US011702429B2

(12) United States Patent
Tzannis et al.

(10) Patent No.: US 11,702,429 B2
(45) Date of Patent: Jul. 18, 2023

(54) MTORC MODULATORS AND USES THEREOF

(71) Applicant: Aeovian Pharmaceuticals, Inc., Walnut Creek, CA (US)

(72) Inventors: Stelios T. Tzannis, Corte Madera, CA (US); Ian J. Massey, Los Altos, CA (US); Alexandre Froidbise, Gardouch (FR); Guillaume Eppe, Toulouse (FR)

(73) Assignee: AEOVIAN PHARMACEUTICALS, INC., Berkeley, CA (US)

( * ) Notice: Subject to any disclaimer, the term of this patent is extended or adjusted under 35 U.S.C. 154(b) by 0 days.

(21) Appl. No.: 17/326,633

(22) Filed: May 21, 2021

(65) Prior Publication Data
US 2023/0013344 A1 Jan. 19, 2023

Related U.S. Application Data

(63) Continuation of application No. 17/024,470, filed on Sep. 17, 2020, now Pat. No. 11,021,492, which is a continuation of application No. PCT/US2020/014671, filed on Jan. 22, 2020.

(60) Provisional application No. 62/795,482, filed on Jan. 22, 2019.

(51) Int. Cl.
  *C07D 498/18* (2006.01)
  *C07D 519/00* (2006.01)
  *A61K 31/436* (2006.01)

(52) U.S. Cl.
  CPC .......... *C07D 498/18* (2013.01); *A61K 31/436* (2013.01); *C07D 519/00* (2013.01)

(58) Field of Classification Search
  CPC .. C07D 498/18; C07D 519/00; A61K 31/436; A61K 9/00; A61K 31/198; A61K 31/375; A61K 38/063; A61K 47/26; A61K 31/439; A61K 31/444; A61P 25/00; A61P 37/00; A61P 37/06; A61P 25/08
  See application file for complete search history.

(56) References Cited

U.S. PATENT DOCUMENTS

| | | | |
|---|---|---|---|
| 10,683,308 B2 | 6/2020 | Saiah et al. | |
| 11,021,492 B2 | 6/2021 | Tzannis et al. | |
| 11,230,557 B2 | 1/2022 | Tzannis et al. | |
| 11,603,377 B2 | 3/2023 | Kincaid | |
| 11,634,432 B2 | 4/2023 | Kincaid | |
| 2016/0138027 A1 | 5/2016 | Gan et al. | |
| 2017/0246305 A1 | 8/2017 | Shokat et al. | |
| 2018/0338918 A1 | 11/2018 | Wang et al. | |
| 2019/0388401 A1 | 12/2019 | Saiah et al. | |
| 2021/0008041 A1 | 1/2021 | Tzannis et al. | |
| 2021/0186935 A1 | 6/2021 | O'Neill et al. | |

FOREIGN PATENT DOCUMENTS

| | | |
|---|---|---|
| EP | 3345601 A1 | 7/2018 |
| EP | 3119425 B1 | 9/2020 |
| WO | WO-9402136 A1 | 2/1994 |
| WO | WO-9516691 A1 | 6/1995 |
| WO | WO-01 14387 A1 | 3/2001 |
| WO | WO-2006136175 A2 | 12/2006 |
| WO | WO-2007085400 A1 | 8/2007 |
| WO | WO-2009131631 A1 | 10/2009 |
| WO | WO-2017044720 A1 | 3/2017 |
| WO | WO-2019064182 A1 | 4/2019 |
| WO | WO-2019241789 A1 | 12/2019 |
| WO | WO-2020076738 A2 | 4/2020 |
| WO | WO-2020128861 A1 | 6/2020 |
| WO | WO-2020154447 A1 | 7/2020 |
| WO | WO-2021113665 A1 | 6/2021 |
| WO | WO-2021195599 A1 | 9/2021 |
| WO | WO-2022020522 A2 | 1/2022 |
| WO | WO-2022159976 A1 | 7/2022 |

OTHER PUBLICATIONS

Bermejo, et al. PAMPA—a drug absorption in vitro model: 7. Comparing rat in situ, Caco-2, and PAMPA permeability of fluoroquinolones. European Journal of Pharmaceutical Sciences 21.4 (2004): 429-441.
Grinfeld et al., "Acid Catalyzed Functionalization of Rapamycin", Tetrahedron Letters, Sep. 12, 1994, 35(37):6835-6838.
National Center for Biotechnology Information. PubChem Compound Summary for CID 124148479. Created Date: Feb. 18, 2017. Available at https://pubchem.ncbi.nlm.nih.gov/compound/124148479. Accessed Nov. 13, 2020.
National Center for Biotechnology Information. PubChem Compound Summary for CID 59032415. Created Date: Aug. 19, 2012. Available at https://pubchem.ncbi.nlm.nih.gov/compound/59032415. Accessed Nov. 13, 2020.
PC/TUS20/14671 International Search Report dated May 19, 2020.
U.S. Appl. No. 17/024,470 Notice of Allowance dated Feb. 18, 2021.
U.S. Appl. No. 17/024,470 Notice of Allowance dated Jan. 27, 2021.
U.S. Appl. No. 17/024,470 Office Action dated Nov. 4, 2020.
U.S. Appl. No. 17/024,486 Examiner's Interview Summary and Advisory Action dated Jun. 15, 2021.
U.S. Appl. No. 17/024,486 Examiner's Interview Summary dated Aug. 13, 2021.
U.S. Appl. No. 17/024,486 Examiner's Interview Summary dated Jul. 8, 2021.
U.S. Appl. No. 17/024,486 Final Office Action dated Mar. 4, 2021.
U.S. Appl. No. 17/024,486 Notice of Allowance dated Sep. 15, 2021.
U.S. Appl. No. 17/024,486 Office Action dated Jan. 13, 2021.

(Continued)

*Primary Examiner* — John M Mauro
(74) *Attorney, Agent, or Firm* — Wilson Sonsini Goodrich & Rosati

(57) ABSTRACT

Novel rapamycin analogs and uses thereof are disclosed herein. The rapamycin analogs of the present disclosure show increased mTORC1 specificity and lowered mTORC2 specificity relative to rapamycin.

20 Claims, No Drawings

(56) References Cited

OTHER PUBLICATIONS

Wong, et al. Antifungal activities of rapamycin and its derivatives, prolylrapamycin, 32-desmethylrapamycin, and 32-desmethoxyrapamycin. The Journal of antibiotics 51.5 (1998): 487-491.
Abdel-Magid, Ahmed F. et al. Rapalogs Potential as Practical Alternatives to Rapamycin. ACS medicinal chemistry letters vol. 10,6 843-845. May 24, 2019, doi:10.1021/acsmedchemlett.9b00215.
Butler, Mark S. et al. Natural product and natural product derived drugs in clinical trials. Natural product reports vol. 31, 11 (2014): 1612-61. doi:10.1039/c4np00064a.
Co-pending U.S. Appl. No. 17/553,409, inventors Tzannis; Stelios T. et al., filed Dec. 16, 2021.
Co-pending U.S. Appl. No. 17/683,549, inventor Kincaid; John, filed Mar. 1, 2022.
PCT/US2021/042644 International Search Report and Written Opinion dated Jan. 19, 2022.
PCT/US21/24536 International Search Report and Written Opinion dated Jun. 9, 2021.
Co-pending U.S. Appl. No. 17/832,240, inventor Kincaid; John, filed Jun. 3, 2022.
EP20745587 Extended European Search Report dated Jul. 22, 2022.
U.S. Appl. No. 17/832,240 Notice of Allowance dated Nov. 8, 2022.
U.S. Appl. No. 17/832,240 Office Action dated Aug. 18, 2022.
U.S. Appl. No. 17/326,633 Notice of Allowance dated Dec. 14, 2022.
Co-pending U.S. Appl. No. 18/180,517, inventor Kincaid; John, filed on Mar. 8, 2023.

MTORC MODULATORS AND USES THEREOF

CROSS-REFERENCE

This application is a continuation of U.S. application Ser. No. 17/024,470, filed Sep. 17, 2020, which claims the benefit of International Application No. PCT/US2020/014671, filed on Jan. 22, 2020, which claims the benefit of U.S. Provisional Patent Application No. 62/795,482 filed on Jan. 22, 2019, each of which is incorporated by reference in its entirety.

BACKGROUND OF THE INVENTION

The therapeutic potential of rapamycin has been established in many chronic diseases, from Alzheimer's and Parkinson's disease to diabetes and cardiovascular disease. However, the prohibitive safety profile of rapamycin for chronic treatment has limited its use for the treatment of various diseases. Rapamycin, an FDA approved compound, inhibits mTOR signaling, leading to extension of lifespan in a number of species, yet it can induce adverse effects, such as peripheral edema, hypercholesterolemia, muscosal ulcerations, abdominal pain, headache, nausea, diarrhea, pain, constipation, hypertriglyceridemia, hypertension, increased creatinine, fever, urinary tract infection, anemia, arthralgia, and thrombocytopenia. Given the complications associated with rapamycin, new agents are needed.

SUMMARY OF THE INVENTION

Rapamycin is believed to inhibit mTORC1 directly and mTORC2 indirectly upon chronic treatment. Recent evidence has revealed that inhibition of mTORC1 is responsible for effects related to lifespan extension, while inhibition of mTORC2 is uncoupled from longevity and is responsible for several of the adverse effects of rapamycin, such as impaired insulin sensitivity, glucose homeostasis, and lipid dysregulation.

The compounds described herein were obtained by synthesizing a library of unique rapamycin analogs (rapalogs) and screening that library in PC3 cells to identify rapalogs that exhibited various degrees of mTORC1 selective inhibitory action (compared to rapamycin). A subset of these rapalogs was selected and the dose-responsiveness of their mTORC1 and mTORC2 inhibitory action was examined, in order to identify compounds that inhibit mTORC1 and show minimal inhibition of mTORC2.

In certain aspects, the disclosure provides a rapamycin analog, wherein the rapamycin analog may be modified at one or both of the C16 and C40 positions relative to rapamycin. The rapamycin analog may have a pIC50 of 9.0 or greater for the mammalian target of rapamycin complex 1 and a pIC50 of 6.0 or less for the mammalian target of rapamycin complex 2.

The rapamycin analog, may be represented by the structure of Formula I.

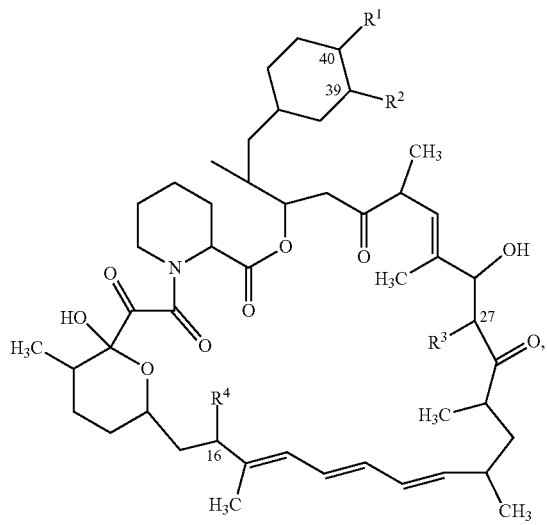

(I)

or a pharmaceutically acceptable salt thereof, wherein:
$R^1$ may be selected from hydroxy,

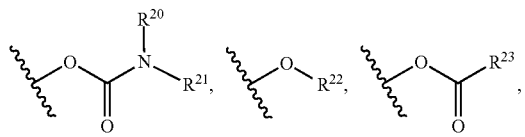

and optionally substituted heteroaryl;

$R^2$ may be selected from hydrogen, an optionally substituted $C_1$-$C_6$ alkoxy group, wherein substituents are independently selected at each occurrence from hydroxy, halogen, cyano, nitro, $C_2$-$C_6$ alkoxy group, cycloalkyl, aryl, heteroaryl, and heterocycloalkyl, wherein cycloalkyl, aryl, heterocyloalkyl, and heteroaryl, are each optionally substituted with one or more substituents independently selected from hydroxy, halogen, cyano, nitro, alkyl, haloalkyl, hydroxyalkyl, alkoxy, and alkoxyalkyl;

$R^3$ may be selected from hydrogen an optionally substituted $C_1$-$C_6$ alkoxy group, wherein the substituents independently selected at each occurrence from hydroxy, halogen, cyano, nitro, $C_2$-$C_6$ alkoxy group, cycloalkyl, aryl, heteroaryl, and heterocycloalkyl, wherein cycloalkyl, aryl, heterocyloalkyl, and heteroaryl, are each optionally substituted with one or more substituents independently selected from hydroxy, halogen, cyano, nitro, alkyl, haloalkyl, hydroxyalkyl, alkoxy, and alkoxyalkyl; and $R^4$ may be selected from methoxy,

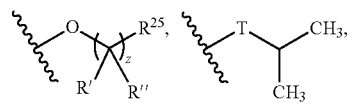

or optionally substituted heteroaryl;

wherein the optionally substituted heteroaryl of $R^1$ may be substituted with one or more substitutents selected from: hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

wherein the optionally substituted heteroaryl of $R^4$ may be substituted with one or more substituents selected from: hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$R^{20}$ may be selected from hydrogen and optionally substituted $C_1$-$C_6$ alkyl;

$R^{21}$ may be selected from optionally substituted $C_1$-$C_6$ alkyl, and optionally substituted 3 to 7 membered heterocycle;

$R^{22}$ may be selected from optionally substituted $C_2$-$C_6$ alkyl, optionally substituted benzyl, —Si($R^{24}$)$_3$, and —P(=O)($R^{24}$)$_2$;

$R^{23}$ may be selected from optionally substituted $C_1$-$C_6$ alkyl and optionally substituted 3 to 7-membered heterocycle;

$R^{24}$ may be optionally substituted $C_1$-$C_6$ alkyl;

wherein the substituents on $R^{20}$, $R^{21}$, $R^{22}$, $R^{23}$, $R^{24}$ may be independently selected at each occurrence from halogen, —OR$^{30}$, —N(R$^{30}$)$_2$, —(O—CH$_2$—(CH$_2$)$_p$)$_n$—W, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN; $C_{1-10}$ alkyl, $C_{2-10}$ alkenyl, $C_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{1-6}$ alkyl, $C_{1-6}$ alkyl-R$^{30}$, $C_{2-6}$ alkenyl, and $C_{2-6}$ alkynyl;

each p may be selected from 1 or 2;

n may be selected from 1-4;

W may be selected from —OH and —CH$_3$, $R^{30}$ may be independently selected at each occurrence from hydrogen, —Si($C_1$-$C_6$ alkyl)$_3$; and $C_{1-10}$ alkyl, $C_{2-10}$ alkenyl, $C_{2-10}$ alkynyl, $C_{3-12}$ carbocycle, and 3- to 12-membered heterocycle, each of which may be optionally substituted with one or more substituents independently selected from halogen, —OH, —OSi($C_1$-$C_6$ alkyl)$_3$, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl;

z may be 0, 1, 2, 3, 4 or 5;

R' and R" may be independently selected from hydrogen, halogen, —OR$^{31}$, and $C_{1-3}$ alkyl optionally substituted with one or more substituents independently selected from halogen and —OR$^{31}$.

T may be S or O;

$R^{25}$ may be selected from —OR$^{31}$, optionally substituted 3- to 10-membered heterocycle, optionally substituted $C_{3-10}$ carbocycle;

wherein substituents on $R^{21}$ may be independently selected at each occurrence from: halogen, —OR$^{31}$, —SR$^{31}$, —N(R$^{31}$)$_2$, —C(O)R$^{31}$, —C(O)N(R$^{31}$)$_2$, N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), and —CN; $C_{1-10}$ alkyl, $C_{2-10}$ alkenyl, $C_{2-10}$ alkynyl, each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$) C(O)R$^{31}$, —C(O)OR$^{31}$, —OC(O)R$^{31}$, —S(O)R$^{31}$, —S(O)$_2$ R$^{31}$, —P(O)(OR$^{31}$)$_2$, —OP(O)(OR$^{31}$)$_2$, —NO$_2$, =O, =S, =N(R$^{31}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR$^{31}$, —SR$^{31}$, —N(R$^{31}$)$_2$, —C(O)R$^{31}$, —C(O)N(R$^{31}$)$_2$, —N(R$^{31}$)C(O)R$^{31}$, —C(O)OR$^{31}$, —OC(O)R$^{31}$, —S(O)R$^{31}$, —S(O)$_2$R$^{31}$, —P(O)(OR$^{31}$)$_2$, —OP(O)(OR$^{31}$)$_2$, —NO$_2$, =O, =S, =N(R$^{31}$), —CN, $C_{1-6}$ alkyl, $C_{2-6}$ alkenyl, $C_{2-6}$ alkynyl; and $R^{31}$ may be independently selected at each occurrence from hydrogen, —Si($C_1$-$C_6$ alkyl)$_3$; and $C_{1-10}$ alkyl, $C_{2-10}$ alkenyl, $C_{2-10}$ alkynyl, $C_{3-12}$ carbocycle, and 3- to 12-membered heterocycle, each of which may be optionally substituted with one or more substituents independently selected from halogen, —OH, —OSi($C_1$-$C_6$ alkyl)$_3$, —CN, —NO$_2$, —NH$_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl.

A compound of the disclosure may be represented by the structure of Formula II:

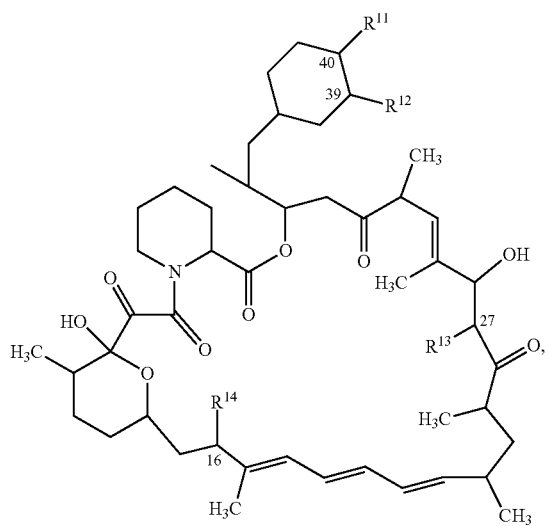

(II)

or a pharmaceutically acceptable salt thereof, wherein:

$R^{11}$ is selected from

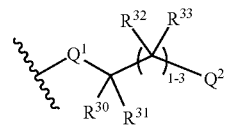

and —OCH$_3$;

$R^{12}$ is selected from hydrogen, hydroxy, and an optionally substituted $C_1$-$C_6$ alkoxy group, wherein substituents on the $C_1$-$C_6$ alkoxy group are independently selected at each occurrence from hydroxy, halogen, cyano, nitro, $C_2$-$C_6$ alkoxy group, optionally substituted carbocycle and optionally substituted heterocycle, wherein substituents on the carbocycle or heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$R^{13}$ is selected from hydrogen, hydroxy, and optionally substituted $C_1$-$C_6$ alkoxy group, wherein the substituents on the $C_1$-$C_6$ alkoxy group are independently selected at each occurrence from hydroxy, halogen, cyano, nitro, $C_2$-$C_6$ alkoxy group, optionally substituted carbocycle and optionally substituted heterocycle, wherein substituents on the carbocycle or heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$R^{14}$ is selected from

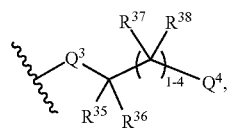

—O—(CH$_2$)$_{0-1}$T and —O—CH(CH$_3$)$_2$;

T is an optionally substituted 3-6-membered heterocycloalkyl wherein substituents are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$Q^1$ and $Q^3$ are independently selected from —O—, —OC(=O)NR$^{41}$—, —S—, and —NR$^{40}$—;

$Q^2$ is selected from optionally substituted $C_{3-6}$ carbocycle, optionally substituted 3-8-membered heterocycle, —OR$^{34}$, —(O—CH$_2$—(CH$_2$)$_p$)$_n$—W, and —N(R$^{39}$)$_2$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$Q^4$ is selected from optionally substituted $C_{3-6}$ carbocycle, optionally substituted 3-8-membered heterocycle, and —OR$^{42}$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$R^{30}$, $R^{31}$, $R^{35}$, and $R^{36}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

each $R^{32}$, $R^{33}$, $R^{37}$, and $R^{38}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

each $R^{34}$ is selected from hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, halogen, cyano, nitro, $C_1$-$C_6$ alkoxy, carbocycle and heterocycle;

each $R^{39}$ is selected from hydrogen, $C_1$-$C_6$ alkyl, haloalkyl, and alkoxy $C_1$-$C_6$ alkyl;

each $R^{40}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle; and each $R^{41}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle;

each $R^{42}$ is selected from hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, halogen, cyano, nitro, $C_1$-$C_6$ alkoxy, carbocycle and heterocycle;

each p is selected from 1 or 2;

n is selected from 2-4;

W is selected from —OH and —OCH$_3$ wherein when $R^{11}$ is

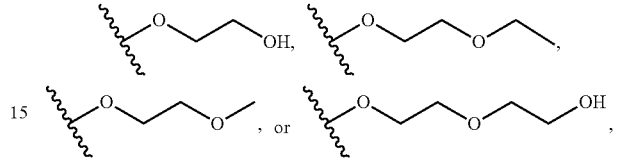

$R^{14}$ is not

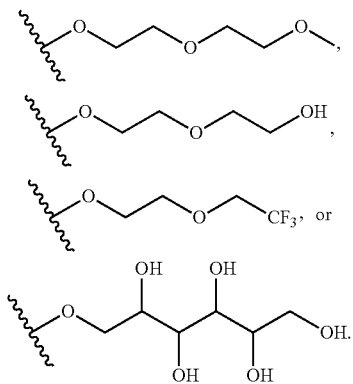

In certain embodiments, the disclosure provides a method of treating disease comprising administering a compound with a pIC50 of 9.0 or greater for the mammalian target of rapamycin complex 1 and a pIC50 of 6.0 or less for the mammalian target of rapamycin complex 2 to a subject in need thereof.

In certain embodiments, the disclosure provides a method of treating disease comprising administering a compound with a pIC50 of 9.5 or greater for the mammalian target of rapamycin complex 1 and a pIC50 of 5.0 or less for the mammalian target of rapamycin complex 2 to a subject in need thereof.

In certain embodiments, the disclosure provides a method of treating disease comprising chronically administering a rapamycin analog or compound described herein to a subject in need thereof.

In certain embodiments, the disclosure provides a method of treating disease, wherein the disease is selected from a chronic disease. The chronic disease may be selected from a disease wherein mTORC1 is hyperactivated. The chronic disease may be selected from a disease wherein the chronic disease would benefit from mTORC1 inhibition. In certain embodiments, the chronic disease may be selected from neurodegenerative disease, a neurocutaneous disease, a neurodevelopmental disorder, mTORopathies, tauopathies, cognitive disorders, epilepsies, autism spectrum disorders, autoimmune diseases, metabolic diseases, cancer, diseases of impaired autophagy, infectious diseases, cardiovascular diseases, muscular atrophy, inflammatory diseases, eye disorders or diseases of aging that result in hyperactivation of mTORC1 including reduced immune activity in the elderly. The chronic disease may be an mTORopathy, e.g., Tuberous Sclerosis.

In certain embodiments, the disclosure provides a method of treating a disease, wherein the compound may be a rapamycin analog.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions).

As used herein, the term "in substantially pure form" means that the compound is provided in a form which is substantially free of other compounds (particularly polyketides or other rapamycin analogues) when produced in fermentation processes, especially a fermentation process involving feeding starter acid as described herein to a rapamycin producing strain that has been genetically altered to remove or inactivate the rapK gene or homologue thereof. For example, the purity of the compound is at least 90%, or at least 95%, or at least 98%, or at least 99% as regards the polyketide content of the form in which is it presented. Hence both prior and post formulation as a pharmaceutical product, in various embodiments, the compounds described herein suitably represent at least 90%, or at least 95%, or at least 98%, or least 99% of the polyketide content of the composition or product.

In certain embodiments, compositions of the disclosure may comprise two or more enantiomers of a compound wherein a single enantiomer accounts for at least about 70% by weight, at least about 80% by weight, at least about 90% by weight, at least about 98% by weight, or at least about 99% by weight or more of the total weight of all stereoisomers. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) *J. Chromatogr.*, 113(3): 283-302). Racemic mixtures of chiral compounds can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R—S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)—. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When stereochemistry is not specified, certain molecules described herein include isomers, such as enantiomers and diastereomers, mixtures of enantiomers, including racemates, mixtures of diastereomers, and other mixtures thereof, to the extent they can be made by one of ordinary skill in the art by routine experimentation. In certain embodiments, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to saturated hydrocarbon groups, including straight-chain alkyl and branched-chain alkyl groups that contain from 1 to 6 carbons. The term —$C_{x-y}$alkylene— refers to a substituted or unsubstituted alkylene chain with from x to y carbons in the alkylene chain. For example —$C_{1-6}$alkylene- may be selected from methylene, ethylene, propylene, butylene, pentylene, and hexylene, any one of which is optionally substituted.

The terms "$C_{x-y}$alkenyl" and "$C_{x-y}$alkynyl" refer to unsaturated aliphatic groups analogous in length and possible substitution to the alkyls described above, but that contain at least one double or triple bond, respectively. The term —$C_{x-y}$alkenylene— refers to a substituted or unsubstituted alkenylene chain with from x to y carbons in the alkenylene chain. For example, —$C_{2-6}$alkenylene—may be selected from ethenylene, propenylene, butenylene, pentenylene, and hexenylene, any one of which is optionally substituted. An alkenylene chain may have one double bond or more than one double bond in the alkenylene chain. The term —$C_{x-y}$alkynylene— refers to a substituted or unsubstituted alkynylene chain with from x to y carbons in the alkynylene chain. For example, —$C_{2-6}$alkynylene—may be selected from ethynylene, propynylene, butynylene, pentynylene, and hexynylene, any one of which is optionally substituted. An alkynylene chain may have one triple bond or more than one triple bond in the alkynylene chain.

"Alkylene" refers to a straight divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). Alkylene chain may be optionally substituted by one or more substituents such as those substituents described herein.

"Alkenylene" refers to a straight divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene). Alkenylene chain may be optionally substituted by one or more substituents such as those substituents described herein.

"Alkynylene" refers to a straight divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene). Alkynylene chain may be optionally substituted by one or more substituents such as those substituents described herein.

The term "carbocycle" as used herein refers to a saturated, unsaturated or aromatic ring in which each atom of the ring is carbon. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Carbocycle may be optionally substituted by one or more substituents such as those substituents described herein. Bicyclic carbocycles may be fused, bridged or spiro-ring systems.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Heterocycle may be optionally substituted by one or more substituents such as those substituents described herein. Bicyclic heterocycles may be fused, bridged or spiro-ring systems.

The term "heteroaryl" includes aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more rings in which two or more carbons are common to two adjoining rings wherein at least one of the rings is heteroaromatic, e.g., the other rings can be aromatic or non-aromatic carbocyclic, or heterocyclic. Heteroaryl groups include, for example, pyrrole, furan, thiophene, imidazole, oxazole, thiazole, pyrazole, pyridine, pyrazine, pyridazine, and pyrimidine, and the like.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2), and —$R^b$—S(O)$_t$N($R^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain. It will be understood by those skilled in the art that substituents can themselves be substituted, if appropriate.

Generally, reference to a certain element, such as hydrogen or H, is meant to include all isotopes of that element. For example, if an R group is defined to include hydrogen or H, it also includes deuterium and tritium. Accordingly, isotopically labeled compounds are within the scope of this invention. The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a compound or salt described herein.

As used herein, "agent" or "biologically active agent" refers to a biological, pharmaceutical, or chemical compound or other moiety. Non-limiting examples include an organic or inorganic molecule, a peptide, a protein, a peptide nucleic acid (PNA), an oligonucleotide (including e.g., aptamer and polynucleotides), an antibody, an antibody derivative, antibody fragment, a vitamin derivative, a carbohydrate, a toxin, a branched chain amino acid in free amino acid form or metabolite thereof, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents.

The terms "administer", "administered", "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used. The term "effective amount" or "therapeutically effective amount" refers to that amount of a compound or salt described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term can also apply to a dose that can induce a particular response in target cells, e.g., reduction of proliferation or down regulation of activity of a target protein. The specific dose can vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including, but not limited to, a therapeutic benefit and/or a prophylactic benefit. In certain embodiments, treatment or treating involves administering a compound or composition disclosed herein to a subject. A therapeutic benefit may include the eradication or amelioration of the underlying disorder being treated. Also, a therapeutic benefit may be achieved with the eradication or amelioration of one or more of the physiological symptoms associated with the underlying disorder, such as observing an improvement in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treating can be used herein to refer to a method that results in some level of treatment or amelioration of the disease or condition, and can contemplate a range of results directed to that end, including but not restricted to prevention of the condition entirely.

In certain embodiments, the tert "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "selective inhibition" or "selectively inhibit" as referred to a biologically active agent refers to the agent's ability to preferentially reduce the target signaling activity as compared to off-target signaling activity, via direct or interact interaction with the target. Rapamycin analogs In some aspects, the present disclosure provides a rapamycin analog, wherein the rapamycin analog is modified, relative to rapamycin, at one or both of the C16 and C40 positions of rapamycin. In certain embodiments a rapamycin analog has a pIC50 of 9.0 or greater for the mammalian target of rapamycin complex 1 (mTORC1) and a pIC50 of 6.0 or less for the mammalian target of rapamycin complex 2 (mTORC 2).

In certain embodiments, the disclosure provides compounds selective for mTORC1 over mTORC2. The compounds of the present disclosure may be mTORC1 selective agents. In certain embodiments, the disclosure provides an mTORC1 selective agent, such as a compound or salt with a pIC50 of 8.0 or greater for the mTORC1 and a pIC50 of 6.0 or less for the mTORC2. The compound may have a pIC50 of 8.0 or greater, 8.5 or greater, 9.0 or greater, 9.5 or greater, 10.0 or greater, 10.5 or greater, 11.0 or greater, for the mTORC1, and may have a pIC50 of 6.0 or less, 5.5 or less, 5.0 or less, 4.5 or less, 4.0 or less, for the mTORC2. In certain embodiments, the mTORC1 selective agent may be a compound or salt with a pIC50 of 9.5 or greater for the mTORC1 and a pIC50 of 5.5 or less for the mTORC2.

In certain embodiments, the compound has a pIC50 for the mTORC1 that may be at least about 6.0, at least about 6.5, at least about 7.0, at least about 7.5, at least about 8.0, at least about 8.5, at least about 9.0, at least about 9.5, at least about 10.0, at least about 10.5, or at least about 11.0, and a pIC50 for the mTORC2 of about 7.0 or less, about 6.5 or less, about 6.0 or less, about 5.5 or less, about 5.0 or less, about 4.5 or less, or about 4.0 or less.

In certain embodiments, the compound has a pIC50 for the mTORC1 that may be at least about 6.0, at least about 6.5, at least about 7.0, at least about 7.5, at least about 8.0, at least about 8.5, at least about 9.0, at least about 9.5, at least about 10.0, at least about 10.5, or at least about 11.0.

In certain embodiments, the compound has a pIC50 for the mTORC1 from about 6.0 to 11.0, 6.0 to 10.0, 6.0 to 9.0, 6.0 to 8.0, 7.0 to 11.0, 7.0 to 10.0, or 7.0 to 9.0.

In certain embodiments, the compound has a pIC50 for the mTORC2 of about 7.0 or less, about 6.5 or less, about 6.0 or less, about 5.5 or less, about 5.0 or less, about 4.5 or less, or about 4.0 or less.

In certain embodiments, the compound has a pIC50 for the mTORC2 of about 4.0 to 7.0, about 4.0 to 6.5, about 4.0 to 6.0, about 4.0 to 5.5, about 4.0 to 5.0, about 4.0 to 4.5, or about 5.0 to 7.0.

In certain embodiments, the compound has a pIC50 for the mTORC1 from about 6.0 to 11.0, about 6.0 to 10.0, about 6.0 to 9.0, about 6.0 to 8.0, about 6.0 to 7.0, and a pIC50 for the mTORC2 from about 4.0 to 7.0, about 4.0 to 6.5, about 4.0 to 6.0, or about 4.0 to 5.5.

In certain embodiments, the rapamycin analog is modified at one of the C16 and C40 positions relative to rapamycin. In certain embodiments, the rapamycin analog is modified at both of the C16 and C40 positions relative to rapamycin. In rapamycin, the C40 position is substituted with a hydroxy group and the C16 position is substituted with a methoxy group. In certain embodiments, for a rapamycin analog described herein, one or both of the substituents at the C16 and C40 positions are substituted with another substituent.

In certain embodiments, a rapamycin analog of the disclosure replaces the C40 hydroxy group with a substituent selected from

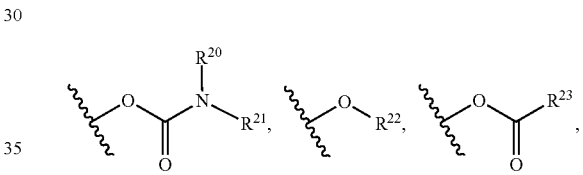

and optionally substituted heteroaryl; wherein the optionally substituted heteroaryl may be substituted with one or more substitutents selected from: hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$R^{20}$ is selected from hydrogen and optionally substituted $C_1$-$C_6$ alkyl;

$R^{21}$ is selected from optionally substituted $C_1$-$C_6$ alkyl, and optionally substituted 3 to 7 membered heterocycle;

$R^{22}$ is selected from optionally substituted $C_2$-$C_6$ alkyl, optionally substituted benzyl, —Si($R^{24}$)$_3$, and —P(=O)($R^{24}$)$_2$;

$R^{23}$ is selected from optionally substituted $C_1$-$C_6$ alkyl and optionally substituted 3 to 7-membered heterocycle;

$R^{24}$ is optionally substituted $C_1$-$C_6$ alkyl;

wherein the substituents on $R^{20}$, $R^{21}$, $R^{22}$, $R^{23}$, $R^{24}$ are independently selected at each occurrence from halogen, —OR$^{30}$, —N(R$^{30}$)$_2$, —(O—CH$_2$—(CH$_2$)$_p$)$_n$—W, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), and —CN;

$C_{1-10}$ alkyl, $C_{2-10}$ alkenyl, $C_{2-10}$ alkynyl, each of which is optionally substituted with one or more substituents independently selected from halogen, —OR$^{30}$, —SR$^{30}$, —N(R$^{30}$)$_2$, —C(O)R$^{30}$, —C(O)N(R$^{30}$)$_2$, —N(R$^{30}$)C(O)R$^{30}$, —C(O)OR$^{30}$, —OC(O)R$^{30}$, —S(O)R$^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —$OR^{30}$, —$SR^{30}$, —$N(R^{30})_2$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, —CN, $C_{1-6}$ alkyl, $C_{1-6}$ alkyl-$R^{30}$, $C_{2-6}$ alkenyl, and $C_{2-6}$ alkynyl;

each p is selected from 1 or 2;

n is selected from 1-4;

W is selected from —OH and —$CH_3$;

$R^{30}$ is independently selected at each occurrence from hydrogen, —Si($C_1$-$C_6$ alkyl)$_3$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)$_3$, —CN, —$NO_2$, —$NH_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl.

In certain embodiments, a rapamycin analog may be modified at additional positions to the C40 position and/or C16 positions, relative to rapamycin.

In certain embodiments, a rapamycin analog of the disclosure replaces the C16 methoxy group of rapamycin with a group selected from

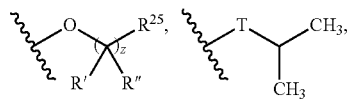

or optionally substituted heteroaryl; wherein the optionally substituted heteroaryl may be substituted with one or more substitutents selected from: hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

z is 0, 1, 2, 3, 4 or 5;

R' and R" are independently selected from hydrogen, halogen, —$OR^{31}$, and $C_{1-3}$ alkyl optionally substituted with one or more substituents independently selected from halogen and —$OR^{31}$.

T is S or O;

$R^{25}$ is selected from —$OR^{31}$, optionally substituted 3- to 10-membered heterocycle, optionally substituted $C_{3-10}$ carbocycle;

wherein substituents on $R^{25}$ are independently selected at each occurrence from: halogen, —$OR^{31}$, —$SR^{31}$, —$N(R^{31})_2$, —$C(O)R^{31}$, —$C(O)N(R^{31})_2$, $N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, =O, =S, =$N(R^{31})$, and —CN;

$C_{1-10}$ alkyl, $C_{2-10}$ alkenyl, $C_{2-10}$ alkynyl, each of which is optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2R^{31}$, —$P(O)(OR^{31})_2$, —$OP(O)(OR^{31})_2$, —$NO_2$, =O, =S, =$N(R^{31})$, —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —$OR^{31}$, —$SR^{31}$, —$N(R^{31})_2$, —$C(O)R^{31}$, —$C(O)N(R^{31})_2$, —$N(R^{31})C(O)R^{31}$, —$C(O)OR^{31}$, —$OC(O)R^{31}$, —$S(O)R^{31}$, —$S(O)_2$ $R^{31}$, —$P(O)(OR^{31})_2$, —$OP(O)(OR^{31})_2$, —$NO_2$, =O, =S, =$N(R^{31})$, —CN, $C_{1-6}$ alkyl, $C_{2-6}$ alkenyl, $C_2$-6 alkynyl; and $R^{31}$ is independently selected at each occurrence from hydrogen, —Si($C_1$-$C_6$ alkyl)$_3$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)$_3$, —CN, —$NO_2$, —$NH_2$, =O, =S, $C_{1-10}$ alkyl, —$C_{1-10}$ haloalkyl, —O—$C_1$-10 alkyl, $C_{2-10}$ alkenyl, $C_{2-10}$ alkynyl, $C_{3-12}$ carbocycle, 3- to 12-membered heterocycle, and haloalkyl.

In some aspects, the rapamycin analog is represented by the structure of Formula (I):

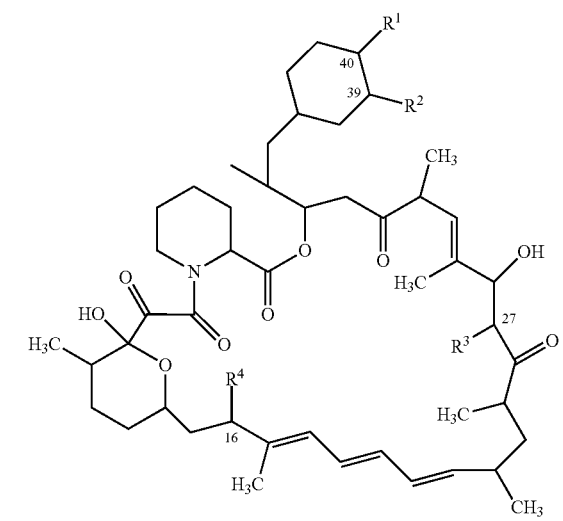

(I)

or a pharmaceutically acceptable salt thereof, wherein:

$R^1$ is selected from hydroxy,

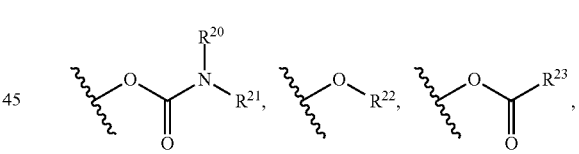

and optionally substituted heteroaryl;

$R^2$ is selected from hydrogen, an optionally substituted $C_1$-$C_6$ alkoxy group, wherein substituents are independently selected at each occurrence from hydroxy, halogen, cyano, nitro, $C_2$-$C_6$ alkoxy group, cycloalkyl, aryl, heteroaryl, and heterocycloalkyl, wherein cycloalkyl, aryl, heterocyloalkyl, and heteroaryl, are each optionally substituted with one or more substituents independently selected from hydroxy, halogen, cyano, nitro, alkyl, haloalkyl, hydroxyalkyl, alkoxy, and alkoxyalkyl;

$R^3$ is selected from hydrogen and an optionally substituted $C_1$-$C_6$ alkoxy group, wherein the substituents are independently selected at each occurrence from hydroxy, halogen, cyano, nitro, $C_2$-$C_6$ alkoxy group, cycloalkyl, aryl, heteroaryl, and heterocycloalkyl, wherein cycloalkyl, aryl, heterocyloalkyl, and heteroaryl, are each optionally substituted with one or more substituents independently selected from hydroxy, halogen, cyano, nitro, alkyl, haloalkyl, hydroxyalkyl, alkoxy, and alkoxyalkyl; and R⁴ is selected from methoxy,

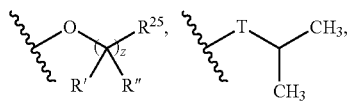

and optionally substituted heteroaryl;

$R^{20}$ is selected from hydrogen and optionally substituted $C_1$-$C_6$ alkyl;

$R^{21}$ is selected from optionally substituted $C_1$-$C_6$ alkyl, and optionally substituted 3 to 7 membered heterocycle;

$R^{22}$ is selected from optionally substituted $C_2$-$C_6$ alkyl, optionally substituted benzyl, —Si(R²⁴)₃, and —P(=O)(R²⁴)₂;

$R^{23}$ is selected from optionally substituted $C_1$-$C_6$ alkyl and optionally substituted 3 to 7-membered heterocycle;

$R^{24}$ is optionally substituted $C_1$-$C_6$ alkyl;

wherein the substituents on $R^{20}$, $R^{21}$, $R^{22}$, $R^{23}$, $R^{24}$ are independently selected at each occurrence from halogen, —OR³⁰, —N(R³⁰)₂, —(O—CH₂—(CH₂)$_p$)$_n$—W, —SR³⁰, —N(R³¹)₂, —C(O)R³⁰, —C(O)N(R³⁰)₂, —N(R³⁰)C(O)R³⁰, —C(O)OR³⁰, —OC(O)R³⁰, —S(O)R³⁰, —S(O)₂R³⁰, —P(O)(OR³⁰)₂, —OP(O)(OR³⁰)₂, —NO₂, =O, =S, =N(R³⁰), and —CN;

$C_{1-10}$ alkyl, $C_{2-10}$ alkenyl, $C_{2-10}$ alkynyl, each of which is optionally substituted with one or more substituents independently selected from halogen, —OR³⁰, —SR³⁰, —N(R³⁰)₂, —C(O)R³⁰, —C(O)N(R³⁰)₂, —N(R³⁰)C(O)R³⁰, —C(O)OR³⁰, —OC(O)R³⁰, —S(O)R³⁰, —S(O)₂R³⁰, —P(O)(OR³⁰)₂, —OP(O)(OR³⁰)₂, —NO₂, =O, =S, =N(R³⁰), —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —OR³⁰, —SR³⁰, —N(R³⁰)₂, —C(O)R³⁰, —C(O)N(R³⁰)₂, —N(R³⁰)C(O)R³⁰, —C(O)OR³⁰, —OC(O)R³⁰, —S(O)R³⁰, —S(O)₂R³⁰, —P(O)(OR³⁰)₂, —OP(O)(OR³⁰)₂, —NO₂, =O, =S, =N(R³⁰), —CN, $C_{1-6}$ alkyl, $C_{1-6}$ alkyl-R³⁰, $C_{2-6}$ alkenyl, and $C_{2-6}$ alkynyl;

each p is selected from 1 or 2;

n is selected from 1-4;

W is selected from —OH and —CH₃;

$R^{30}$ is independently selected at each occurrence from hydrogen, —Si($C_1$-$C_6$ alkyl)₃; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)₃, —CN, —NO₂, —NH₂, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl;

z is 0, 1, 2, 3, 4 or 5;

R' and R" are independently selected from hydrogen, halogen, —OR³¹, and $C_{1-3}$ alkyl optionally substituted with one or more substituents independently selected from halogen and —OR³¹.

T is S or O;

$R^{25}$ is selected from —OR³¹, optionally substituted 3- to 10-membered heterocycle, optionally substituted $C_{3-10}$ carbocycle;

wherein substituents on $R^{25}$ are independently selected at each occurrence from: halogen, —OR³¹, —SR³¹, —N(R³¹)₂, —C(O)R³¹, —C(O)N(R³¹)₂, N(R³¹)C(O)R³¹, —C(O)OR³¹, —OC(O)R³¹, —S(O)R³¹, —S(O)₂R³¹, —P(O)(OR³¹)₂, —OP(O)(OR³¹)₂, —NO₂, =O, =S, =N(R³¹), and —CN;

$C_{1-10}$ alkyl, $C_{2-10}$ alkenyl, $C_{2-10}$ alkynyl, each of which is optionally substituted with one or more substituents independently selected from halogen, —OR³¹, —SR³¹, —N(R³¹)₂, —C(O)R³¹, —C(O)N(R³¹)₂, —N(R³¹)C(O)R³¹, —C(O)OR³¹, —OC(O)R³¹, —S(O)R³¹, —S(O)₂R³¹, —P(O)(OR³¹)₂, —OP(O)(OR³¹)₂, —NO₂, =O, =S, =N(R³¹), —CN, $C_{3-10}$ carbocycle and 3- to 10-membered heterocycle; and $C_{3-10}$ carbocycle and 3- to 10-membered heterocycle each of which is optionally substituted with one or more substituents independently selected from halogen, —OR³¹, —SR³¹, —N(R³¹)₂, —C(O)R³¹, —C(O)N(R³¹)₂, —N(R³¹)C(O)R³¹, —C(O)OR³¹, —OC(O)R³¹, —S(O)R³¹, —S(O)₂R³¹, —P(O)(OR³¹)₂, —OP(O)(OR³¹)₂, —NO₂, =O, =S, =N(R³¹), —CN, $C_{1-6}$ alkyl, $C_{2-6}$ alkenyl, $C_{2-6}$ alkynyl; and $R^{31}$ is independently selected at each occurrence from hydrogen, —Si($C_1$-$C_6$ alkyl)₃; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)₃, —CN, —NO₂, —NH₂, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl.

In some aspects, the compound or salt of Formula (I) is represented by the structure of Formula (I-A):

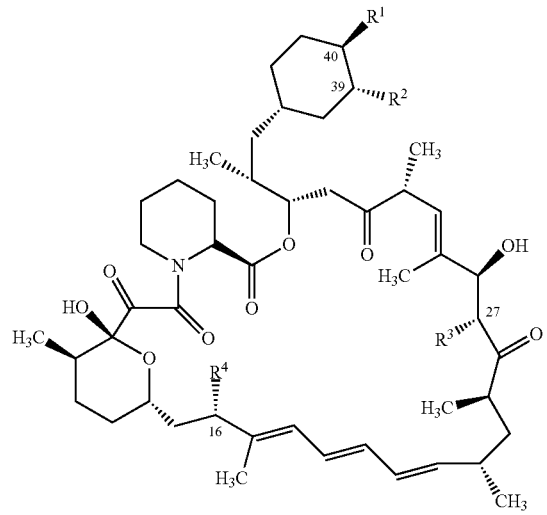

(I-A)

or a pharmaceutically acceptable salt thereof.

In some embodiments, R¹ is not —OH,

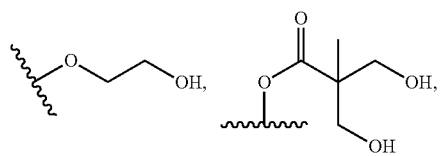

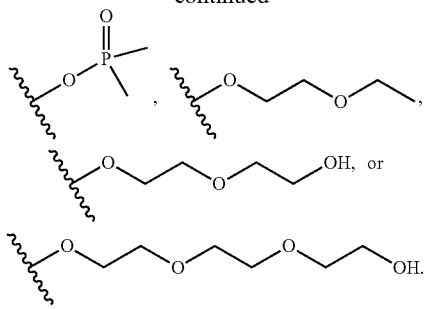

In some embodiments, $R^1$ is

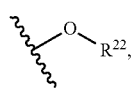

wherein $R^{22}$ is selected from optionally substituted $C_2$-$C_6$ alkyl, optionally substituted benzyl, —Si($R^{24}$)$_3$, and —P(=O)($R^{24}$)$_2$. In some embodiments, $R^{22}$ is an optionally substituted $C_2$-$C_6$ alkyl. In some embodiments, $R^{22}$ is $C_2$-$C_6$ alkyl substituted with one or more substituents selected from halogen, —C(O)O$R^{30}$, —OC(O)$R^{30}$, —S$R^{30}$, —N($R^{30}$)$_2$, —(O—CH$_2$—(CH$_2$)$_p$)$_n$—W, —O$R^{30}$, optionally substituted $C_{1-10}$ alkyl, optionally substituted $C_{2-10}$ alkenyl, optionally substituted $C_{3-10}$ carbocycle and optionally substituted 3- to 10-membered heterocycle. In some embodiments, $R^{22}$ may be $C_2$-$C_6$ alkyl substituted with one or more substituents selected from —N($R^{30}$)$_2$, —(O—CH$_2$—(CH$_2$)$_p$)$_n$—W, —O$R^{30}$, optionally substituted $C_3$-10 carbocycle and optionally substituted 3- to 10-membered heterocycle, and wherein $R^{30}$ is selected from hydrogen, —Si($C_1$-$C_6$ alkyl)$_3$, optionally substituted $C_{1-10}$ alkyl, and optionally substituted $C_{1-10}$ alkyl. In some embodiments, $R^{22}$ may be $C_2$-$C_6$ alkyl substituted with one or more substituents selected from —N($R^{30}$)$_2$, —(O—CH$_2$—(CH$_2$)$_p$)$_n$—W, —O$R^{30}$, optionally substituted $C_{3-10}$ carbocycle and optionally substituted 3- to 10-membered heterocycle, and wherein $R^{30}$ is selected from hydrogen, —Si($C_1$-$C_6$ alkyl)$_3$ and optionally substituted $C_{1-10}$ alkyl.

In some embodiments, $R^{22}$ may be $C_2$-$C_6$ alkyl substituted with one or more substituents selected from —N($R^{30}$)$_2$. In some embodiments, $R^1$ is

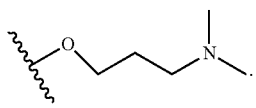 [SMILES: *OCCCN(C)C]

In some embodiments, $R^{22}$ is $C_2$-$C_6$ alkyl substituted with one or more substituents selected from —(O—CH$_2$—(CH$_2$)$_p$)$_n$—W and —O$R^{30}$. In some embodiments, $R^1$ is selected from:

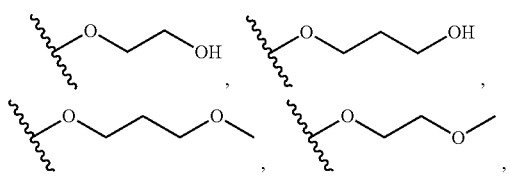

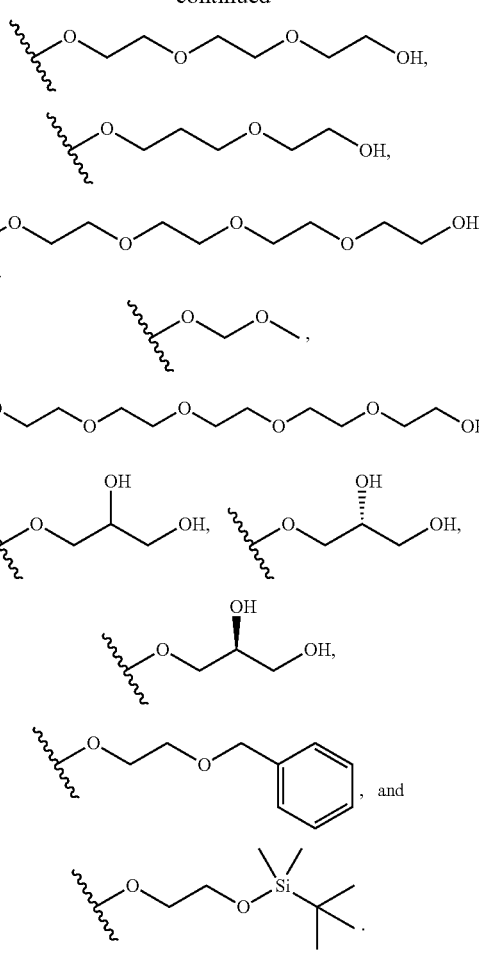

In some embodiments, $R^{22}$ is $C_2$-$C_6$ alkyl substituted with one or more substituents selected from —O$R^{30}$. In some embodiments, $R^1$ is selected from:

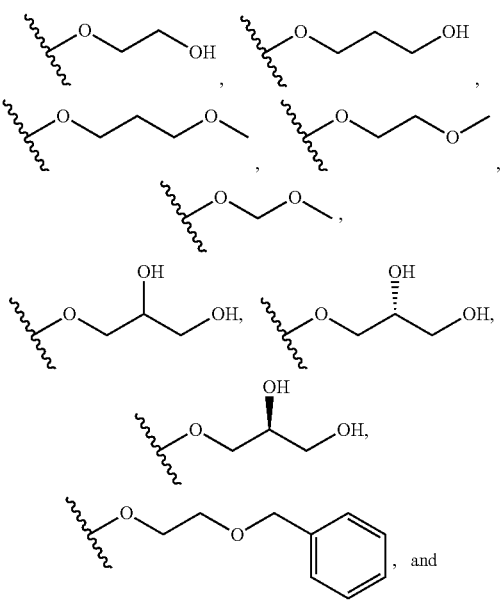

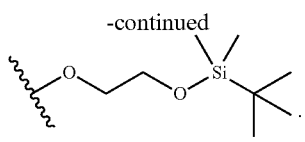

In some embodiments, $R^{22}$ is $C_2$-$C_6$ alkyl substituted with one substituent selected from —$OR^{30}$. In some embodiments, $R^1$ is selected from:

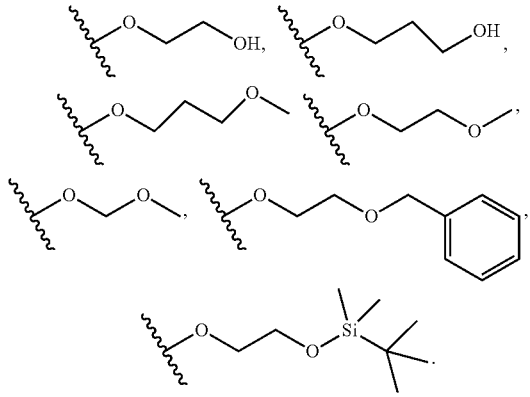

In some embodiments, $R^{22}$ is $C_2$-$C_6$ alkyl substituted with one or more substituents selected from optionally substituted $C_{3-6}$ carbocycle.

In some embodiments, $R^1$ is selected from:

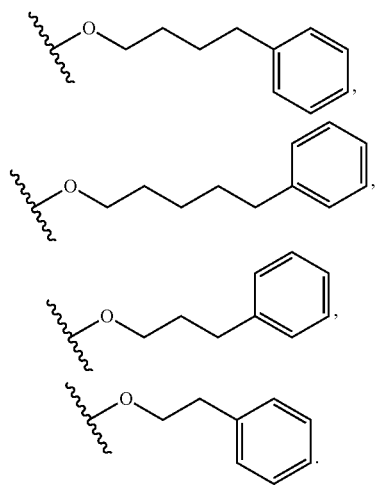

In some embodiments, $R^{22}$ is $C_2$-$C_6$ alkyl substituted with one or more substituents selected from —(O—$CH_2$—$(CH_2)_p)_n$—W. In some embodiments, $R^1$ is selected from:

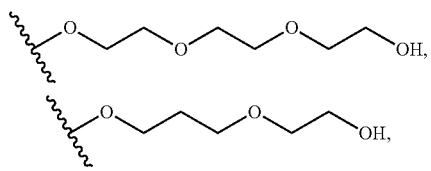

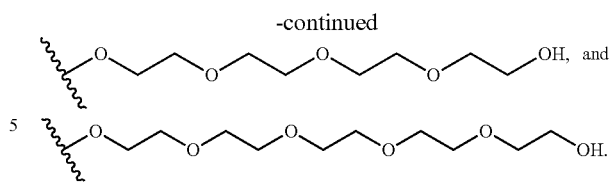

In some embodiments, $R^{30}$ is selected from hydrogen and $C_{1-10}$ alkyl.

In some embodiments, $R^1$ is selected from:

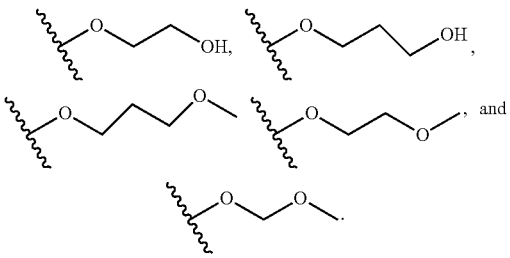

In some embodiments, $R^{22}$ is $C_2$-$C_6$ alkyl substituted with one or more substituents selected from optionally substituted $C_{3-6}$ carbocycle. In some embodiments, $R^{22}$ is $C_2$-$C_6$ alkyl substituted with one or more $C_{3-6}$ carbocycle that may be selected from:

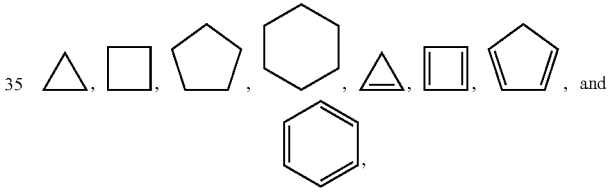

any one of which is optionally substituted. In some embodiments, $R^{22}$ may be $C_2$-$C_6$ alkyl substituted with one or more optionally substituted phenyl. In some embodiments, $R^{22}$ may be $C_2$-$C_6$ alkyl substituted with phenyl.

In some embodiments, $R^1$ is selected from:

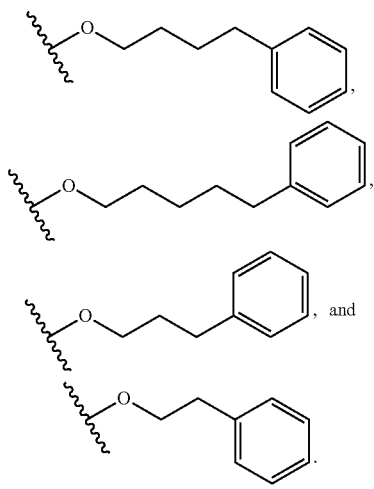

In some embodiments, $R^1$ is selected from:

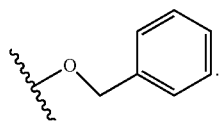 [SMILES: *OCc1ccccc1]

In some embodiments, $R^{22}$ is $C_2$-$C_6$ alkyl substituted with one or more substituents selected from optionally substituted 3- to 6-membered heterocycle. In some embodiments, the 3- to 6-membered heterocycle comprises at least one heteroatom selected from N and O. In some embodiments, the 3- to 6-membered heterocycle is substituted with one or more substituents selected from $C_{1-6}$ alkyl and —$OR^{30}$.

In some embodiments, $R^{22}$ is $C_2$-$C_6$ alkyl substituted with one or more 3- to 6-membered heterocycle that may be selected from:

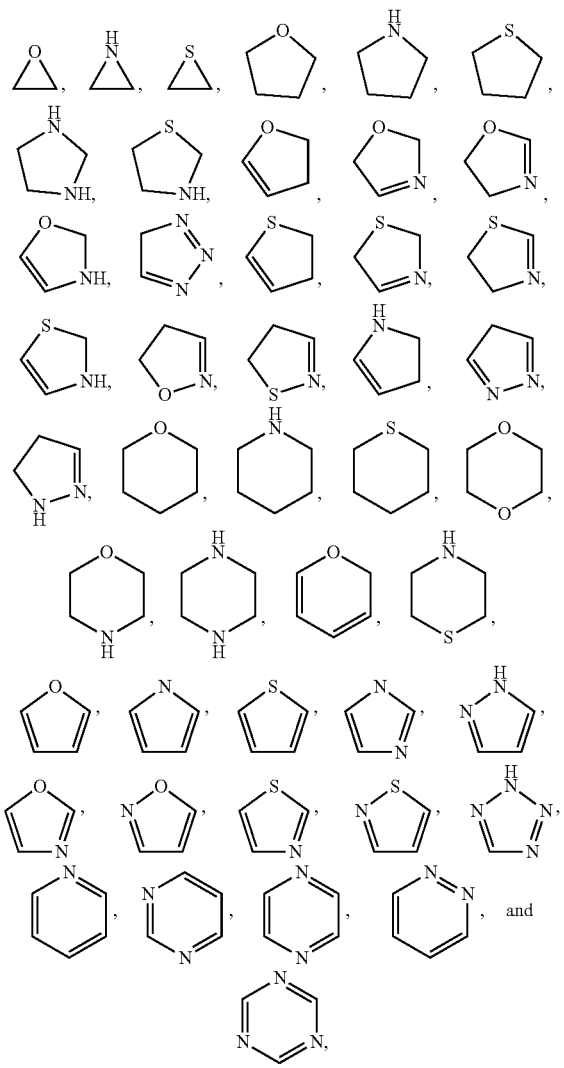

which is optionally substituted.

In some embodiments, $R^{22}$ is $C_2$-$C_6$ alkyl substituted with one or more substituents selected from optionally substituted 3- to 6-membered heterocycle. In some embodiments, $R^{22}$ is $C_2$-$C_6$ alkyl substituted with one or more substituents selected from optionally substituted 3- to 6-membered heterocycle, wherein the 3- to 6-membered heterocycle comprises at least 1, 2, 3, 4, or 5 heteroatoms independently selected from N and O. In some embodiments, $R^{22}$ is $C_2$-$C_6$ alkyl substituted with one or more substituents selected from optionally substituted 3- to 6-membered heterocycle, wherein the 3- to 6-membered heterocycle comprises at most 5, 4, 3, 2, or 1 heteroatoms independently selected from N and O. In some embodiments, $R^{22}$ is $C_2$-$C_6$ alkyl substituted with one or more substituents selected from optionally substituted 3- to 6-membered heterocycle, wherein the 3- to 6-membered heterocycle comprises 1 to 5, 1 to 4, 1 to 3, 1 to 2, 2 to 5, 2 to 4, 2 to 3, 3 to 5, 3 to 4, or 4 to 5 heteroatoms selected from N and O.

In some embodiments, $R^{22}$ is $C_2$-$C_6$ alkyl substituted with one or more substituents selected from optionally substituted 3- to 6-membered heterocycle, wherein the 3- to 6-membered heterocycle may be substituted with one or more substituents selected from optionally substituted $C_{1-6}$ alkyl and —$OR^{30}$. In some embodiments, $R^{22}$ is $C_2$-$C_6$ alkyl substituted with one or more substituents selected from optionally substituted 3- to 6-membered heterocycle, wherein the 3- to 6-membered heterocycle may be substituted with one or more substituents selected from optionally substituted $C_{1-3}$ alkyl and —$OR^{30}$. In some embodiments, $R^{30}$ is selected from hydrogen, $C_{1-10}$ alkyl, $C_{3-12}$ carbocycle, and 3- to 12-membered heterocycle. In some embodiments, $R^{30}$ may be selected from hydrogen and $C_{1-10}$ alkyl. In some embodiments, $R^{30}$ may be hydrogen.

In some embodiments, $R^1$ is selected from:

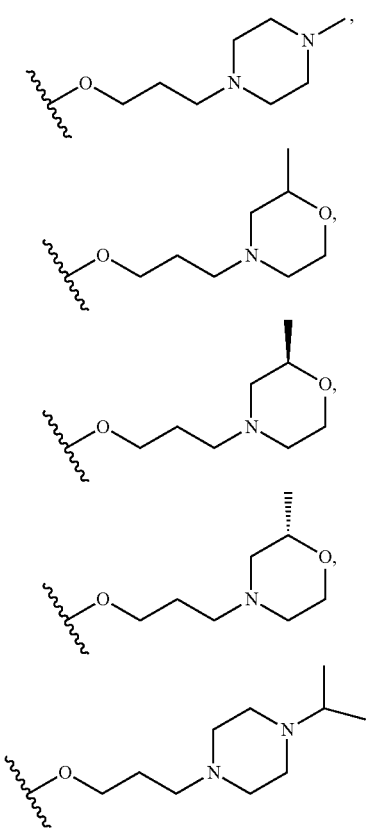

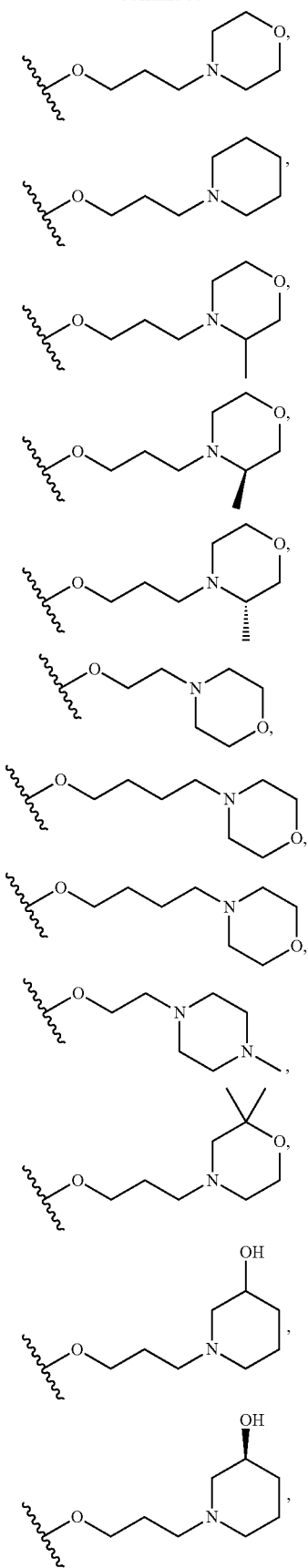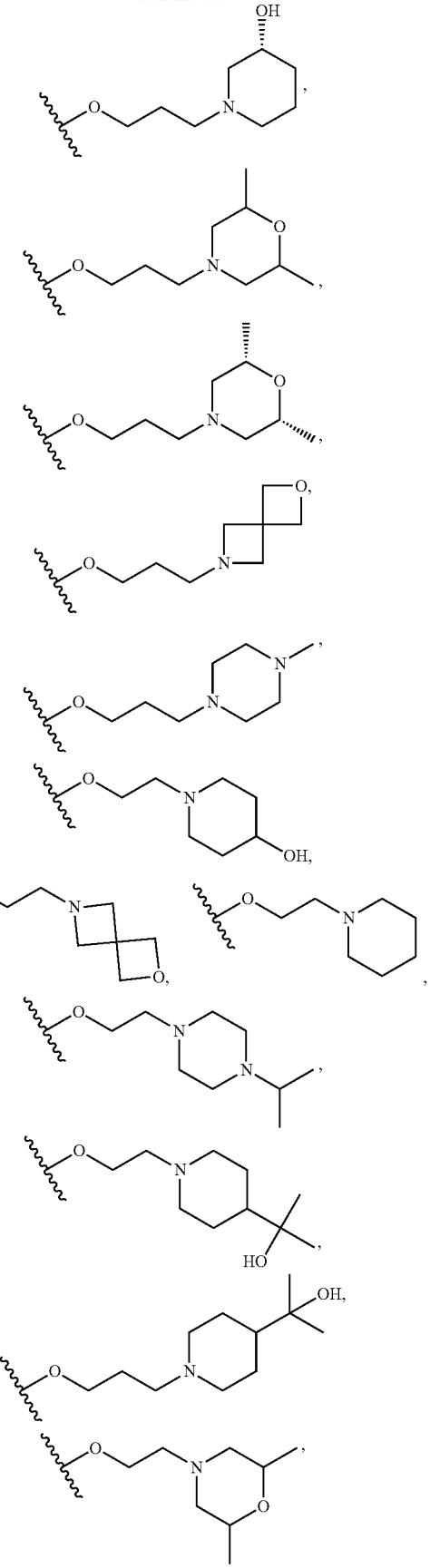

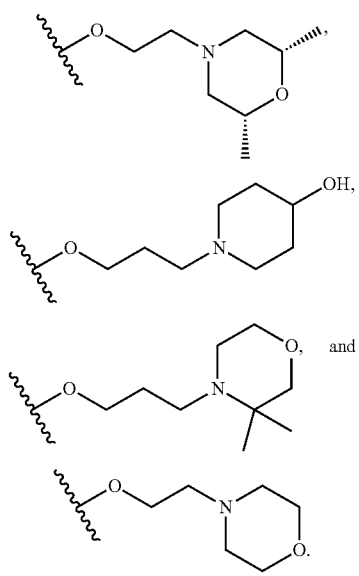
In some embodiments, $R^{22}$ is $C_2$-$C_6$ alkyl substituted with 3- to 6-membered heterocycle substituted with one or more $C_{1-6}$ alkyl. In some embodiments, $R^{22}$ is $C_2$-$C_6$ alkyl substituted with 3- to 6-membered heterocycle substituted with one or more $C_{1-3}$ alkyl. In some embodiments, $R^1$ is selected from:
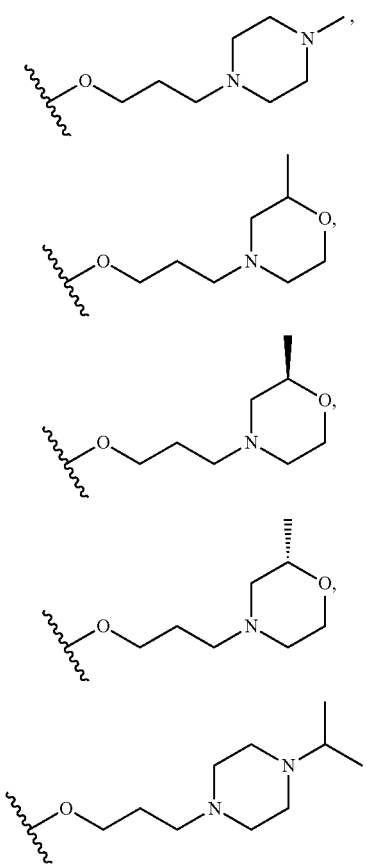
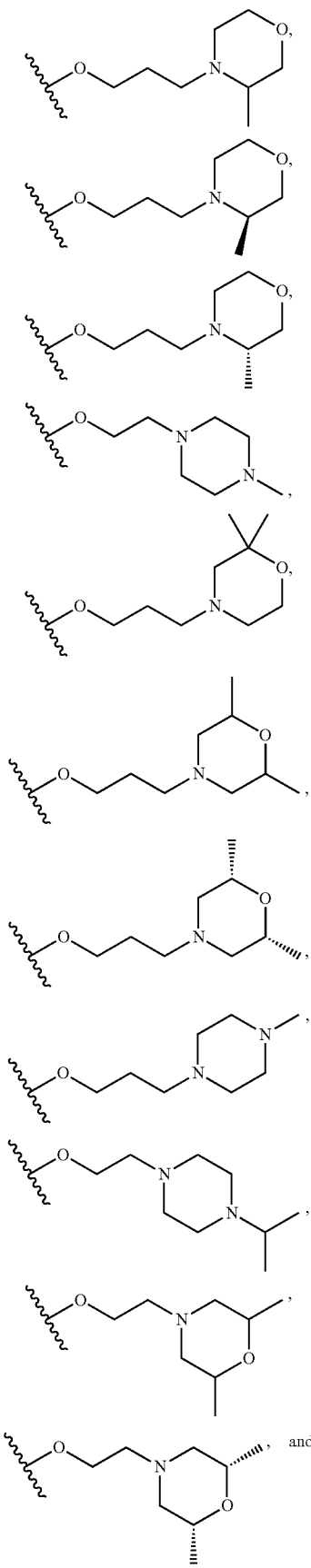

31
-continued

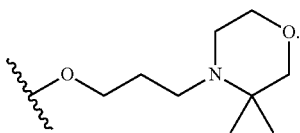

In some embodiments, the 3- to 6-membered heterocycle of $R^{22}$ is substituted with one or more —$OR^{30}$. In some embodiments, the 3- to 6-membered heterocycle of $R^{22}$ is substituted with one —$OR^{30}$. In some embodiments, $R^{30}$ may be selected from hydrogen and $C_{1-10}$ alkyl. In some embodiments, $R^{30}$ may be hydrogen. In some embodiments, $R^1$ is selected from:

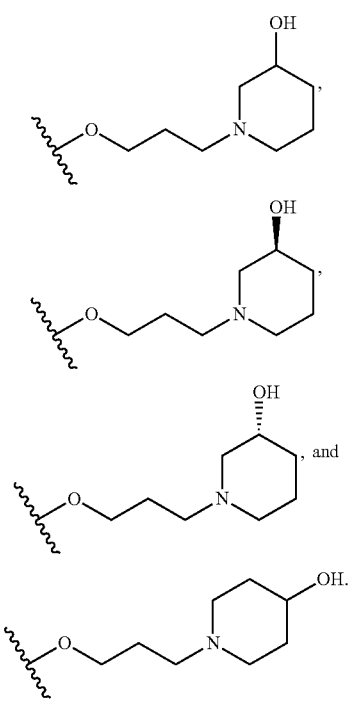

In some embodiments, the 3- to 6-membered heterocycle of $R^{22}$ is substituted with one or more substituents selected from optionally substituted $C_{1-6}$ alkyl. In some embodiments, the 3- to 6-membered heterocycle of $R^{22}$ is substituted with one or more substituents selected from optionally substituted $C_{1-6}$ alkyl, the $C_{1-6}$ alkyl may be substituted with —$OR^{30}$ and $C_{1-6}$ alkyl. In some embodiments, $R^{30}$ may be selected from hydrogen and $C_{1-6}$ alkyl. In some embodiments, $R^{30}$ may be hydrogen.

In some embodiments, $R^1$ is selected from:

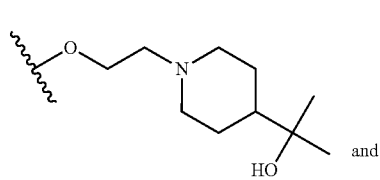

32
-continued

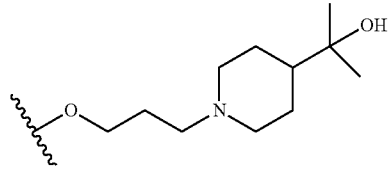

In some embodiments, $R^{22}$ is —$Si(R^{24})_3$, wherein $R^{24}$ is selected from optionally substituted $C_{1-10}$ alkyl, halogen, —$OR^{30}$, —$N(R^{30})_2$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, and —CN. In some embodiments, $R^{24}$ may be selected from optionally substituted $C_{1-10}$ alkyl, —$N(R^{30})_2$, —$NO_2$, =O, =S, =$N(R^{30})$, and —CN. In some embodiments, $R^{24}$ may be selected from optionally substituted $C_{1-10}$ alkyl. In some embodiments, $R^1$ is selected from:

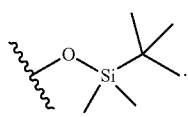 [SMILES: *O[Si](C)(C)C(C)(C)C]

In some embodiments, $R^{22}$ is —$P(=O)(R^{24})_2$, wherein $R^{24}$ is selected from optionally substituted $C_{1-10}$ alkyl, halogen, —$OR^{30}$, —$N(R^{30})_2$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, and —CN. In some embodiments, $R^{24}$ may be selected from optionally substituted $C_{1-10}$ alkyl, —$N(R^{30})_2$, —$NO_2$, =O, =S, =$N(R^{30})$, and —CN. In some embodiments, $R^{24}$ may be selected from optionally substituted $C_{1-10}$ alkyl. $R^{24}$ may be selected from optionally substituted $C_{1-6}$ alkyl. $R^{24}$ may be selected from optionally substituted $C_{1-3}$ alkyl. In some embodiments, $R^1$ is selected from:

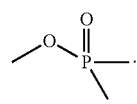

In some embodiments, $R^1$ is an optionally substituted heteroaryl. In some embodiments, the optionally substituted heteroaryl comprises at least 1, 2, 3, 4, or 5 heteroatoms that are nitrogen. In some embodiments, the optionally substituted heteroaryl comprises at most 5, 4, 3, 2 or 1 heteroatoms that are nitrogen. In some embodiments, the optionally substituted heteroaryl comprises from 1 to 5, 1 to 4, 1 to 3, 1 to 2, 2 to 5, 2 to 4, 2 to 3, 3 to 5, 3 to 4, or 4 to 5 heteroatoms that are nitrogen. In some embodiments, the optionally substituted heteroaryl is a 4- to 6-membered heteroaryl. In some embodiments, $R^1$ is selected from:

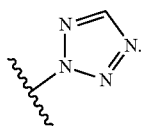

In some embodiments, the optionally substituted heteroaryl of $R^1$ may be substituted with one or more substitutents selected from: hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments, the optionally substituted heteroaryl of $R^4$ may be substituted with one or more substitutents selected from: hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments, the optionally substituted heteroaryl of R is an optionally substituted 5- to 7-membered heteroaryl. In some embodiments, $R^1$ is selected from:

where the heteroaryl may be selected from:

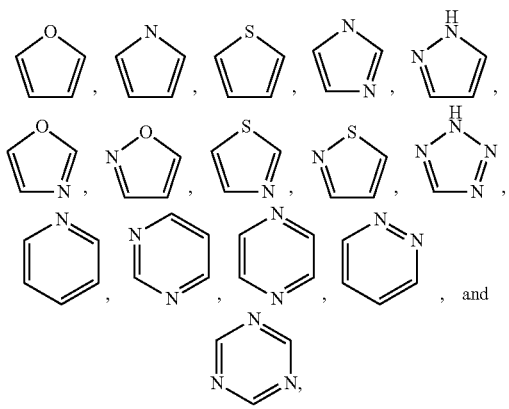

any one of which is optionally substituted.

In some embodiments, $R^1$ is selected from:

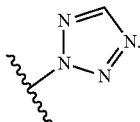 [SMILES: *n1ncnn1]

In some embodiments, the optionally substituted heteroaryl of $R^4$ is an optionally substituted 5- to 7-membered heteroaryl. In some embodiments, $R^1$ is selected from:

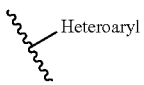

where the heteroaryl may be selected from:

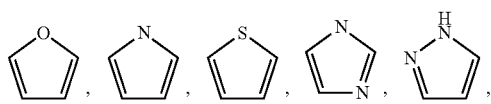

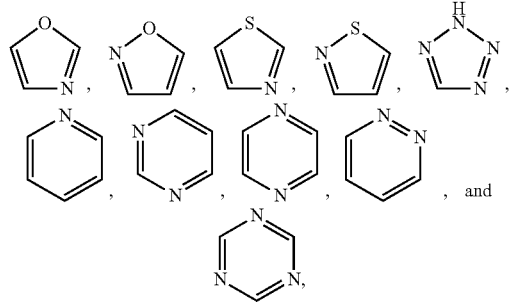

any one of which is optionally substituted.

In some embodiments, $R^1$ is selected from:

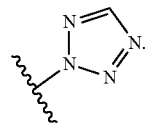

In some embodiments, $R^1$ is

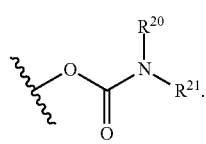

In some embodiments, $R^{20}$ is selected from hydrogen and optionally substituted $C_1$-$C_5$ alkyl. In some embodiments, $R^{20}$ may be selected from hydrogen and optionally substituted $C_1$-$C_4$ alkyl. In some embodiments, $R^{20}$ may be selected from hydrogen and optionally substituted $C_1$-$C_3$ alkyl. In some embodiments, $R^{20}$ is hydrogen. In some embodiments, $R^{20}$ is optionally substituted $C_1$-$C_3$ alkyl. In some embodiments, $R^{21}$ is an optionally substituted $C_{1-6}$ alkyl. In some embodiments, $C_{1-6}$ alkyl of $R^{21}$ may be substituted with one or more substituents selected from —OC(O)$R^{30}$, —S(O)$R^{30}$, —S(O)$_2R^{30}$, —P(O)(O$R^{30}$)$_2$, —OP(O)(O$R^{30}$)$_2$, —NO$_2$, =O, =S, =N($R^{30}$), —CN, —O$R^{30}$, —N($R^{30}$)$_2$, —(O—CH$_2$—(CH$_2$)$_p$)$_n$—W, optionally substituted $C_{3-10}$ carbocycle and optionally substituted 3- to 10-membered heterocycle. In some embodiments, $C_{1-6}$ alkyl of $R^{21}$ may be substituted with one or more substituents selected from —NO$_2$, =O, =S, =N($R^{30}$), —CN, —O$R^{30}$, —N($R^{30}$)$_2$, —(O—CH$_2$—(CH$_2$)$_p$)$_n$—W, optionally substituted $C_{3-10}$ carbocycle and optionally substituted 3- to 10-membered heterocycle. In some embodiments, $C_{1-6}$ alkyl of $R^{21}$ may be substituted with one or more substituents selected from —O$R^{30}$, —N($R^{30}$)$_2$, —(O—CH$_2$—(CH$_2$)$_p$)$_n$—W, optionally substituted $C_{3-10}$ carbocycle and optionally substituted 3- to 10-membered heterocycle. In some embodiments, $R^{30}$ may be selected from hydrogen and $C_{1-3}$ alkyl.

In some embodiments, $R^1$ is selected from:

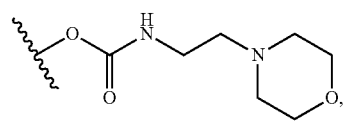

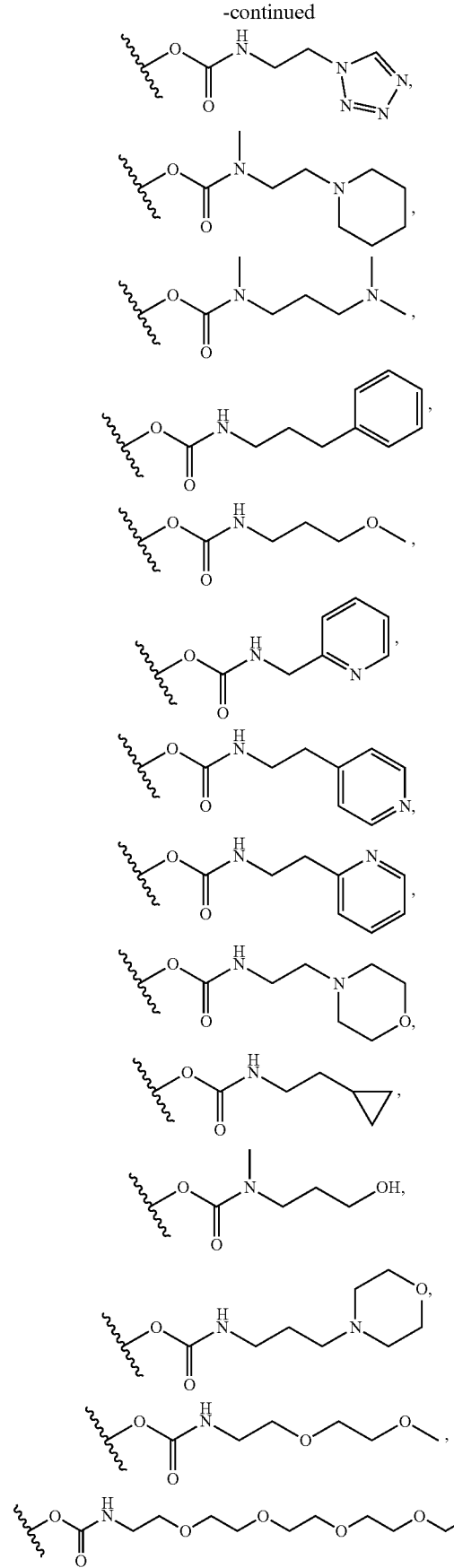
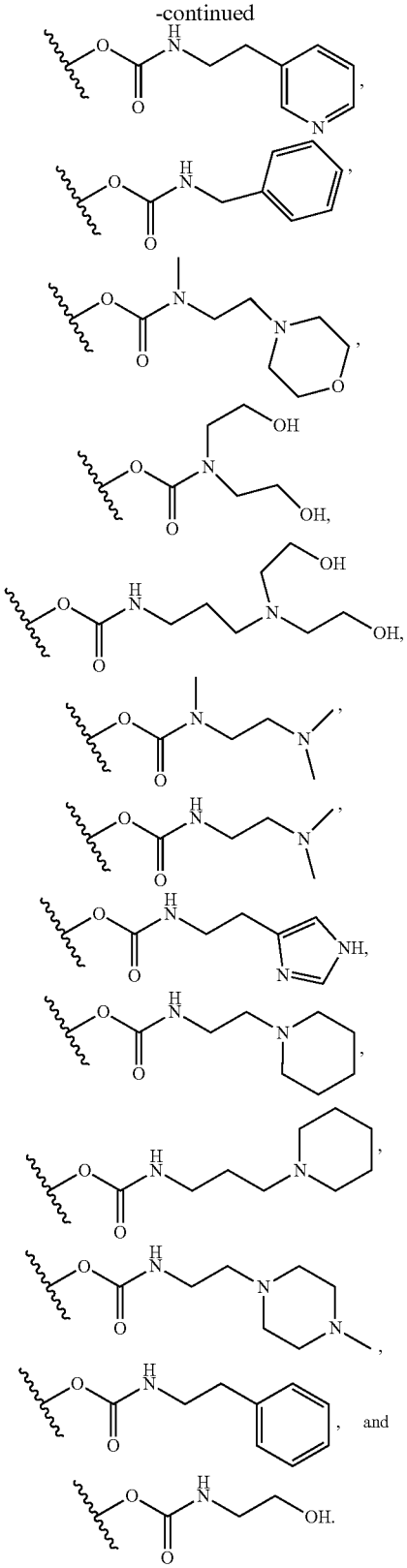
In some embodiments, $R^{21}$ is $C_{1-6}$ alkyl substituted with one or more substituents selected from —$OR^{30}$. In some embodiments, $R^{30}$ may be selected from hydrogen, optionally substituted $C_{1-10}$ alkyl, optionally substituted $C_{3-10}$ carbocycle, and optionally substituted 3- to 10-membered heterocycle. In some embodiments, $R^{30}$ may be selected from hydrogen and optionally substituted $C_{1-10}$ alkyl. In some embodiments, $R^{30}$ may be selected from hydrogen and optionally substituted $C_{1-6}$ alkyl. In some embodiments, $R^{30}$ may be selected from hydrogen and $C_{1-6}$ alkyl. In some embodiments, $R^1$ is selected from:

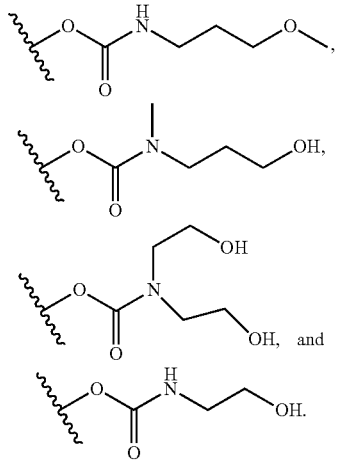

In some embodiments, $R^{21}$ is $C_{1-6}$ alkyl substituted with one or more substituents selected from —N($R^{30}$)$_2$. In some embodiments, $R^{30}$ may be selected from hydrogen and optionally substituted $C_{1-10}$ alkyl. In some embodiments, the $C_{1-10}$ alkyl of $R^{30}$ may be substituted with and selected from $C_{1-6}$ alkyl, —O—$C_{1-6}$ alkyl, and —OH. In some embodiments, $R^1$ is selected from:

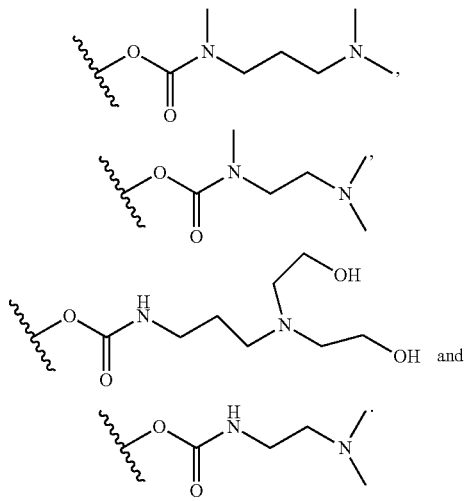

In some embodiments, $R^{21}$ is an optionally substituted 3- to 7-membered heterocycle. In some embodiments, the 3- to 7-membered heterocycle of $R^{21}$ is substituted with one or more substituents selected from —OR$^{30}$ and optionally substituted $C_{1-10}$ alkyl. In some embodiments, $R^{30}$ may be selected from hydrogen and optionally substituted $C_{1-10}$ alkyl. In some embodiments, $R^{30}$ may be hydrogen. In some embodiments, the 3- to 7-membered heterocycle of $R^{21}$ is substituted with one or more $C_{1-10}$ alkyl, substituted with one or more selected from —OH. In some embodiments, $R^1$ is selected from:

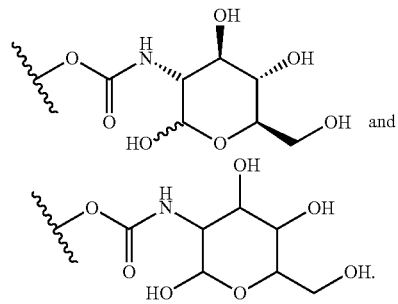

In some embodiments, $R^1$ is

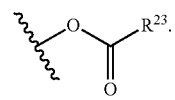

In some embodiments, $R^{23}$ is optionally substituted $C_1$-$C_6$ alkyl. In some embodiments, $R^{23}$ may be an optionally substituted $C_1$-$C_6$ alkyl, optionally substituted with one or more substituents selected from —OR$^{30}$, —N($R^{30}$)$_2$, —(O—CH$_2$—(CH$_2$)$_p$)$_n$—W, —S(O)$R^{30}$, —S(O)$_2$R$^{30}$, —P(O)(OR$^{30}$)$_2$, —OP(O)(OR$^{30}$)$_2$, —NO$_2$, =O, =S, =N(R$^{30}$), —CN, optionally substituted $C_{1-10}$ alkyl, optionally substituted $C_{3-10}$ carbocycle and 3 to 10 membered heterocycle. In some embodiments, $R^{23}$ is an optionally substituted $C_1$-$C_6$ alkyl, optionally substituted with one or more substituents selected from —OR$^{30}$, —N($R^{30}$)$_2$, —(O—CH$_2$—(CH$_2$)$_p$)$_n$—W, optionally substituted $C_{1-10}$ alkyl, optionally substituted $C_{3-10}$ carbocycle and 3- to 10-membered heterocycle. In some embodiments, $R^{30}$ may be selected from hydrogen and $C_{1-10}$ alkyl. In some embodiments, $R^{23}$ is an optionally substituted $C_{1-10}$ alkyl, optionally substituted with —OR$^{30}$. In some embodiments, $R^{30}$ of —OR$^{30}$ may be selected from hydrogen and $C_{1-10}$ alkyl. In some embodiments, $R^{30}$ of —OR$^{30}$ may be hydrogen. In some embodiments, $R^{30}$ of —N($R^{30}$)$_2$ may be selected from hydrogen and $C_{1-10}$ alkyl. In some embodiments, $R^{30}$ of —N($R^{30}$)$_2$ may be hydrogen.

In some embodiments, $R^1$ is selected from:

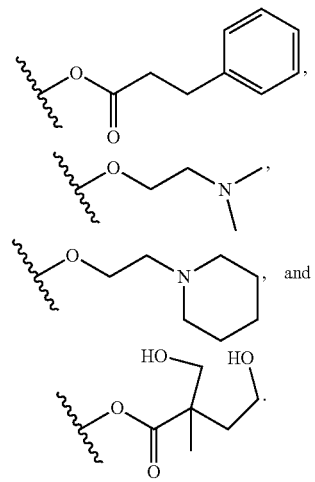

In some embodiments, $R^1$ is selected from:

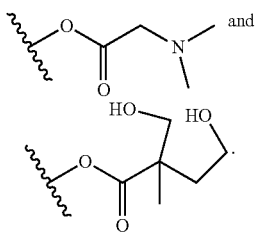

and

In some embodiments, $R^{23}$ is $C_1$-$C_6$ alkyl optionally substituted with one or more substituents selected from optionally substituted $C_{3-10}$ carbocycle and 3 to 10 membered heterocycle. In some embodiments, the $C_1$-$C_6$ alkyl of $R^{23}$ may be substituted with one or more substituents selected from optionally substituted $C_{3-6}$ carbocycle and 3- to 6-membered heterocycle, each of which is optionally substituted with —$OR^{30}$, —$N(R^{30})_2$, and $C_{1-6}$ alkyl. In some embodiments, $R^{30}$ of —$OR^{30}$ may be selected from hydrogen and $C_1$-$C_6$ alkyl. In some embodiments, $R^{30}$ of —$N(R^{30})_2$ may be selected from hydrogen and $C_1$-$C_6$ alkyl. In some embodiments, the $C_1$-$C_6$ alkyl of $R^{23}$ may be substituted with one or more optionally substituted $C_{3-6}$ carbocycle. In some embodiments, the $C_1$-$C_6$ alkyl of $R^{23}$ may be substituted with one or more optionally substituted $C_6$ aryl. In some embodiments, the $C_1$-$C_6$ alkyl of $R^{23}$ may be substituted with one or more unsubstituted $C_6$ aryl. In some embodiments, the $C_1$-$C_6$ alkyl of $R^{23}$ may be substituted with one phenyl. In some embodiments, $C_1$-$C_6$ alkyl of $R^{23}$ may be substituted with one or more 3- to 6-membered heterocycle. In some embodiments, the 3- to 6-membered heterocycle may be unsaturated. In some embodiments, $R^1$ is selected from:

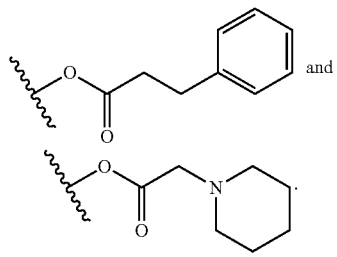

In some embodiments, $R^{23}$ is $C_1$-$C_6$ alkyl optionally substituted with one or more —$OR^{30}$.

In some embodiments, $R^{23}$ is $C_1$-$C_6$ alkyl optionally substituted with one or more —$N(R^{30})_2$. In some embodiments, $R^{30}$ may be selected from hydrogen and $C_1$-$C_6$ alkyl. In some embodiments, $R^{30}$ may be $C_1$-$C_6$ alkyl. In some embodiments, $R^1$ is

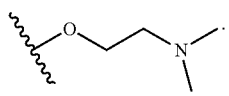 [SMILES: *OCCN(C)C]

In some embodiments, $R^{23}$ is $C_1$-$C_6$ alkyl substituted with one or more optionally substituted $C_{3-10}$ carbocycle. In some embodiments, $C_1$-$C_6$ alkyl of $R^{23}$ may be substituted with one optionally substituted $C_{3-10}$ carbocycle. In some embodiments, $C_1$-$C_6$ alkyl of $R^{23}$ may be substituted with one optionally substituted $C_{3-6}$ carbocycle. In some embodiments, the $C_{3-6}$ carbocycle substituted on $C_1$-$C_6$ alkyl of $R^{23}$ may be substituted with —$OR^{30}$, —$N(R^{30})_2$, and $C_{1-6}$ alkyl. In some embodiments, $R^{30}$ may be selected from hydrogen and $C_1$-$C_6$ alkyl. In some embodiments, $R^1$ is

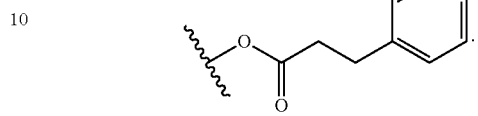

In some embodiments, $R^{23}$ is $C_1$-$C_6$ alkyl substituted with one or more 3- to 10-membered heterocycle. In some embodiments, $R^{23}$ is $C_1$-$C_6$ alkyl substituted with one or more 3- to 6-membered heterocycle. In some embodiments, the 3- to 6-membered heterocycle substituted on $C_1$-$C_6$ alkyl of $R^{23}$ may be selected from:

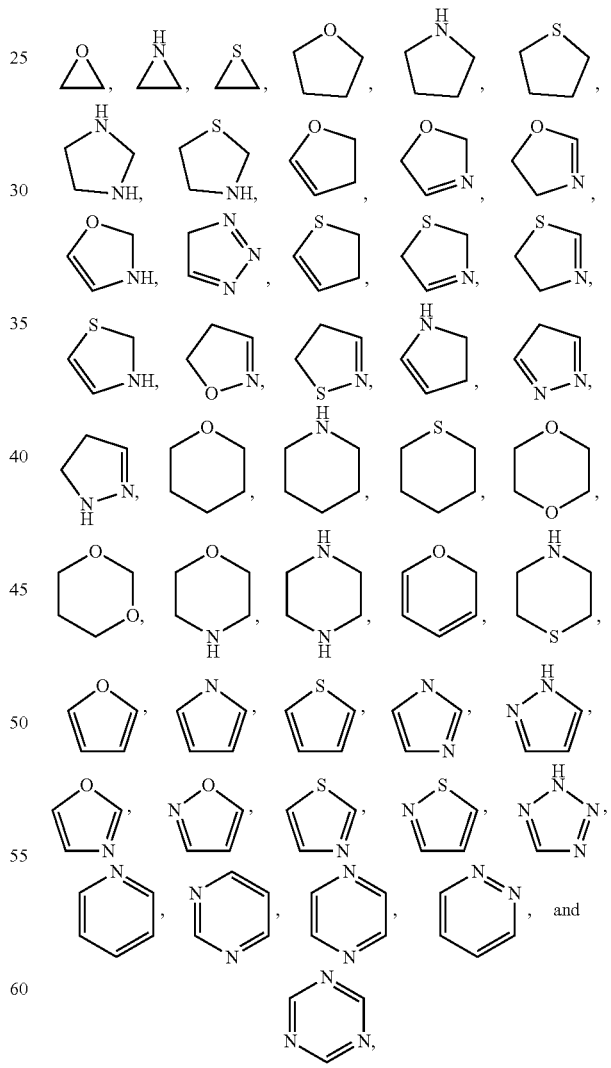

any one of which is optionally substituted. In some embodiments, the 3- to 6-membered heterocycle substituted on $C_1$-$C_6$ alkyl of $R^{23}$ may be substituted with —$OR^{30}$, —N($R^{30}$)$_2$, and $C_{1-6}$ alkyl. $R^{30}$ may be selected from hydrogen and $C_1$-$C_6$ alkyl. In some embodiments, the 3- to 6-membered heterocycle substituted on $C_1$-$C_6$ alkyl of $R^{23}$ may be unsubstituted. In certain embodiments, the 3- to 6-membered heterocycle is unsaturated. In some embodiments, $R^1$ is

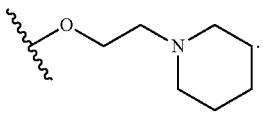 [SMILES: *OCCN1CCCCC1]

In some embodiments, $R^{23}$ is optionally substituted 3- to 7-membered heterocycle. In some embodiments, the 3- to 7-membered heterocycle may be substituted with one or more substituents selected from optionally substituted $C_{1-10}$ alkyl. In some embodiments, the 3- to 7-membered heterocycle of $R^{23}$ comprises at least 1, 2, 3, 4, or 5 heteroatoms independently selected from N, S, and O. In some embodiments, the 3- to 7-membered heterocycle of $R^{23}$ comprises at least 1, 2, or 3 heteroatoms independently selected from N, S, and O. In some embodiments 3- to 7-membered heterocycle may be selected from:

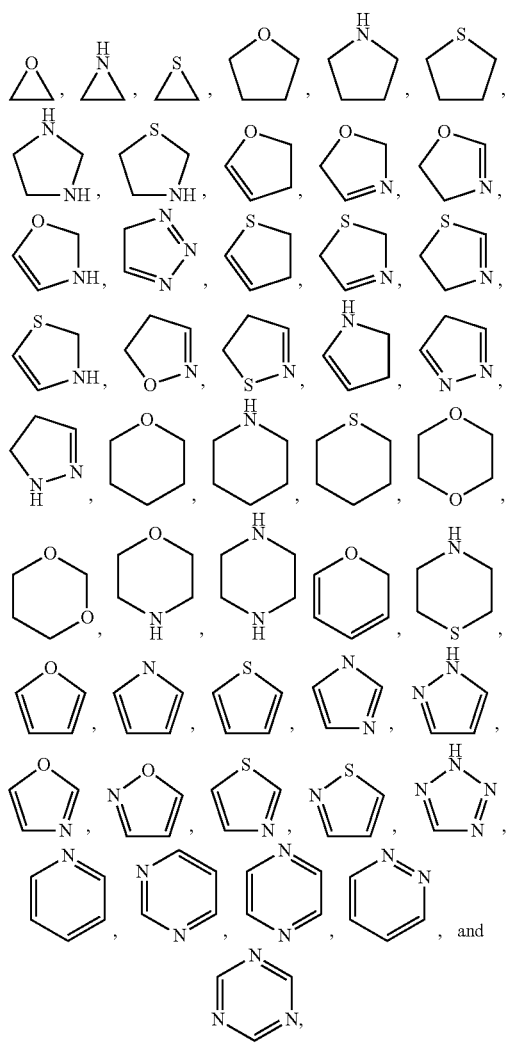

any one of which is optionally substituted. In some embodiments, the 3- to 7-membered heterocycle of $R^{23}$ may be substituted with one or more substituents selected from optionally substituted $C_{1-6}$ alkyl. In some embodiments, the 3- to 7-membered heterocycle of $R^{23}$ may be substituted with one or more substituents selected from $C_{1-6}$ alkyl. In some embodiments, $R^1$ is selected from:

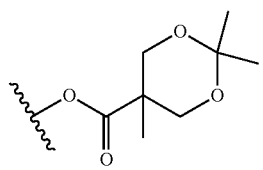 [SMILES: *OC(=O)C1(C)COC(C)(C)OC1]

In some embodiments, $R^1$ is selected from is selected from:

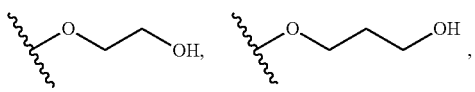

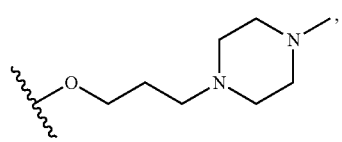

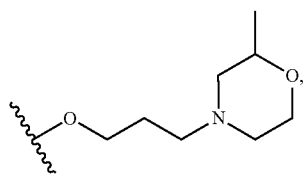

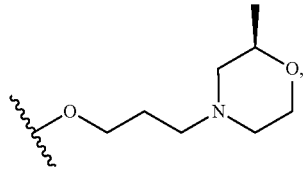

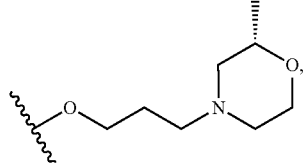

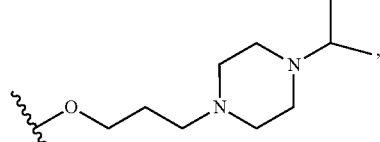

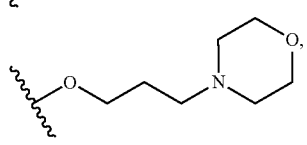

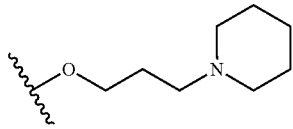

-continued
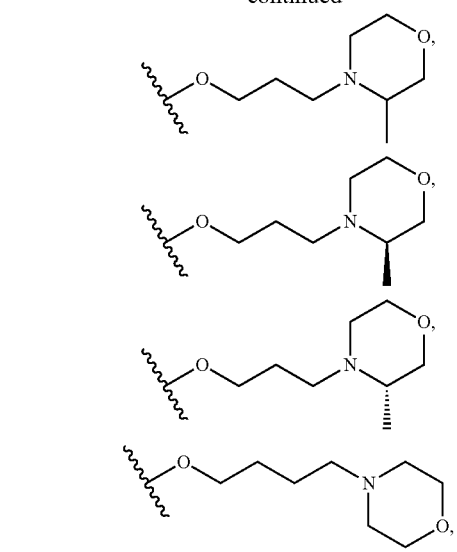
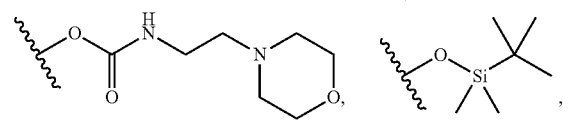
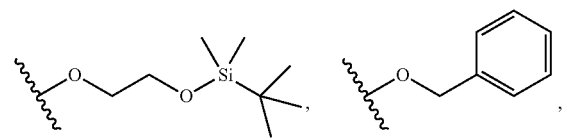
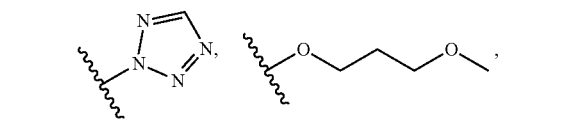
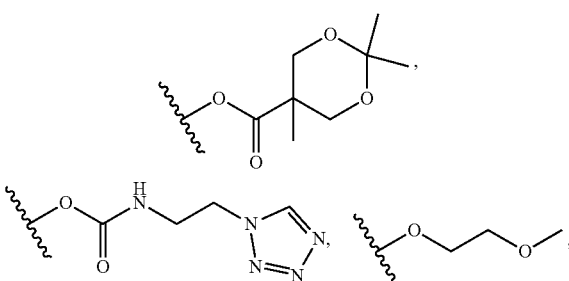
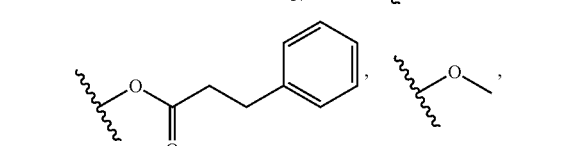
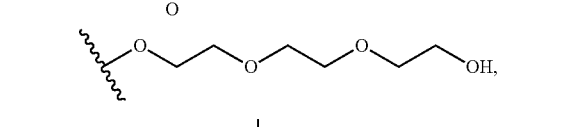
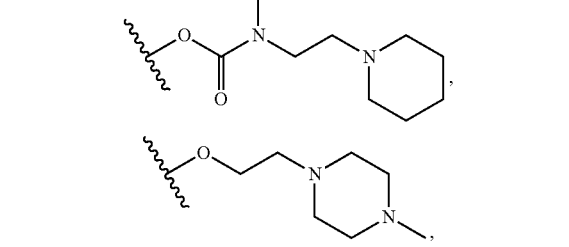
-continued
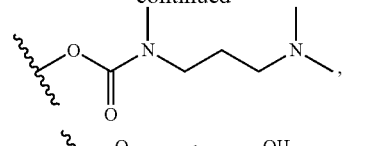
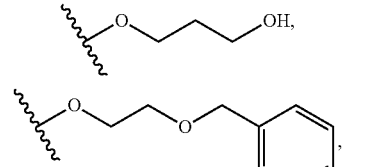
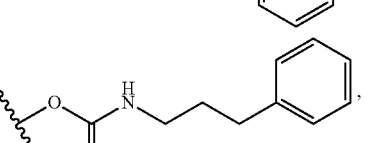
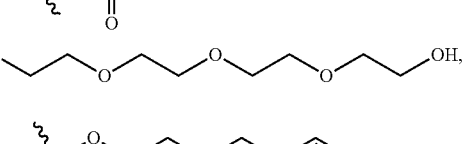
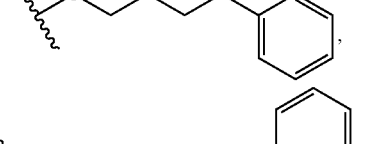
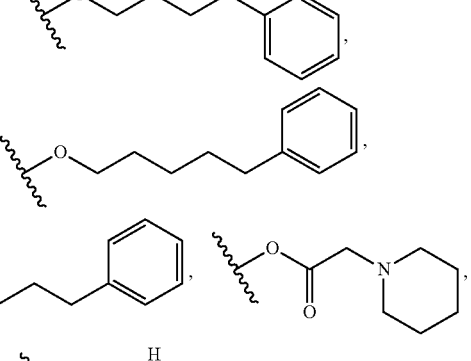
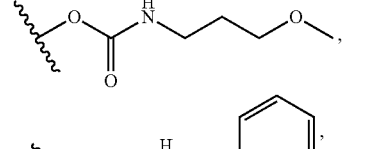
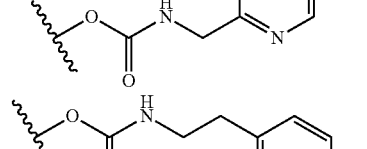
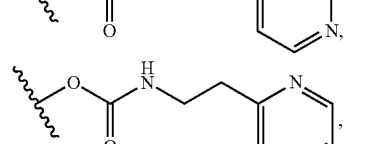
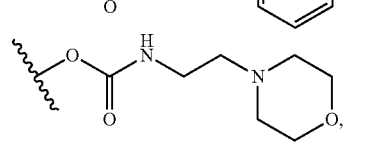
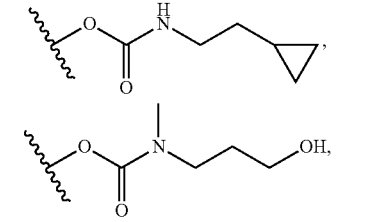

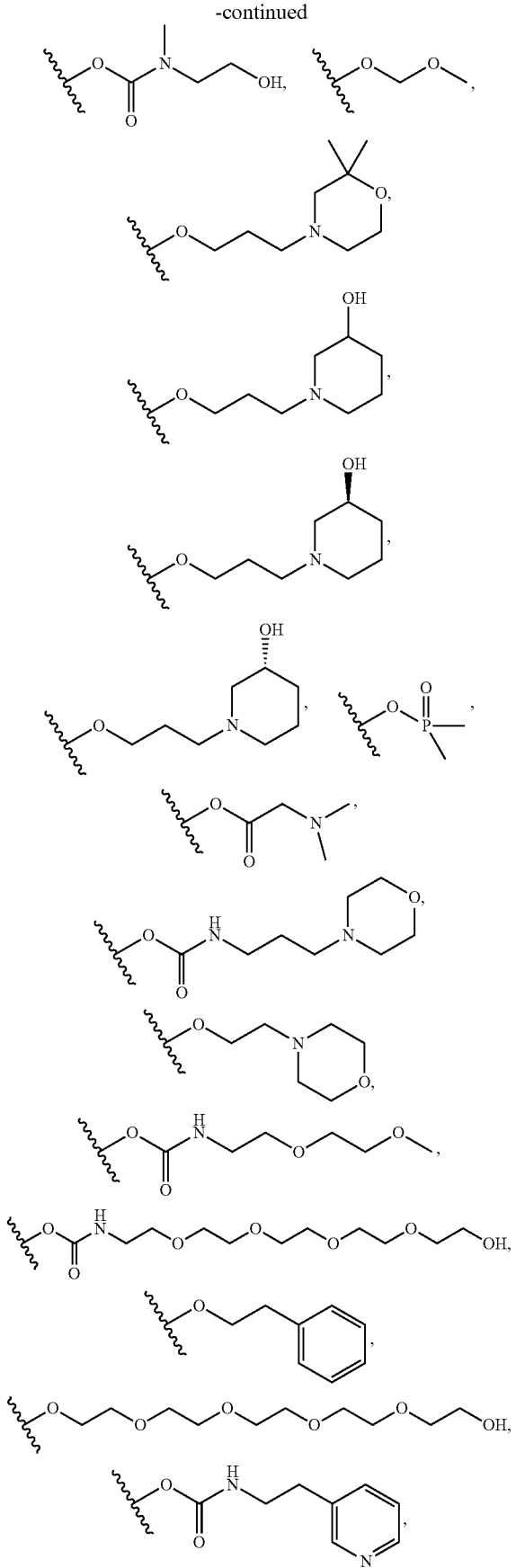
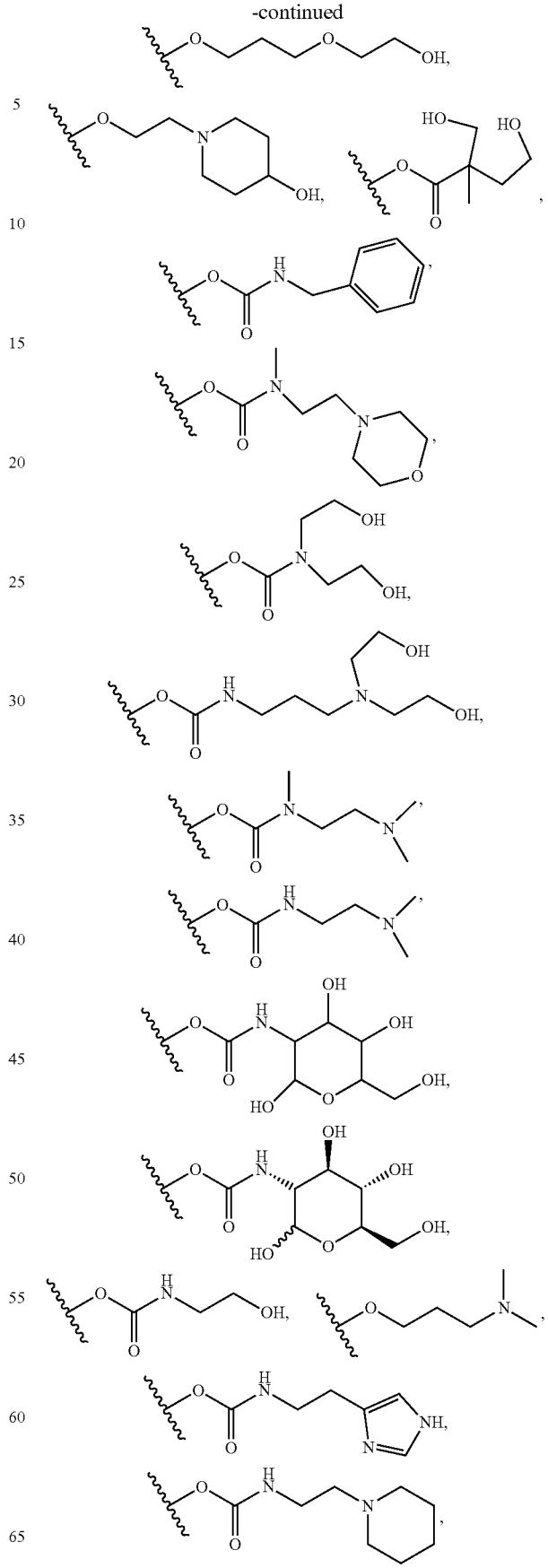

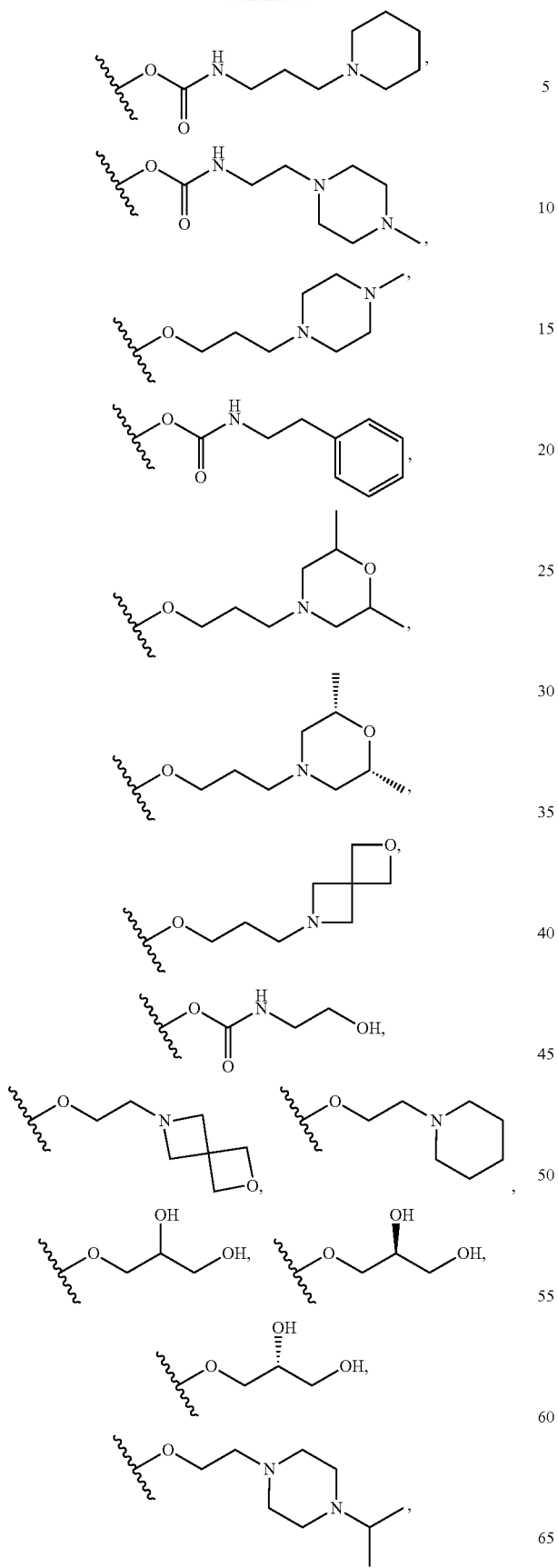
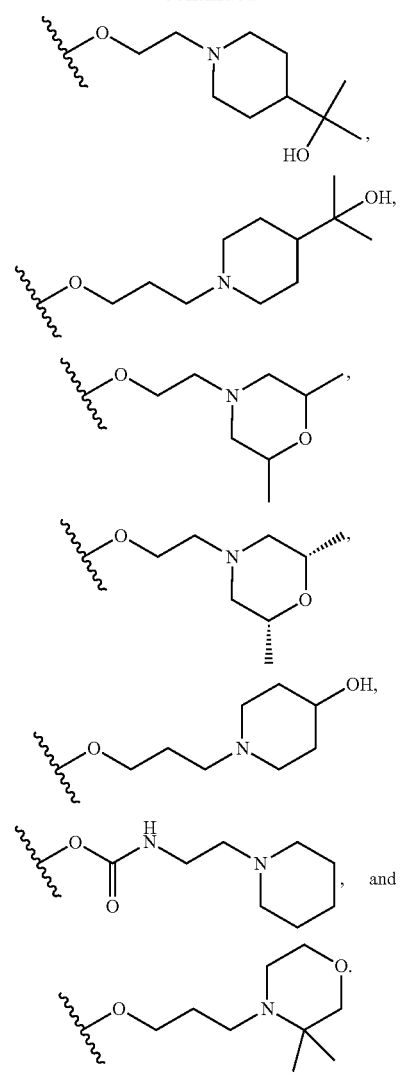
In some embodiments, R$^1$ is selected from:
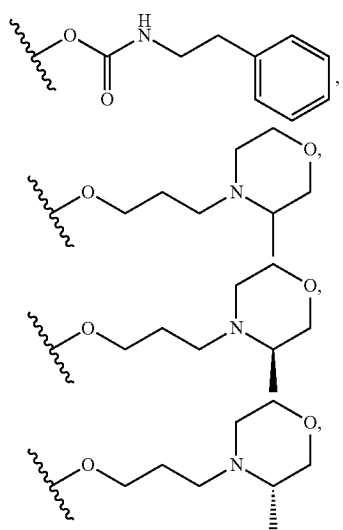

-continued
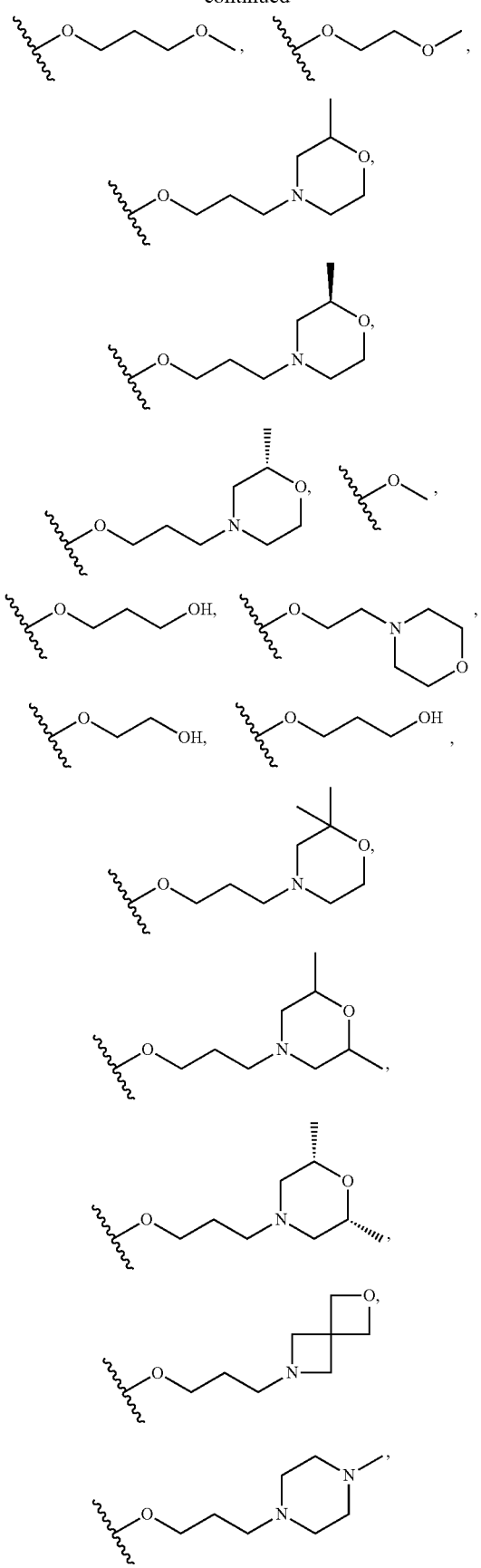
-continued
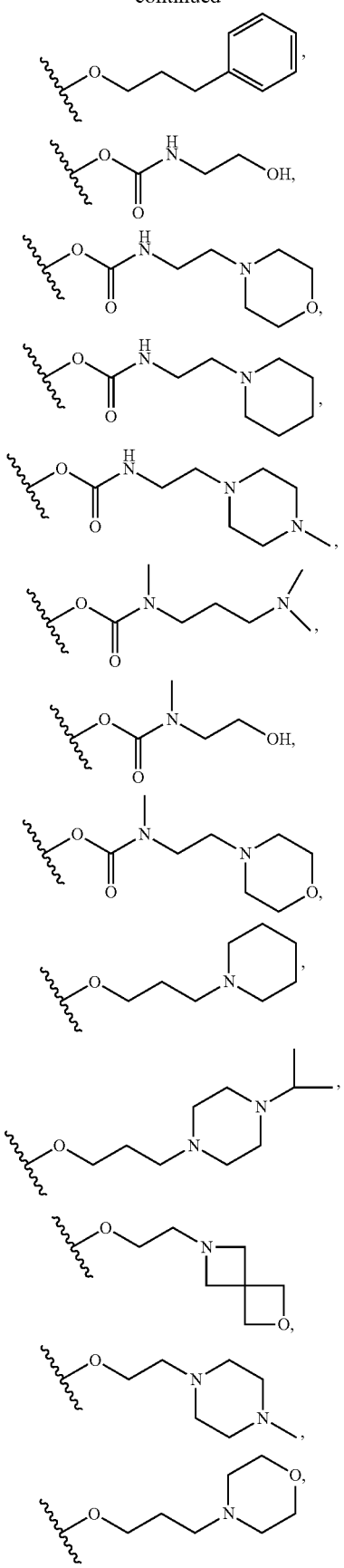

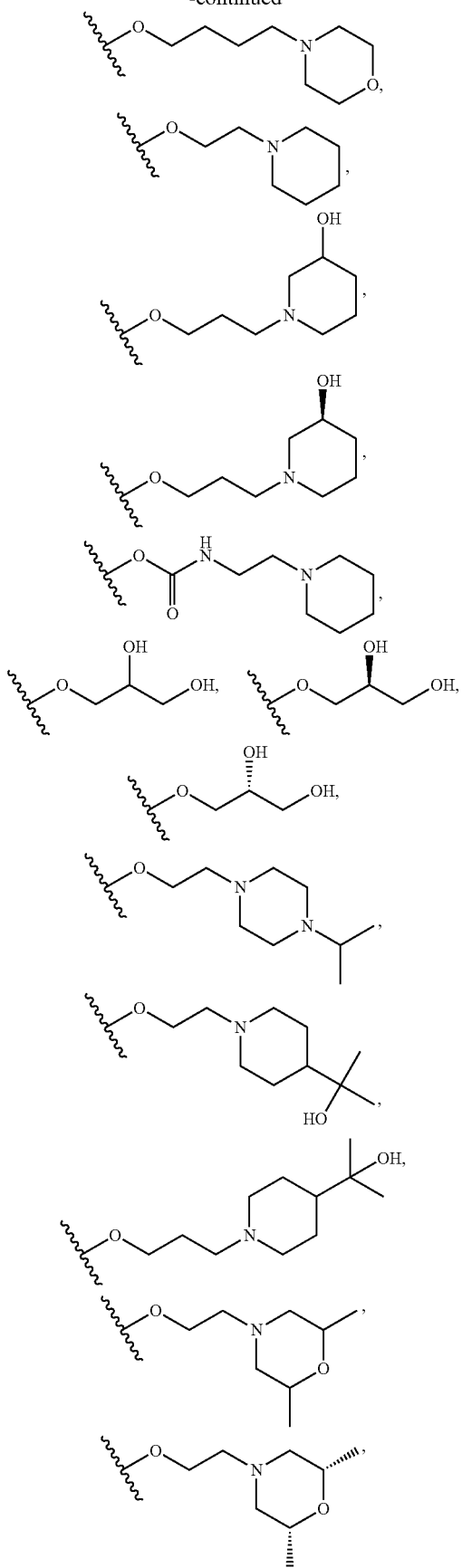
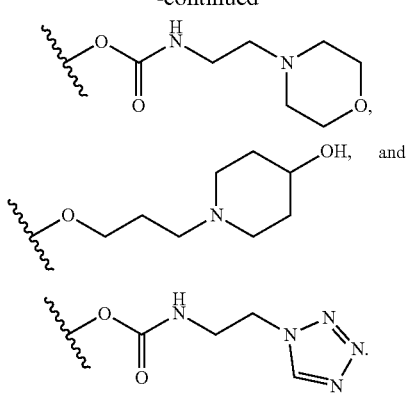
In some embodiments, $R^1$ is selected from:
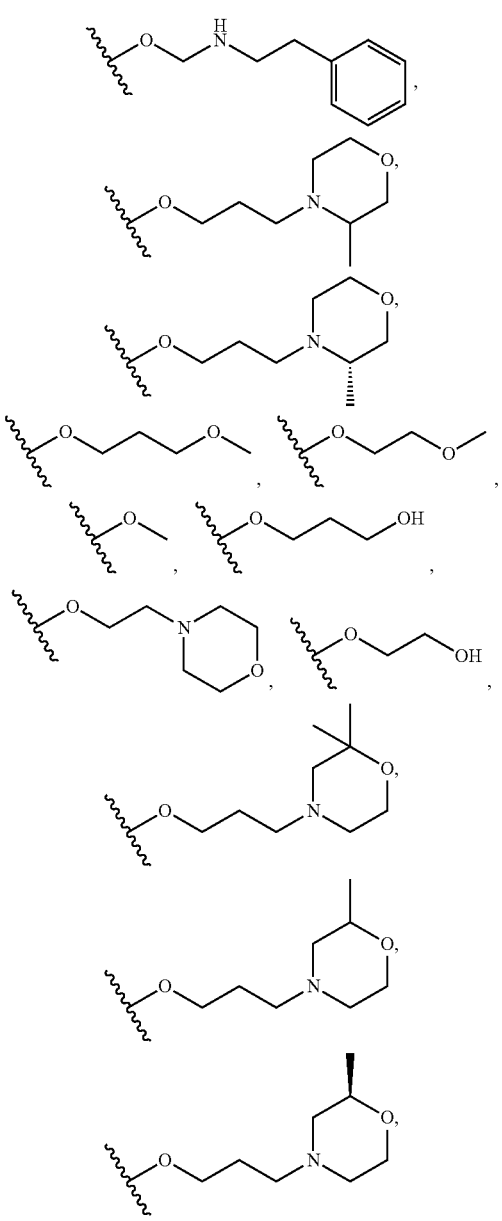

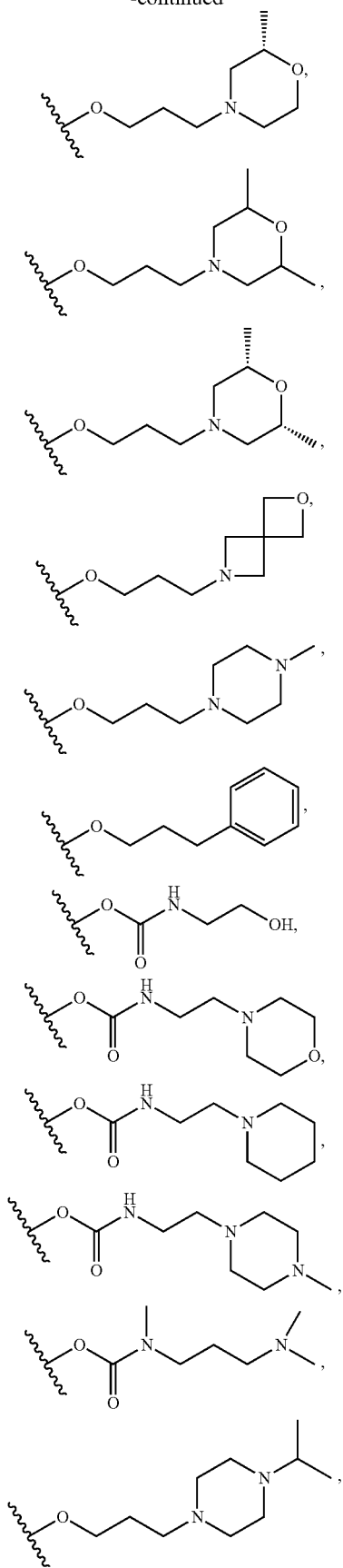

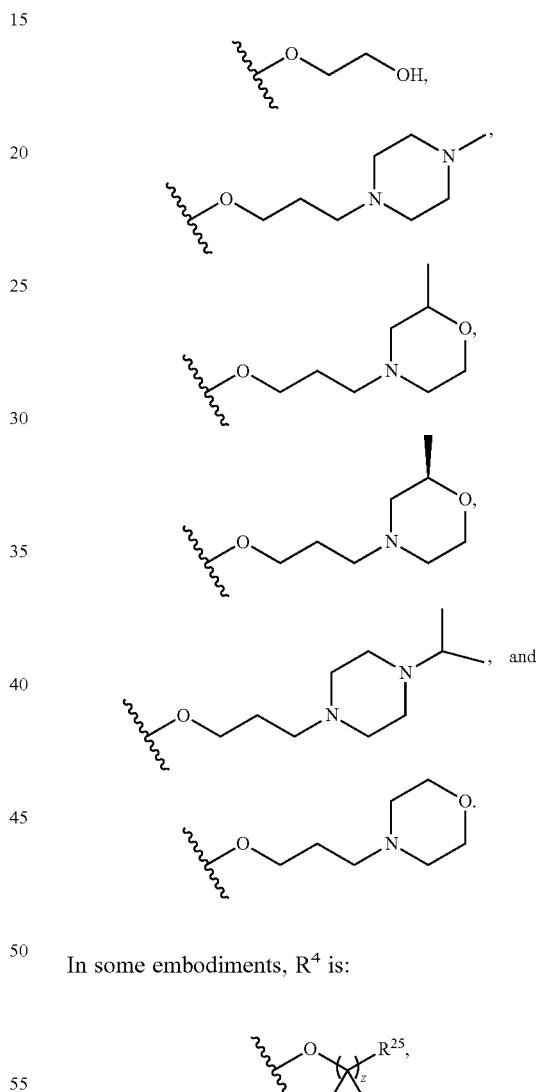

In some embodiments, $R^1$ is selected from:

In some embodiments, $R^4$ is:

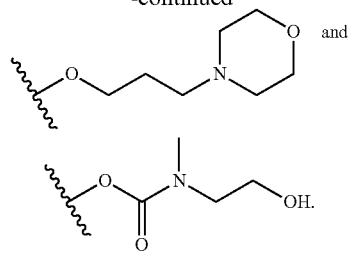

and wherein z is 0, 1, 2, 3, 4 or 5.

In some embodiments, z may be 0, 1, 2, 3, or 4. z may be 0, 1, 2, or 3. z may be 0, 1, or 2. z may be 0 or 1. z may be 0.

In some embodiments, each R' and R" are independently selected from hydrogen, —$OR^{31}$, and $C_{1-3}$ alkyl optionally substituted with one or more —$OR^{31}$. In some embodiments, R' is hydrogen. In some embodiments, R" is hydrogen. R' and R" may each be hydrogen.

In some embodiments, $R^{25}$ is selected from $-OR^{31}$, optionally substituted 3- to 10-membered heterocycle, and optionally substituted $C_{3-10}$ carbocycle. In some embodiments, $R^{25}$ may be $-OR^{31}$.

In some embodiments, $R^{31}$ is selected from hydrogen and optionally substituted $C_{1-10}$ alkyl.

In some embodiments, $R^4$ is selected from:

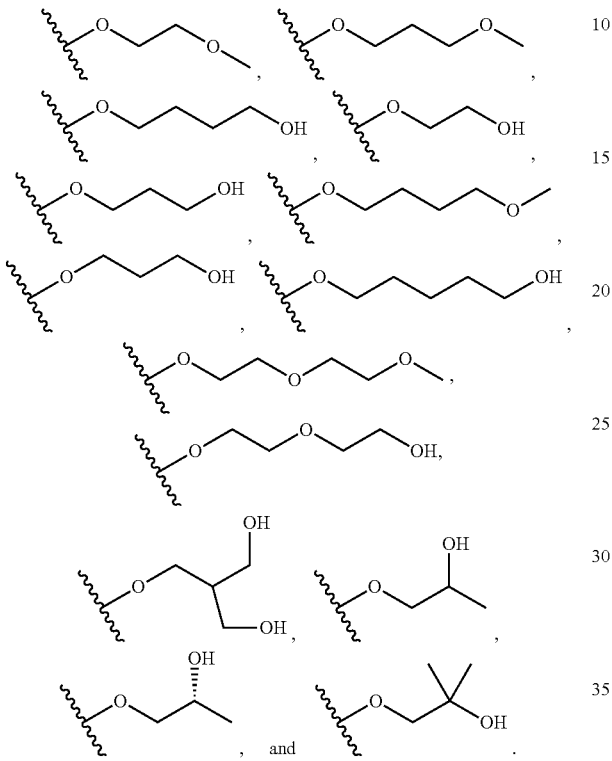

In some embodiments, $R^4$ is selected from:

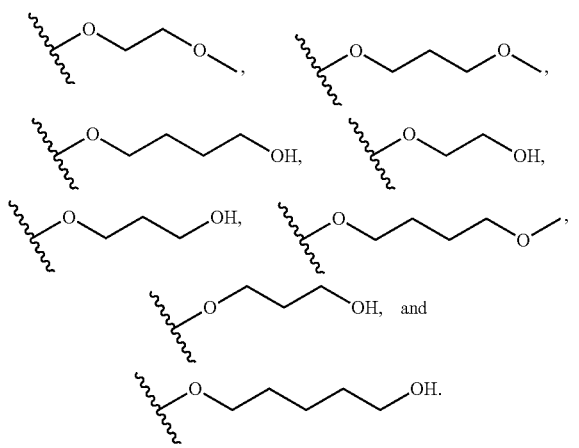

In some embodiments, $R^4$ is selected from:

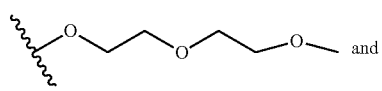

-continued

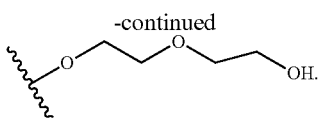

In some embodiments, $R^4$ is selected from:

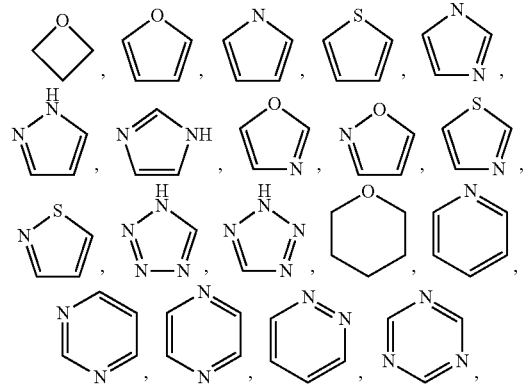

In some embodiments, $R^{25}$ is an optionally substituted 3- to 8-membered heterocycle. $R^{25}$ may be an optionally substituted 3- to 7-membered heterocycle. In some embodiments, $R^{25}$ may be an optionally substituted 3- to 6-membered heterocycle. In some embodiments, the optionally substituted 3- to 6-membered heterocycle of $R^{23}$ may comprise at least three heteroatoms selected from S, N and O, wherein the 3- to 6-membered heterocycle is optionally substituted with $C_{1-10}$ alkyl. In some embodiments, the optionally substituted 3- to 6-membered heterocycle of $R^{23}$ may comprise at least two heteroatoms selected from N and O, wherein the 3- to 6-membered heterocycle is optionally substituted with $C_{1-10}$ alkyl. In some embodiments, the optionally substituted 3- to 6-membered heterocycle of $R^{23}$ may comprise at least one heteroatom selected from N and O, wherein the 3- to 6-membered heterocycle is optionally substituted with $C_{1-10}$ alkyl. In some embodiments, the optionally substituted 3- to 6-membered heterocycle of $R^{23}$ may comprise at least one heteroatom selected from N and O, wherein the 3- to 6-membered heterocycle is optionally substituted with $C_{1-6}$ alkyl. In some embodiments, the optionally substituted heterocycle is selected from:

-continued

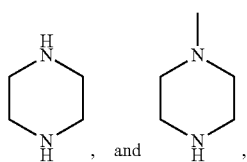

any one of which is optionally substituted.

In some embodiments, $R^4$ is selected from:

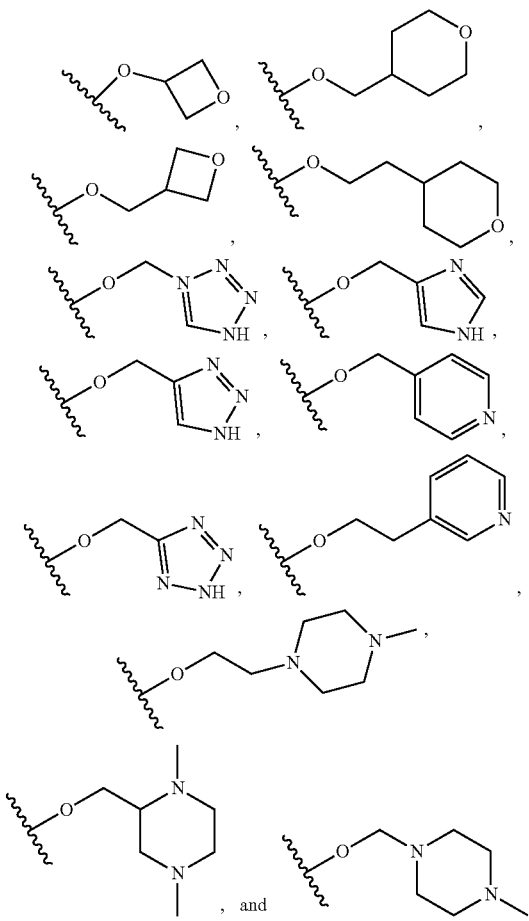

In some embodiments, $R^{25}$ is an optionally substituted 3- to 6-membered heterocycle comprising at least one heteroatom that is oxygen, wherein the 3- to 6-membered heterocycle is optionally substituted with $C_{1-6}$ alkyl. In some embodiments, the 3- to 6-membered heterocycle of $R^{25}$ may comprise at least one O, and wherein the 3- to 6-membered heterocycle is unsubstituted.

In some embodiments, $R^4$ is selected from:

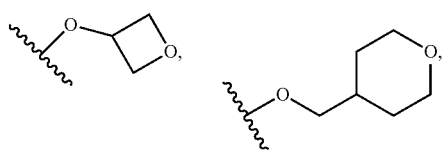

-continued

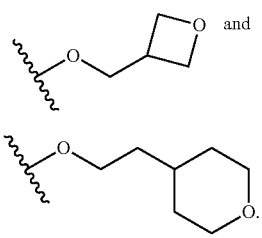

In some embodiments, $R^{25}$ is an optionally substituted 3- to 6-membered heterocycle comprising at least 1 heteroatom that is nitrogen, wherein the 3- to 6-membered heterocycle is optionally substituted with $C_{1-6}$ alkyl. In some embodiments, $R^4$ is selected from:

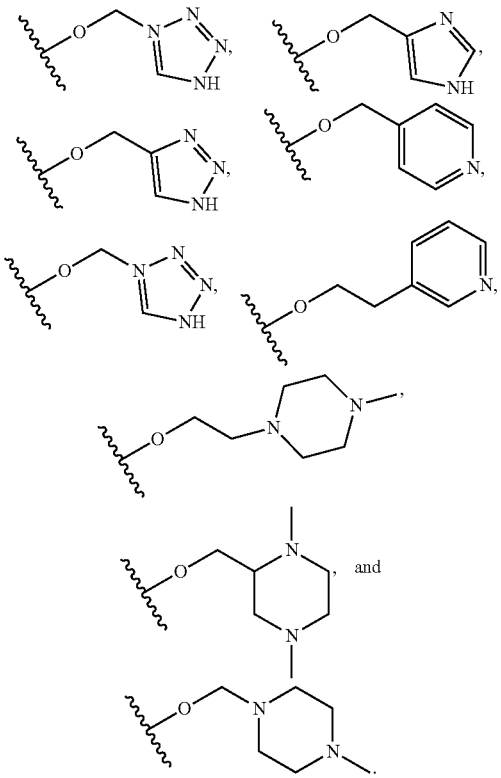

In some embodiments, $R^{25}$ is a 3- to 6-membered heterocycle comprising at least 1 heteroatom that is selected from N and O, wherein the 3- to 6-membered heterocycle is unsubstituted. In some embodiments, $R^4$ is selected from:

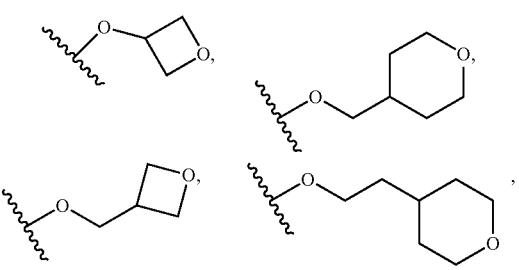

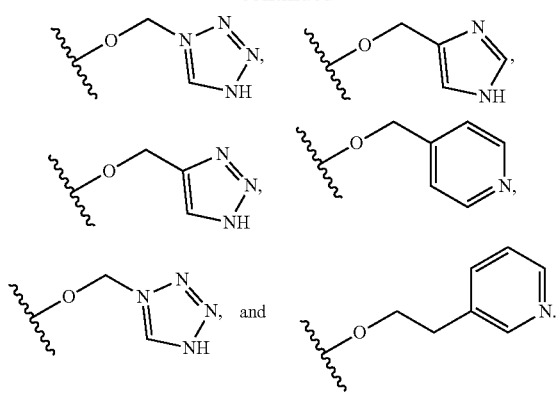

In some embodiments, $R^{25}$ is a 3- to 6-membered heterocycle comprising at least 1 heteroatom that is nitrogen, wherein the 3- to 6-membered heterocycle may be unsubstituted. In some embodiments, $R^4$ is selected from:

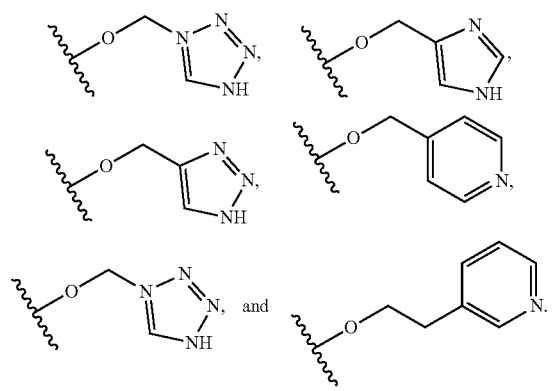

In some embodiments, $R^{25}$ is a 3- to 6-membered heterocycle comprising at least 1 heteroatom that is nitrogen, wherein the 3- to 6-membered heterocycle is an optionally substituted heteroaryl. In some embodiments, the 3- to 6-membered heterocycle of $R^{25}$ comprises at least 1 heteroatom that is nitrogen, wherein the 3- to 6-membered heterocycle is not optionally substituted heteroaryl. In some embodiments, $R^4$ is selected from:

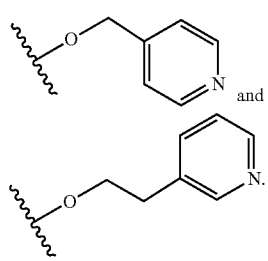

In some embodiments, $R^{25}$ is an optionally substituted 3- to 6-membered heterocycle comprising at least 1 heteroatom that is nitrogen, wherein the 3- to 6-membered heterocycle is a saturated heterocycle. In some embodiments, $R^4$ is selected from:

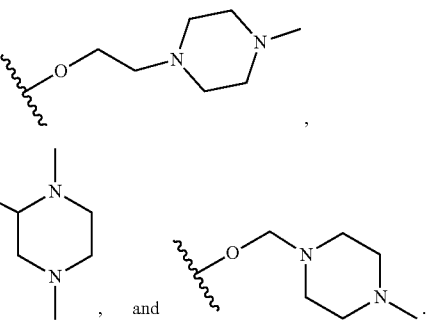

In some embodiments, $R^{25}$ is an optionally substituted $C_{3-10}$ carbocycle. In some embodiments, $R^4$ is selected from:

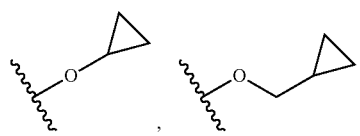

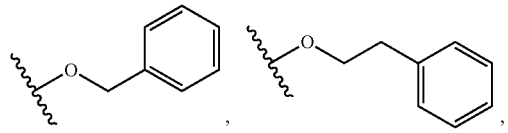

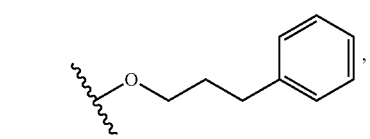

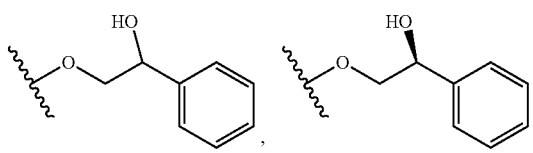

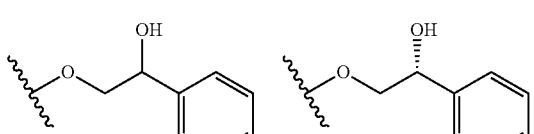

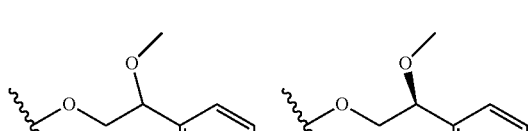

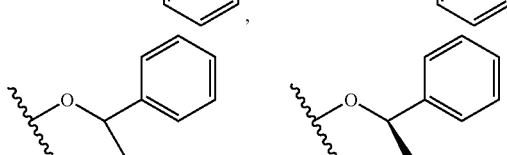

In some embodiments, $R^{25}$ is an optionally substituted saturated carbocycle, e.g., $R^4$ is selected from:

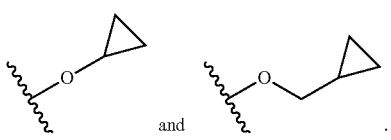 [SMILES: *OC1CC1 ; *OCC1CC1]

and

In some embodiments, $R^{25}$ is an optionally substituted phenyl, e.g., $R^4$ is selected from:

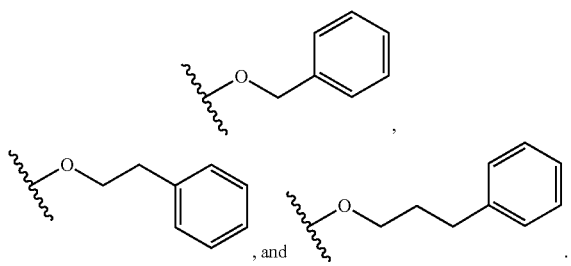

, and

In some embodiments, each R' and R'' are independently selected from hydrogen and $-OR^{31}$.

In some embodiments, $R^4$ is selected from:

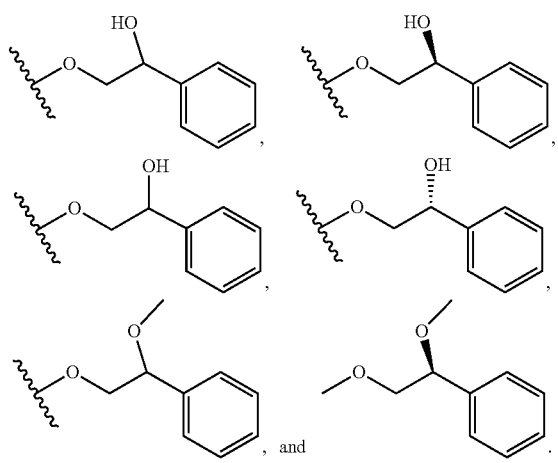

, and

In some embodiments, R' and R'' are independently selected from hydrogen and $C_{1-3}$ alkyl optionally substituted with one or more $-OR^{31}$. In some embodiments, $R^{31}$ may be selected from hydrogen and $C_{1-3}$ alkyl. In some embodiments, $R^4$ is selected from:

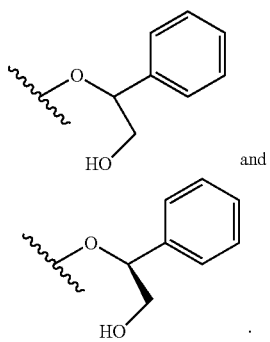

and

In some embodiments, $R^4$ is:

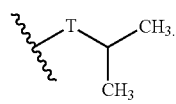

In some embodiments, T is S. In some embodiments, $R^4$ is:

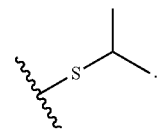 [SMILES: *SC(C)C]

In some embodiments, T is O. In some embodiments, $R^4$ is:

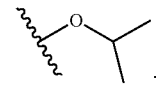

In some embodiments, $R^4$ is an optionally substituted heteroaryl. In some embodiments, the optionally substituted heteroaryl comprises at least one heteroatom selected from S, N and O. In some embodiments, $R^4$ is selected from

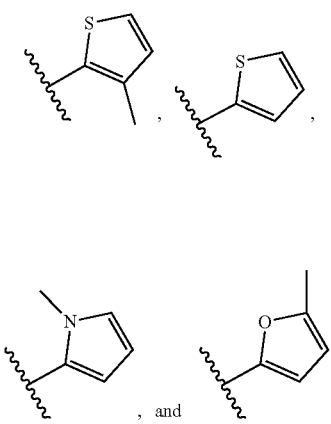

, and

In some embodiments, the optionally substituted heteroaryl comprises at least one heteroatom selected from N and O. In some embodiments, $R^4$ is selected from

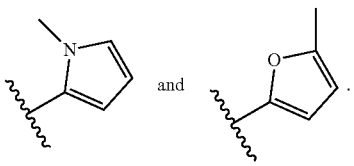

and

In some embodiments, the optionally substituted heteroaryl comprises at least one heteroatom that is sulfur, e.g., $R^4$ is selected from

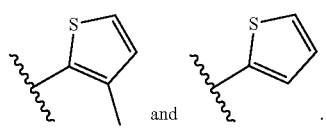
In some embodiments, R⁴ is an optionally substituted heteroaryl comprising at least one heteroatom that is nitrogen, e.g., R⁴ is
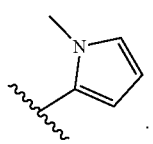 [SMILES: *c1cccn1C]
In some embodiments, R⁴ is an optionally substituted heteroaryl comprising at least one heteroatom that is oxygen, e.g., R⁴ is
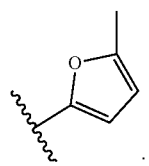 [SMILES: *c1ccc(C)o1]
In some embodiments, R⁴ is selected from:
-continued
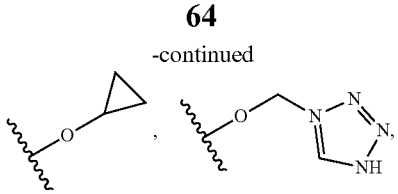
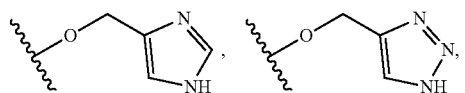
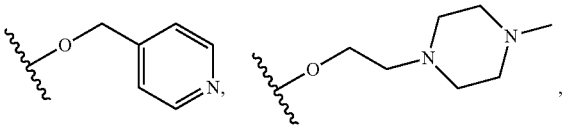
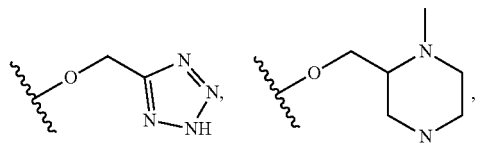
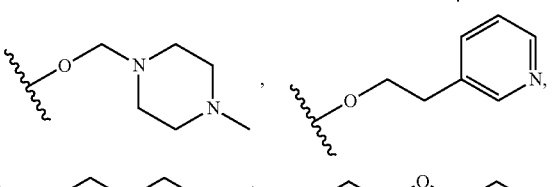
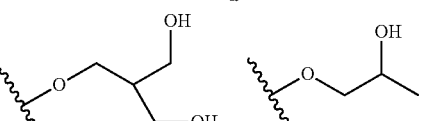
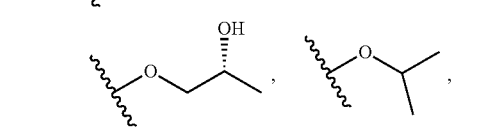
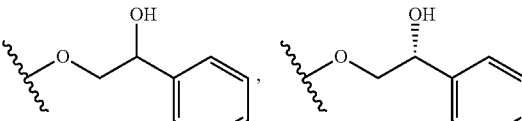
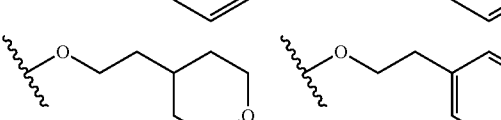
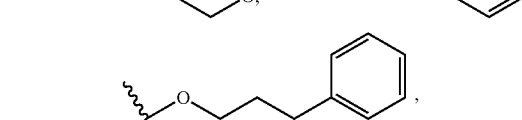
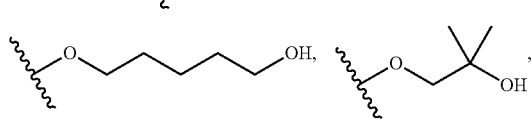

-continued
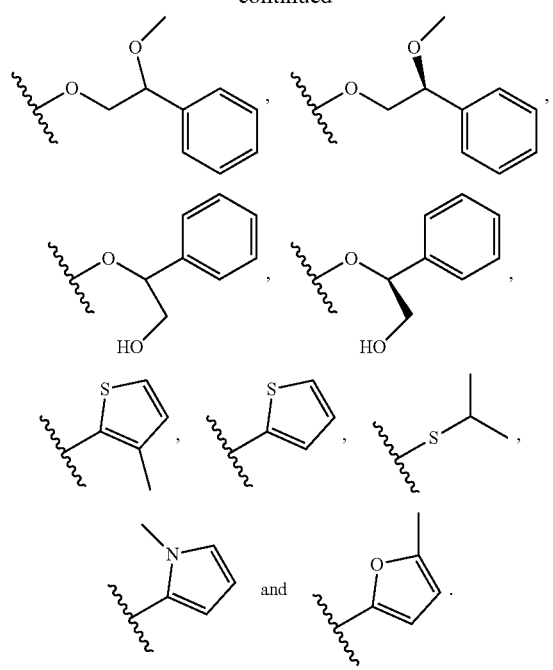
In some embodiments, $R^4$ is selected from:
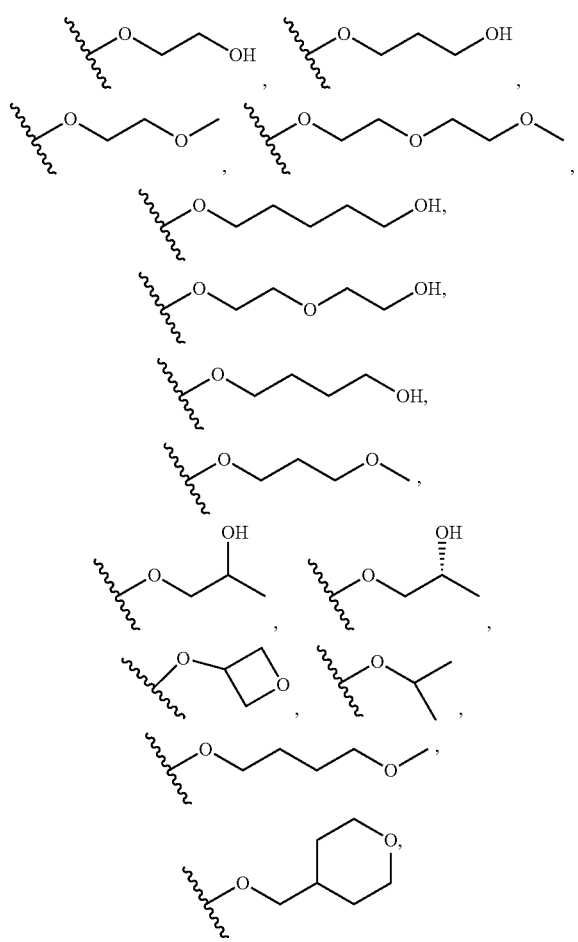
-continued
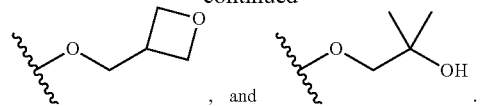
In some embodiments $R^4$ is selected from:
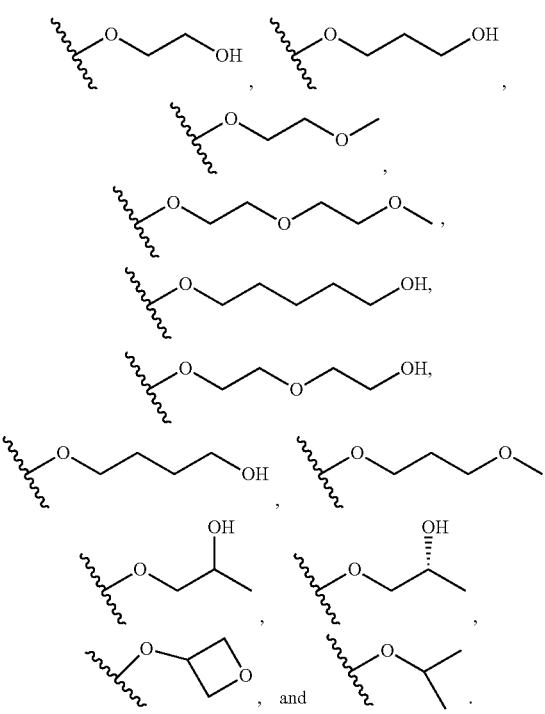
In some embodiments, $R^4$ is selected from:
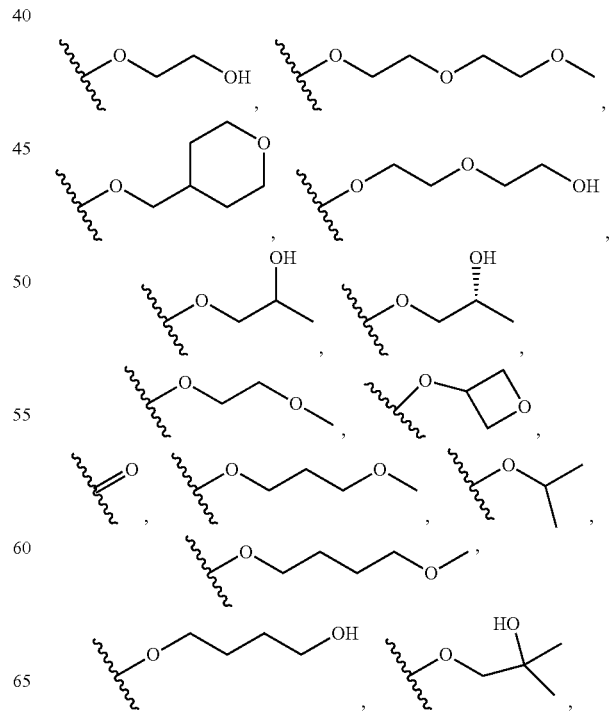

-continued

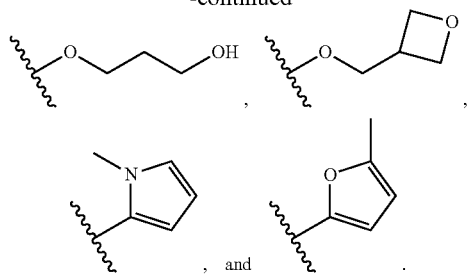

In some embodiments, $R^4$ is selected from:

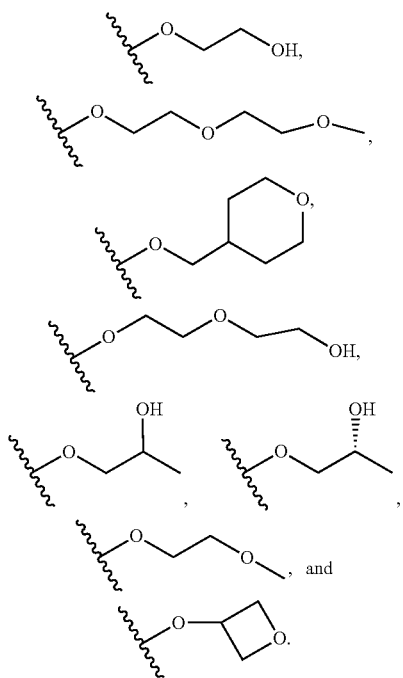

In some embodiments, $R^1$ is selected from:

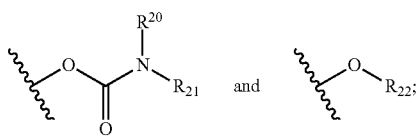

and $R^4$ is selected from:

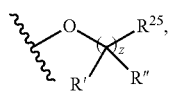

and wherein z is 0, 1, 2, 3, 4 or 5. In some embodiments, $R^{21}$ is an optionally substituted $C_1$-$C_6$ alkyl. In some embodiments, $R^{21}$ may be $C_1$-$C_6$ alkyl substituted with one or more substituents selected from optionally substituted $C_{3-10}$ carbocycle and optionally substituted 3- to 10-membered heterocycle. In some embodiments, $R^{21}$ may be $C_1$-$C_6$ alkyl substituted with one or more substituents selected from $C_{3-6}$ aryl and 3- to 6-membered heterocycle. In some embodiments, $C_{3-6}$ aryl of $R^{21}$ may be phenyl. In some embodiments, the 3- to 6-membered heterocycle of $R^{21}$ comprises at least two heteroatoms selected from N and O. In some embodiments, $R^{22}$ is an optionally substituted $C_2$-$C_6$ alkyl. In some embodiments, $R^{22}$ may be $C_2$-$C_6$ alkyl substituted with one or more substituents selected from $-OR^{30}$ and optionally substituted 3- to 10-membered heterocycle. In some embodiments, $R^{22}$ may be $C_2$-$C_6$ alkyl substituted with one or more substituents selected from $-OR^{30}$ and optionally substituted 3- to 6-membered heterocycle. In some embodiments, $R^{30}$ may be selected from hydrogen and $C_1$-$C_3$ alkyl. In some embodiments, the optionally substituted 3- to 6-membered heterocycle of $R^{22}$ comprises at least two heteroatoms selected from N and O. In some embodiments, the 3- to 7-membered heterocycle of $R^{22}$ may be substituted with one or more $C_{1-3}$ alkyl. In some embodiments, R' and R" are hydrogen. In some embodiments, $R^{25}$ is selected from $-OR^{31}$, optionally substituted 3- to 10-membered heterocycle, and optionally substituted $C_{3-10}$ carbocycle. In some embodiments, $R^{31}$ may be selected from hydrogen and $C_{1-10}$ alkyl which is optionally substituted with one or more substituents independently selected from $-OH$ and $-O-C_{1-10}$ alkyl.

In some embodiments, $R^1$ is selected from:

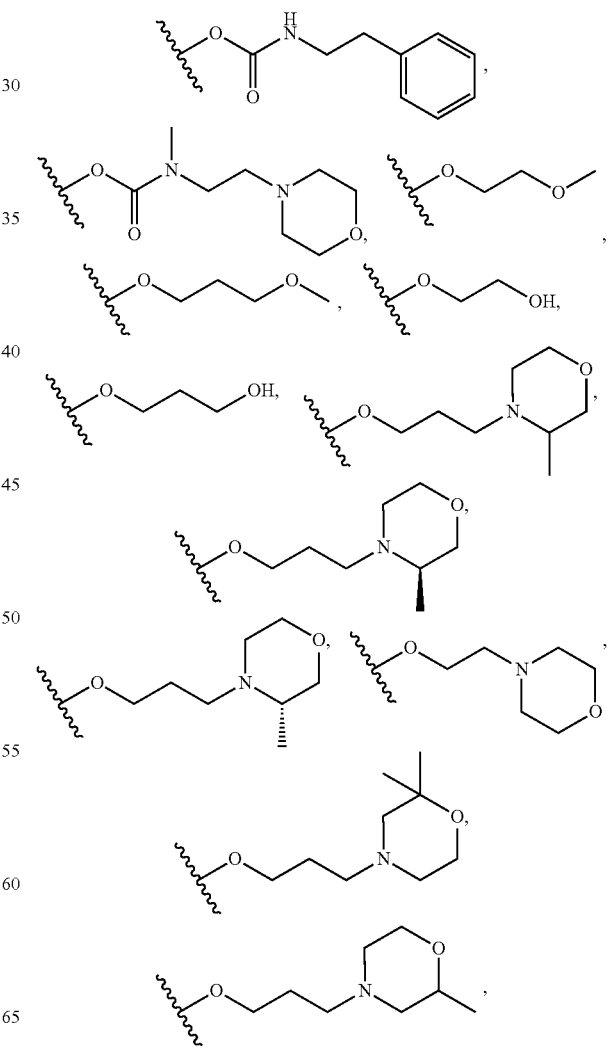

-continued
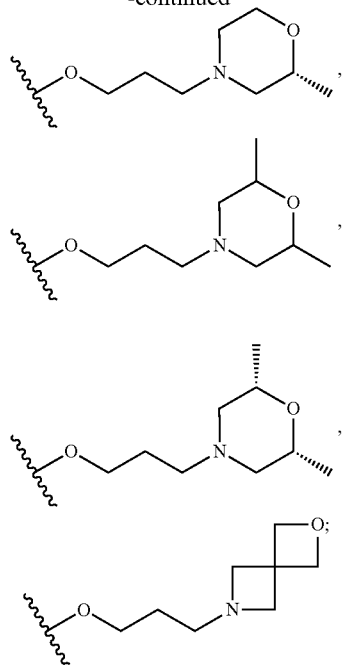
and R⁴ is selected from:
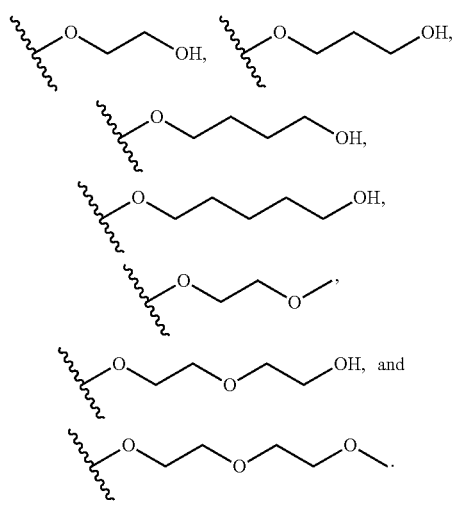
In some embodiments, R¹ is
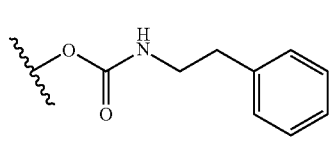
and R⁴ is
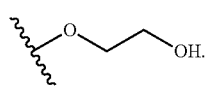
In some embodiments, R¹ is
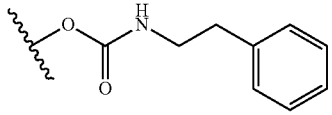 [SMILES: *OC(=O)NCCc1ccccc1]
and R⁴ is
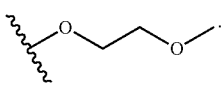 [SMILES: *OCCOC]
In some embodiments, R¹ is
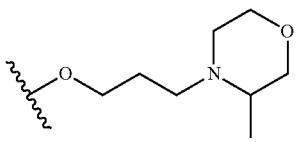 [SMILES: *OCCCN1CCOCC1C]
and R⁴ is
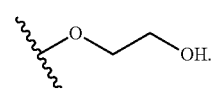 [SMILES: *OCCO]
In some embodiments, R¹ is
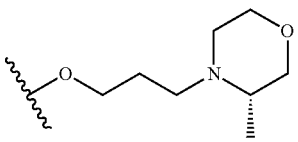 [SMILES: *OCCCN1CCOC[C@@H]1C]
and R⁴ is
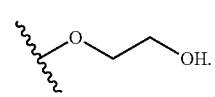 [SMILES: *OCCO]
In some embodiments, R¹ is
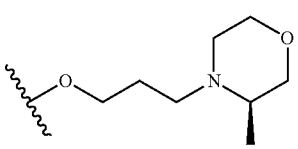 [SMILES: *OCCCN1CCOC[C@H]1C]
and R⁴ is
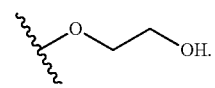 [SMILES: *OCCO]

In some embodiments, R¹ is
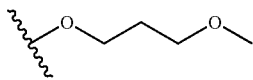
and R⁴ is
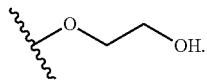 [SMILES: *OCCO]
In some embodiments, R¹ is
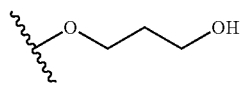 [SMILES: *OCCCO]
and R⁴ is
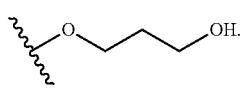 [SMILES: *OCCCO]
In some embodiments, R¹ is
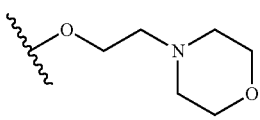 [SMILES: *OCCN1CCOCC1]
and R⁴ is
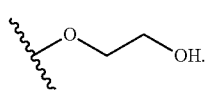 [SMILES: *OCCO]
In some embodiments, R¹ is
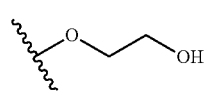 [SMILES: *OCCO]
and R⁴ is
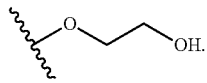 [SMILES: *OCCO]
In some embodiments, R¹ is
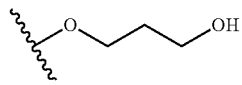 [SMILES: *OCCCO]
and R⁴ is
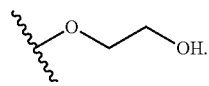 [SMILES: *OCCO]
In some embodiments, R¹ is
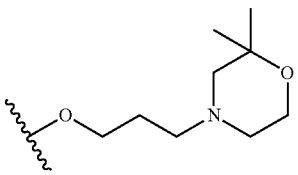 [SMILES: *OCCCN1CCOC(C)(C)C1]
and R⁴ is
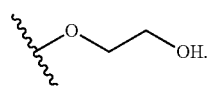 [SMILES: *OCCO]
In some embodiments, R¹ is
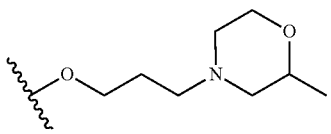 [SMILES: *OCCCN1CCOC(C)C1]
and R⁴ is
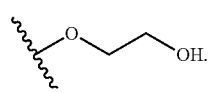 [SMILES: *OCCO]
In some embodiments, R¹ is
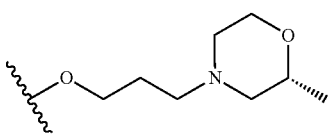 [SMILES: *OCCCN1CCO[C@H](C)C1]
and R⁴ is
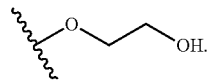 [SMILES: *OCCO]

In some embodiments, $R^1$ is
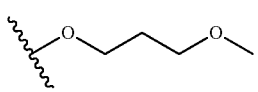
and $R^4$ is
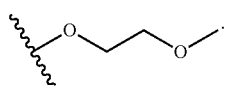 [SMILES: *OCCOC]
In some embodiments, $R^1$ is
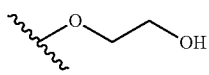
and $R^4$ is
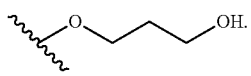 [SMILES: *OCCCO]
In some embodiments, $R^1$ is
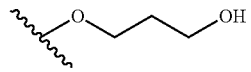 [SMILES: *OCCCO]
and $R^4$ is
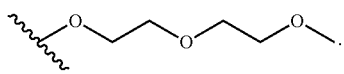 [SMILES: *OCCOCCOC]
In some embodiments, $R^1$ is
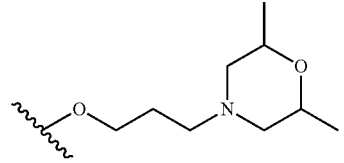 [SMILES: *OCCCN1CC(C)OC(C)C1]
and $R^4$ is
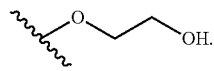 [SMILES: *OCCO]
In some embodiments, $R^1$ is
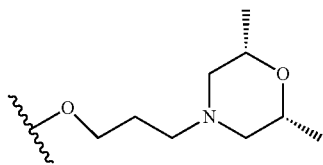 [SMILES: *OCCCN1C[C@@H](C)O[C@@H](C)C1]
and $R^4$ is
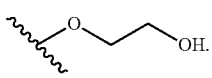 [SMILES: *OCCO]
In some embodiments, $R^1$ is
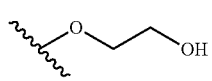 [SMILES: *OCCO]
and $R^4$ is
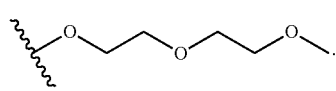 [SMILES: *OCCOCCOC]
In some embodiments, $R^1$ is
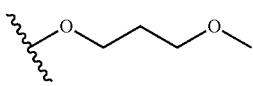 [SMILES: *OCCCOC]
and $R^4$ is
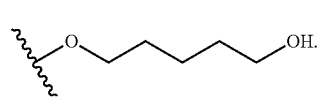 [SMILES: *OCCCCCO]
In some embodiments, $R^1$ is
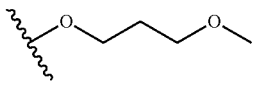 [SMILES: *OCCCOC]
and $R^4$ is
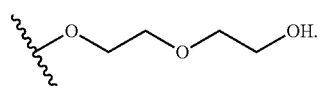 [SMILES: *OCCOCCO]
In some embodiments, $R^1$ is
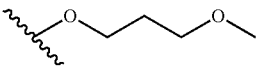 [SMILES: *OCCCOC]

and R⁴ is

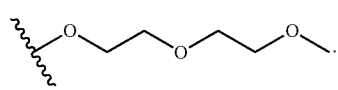 [SMILES: *OCCOCCOC]

In some embodiments, R is an optionally substituted $C_1$-$C_3$ alkoxy group. In some embodiments, $R^2$ is —$OCH_3$.

In some aspects, the compound of Formula (I) is represented by the structure of Formula (I-B):

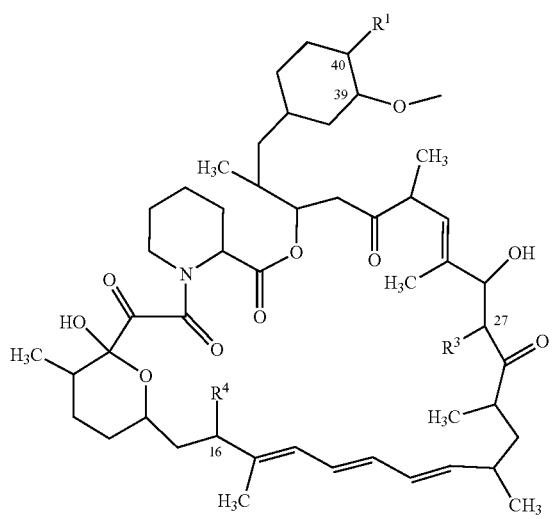

(I-B)

or a pharmaceutically acceptable salt thereof.

In some aspects, the compound of Formula (I) is represented by the structure of Formula (I-C):

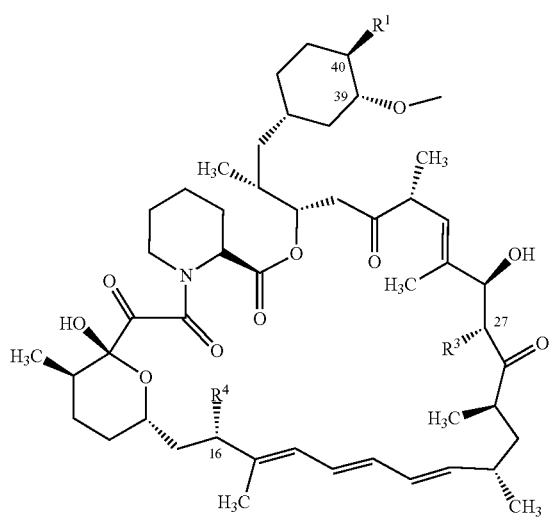

(I-C)

or a pharmaceutically acceptable salt thereof.

In some aspects, the compound of Formula (I) is represented by the structure of Formula (I-C2):

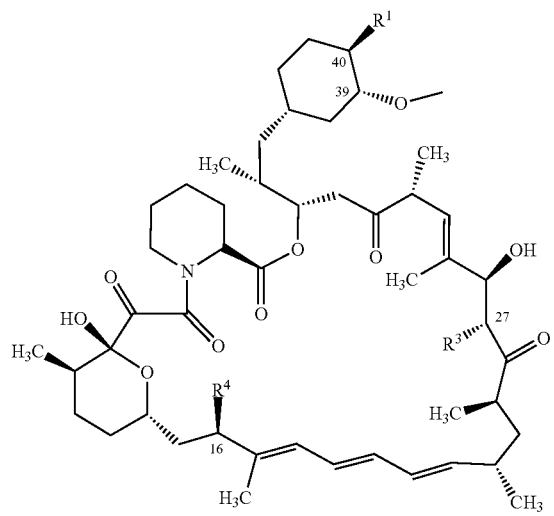

(I-C2)

or a pharmaceutically acceptable salt thereof.

In some embodiments, $R^3$ is an optionally substituted $C_1$-$C_3$ alkoxy group.

In some embodiments, $R^3$ is —$OCH_3$.

In some aspects, the compound of Formula (I) is represented by the structure of Formula (I-D):

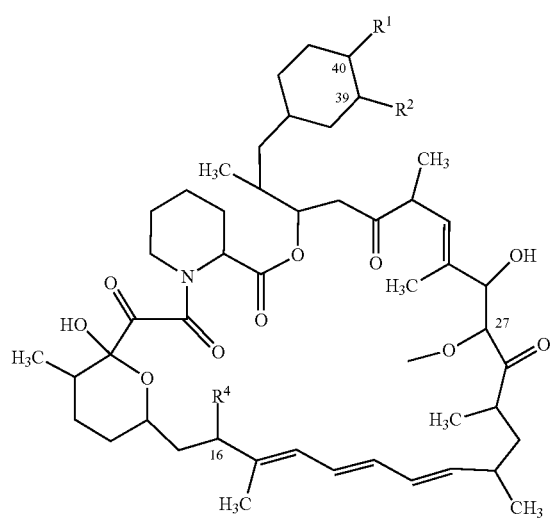

(I-D)

or a pharmaceutically acceptable salt thereof.

In some aspects, the compound of Formula (I) is represented by the structure of Formula (I-E):

In some aspects, the compound of Formula (I) is represented by the structure of Formula (I-F):

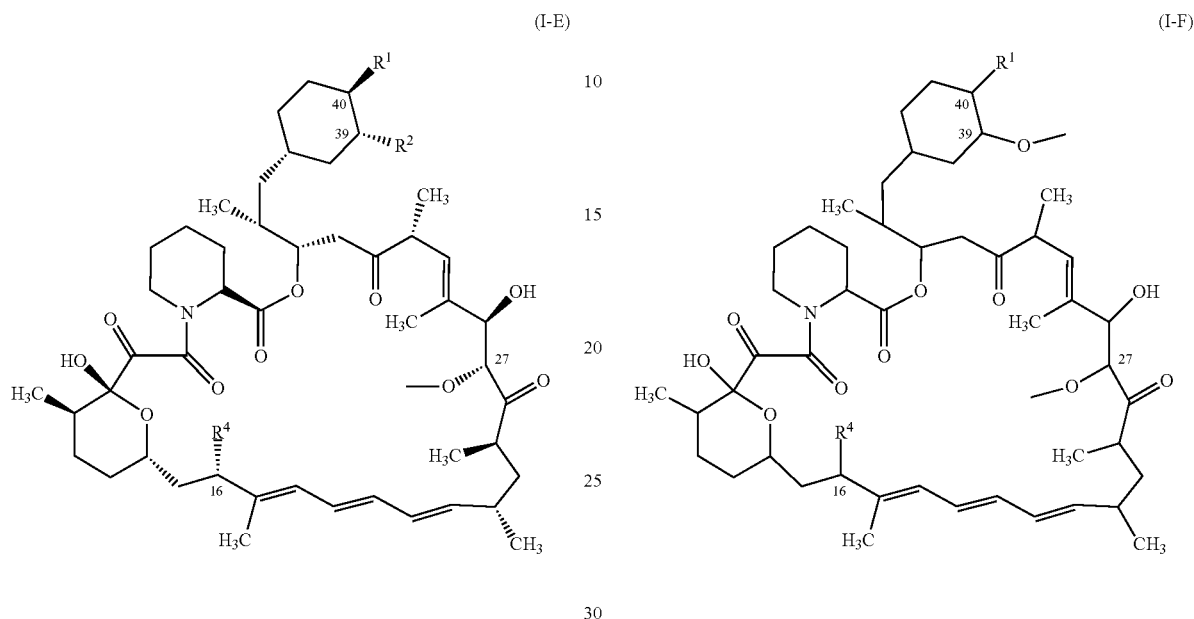

or a pharmaceutically acceptable salt thereof.

In some aspects, the compound of Formula (I) is represented by the structure of Formula (I-E2):

or a pharmaceutically acceptable salt thereof.

In some aspects, the compound of Formula (I) is represented by the structure of Formula (I-G):

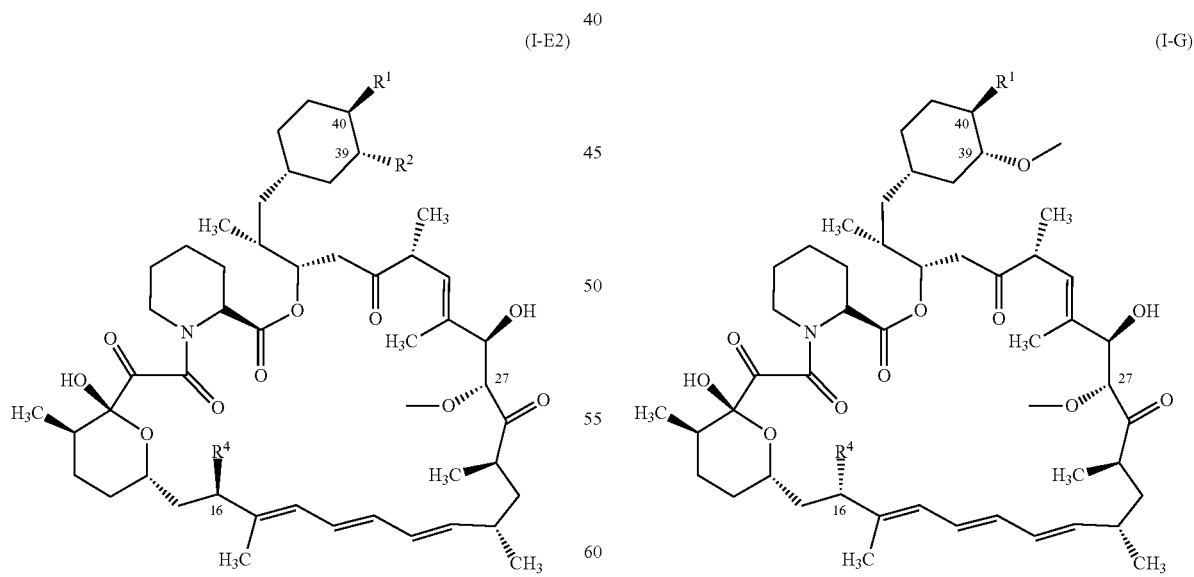

or a pharmaceutically acceptable salt thereof.

or a pharmaceutically acceptable salt thereof.-

In some aspects, the compound of Formula (I) is represented by the structure of Formula (I-G2):

(I-G2)

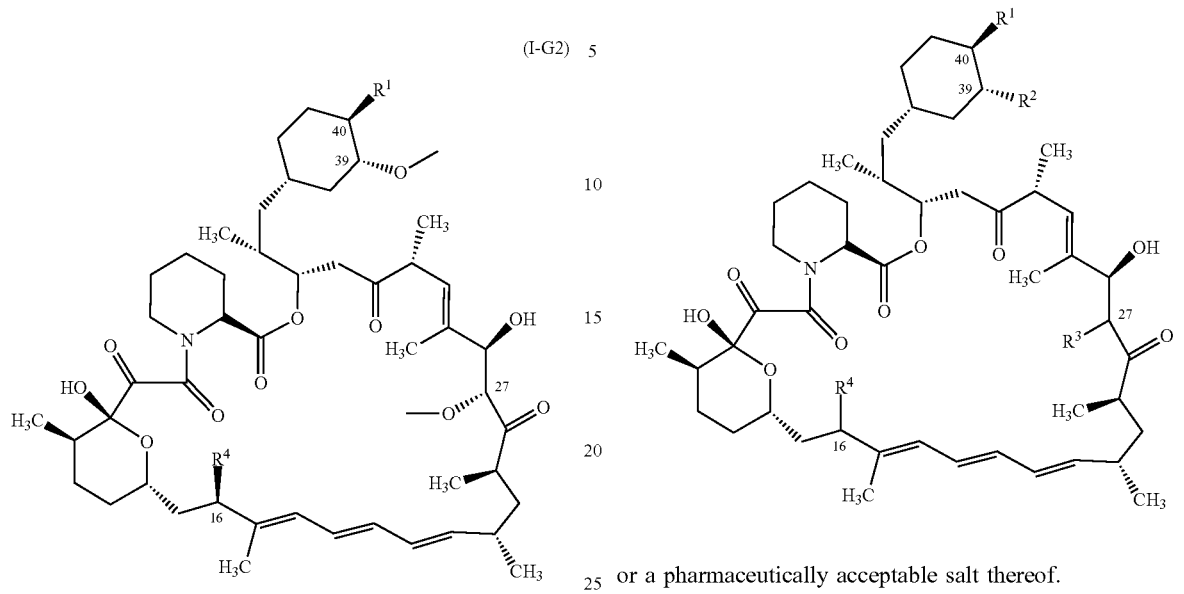

or a pharmaceutically acceptable salt thereof.

In some aspects, the compound of Formula (I) is represented by the structure of Formula (I-H):

(I-H)

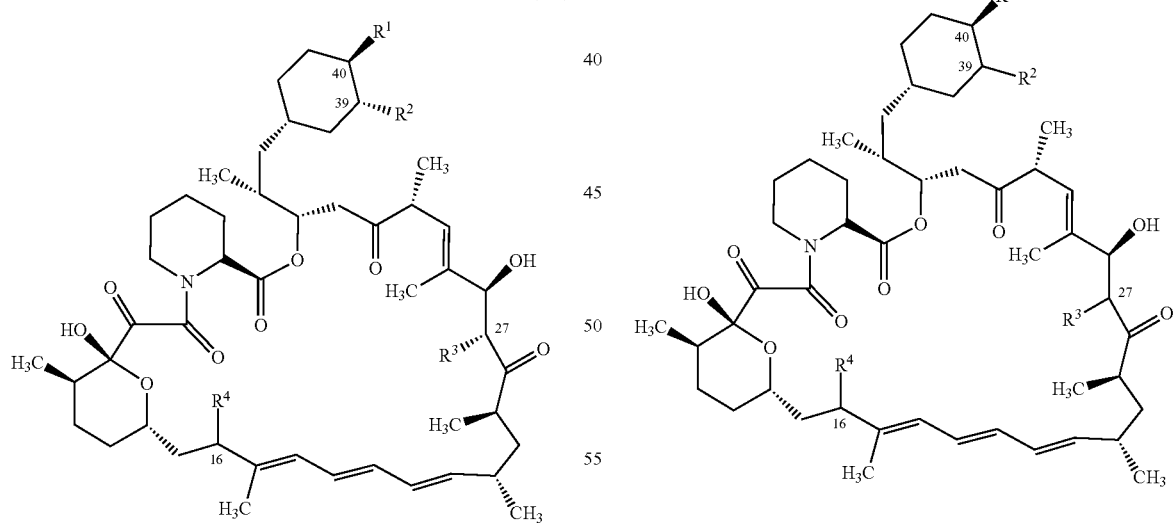

or a pharmaceutically acceptable salt thereof.

In some aspects, the compound of Formula (I) is represented by the structure of Formula (I-I):

(I-I)

or a pharmaceutically acceptable salt thereof.

In some aspects, the compound of Formula (I) is represented by the structure of Formula (I-J):

(I-J)

or a pharmaceutically acceptable salt thereof.

In some aspects, the compound of Formula (I) is represented by the structure of Formula (I-K):

(I-K)

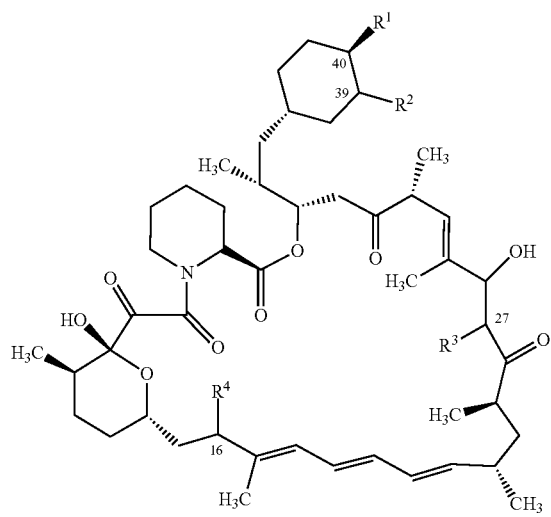

or a pharmaceutically acceptable salt thereof.

In some aspects, the compound of Formula (I) is represented by the structure of Formula (I-L):

(I-L)

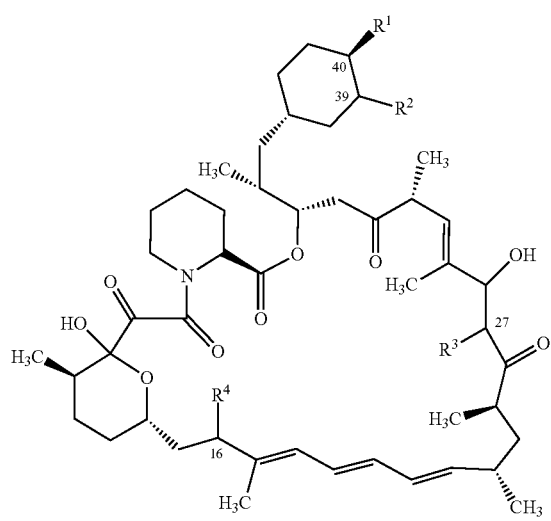

or a pharmaceutically acceptable salt thereof.

In some aspects, a compound of the disclosure, may be represented by the structure of Formula II:

(II)

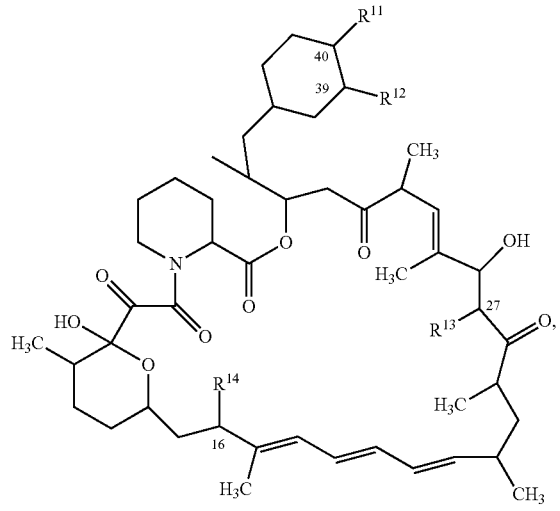

or a pharmaceutically acceptable salt thereof, wherein: $R^{11}$ is selected from

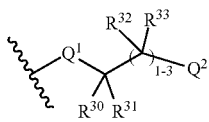

and —OCH$_3$;

$R^{12}$ is selected from hydrogen, hydroxy, and an optionally substituted C$_1$-C$_6$ alkoxy group, wherein substituents on the C$_1$-C$_6$ alkoxy group are independently selected at each occurrence from hydroxy, halogen, cyano, nitro, C$_2$-C$_6$ alkoxy group, optionally substituted carbocycle and optionally substituted heterocycle, wherein substituents on the carbocycle or heterocycle are independently selected from hydroxy, halogen, cyano, nitro, C$_1$-C$_6$ alkyl, haloalkyl, hydroxy C$_1$-C$_6$ alkyl, alkoxy, and alkoxy C$_1$-C$_6$ alkyl;

$R^{13}$ is selected from hydrogen, hydroxy, and optionally substituted C$_1$-C$_6$ alkoxy group, wherein the substituents on the C$_1$-C$_6$ alkoxy group are independently selected at each occurrence from hydroxy, halogen, cyano, nitro, C$_2$-C$_6$ alkoxy group, optionally substituted carbocycle and optionally substituted heterocycle, wherein substituents on the carbocycle or heterocycle are independently selected from hydroxy, halogen, cyano, nitro, C$_1$-C$_6$ alkyl, haloalkyl, hydroxy C$_1$-C$_6$ alkyl, alkoxy, and alkoxy C$_1$-C$_6$ alkyl;

$R^{14}$ is selected from

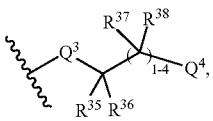

—O—(CH$_2$)$_{0-1}$T and —O—CH(CH$_3$)$_2$;

T is an optionally substituted 3-6-membered heterocyloalkyl wherein substituents are independently selected from hydroxy, halogen, cyano, nitro, C$_1$-C$_6$ alkyl, haloalkyl, hydroxy C$_1$-C$_6$ alkyl, alkoxy, and alkoxy C$_1$-C$_6$ alkyl;

$Q^1$ and $Q^3$ are independently selected from —O—, —OC(=O)NR$^{41}$—, —S—, and —NR$^{40}$—;

$Q^2$ is selected from optionally substituted $C_{3-6}$ carbocycle, optionally substituted 3-8-membered heterocycle, —OR$^{34}$, —(O—CH$_2$—(CH$_2$)$_p$)$_n$—W, and —N(R$^{39}$)$_2$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl; $Q^4$ is selected from optionally substituted $C_{3-6}$ carbocycle, optionally substituted 3-8-membered heterocycle, and —OR$^{42}$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$R^{30}$, $R^{31}$, $R^{35}$, and $R^{36}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

each $R^{32}$, $R^{33}$, $R^{37}$, and $R^{38}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

each $R^{34}$ is selected from hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, halogen, cyano, nitro, $C_1$-$C_6$ alkoxy, carbocycle and heterocycle;

each $R^{39}$ is selected from hydrogen, $C_1$-$C_6$ alkyl, haloalkyl, and alkoxy $C_1$-$C_6$ alkyl;

each $R^{40}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle; and each $R^{41}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle;

each $R^{42}$ is selected from hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, halogen, cyano, nitro, $C_1$-$C_6$ alkoxy, carbocycle and heterocycle;

each p is selected from 1 or 2;

n is selected from 2-4;

W is selected from —OH and —CH3 wherein when $R^{11}$ is

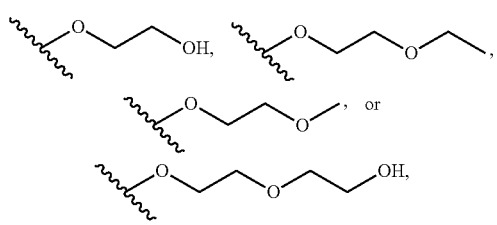

$R^{14}$ is not

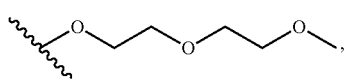

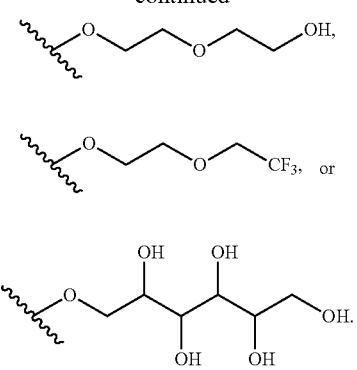

In some embodiments, when $R^{11}$ is

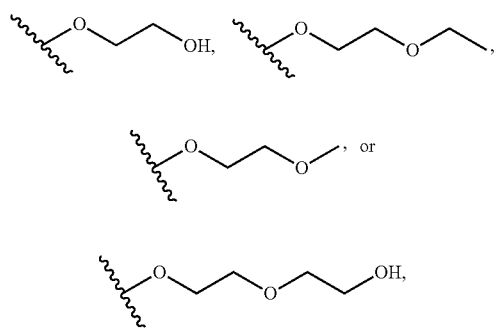

$R^{14}$ is not

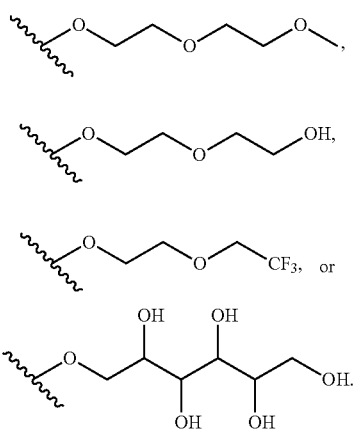

In some embodiments, $R^{11}$ is not

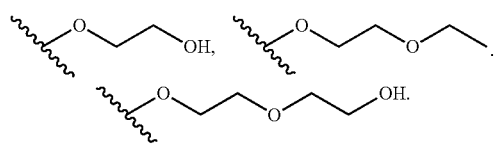

In some aspects, the compound of Formula (II) is represented by the structure of Formula (II-A):

(II-A)

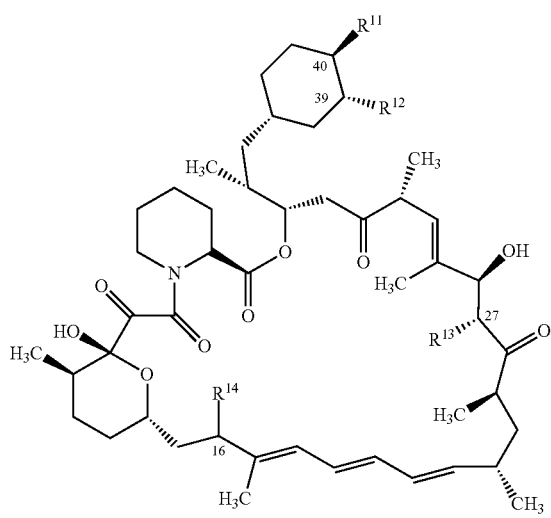

or a pharmaceutically acceptable salt thereof. In certain embodiments, the compound of Formula (II-A) is represented by Formula (II-A1) or (II-A2):

(II-A1)

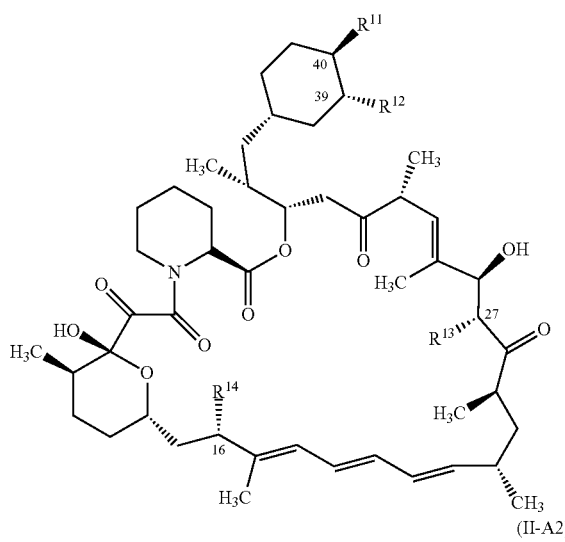

(II-A2)

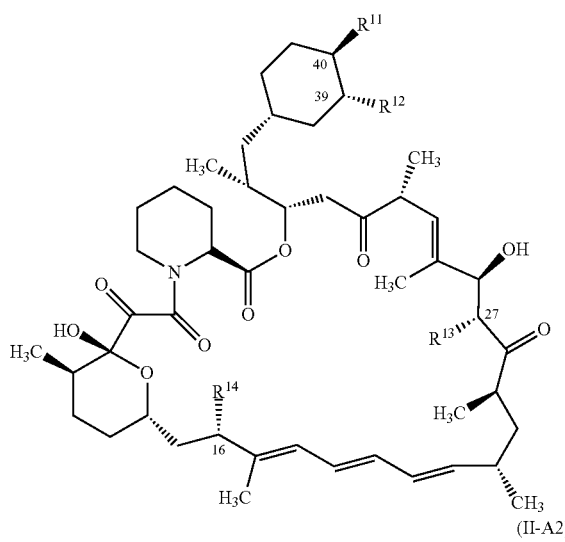

In some embodiments for a compound of Formula (II), (II-A), (II-A1) or (II-A2), $R^{12}$ is selected from optionally substituted $C_1$-$C_6$ alkoxy group. In some embodiments, $R^{12}$ is a $C_1$-$C_6$ alkoxy group. In some embodiments, $R^{12}$ is a $C_1$-$C_3$ alkoxy group. In some embodiments, $R^{12}$ is a $C_1$ alkoxy group. In some embodiments, $R^{12}$ is a —$OCH_3$.

In some embodiments for a compound of Formula (II), (II-A), (II-A1) or (II-A2), $R^{13}$ is selected from an optionally substituted $C_1$-$C_6$ alkoxy group. In some embodiments, $R^{13}$ is a $C_1$-$C_6$ alkoxy group. In some embodiments, $R^{13}$ is a $C_1$-$C_3$ alkoxy group. In some embodiments, $R^{13}$ is a $C_1$ alkoxy group. In some embodiments, $R^{13}$ is a —$OCH_3$.

In some embodiments for a compound of Formula (II), (II-A), (II-A1) or (II-A2), $R^{11}$ is selected from:

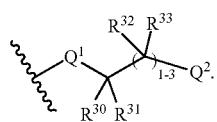

In some embodiments, $R^{11}$ is selected from:

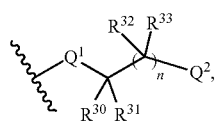

wherein n is 0, 1, 2, 3, 4 or 5. In some embodiments, n of

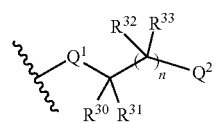

of $R^{11}$ is 0, 1, 2, or 3.
In some embodiments, n of

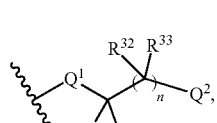

of $R^{11}$ is 0, 1, or 2. In some embodiments, n of

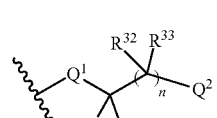

of $R^{11}$ is 0, 1, or 2. In some embodiments, n of

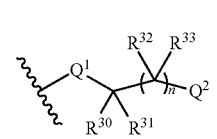

of $R^{11}$ is 0.

In some embodiments, n of

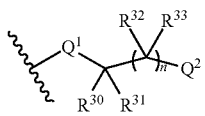

of $R^{11}$ is 1. In some embodiments, n of

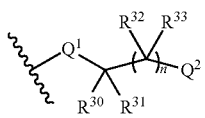

of $R^{11}$ is 2.

In some embodiments for a compound of Formula (II), (II-A), (II-A1) or (II-A2), $Q^2$ is selected from optionally substituted phenyl, optionally substituted 5-7-membered heterocycle, and —N($R^{39}$)$_2$, wherein substituents on phenyl and 5-7-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), when $Q^1$ is —O—, $Q^2$ is selected from optionally substituted phenyl, optionally substituted 5-7-membered heterocycle, and —N($R^{39}$)$_2$, wherein substituents on phenyl and 5-7-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^2$ is selected from optionally substituted phenyl and optionally substituted 5- or 6-membered heterocycle wherein substituents on phenyl and 5- or 6-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^2$ is selected from optionally substituted phenyl and optionally substituted 5- or 6-membered saturated heterocycle wherein substituents on phenyl and 5- or 6-membered saturated heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^2$ is selected from optionally substituted phenyl, optionally substituted piperidine, optionally substituted morpholine, optionally substituted piperazine, optionally substituted pyrrolidine, optionally substituted pyrazolidine, optionally substituted oxazolidine, and optionally substituted isooxazolidine, wherein substituents on phenyl, morpholine, piperidine, pyrrolidine, pyrazolidine, oxazolidine, isooxazolidine, and piperazine are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^2$ is selected from optionally substituted phenyl, optionally substituted piperidine, optionally substituted morpholine, and optionally substituted piperazine, wherein substituents on phenyl, morpholine, piperidine, and piperazine are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^1$ of $R^{11}$ is selected from —O— and —OC(=O)N$R^{41}$—. In some embodiments, $Q^1$ of $R^{11}$ is selected from —O— and —OC(=O)N$R^{41}$—, and $R^{41}$ is selected from hydrogen and $C_1$-$C_3$ alkyl group wherein the substituents are independently selected at each occurrence from halogen, hydroxy, carbocycle and heterocycle. In some embodiments, the carbocycle of optionally substituted $C_1$-$C_3$ alkyl group of $R^{41}$ is $C_{3-6}$ carbocycle. In some embodiments, the $C_{3-6}$ carbocycle is aromatic. In some embodiments, the heterocycle of optionally substituted $C_1$-$C_3$ alkyl group of $R^{41}$ is 3- to 6-membered heterocycle. In some embodiments, the 3- to 6-membered heterocycle is aromatic. In some embodiments, $Q^1$ of $R^{11}$ is selected from —O— and —OC(=O)N$R^{41}$—, and $R^{41}$ is selected from hydrogen and $C_1$-$C_3$ alkyl group wherein the substituents are independently selected at each occurrence from halogen or hydroxy. In some embodiments, $Q^1$ of $R^{11}$ is selected from —O— and —OC(=O)N$R^{41}$—, and $R^{41}$ is selected from hydrogen and $C_1$-$C_3$ alkyl group. In some embodiments, $Q^1$ of $R^{11}$ is selected from —O— and —OC(=O)N$R^{41}$—, and $R^{41}$ is selected from hydrogen and $C_1$ alkyl group. In some embodiments, $Q^1$ of $R^{11}$ is —OC(=O)N$R^{41}$—, and $R^{41}$ is selected from hydrogen and $C_{1-3}$ alkyl group.

In some embodiments for a compound of Formula (II), (II-A), (II-A1) or (II-A2), $Q^1$ of $R^{11}$ is selected from —O—, —OC(=O)NH—, and —OC(=O)N(CH$_3$)—. In some embodiments, $Q^1$ of $R^{11}$ is from —O—. In some embodiments, $Q^1$ of $R^{11}$ is —OC(=O)NH—. In some embodiments, $Q^1$ of $R^{11}$ is and —OC(=O)N(CH$_3$)—. In some embodiments, $Q^1$ of $R^{11}$ is and —OC(=O)N(CH$_2$CH$_3$)—. In some embodiments, $Q^1$ of $R^{11}$ is and —OC(=O)N(CH$_2$CH$_2$CH$_3$)—. In some embodiments, $Q^1$ of $R^{11}$ is and —OC(=O)N(CH$_2$CH$_2$CH$_2$CH$_3$)—.

In some embodiments for a compound of Formula (II), (II-A), (II-A1) or (II-A2), each of $R^{30}$, $R^{31}$, $R^{32}$ and $R^{33}$ of $R^{11}$ are independently selected from hydrogen, hydroxy, halogen, cyano, nitro, and $C_1$-$C_6$ alkyl. In some embodiments, each of $R^{30}$, $R^{31}$, $R^{32}$ and $R^{33}$ of $R^{11}$ are independently selected from hydrogen, hydroxy, halogen, cyano, nitro, and $C_1$-$C_3$ alkyl. In some embodiments, each of $R^{30}$, $R^{31}$, $R^{32}$ and $R^{33}$ of $R^{11}$ are independently selected from hydrogen, hydroxy, and $C_1$-$C_3$ alkyl.

In some embodiments for a compound of Formula (II), (II-A), (II-A1) or (II-A2), each of $R^{30}$, $R^{31}$, $R^{32}$ and $R^{33}$ of $R^{11}$ are independently selected from hydrogen, hydroxy, and methyl. In some embodiments, one of $R^{30}$, $R^{31}$, $R^{32}$ and $R^{33}$ of $R^{11}$ is hydroxy or methyl and the rest of $R^{30}$, $R^{31}$, $R^{32}$ and $R^{33}$ are each hydrogen. In some embodiments, one of $R^{30}$, $R^{31}$, $R^{32}$ and $R^{33}$ of $R^{11}$ is hydroxy and the rest of $R^{30}$, $R^{31}$, $R^{32}$ and $R^{33}$ are each hydrogen. In some embodiments, each $R^{30}$, $R^{31}$, $R^{32}$ and $R^{33}$ of $R^{11}$ is hydrogen.

In some embodiments for a compound of Formula (II), (II-A), (II-A1) or (II-A2), $Q^2$ of $R^{11}$ is selected from optionally substituted $C_{3-6}$ carbocycle, optionally substituted 5-7-membered heterocycle, —O$R^{34}$, —(O—CH$_2$—(CH$_2$)$_p$)$_n$—W, and —N($R^{39}$)$_2$, wherein substituents on $C_{3-6}$ carbocycle and 5-7-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, $Q^2$ of $R^{11}$ is selected from optionally substituted phenyl, optionally substituted 5-7-membered heterocycle, —O$R^{34}$, —(O—CH$_2$—(CH$_2$)$_p$)$_n$—W, and —N($R^{39}$)$_2$, wherein substituents on phenyl and 5-7-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^2$ of $R^{11}$ is selected from optionally substituted 5-7-membered heterocycle, and —$OR^{34}$. In some embodiments, $Q^2$ of $R^{11}$ is selected from —$OR^{34}$, and $R^{34}$ is selected from hydrogen and optionally substituted $C_1$-$C_6$ alkyl. In some embodiments, $Q^2$ of $R^{11}$ is selected from —$OR^{34'}$ and $R^{34}$ is selected from hydrogen and $C_1$-$C_6$ alkyl. In some embodiments, $Q^2$ of $R^{11}$ is selected from —$OR^{34}$, and $R^{34}$ is selected from hydrogen, methyl, ethyl and propyl.

In some embodiments for a compound of Formula (II), (II-A), (II-A1) or (II-A2), $Q^2$ of $R^{11}$ is selected from optionally substituted carbocycle or optionally substituted heterocycle. In some embodiments, the carbocycle of $Q^2$ of $R^{11}$ may be selected from:

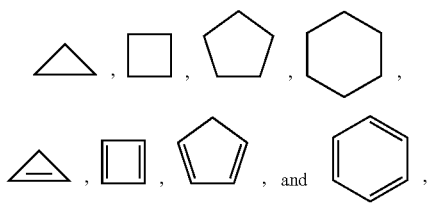

any one of which is optionally substituted. In some embodiments, the heterocycle of $Q^2$ of $R^{11}$ may be selected from:

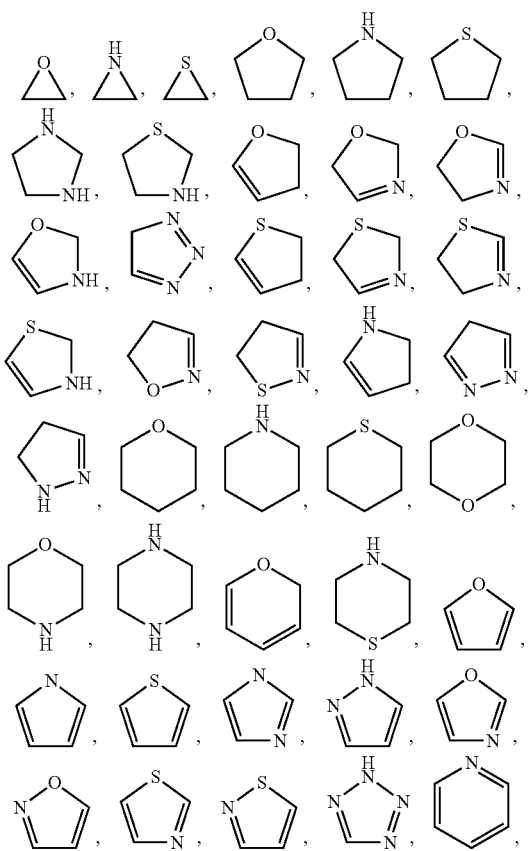

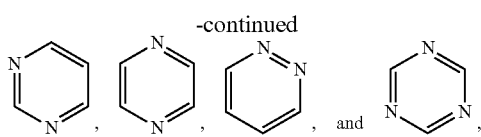

any one of which is optionally substituted.

In some embodiments for a compound of Formula (II), (II-A), (II-A1) or (II-A2), $Q^2$ of $R^{11}$ is optionally substituted carbocycle. In some embodiments, substituents on carbocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, $Q^2$ of $R^{11}$ is optionally substituted $C_{3-6}$ carbocycle. In some embodiments, substituents on $C_{3-6}$ carbocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, $C_{3-6}$ carbocycle is substituted with one substituent selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, $C_{3-6}$ carbocycle is substituted with one substituent selected from hydroxy, $C_1$-$C_6$ alkyl, hydroxy $C_1$-$C_6$ alkyl, alkoxy, and alkoxy $C_1$-$C_6$ alkyl. In some embodiments, $Q^2$ of $R^{11}$ is optionally substituted phenyl. In some embodiments, substituents on phenyl of $Q^2$ of $R^{11}$ of are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, phenyl of $Q^2$ of $R^{11}$ is substituted with one substituent selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^2$ of $R^{11}$ is optionally substituted 5-7-membered heterocycle. In some embodiments, substituents on 5-7-membered heterocycle of $Q^2$ of $R^{11}$ are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, substituents on 5-7-membered heterocycle of $Q^2$ of $R^{11}$ are independently selected from hydroxy, $C_1$-$C_6$ alkyl, hydroxy $C_1$-$C_6$ alkyl, alkoxy, and alkoxy $C_1$-$C_6$ alkyl. In some embodiments, 5-7-membered heterocycle of $Q^2$ of $R^{11}$ is substituted one substituent selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, 5-7-membered heterocycle of $Q^2$ of $R^{11}$ is substituted two substituents independently selected at each occurrence from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, 5-7-membered heterocycle of $Q^2$ of $R^{11}$ is substituted with one, two, or three substituents independently selected at each occurrence from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some embodiments, 5-7-membered heterocycle of $Q^2$ of $R^{11}$ is substituted with one or two substituents independently selected at each occurrence from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl. In some cases, the $C_1$-$C_6$ alkyl of the independently selected at each occurrence $C_1$-$C_6$ alkyl of the 5-7-membered heterocycle of $Q^2$ of $R^{11}$ may be substituted with a substituent independently selected at each occurrence from hydroxy, $C_1$-$C_6$ alkyl, and alkoxy.

In some embodiments for a compound of Formula (II), (II-A), (II-A1) or (II-A2), $Q^2$ of $R^{11}$ is —$OR^{34}$. In some embodiments, $Q^2$ of $R^{11}$ is —$OR^{34}$, and $R^{34}$ is selected from hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, $C_1$-$C_6$ alkoxy, carbocycle and heterocycle. In some embodiments, the optionally substituted carbocycle of $R^{34}$ of —$OR^{34}$ is a $C_{3-6}$ carbocycle. In some embodiments, the optionally substituted heterocycle of $R^{34}$ of —$OR^{34}$ is a 3-7-membered heterocycle.

In some embodiments for a compound of Formula (II), (II-A), (II-A1) or (II-A2), $R^{11}$ is selected from

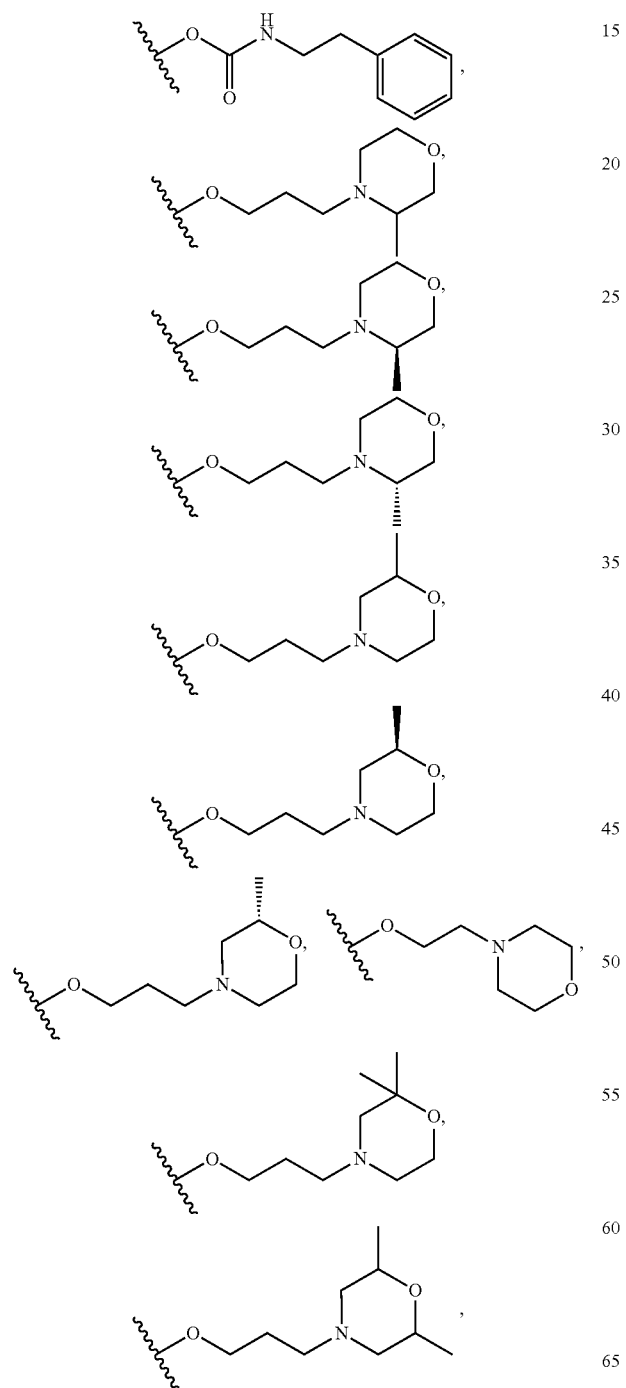

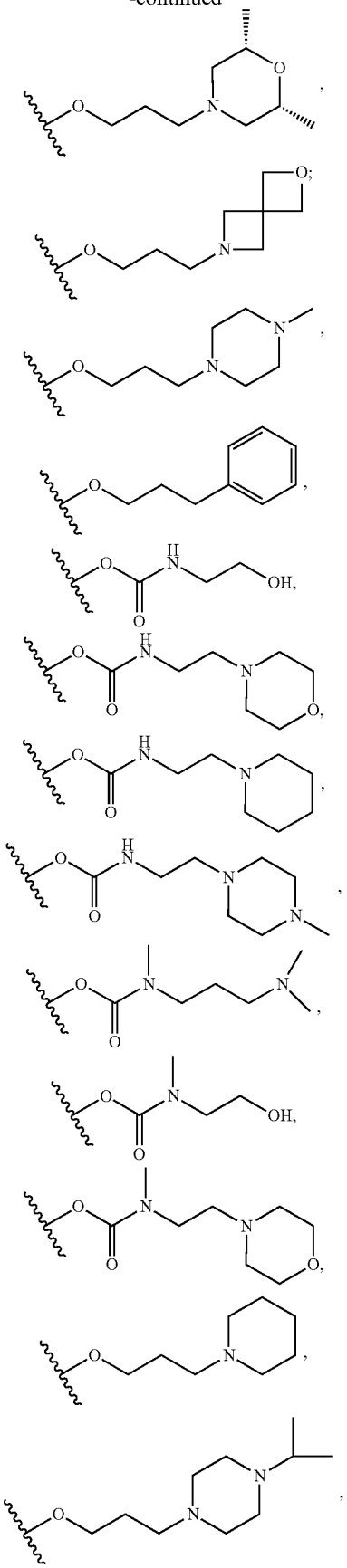

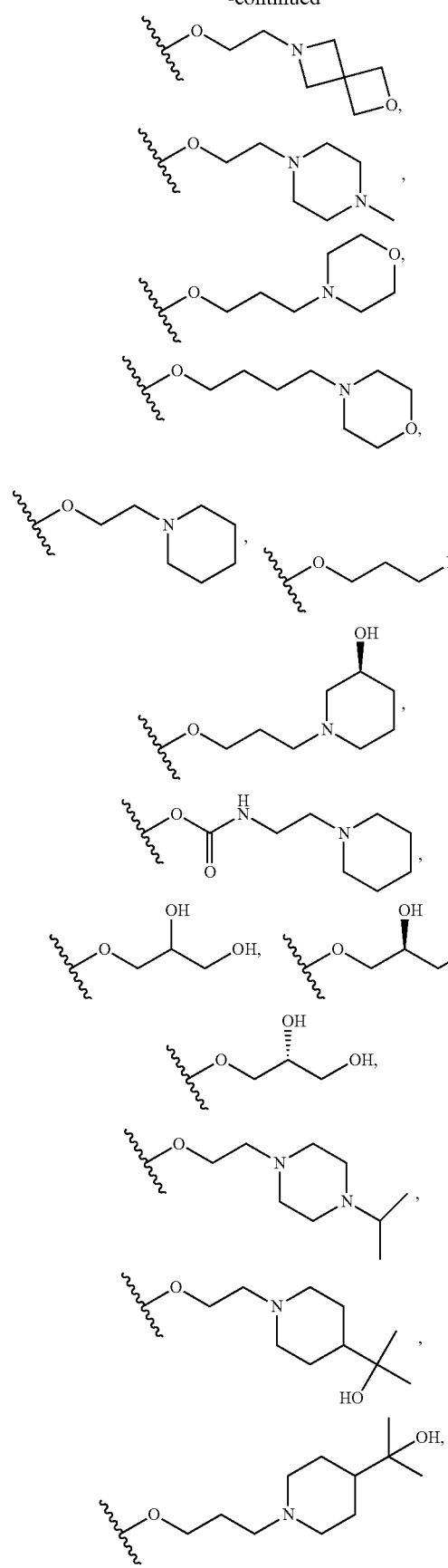
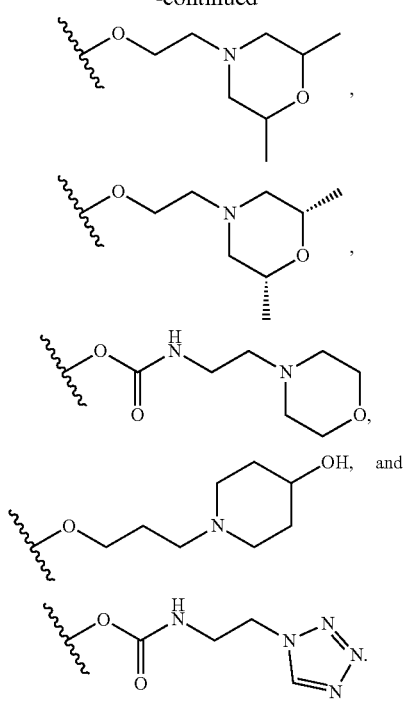
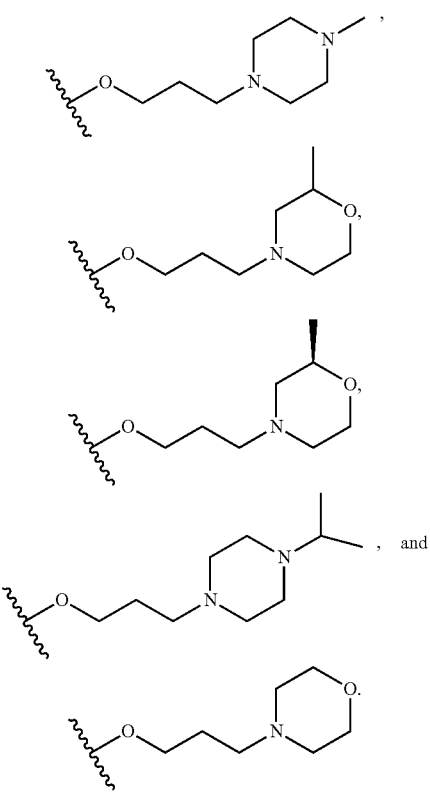
In some embodiments for a compound of Formula (II), (II-A), (II-A1) or (II-A2), $R^{11}$ is selected from:
In some embodiments for a compound of Formula (II), (II-A), (II-A1) or (II-A2), $R^{11}$ is

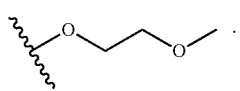 [SMILES: *OCCOC]

In some embodiments for a compound of Formula (II), (II-A), (II-A1) or (II-A2), $R^{11}$ is

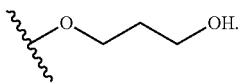 [SMILES: *OCCCO]

In some embodiments for a compound of Formula (II), (II-A), (II-A1) or (II-A2), the carbocycle of $R^{34}$ of —$OR^{34}$ may be selected from:

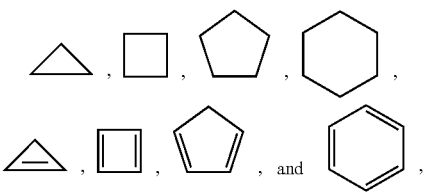

any one of which is optionally substituted.

In some embodiments for a compound of Formula (II), (II-A), (II-A1) or (II-A2), the heterocycle of $R^{34}$ of —$OR^{34}$ may be selected from:

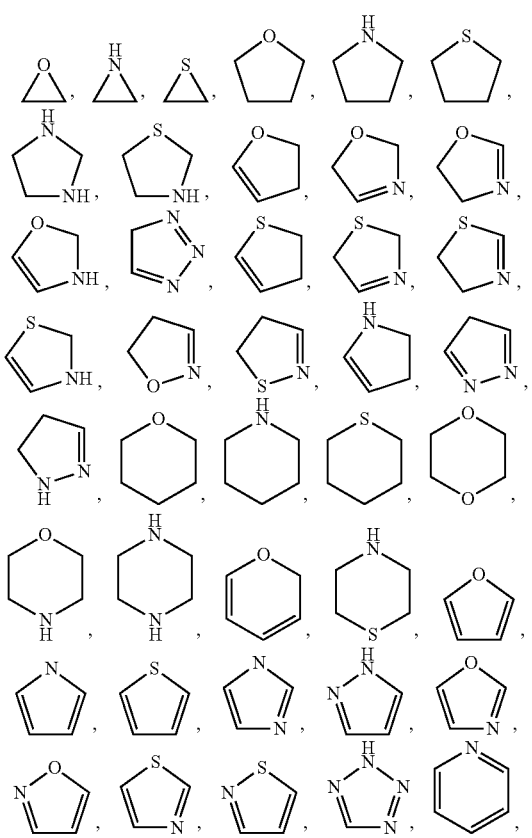

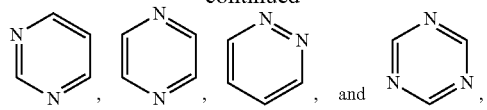

any one of which is optionally substituted.

In some embodiments for a compound of Formula (II), (II-A), (II-A1) or (II-A2), $Q^2$ of $R^{11}$ is —$OR^{34}$, and $R^{34}$ is selected from hydrogen, $C_1$-$C_6$ alkyl, carbocycle, and heterocycle. In some embodiments, the carbocycle of $R^{34}$ of —$OR^{34}$ is a $C_{3-6}$ carbocycle. In some embodiments, $Q^2$ of $R^{11}$ is selected from —$OR^{34}$, and $R^{34}$ is selected from hydrogen and optionally substituted $C_1$—$C_6$ alkyl. In some embodiments, $Q^2$ of $R^{11}$ is selected from —$OR^{34}$, and $R^{34}$ is selected from hydrogen and $C_1$-$C_6$ alkyl. In some embodiments, $Q^2$ of $R^{11}$ is selected from —$OR^{34}$, and $R^{34}$ is selected from hydrogen, methyl, ethyl and propyl.

In some embodiments for a compound of Formula (II), (II-A), (II-A1) or (II-A2), $R^{11}$ is selected from

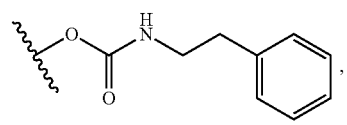

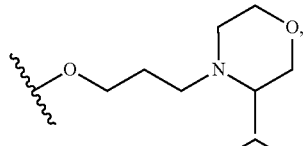

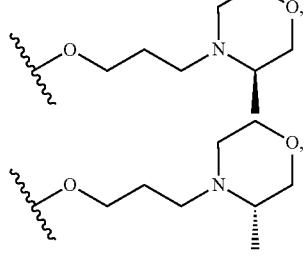

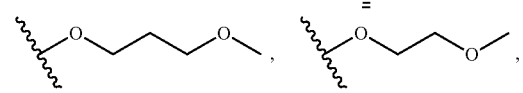

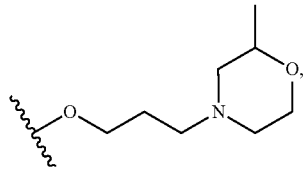

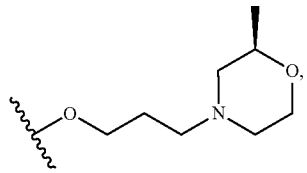

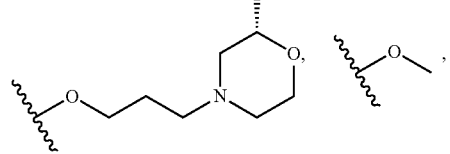

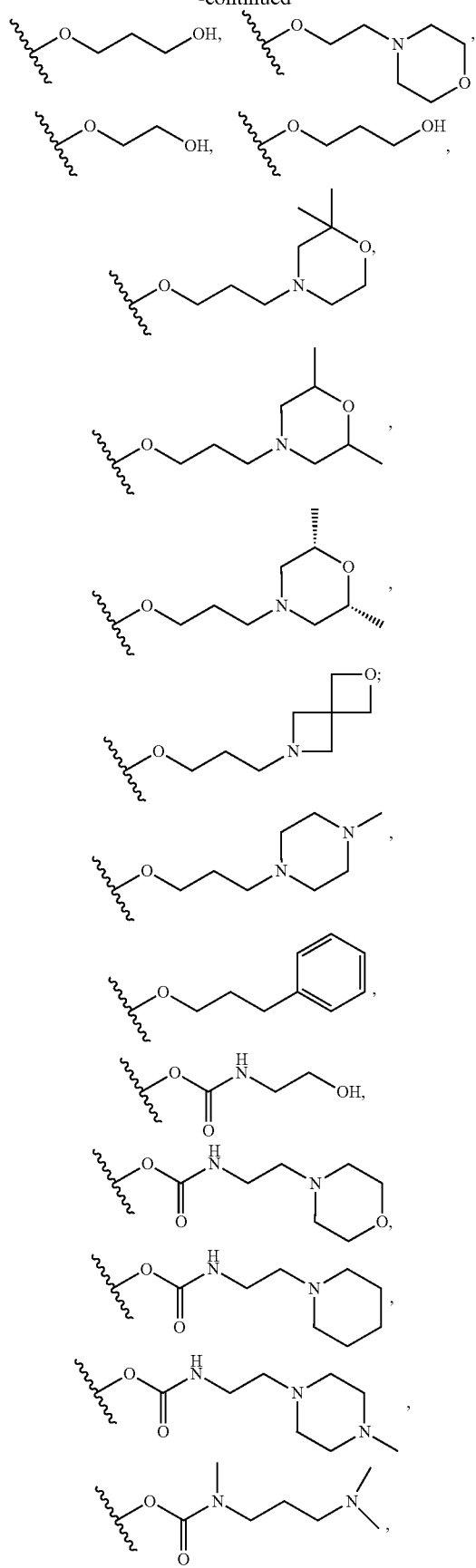
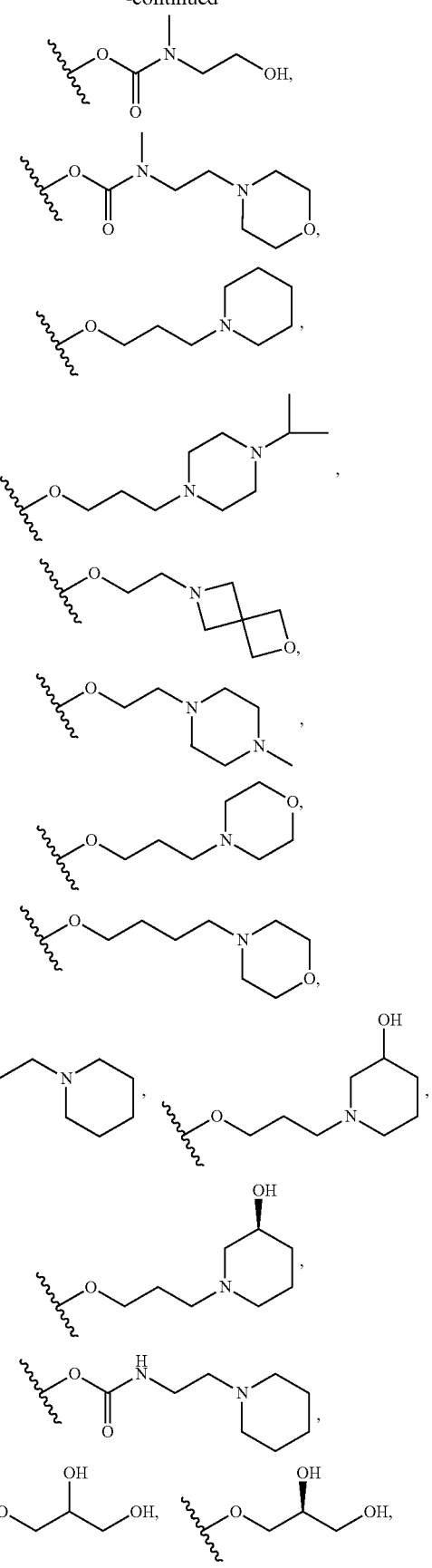

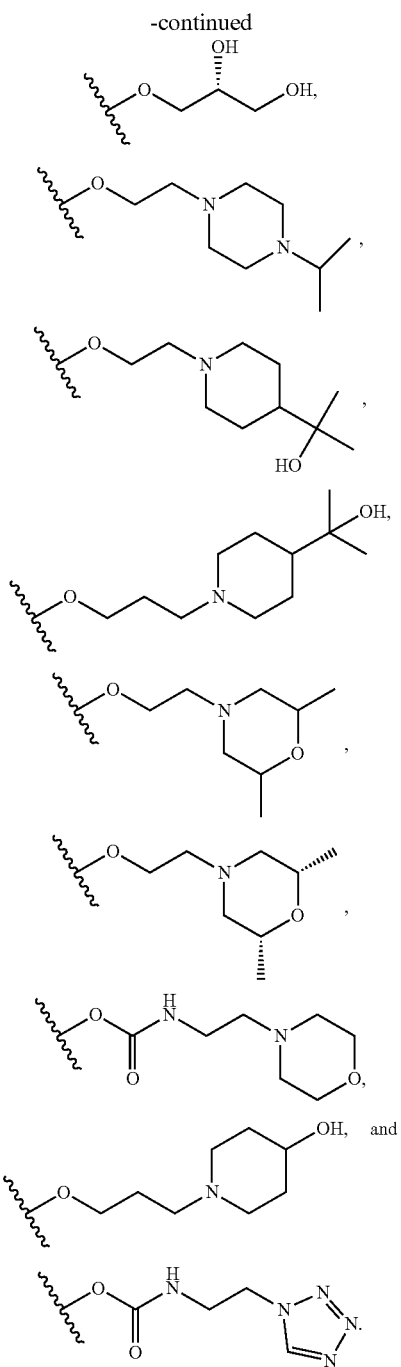

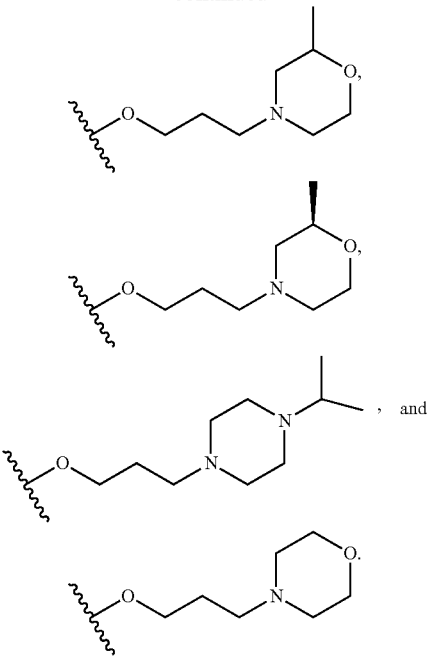

In some embodiments for a compound of Formula (II), (II-A), (II-A1) or (II-A2), $R^{14}$ is selected from

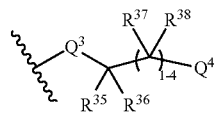

and —O—$(CH_2)_{0-1}$T.

In some embodiments for a compound of Formula (II), (II-A), (II-A1) or (II-A2), $R^{14}$ is —O—$(CH_2)_{0-1}$T. In some embodiments, T of —O—$(CH_2)_{0-1}$T is an optionally substituted 3-6-membered heterocycloalkyl wherein substituents are independently selected from hydroxy, $C_1$-$C_6$ alkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $R^{14}$ is selected from

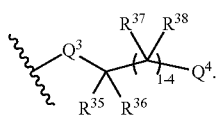

In some embodiments, $Q^3$ of $R^{14}$ is —O—.

In some embodiments for a compound of Formula (II), (II-A), (II-A1) or (II-A2), each of $R^{35}$, $R^{36}$, $R^{37}$ and $R^{38}$ of $R^{14}$ are independently selected from hydrogen, hydroxy, halogen, cyano, nitro, and $C_1$-$C_3$ alkyl. In some embodiments, each of $R^{35}$, $R^{36}$, $R^{37}$ and $R^{38}$ of $R^{14}$ are independently selected from hydrogen, hydroxy, and methyl.

In some embodiments for a compound of Formula (II), (II-A), (II-A1) or (II-A2), one or two of $R^{35}$, $R^{36}$, $R^{37}$ and $R^{38}$ of $R^{14}$ is selected from hydroxy and methyl and the rest of $R^{35}$, $R^{36}$, $R^{37}$ and $R^{38}$ are each hydrogen.

In some embodiments for a compound of Formula (II), (II-A), (II-A1) or (II-A2), each of $R^{35}$, $R^{36}$, $R^{37}$, and $R^{38}$ are In some embodiments for a compound of Formula (II), (II-A), (II-A1) or (II-A2), $R^{11}$ is selected from:

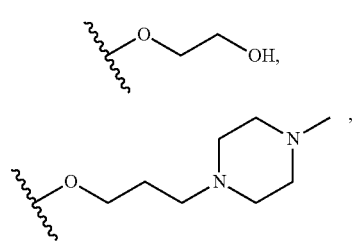

independently selected from hydrogen, hydroxy, halogen, cyano, nitro, $C_1$-$C_6$ alkyl, haloalkyl, hydroxy $C_{1-6}$ alkyl, alkoxy, and alkoxy $C_1$-$C_6$ alkyl, wherein no more than three of $R^{35}$, $R^{36}$, $R^{37}$, and $R^{38}$ are hydroxy, halogen, cyano, nitro, $C_1$-$C_6$ alkyl, haloalkyl, hydroxy $C_{1-6}$ alkyl, alkoxy, and alkoxy $C_1$-$C_6$ alkyl and the others are hydrogen.

In some embodiments for a compound of Formula (II), (II-A), (II-A1) or (II-A2), each of $R^{35}$, $R^{36}$, $R^{37}$, and $R^{38}$ are independently selected from hydrogen, hydroxy, halogen, cyano, nitro, $C_1$-$C_6$ alkyl, haloalkyl, hydroxy $C_{1-6}$ alkyl, alkoxy, and alkoxy $C_1$-$C_6$ alkyl, wherein no more than three of $R^{35}$, $R^{36}$, $R^{37}$, and $R^{38}$ are hydroxy.

In some embodiments for a compound of Formula (II), (II-A), (II-A1) or (II-A2), each of $R^{35}$, $R^{36}$, $R^{37}$, and $R^{38}$ are independently selected from hydrogen, hydroxy, halogen, cyano, nitro, $C_1$-$C_6$ alkyl, haloalkyl, hydroxy $C_{1-6}$ alkyl, alkoxy, and alkoxy $C_1$-$C_6$ alkyl, wherein no more than two of $R^{35}$, $R^{36}$, $R^{37}$, and $R^{38}$ are hydroxy.

In some embodiments for a compound of Formula (II), (II-A), (II-A1) or (II-A2), $Q^4$ of $R^{14}$ is selected from optionally substituted phenyl, and —$OR^{42}$, wherein substituents on phenyl are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl.

In some embodiments for a compound of Formula (II), (II-A), (II-A1) or (II-A2), $Q^4$ of $R^{14}$ is selected from phenyl and —$OR^{42}$, and $R^{42}$ is selected from hydrogen and optionally substituted $C_1$-$C_6$ alkyl.

In some embodiments for a compound of Formula (II), (II-A), (II-A1) or (II-A2), $Q^4$ of $R^{14}$ is selected from phenyl and —$OR^{42}$, and $R^{42}$ is selected from hydrogen, methyl, hydroxyethyl, and methoxyethyl.

In some embodiments for a compound of Formula (II), (II-A), (II-A1) or (II-A2), $R^{14}$ is selected from:

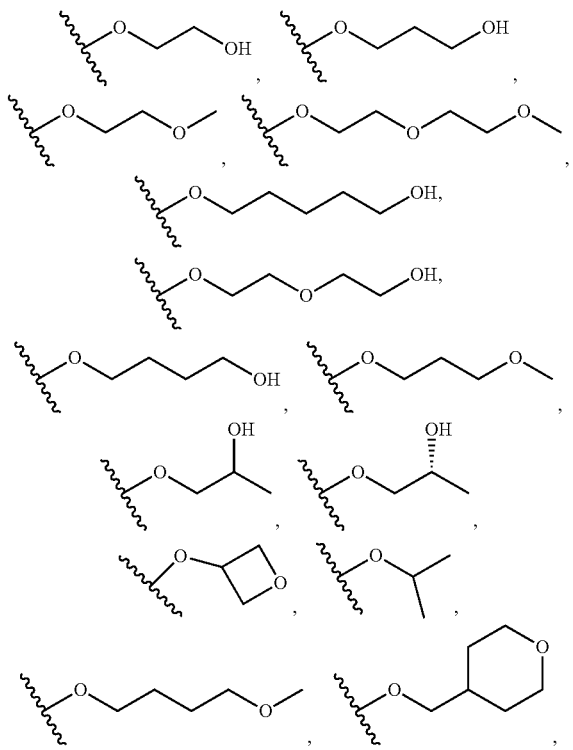

In some embodiments for a compound of Formula (II), (II-A), (II-A1) or (II-A2), $R^{14}$ is selected from:

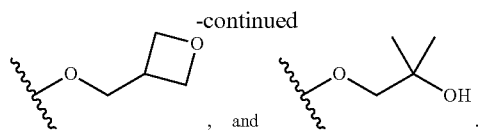
, and

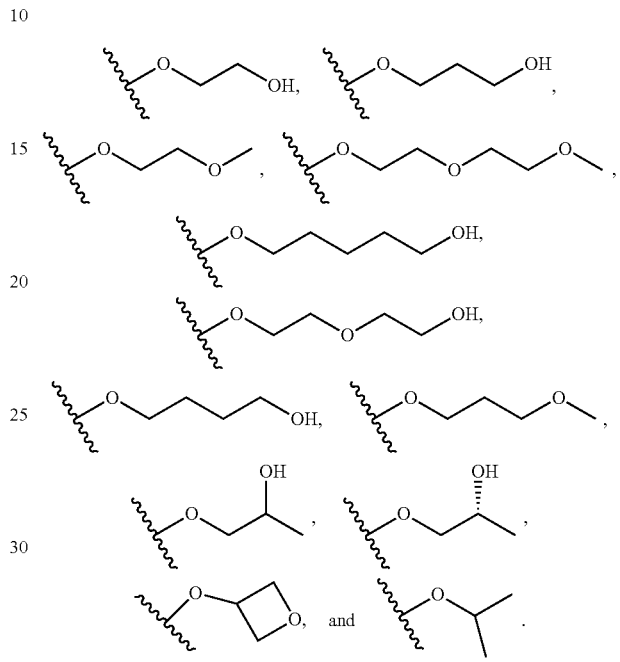
, and

In certain embodiments, for a compound of Formula (II), (II-A), (II-A1) or (II-A2):

$R^{11}$ is selected from

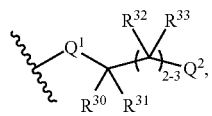

and —$OCH_3$;

$R^{12}$ is selected from optionally substituted $C_1$-$C_6$ alkoxy group, such as $R^{12}$ is a $C_1$-$C_6$ alkoxy group, and preferably $R^{12}$ is —$OCH_3$;

$R^{13}$ is selected from an optionally substituted $C_1$-$C_6$ alkoxy group, such as $R^{12}$ is a $C_1$-$C_6$ alkoxy group, and preferably $R^{12}$ is —$OCH_3$;

$R^{14}$ is selected from

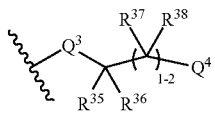

and —O—$(CH_2)_{0-1}$T;

T is an optionally substituted 4-6-membered heterocycloalkyl wherein substituents are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, such as T is selected from optionally substituted oxetane and optionally substituted pyran;

$Q^1$ and $Q^3$ are independently selected from —O—, —OC(=O)$NR^{41}$—, —S—, and —$NR^{40}$—, preferably $Q^1$ and $Q^3$ are each —O—;

$Q^2$ is selected from optionally substituted $C_{3-6}$ carbocycle, optionally substituted 3-8-membered heterocycle, —$OR^{34}$, and —$N(R^{39})_2$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, preferably $Q^2$ is —$OR^{34}$;

$Q^4$ is selected from optionally substituted $C_{3-6}$ carbocycle, optionally substituted 3-8-membered heterocycle, and —$OR^{42}$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, preferably $Q^4$ is —$OR^{42}$;

$R^{30}$, $R^{31}$, $R^{35}$, and $R^{36}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, and preferably each of $R^{30}$, $R^{31}$, $R^{35}$, and $R^{36}$ is hydrogen;

each $R^{32}$, $R^{33}$, $R^{37}$, and $R^{38}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, wherein no more than two of $R^{35}$, $R^{36}$ $R^{37}$, and $R^{38}$ are hydroxy, such as preferably each of $R^{32}$, $R^{33}$, $R^{37}$, and $R^{38}$ are hydrogen;

$R^{34}$ is selected from hydrogen and optionally substituted $C_1$-$C_6$ alkyl, hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, halogen, cyano, nitro, $C_1$-$C_6$ alkoxy, carbocycle and heterocycle, preferably $R^{34}$ is hydrogen or $CH_3$;

each $R^{39}$ is selected from hydrogen, $C_1$-$C_6$ alkyl, haloalkyl, and alkoxy $C_1$-$C_6$ alkyl;

each $R^{40}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle;

each $R^{41}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle; and each $R^{42}$ is selected from hydrogen, optionally substituted $C_1$-$C_2$ alkyl, optionally substituted carbocycle, and optionally substituted heterocycle, wherein the substituents on $C_1$-$C_2$ alkyl, carbocycle, and heterocycle are independently selected at each occurrence from hydroxy, halogen, cyano, nitro, $C_1$-$C_2$ alkoxy, carbocycle and heterocycle.

In certain embodiments, for a compound of Formula (II), (II-A), (II-A1) or (II-A2):

$R^{11}$ is selected from

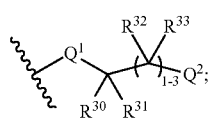

$R^{12}$ is selected from optionally substituted $C_1$-$C_6$ alkoxy group, such as $R^{12}$ is a $C_1$-$C_6$ alkoxy group, and preferably $R^{12}$ is —$OCH_3$;

$R^{13}$ is selected from an optionally substituted $C_1$-$C_6$ alkoxy group, such as $R^{12}$ is a $C_1$-$C_6$ alkoxy group, and preferably $R^{12}$ is —$OCH_3$;

$R^{14}$ is selected from

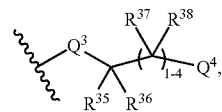

—O—$(CH_2)_{0-1}$T and —O—$CH(CH_3)_2$;

T is an optionally substituted 3-6-membered heterocycloalkyl wherein substituents are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$Q^1$ selected from —OC(=O)$NR^{41}$—, —S—, and —$NR^{40}$—, preferably $Q^1$ is —OC(=O)$NR^{41}$—;

$Q^3$ is selected from —O—, —OC(=O)$NR^{41}$—, —S—, and —$NR^{40}$—, preferably $Q^3$ is —O—;

$Q^2$ is selected from optionally substituted phenyl, optionally substituted 3-6-membered saturated heterocycle, —$OR^{34}$, and —$N(R^{39})_2$, wherein substituents on phenyl and 3-6-membered saturated heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$Q^4$ is selected from optionally substituted $C_{3-6}$ carbocycle, optionally substituted 3-8-membered heterocycle, and —$OR^{42}$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, preferably $Q^4$ is —$OR^{42}$;

$R^{30}$, $R^{31}$, $R^{35}$, and $R^{36}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, and preferably each of $R^{30}$, $R^{31}$, $R^{35}$, and $R^{36}$ is hydrogen;

each $R^{32}$, $R^{33}$, $R^{37}$, and $R^{38}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, wherein no more than two of $R^{35}$, $R^{36}$, $R^{37}$, and $R^{38}$ are hydroxy, such as preferably each of $R^{32}$, $R^{33}$, $R^{37}$, and $R^{38}$ are hydrogen;

each $R^{34}$ is selected from hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, halogen, cyano, nitro, $C_1$-$C_6$ alkoxy, carbocycle and heterocycle, preferably $R^{34}$ is hydrogen or $CH_3$;

each $R^{39}$ is selected from hydrogen, $C_1$-$C_6$ alkyl, haloalkyl, and alkoxy $C_1$-$C_6$ alkyl;

each $R^{40}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle;

each $R^{41}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle; and each $R^{42}$ is selected from hydrogen, optionally substituted $C_1$-$C_2$ alkyl, optionally substituted carbocycle, and optionally substituted heterocycle, wherein the substituents on $C_1$-$C_2$ alkyl, carbocycle, and heterocycle are independently selected at each occurrence from hydroxy, halogen, cyano, nitro, $C_1$-$C_2$ alkoxy, carbocycle and heterocycle.

In certain embodiments, for a compound or salt of Formula (II), (II-A), (II-A1) or (II-A2), $R^{11}$ is selected from

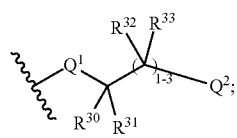

$R^{12}$ is selected from optionally substituted $C_1$-$C_6$ alkoxy group, such as $R^{12}$ is a $C_1$-$C_6$ alkoxy group, and preferably $R^{12}$ is —$OCH_3$;

$R^{13}$ is selected from an optionally substituted $C_1$-$C_6$ alkoxy group, such as $R^{12}$ is a $C_1$-$C_6$ alkoxy group, and preferably $R^{12}$ is —$OCH_3$;

$R^{14}$ is selected from

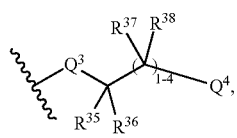

—O—$(CH_2)_{0-1}$T and —O—$CH(CH_3)_2$;

T is an optionally substituted 3-6-membered heterocycloalkyl wherein substituents are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$Q^1$ selected from —O—, —OC(=O)$NR^{41}$—, and —$NR^{40}$—, preferably $Q^1$ is —O—;

$Q^3$ is selected from —O—, —OC(=O)$NR^{41}$—, —S—, and —$NR^{40}$—, preferably $Q^3$ is —O—;

$Q^2$ is selected from optionally substituted phenyl, optionally substituted 3-8-membered saturated heterocycle, and —$N(R^{39})_2$, wherein substituents on phenyl and 3-8-membered saturated heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl;

$Q^4$ is selected from optionally substituted $C_{3-6}$ carbocycle, optionally substituted 3-8-membered heterocycle, and —$OR^{42}$, wherein substituents on $C_{3-6}$ carbocycle and 3-8-membered heterocycle are independently selected from hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, preferably $Q^4$ is —$OR^{42}$;

$R^{30}$, $R^{31}$, $R^{35}$, and $R^{36}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, and preferably each of $R^{30}$, $R^{31}$, $R^{35}$, and $R^{36}$ is hydrogen;

each $R^{32}$, $R^{33}$, $R^{37}$, and $R^{38}$ are independently selected from hydrogen, hydroxy, halogen, cyano, nitro, $C_1$-$C_6$ alkyl, haloalkyl, hydroxy $C_1$-$C_6$ alkyl, alkoxy, and alkoxy $C_1$-$C_6$ alkyl, wherein no more than two of $R^{35}$, $R^{36}$, $R^{37}$, and $R^{38}$ are hydroxy, such as preferably each of $R^{32}$, $R^{33}$, $R^{37}$, and $R^{38}$ are hydrogen;

each $R^{34}$ is selected from hydrogen, optionally substituted $C_1$-$C_6$ alkyl, optionally substituted carbocycle, and optionally substituted heterocycle, wherein the substituents on $C_1$-$C_6$ alkyl, carbocycle, and heterocycle are independently selected at each occurrence from hydroxy, halogen, cyano, nitro, $C_1$-$C_6$ alkoxy, carbocycle and heterocycle, preferably $R^{34}$ is hydrogen or $CH_3$;

each $R^{39}$ is selected from hydrogen, $C_1$-$C_6$ alkyl, haloalkyl, and alkoxy $C_1$-$C_6$ alkyl;

each $R^{40}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle; and each $R^{41}$ is selected from hydrogen and an optionally substituted $C_1$-$C_6$ alkyl group, wherein the substituents are independently selected at each occurrence from hydroxy, halogen, cyano, nitro, $C_2$-$C_6$ alkoxy group, carbocycle and heterocycle; and each $R^{42}$ is selected from hydrogen, optionally substituted $C_1$-$C_2$ alkyl, optionally substituted carbocycle, and optionally substituted heterocycle, wherein the substituents on $C_1$-$C_2$ alkyl, carbocycle, and heterocycle are independently selected at each occurrence from hydroxy, halogen, cyano, nitro, $C_1$-$C_2$ alkoxy, carbocycle and heterocycle.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

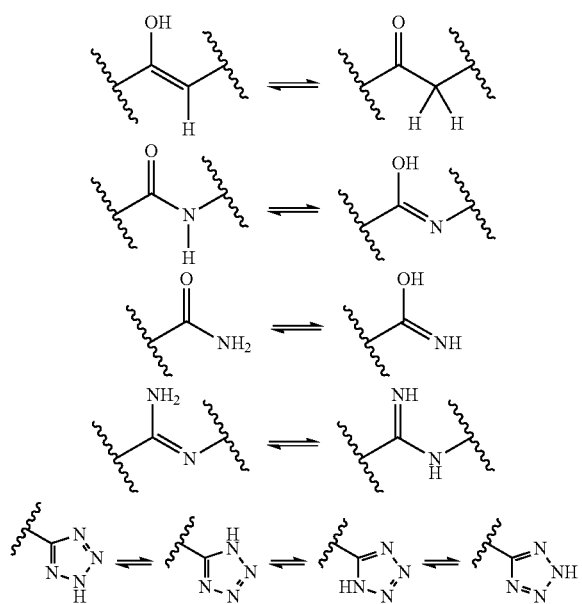

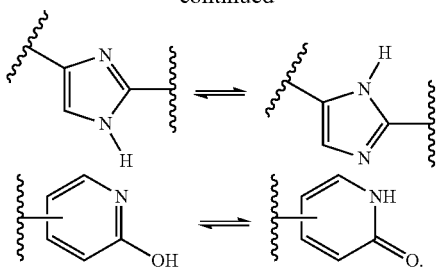

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$— or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.*, 269:G210-218 (1995); McLoed et al., *Gastroenterol,* 106:

405-413 (1994); Hochhaus et al., *Biomed. Chrom.*, 6:283-286 (1992); J. Larsen and H. Bundgaard, *Int. J Pharmaceutics*, 37, 87 (1987); J. Larsen et al., *Int. J Pharmaceutics*, 47, 103 (1988); Sinkula et al., *J Pharm. Sci.*, 64:181-210 (1975); T. Higuchi and V. Stella, *Pro-drugs as Novel Delivery Systems*, Vol. 14 of the *A.C.S. Symposium Series*; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Methods of Treatment

In some aspects, the present disclosure provides a method of treating a disease. A method comprising administering a compound or salt disclosed here or a pharmaceutical composition.

In some aspects, the present disclosure provides a method of treating a disease. A method comprising administering a compound with a pIC50 of 9.0 or greater for the mammalian target of rapamycin complex 1 and a pIC50 of 6.0 or less for the mammalian target of rapamycin complex 2 to a subject in need thereof.

In some embodiments, the method comprises, administering a compound with a pIC50 for the mammalian target of rapamycin complex 1 of at least about 6.0, at least about 6.5, at least about 7.0, at least about 7.5, at least about 8.0, at least about 8.5, at least about 9.0, at least about 9.5, at least about 10.0, at least about 10.5, or at least about 11.0.

In some embodiments, the method comprises, administering a compound with a pIC50 for the mammalian target of rapamycin complex 1 from about 5.0 to 12.0, 5.0 to 11.0, 5.0 to 10.0, 5.0 to 9.0, 5.0 to 8.0, 5.0 to 7.0, 6.0 to 12.0, 6.0 to 11.0, 6.0 to 10.0, 6.0 to 9.0, 6.0 to 8.0, 7.0 to 12.0, 7.0 to 11.0, 7.0 to 10.0, 7.0 to 9.0, 8.0 to 12.0, 8.0 to 11.0, 8.0 to 10.0, 9.0 to 12.0, 9.0 to 11.0, 9.0 to 10.5, or 9.0 to 10.0 and with a pIC50 for the mammalian target of rapamycin complex 2 from about 3.0 to 7.0, 3.0 to 6.0, 3.0 to 5.0, 3.0 to 4.0, 4.0 to 7.0, or 4.0 to 6.0. The ranges may be a combination thereof, for example, the method may comprise administering a compound with a pIC50 for the mammalian target of rapamycin complex 1 from about 5.0 to 12.0 and a pIC50 for the mammalian target of rapamycin complex 2 from about 3.0 to 7.0, the method may comprise administering a compound with a pIC50 for the mammalian target of rapamycin complex 1 from about 5.0 to 12.0 and a pIC50 for the mammalian target of rapamycin complex 2 from about 3.0 to 6.0, etc.

In some embodiments, the method comprises, administering a compound with a pIC50 for the mammalian target of rapamycin complex 1 from about 5.0 to 12.0, 5.0 to 11.0, 5.0 to 10.0, 5.0 to 9.0, 5.0 to 8.0, 5.0 to 7.0, 6.0 to 11.0, 6.0 to 10.0, 6.0 to 9.0, 7.0 to 12.0, 7.0 to 11.0, 7.0 to 10.0, 7.0 to 9.0, 7.0 to 8.0, 8.0 to 12.0, 8.0 to 11.0, or 8.0 to 10.0.

In some embodiments, the method comprises, administering a compound with a pIC50 for the mammalian target of rapamycin complex 2 of about 7.0 or less, about 6.5 or less, about 6.0 or less, about 5.5 or less, about 5.0 or less, about 4.5 or less, or about 4.0 or less.

In some embodiments, the method comprises, administering a compound with a pIC50 for the mammalian target of rapamycin complex 2 from about 3.0 to 7.0, 3.0 to 6.0, 3.0 to 5.0, 4.0 to 7.0, 4.0 to 6.0, 5.0 to 7.0, or 5.0 to 6.0.

In some embodiments, the method comprises, administering a compound with a pIC50 for the mammalian target of rapamycin complex 1 of at least about 6.0, at least about 6.5, at least about 7.0, at least about 7.5, at least about 8.0, at least about 8.5, at least about 9.0, at least about 9.5, at least about 10.0, at least about 10.5, or at least about 11.0 and administering a compound with a pIC50 for the mammalian target of rapamycin complex 2 of about 7.0 or less, about 6.5 or less, about 6.0 or less, about 5.5 or less, about 5.0 or less, about 4.5 or less, or about 4.0 or less. The ranges may be a combination thereof, for example, the method may comprise administering a compound with a pIC50 for the mammalian target of rapamycin complex 1 of at least about 6.0 and administering a compound with a pIC50 for the mammalian target of rapamycin complex 2 of about 7.0 or less, the method may comprise administering a compound with a pIC50 for the mammalian target of rapamycin complex 1 of at least about 6.0 and administering a compound with a pIC50 for the mammalian target of rapamycin complex 2 of about 6.5 or less, etc.

In some embodiments, the method comprises the compound or salt disclosed herein.

In some embodiments, the method comprises, chronically administering. Chronically administering comprises administering the compound or salt disclosed herein daily, every other day, every third day, once a week, or once a month.

In some embodiments, the method comprises chronically administering. Chronically administering the compound daily, every other day, every third day, once a week, or once a month.

In some embodiments, the method comprises chronically administering. Chronically administering the compound at least daily, every other day, every third day, once a week, or once a month.

In some embodiments, the method comprises chronically administering. Chronically administering the compound at most once a month, once a week, every third day, or every other day.

In some embodiments, the method comprises chronically administering. Chronically administering the compound at least one time a day, two times a day, three times a day, four times a day, five times a day, six times a day, seven times a day, eight times a day, nine times a day, ten times a day, or more.

In some embodiments, the method comprises chronically administering. Chronically administering the compound at most ten times a day, nine times a day, eight times a day, seven times a day, six times a day, five times a day, four times a day, three times a day, two times a day, or less.

In some embodiments, the method comprises chronically administering. Chronically administering the compound from about one to ten times a day, one to nine times a day, one to eight times a day, one to seven times a day, one to six times a day, one to five times a day, one to four times a day, one to three times a day, or one to two times a day.

In some embodiments, the method comprises chronically administering. Chronically administering the compound at least every other one day, second day, third day, fourth day, fifth day, sixth day, seventh day, or more.

In some embodiments, the method comprises chronically administering. Chronically administering the compound at most every other seventh day, sixth day, fifth day, fourth day, third day, second day, or less.

In some embodiments, the method comprises chronically administering. Chronically administering the compound from about every other one day to seventh day, one day to sixth day, one day to fifth day, one day to fourth day, one day to third day, or one day to second day.

In some embodiments, the method comprises chronically administering. Chronically administering the compound at least one time a week, two times a week, three times a week, four times a week, five times a week, six times a week, seven times a week, eight times a week, nine times a week, ten times a week, or more.

In some embodiments, the method comprises chronically administering. Chronically administering the compound at most ten times a week, nine times a week, eight times a week, seven times a week, six times a week, five times a week, four times a week, three times a week, two times a week, or less.

In some embodiments, the method comprises chronically administering. Chronically administering the compound from about one time a week to ten times a week, one time a week to nine times a week, one time a week to eight times a week, one time a week to seven times a week, one time a week to six times a week, one time a week to five times a week, one time a week to four times a week, one time a week to three times a week, or one time a week to two times a week.

In some embodiments, the method comprises chronically administering. Chronically administering the compound at least one time a month, two times a month, three times a month, four times a month, five times a month, six times a month, seven times a month, eight times a month, nine times a month, ten times a month, twenty times a month, thirty times a month, sixty times a month, ninety times a month, or more.

In some embodiments, the method comprises chronically administering. Chronically administering the compound at most ninety times a month, sixty times a month, thirty times a month, twenty times a month, ten times a month, nine times a month, eight times a month, seven times a month, six times a month, five times a month, four times a month, three times a month, two times a month, or less.

In some embodiments, the method comprises chronically administering. Chronically administering comprises administering the compound from about one time to ninety times a month, one time to sixty times a month, one time to thirty times a month, one time to twenty times a month, one time to ten times a month, one time to nine times a month, one time to eight times a month, one time to seven times a month, one time to six times a month, one time to five times a month, one time to four times a month, one time to three times a month, or one time to two times a month.

In some embodiments, the method comprises chronically administering. Chronically administering comprises administrating said compound over the course of 60 days or more.

In some embodiments, the method comprises chronically administering. Chronically administering comprises administrating said compound over the course of 90 days or more.

In some embodiments, the method comprises chronically administering. Chronically administering comprises administrating said compound over the course of 180 days or more.

In some embodiments, the method comprises chronically administering. Chronically administrating comprises administering the compound over the course of at least about 30 days, 60 days, 120 days, 180 days, 240 days, 300 days, 360 days, 720 days, 1440 days, 2880 days 5760 days, 11520 days or more.

In some embodiments, the method comprises chronically administering. Chronically administrating comprises administering the compound over the course from about 30 days to 11520 days, 30 days to 5760 days, 30 days to 2880 days, 30 day to 1440 days, 30 days to 720 days, 30 days to 360 days, 30 days to 300 days, 30 days to 240 days, 30 days to 180 days, 30 days to 60 days, 180 days to 11520 days, 180 days to 5760 days, 180 days to 2880 days, 180 day to 1440 days, 180 days to 720 days, 180 days to 360 days, 180 days to 300 days, 180 days to 240 days 360 days to 11520 days, 360 days to 5760 days, 360 days to 2880 days, 360 day to 1440 days, 360 days to 720 days, 1440 days to 11520 days, 1440 days to 5760 days, or 1440 days to 2880 days.

In some embodiments, the disease of the methods described herein is selected from a chronic disease.

In some embodiments, the chronic disease of the methods described herein is selected from a disease wherein mTORC1 is hyperactivated or a disease that would benefit from inhibition of the activity of mTORC1.

In some embodiments, the chronic disease of the methods described herein is selected from a disease wherein the chronic disease would benefit from mTORC1 inhibition. For example, a benefit would be an improvement of one symptoms associated with a chronic disease.

In some embodiments, the chronic disease of the methods described herein is selected from a disease wherein the chronic disease would benefit from selective mTORC1 inhibition over mTORC2 inhibition.

In some embodiments, the chronic disease of the methods described herein is selected from a neurodegenerative disease, a neurocutaneous disease, a neurodevelopmental disorder, mTORopathies, tauopathies, cognitive disorders, epilepsies, autism spectrum disorders, autoimmune diseases, metabolic diseases, cancer, diseases of impaired autophagy, infectious diseases, cardiovascular diseases, muscular atrophy, inflammatory diseases, eye disorders or diseases of aging that result in hyperactivation of mTORC1 including reduced immune activity in the elderly.

In some embodiments, the chronic disease of the methods described herein is an mTORopathy.

In some embodiments, the mTORopathy of the methods described herein is Tuberous Sclerosis.

In some embodiments, the mTORopathy of the methods described herein is Tuberous Sclerosis, Focal Cortical Dysplasia, or a PTEN (Phosphatase and tensin homolog) disease.

In some embodiments, a symptom of the chronic disease may be epileptiform activity.

In some embodiments, the chronic disease may be characterized by the accumulation of at least one aberrant protein. In some cases, the abberant protein may be selected from alpha-synuclein, Tau, amyloid beta, TDP-43 and BRCA1. In some cases, the abberant protein may be selected from but not limited to alpha-synuclein, Tau, amyloid beta, TDP-43 and/or BRCA1.

In some embodiments, the disease may be selected from the disease is selected from a neurodegenerartive or neurodevelopmental disease.

In another aspect, the method may further comprise administering a mTORC1 selective agent with a $\Delta pIC50$ of 5.0 or greater, wherein the $\Delta pIC50$ is the difference between the pIC50 for mTORC1 and the pIC50 for mTORC2.

In some embodiments, the method may comprise administering a compound with a ΔpIC50 of 4.5 or greater.

In some embodiments, the method may comprise administering a compound with a ΔpIC50 of at least about 2.0, at least about 2.5, at least about 3.0, at least about 3.5, at least about 4.0, at least about 4.5, at least about 5.0, at least about 5.5, or at least about 6.0.

In some embodiments, the method may further comprise administering a compound with a ΔpIC50 from about 2.0 to 7.0, 2.0 to 6.0, 2.0 to 5.0, 2.0 to 4.0, 3.0 to 7.0, 3.0 to 6.0, 3.0 to 5.0, 4.0 to 7.0, 4.0 to 6.0, or 5.0 to 7.0.

Pharmaceutical Formulations

The compositions and methods described herein can be considered useful as pharmaceutical compositions for administration to a subject in need thereof. Pharmaceutical compositions can comprise at least the compounds or salts described herein and one or more pharmaceutically acceptable carriers, diluents, excipients, stabilizers, dispersing agents, suspending agents, and/or thickening agents.

Pharmaceutical compositions can be formulated using one or more physiologically-acceptable carriers comprising excipients and auxiliaries. Formulation can be modified depending upon the route of administration chosen. Pharmaceutical compositions comprising a compound or salt as described herein can be manufactured, for example, by lyophilizing the compound or salt, mixing, dissolving, emulsifying, encapsulating or entrapping the compound or salts. The pharmaceutical compositions can also include the compounds or salts, described herein in a free-base form or pharmaceutically-acceptable salt form.

Pharmaceutical compositions described herein can comprise at least one active ingredient (e.g., a compound or salts). The active ingredients can be entrapped in microcapsules prepared, for example, by coacervation techniques or by interfacial polymerization (e.g., hydroxymethylcellulose or gelatin microcapsules and poly-(methylmethacylate) microcapsules, respectively), in colloidal drug-delivery systems (e.g., liposomes, albumin microspheres, microemulsions, nano-particles and nanocapsules) or in macroemulsions.

Pharmaceutical compositions as described herein often further can comprise more than one active compound (e.g., a compound or salt and other agents) as necessary for the particular indication being treated. The active compounds can have complementary activities that do not adversely affect each other. For example, the composition can also comprise a chemotherapeutic agent, cytotoxic agent, cytokine, growth-inhibitory agent, anti-hormonal agent, anti-angiogenic agent, and/or cardioprotectant. Such molecules can be present in combination in amounts that are effective for the purpose intended.

The compositions and formulations can be sterilized. Sterilization can be accomplished by filtration through sterile filtration.

The compositions described herein can be formulated for administration as an injection. Non-limiting examples of formulations for injection can include a sterile suspension, solution or emulsion in oily or aqueous vehicles. Suitable oily vehicles can include, but are not limited to, lipophilic solvents or vehicles such as fatty oils or synthetic fatty acid esters, or liposomes. Aqueous injection suspensions can contain substances which increase the viscosity of the suspension. The suspension can also contain suitable stabilizers. Injections can be formulated for bolus injection or continuous infusion. Alternatively, the compositions described herein can be lyophilized or in powder form for reconstitution with a suitable vehicle, e.g., sterile pyrogen-free water, before use.

For parenteral administration, the compounds or salts can be formulated in a unit dosage injectable form (e.g., use letter solution, suspension, emulsion) in association with a pharmaceutically acceptable parenteral vehicle. Such vehicles can be inherently non-toxic, and non-therapeutic. Vehicles can be water, saline, Ringer's solution, dextrose solution, and 5% human serum albumin. Non-aqueous vehicles such as fixed oils and ethyl oleate can also be used. Liposomes can be used as carriers. The vehicle can contain minor amounts of additives such as substances that enhance isotonicity and chemical stability (e.g., buffers and preservatives).

Sustained-release preparations can also be prepared. Examples of sustained-release preparations can include semipermeable matrices of solid hydrophobic polymers that can contain the compound or salt, and these matrices can be in the form of shaped articles (e.g., films or microcapsules). Examples of sustained-release matrices can include polyesters, hydrogels (e.g., poly(2-hydroxyethyl-methacrylate), or poly (vinyl alcohol)), polylactides, copolymers of L-glutamic acid and γ ethyl-L-glutamate, non-degradable ethylene-vinyl acetate, degradable lactic acid-glycolic acid copolymers such as the LUPRON DEPO™ (i.e., injectable microspheres composed of lactic acid-glycolic acid copolymer and leuprolide acetate), and poly-D-(−)-3-hydroxybutyric acid.

Pharmaceutical formulations described herein can be prepared for storage by mixing a compound or salt with a pharmaceutically acceptable carrier, excipient, and/or a stabilizer. This formulation can be a lyophilized formulation or an aqueous solution. Acceptable carriers, excipients, and/or stabilizers can be nontoxic to recipients at the dosages and concentrations used. Acceptable carriers, excipients, and/or stabilizers can include buffers such as phosphate, citrate, and other organic acids; antioxidants including ascorbic acid and methionine; preservatives, polypeptides; proteins, such as serum albumin or gelatin; hydrophilic polymers; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

In some embodiments the drug delivery composition may be incorporated into a system comprising a substrate that carries the composition to the administration site or delivery site or treatment site. The substrate may remain with the composition upon administration (or upon delivery of the composition) and for any amount of time or indefinitely thereafter, or be removed upon administration (or upon delivery of the composition) leaving the composition at the administration site or delivery site or treatment site.

The rapamycin analog(s) can be administered in the "native" form or, if desired, in the form of salts, esters, amides, prodrugs, clathrates, derivatives, and the like, provided the salt, ester, amide, prodrug, clathrate, or derivative is pharmacologically suitable, e.g., effective in treatment of a pathology and/or various symptoms thereof, e.g., as described herein. Salts, esters, amides, clathrates, prodrugs and other derivatives of the rapamycin analogs can be prepared using standard procedures known to those skilled in the art of synthetic organic chemistry and described, for example, by March (1992) *Advanced Organic Chemistry;*

*Reactions, Mechanisms and Structure,* 4th Ed. N.Y. Wiley-Interscience, and as described above.

For example, a pharmaceutically acceptable salt can be prepared for any of the rapamycin analogs described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically rapamycin analogs as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the rapamycin analogs herein include halide salts, such as may be prepared using hydrochloric or hydrobromic acids. Conversely, preparation of basic salts of the rapamycin analogs of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzenesulfonate, benzoate, benzylate, bicarbonate, bitartrate, bitartrate, bromide, calcium edetate, camsylateh, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionatei, lactate, lactobionate, malate, maleate, mandelate, mesylate, methylbromide, methylnitrate, methylsulfate, mucate, napsylate, nitrate, pamoate (embonate), pantothenate, phosphate and diphosphate, polygalacturonate, salicylate and disalicylate, stearate, subacetate, succinate, sulfate, tannate, tartrate, teoclate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like. Suitable cationic salt forms include, but are not limited to Benzathine, chloroprocaine, choline, diethanolamine, ethylenediamine, meglumine, procaine, aluminum, calcium, lithium, magnesium, potassium, sodium, zinc, and the like.

Preparation of esters typically involves functionalization of hydroxyl and/or carboxyl groups that are present within the molecular structure of the rapamycin analog. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the rapamycin analogs described herein (e.g. compound represented by the structure of Formula I and the like) are useful for parenteral administration, topical administration, oral administration, nasal administration (or otherwise inhaled), rectal administration, or local administration, such as by aerosol or transdermally, for prophylactic and/or therapeutic treatment of one or more of the pathologies/indications described herein (e.g., pathologies characterized by excess amyloid plaque formation and/or deposition or undesired amyloid or pre-amyloid processing).

The rapamycin analogs described herein can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., atablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g. compound represented by the structure of Formula I and the like)) and the resulting composition is compressed. Where necessary the compressed product is coated, e.g., using known methods for masking the taste or for enteric dissolution or sustained release. Suitable coating materials include, but are not limited to ethyl-cellulose, hydroxymethylcellulose, POLYOX® yethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s). In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

Pharmaceutical compositions comprising the rapamycin analogs described herein (e.g. compound represented by the structure of Formula I and the like) can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the active agent(s) into preparations that can be used pharmaceutically. Proper formulation is dependent upon the route of administration chosen.

In certain embodiments, the active agents described herein are formulated for oral administration. For oral administration, suitable formulations can be readily formulated by combining the active agent(s) with pharmaceutically acceptable carriers suitable for oral delivery well known in the art. Such carriers enable the active agent(s) described herein to be formulated as tablets, pills, dragees, caplets, lizenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

For administration by inhalation, the active agent(s) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the compound and a suitable powder base such as lactose or starch.

In various embodiments the active agent(s) can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) *Suppositories*, Pharmaceutical Press) and typically involve combining the active agents with a suitable base (e.g., hydrophilic (PEG), lipophilic materials such as cocoa butter or Witepsol W45), amphiphilic materials such as Suppocire AP and polyglycolized glyceride, and the like). The base is selected and compounded for a desired melting/delivery profile.

For topical administration the rapamycin analogs described herein (e.g. compound represented by the structure of Formula I and the like) can be formulated as solutions, gels, ointments, creams, suspensions, and the like as are well-known in the art.

In certain embodiments the rapamycin analogs described herein are formulated for systemic administration (e.g., as an injectable) in accordance with standard methods well known to those of skill in the art. Systemic formulations include, but are not limited to, those designed for administration by injection, e.g. subcutaneous, intravenous, intramuscular, intrathecal or intraperitoneal injection, as well as those designed for transdermal, transmucosal oral or pulmonary administration. For injection, the active agents described herein can be formulated in aqueous solutions, preferably in physiologically compatible buffers such as Hanks solution, Ringer's solution, or physiological saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. Such penetrants are generally known in the art. Injectable formulations and inhalable formulations are generally provided as a sterile or substantially sterile formulation.

In addition to the formulations described previously, the active agent(s) may also be formulated as a depot preparations. Such long acting formulations can be administered by implantation (for example subcutaneously or intramuscularly) or by intramuscular injection. Thus, for example, the active agent(s) may be formulated with suitable polymeric or hydrophobic materials (for example as an emulsion in an acceptable oil) or ion exchange resins, or as sparingly soluble derivatives, for example, as a sparingly soluble salt.

In certain embodiments the active agent(s) described herein can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Alternatively, other pharmaceutical delivery systems can be employed. For example, liposomes, emulsions, and microemulsions/nanoemulsions are well known examples of delivery vehicles that may be used to protect and deliver pharmaceutically active compounds. Certain organic solvents such as dimethylsulfoxide also can be employed, although usually at the cost of greater toxicity.

In certain embodiments the rapamycin analogs described herein (e.g. compound represented by the structure of Formula I and the like) are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and mini-emulsion are used as synonyms.

Illustrative oil in water (O/W) nanoemulsions include, but are not limited to: Surfactant micelles—micelles composed of small molecules surfactants or detergents (e.g., SDS/PBS/2-propanol); Polymer micelles—micelles composed of polymer, copolymer, or block copolymer surfactants (e.g., Pluronic L64/PBS/2-propanol); Blended micelles—micelles in which there is more than one surfactant component or in which one of the liquid phases (generally an alcohol or fatty acid compound) participates in the formation of the micelle (e.g., octanoic acid/PBS/EtOH); Integral micelles—blended micelles in which the active agent(s) serve as an auxiliary surfactant, forming an integral part of the micelle; and Pickering (solid phase) emulsions—emulsions in which the active agent(s) are associated with the exterior of a solid nanoparticle (e.g., polystyrene nanoparticles/PBS/no oil phase).

Illustrative water in oil (W/O) nanoemulsions include, but are not limited to: Surfactant micelles—micelles composed of small molecules surfactants or detergents (e.g., dioctyl sulfosuccinate/PBS/2-propanol, isopropylmyristate/PBS/2-propanol, etc.); Polymer micelles—micelles composed of polymer, copolymer, or block copolymer surfactants (e.g., PLURONIC® L121/PBS/2-propanol); Blended micelles — micelles in which there is more than one surfactant component or in which one of the liquid phases (generally an alcohol or fatty acid compound) participates in the formation of the micelle (e.g., capric/caprylic diglyceride/PBS/EtOH); Integral micelles—blended micelles in which the active agent(s) serve as an auxiliary surfactant, forming an integral part of the micelle (e.g., active agent/PBS/polypropylene glycol); and Pickering (solid phase) emulsions—emulsions in which the active agent(s) are associated with the exterior of a solid nanoparticle (e.g., chitosan nanoparticles/no aqueous phase/mineral oil).

As indicated above, in certain embodiments the nanoemulsions comprise one or more surfactants or detergents. In some embodiments the surfactant is a non-anionic detergent (e.g., a polysorbate surfactant, a polyoxyethylene ether, etc.). Surfactants that find use in the present invention include, but are not limited to surfactants such as the TWEEN®, TRITON®, and TYLOXAPOL® families of compounds.

In certain embodiments the emulsions further comprise one or more cationic halogen containing compounds, including but not limited to, cetylpyridinium chloride. In still further embodiments, the compositions further comprise one or more compounds that increase the interaction ("interaction enhancers") of the composition with microorganisms (e.g., chelating agents like ethylenediaminetetraacetic acid, or ethylenebis(oxyethylenenitrilo)tetraacetic acid in a buffer).

In some embodiments, the nanoemulsion further comprises an emulsifying agent to aid in the formation of the emulsion. Emulsifying agents include compounds that aggregate at the oil/water interface to form a kind of continuous membrane that prevents direct contact between two adjacent droplets. Certain embodiments of the present invention feature oil-in-water emulsion compositions that may readily be diluted with water to a desired concentration without impairing their anti-pathogenic properties.

In addition to discrete oil droplets dispersed in an aqueous phase, certain oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces that drive apolar residues (e.g., long hydrocarbon chains) away from water. The above lipid preparations can generally be described as surfactant lipid preparations (SLPs). SLPs are minimally toxic to mucous membranes and are believed to be metabolized within the small intestine (see e.g., Hamouda et al., (1998) *J Infect. Disease* 180: 1939).

In certain embodiments the emulsion comprises a discontinuous oil phase distributed in an aqueous phase, a first component comprising an alcohol and/or glycerol, and a second component comprising a surfactant or a halogen-containing compound. The aqueous phase can comprise any type of aqueous phase including, but not limited to, water (e.g., dionized water, distilled water, tap water) and solutions (e.g., phosphate buffered saline solution, or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In certain embodiments, the oil phase comprises 30-90 vol % of the oil-in-water emulsion (i.e., constitutes 30-90% of the total volume of the final emulsion), more preferably 50-80%. The formulations need not be limited to particular surfactants, however in certain embodiments, the surfactant is a polysorbate surfactant (e.g., TWEEN 20®, TWEEN 40®, TWEEN 60®, and TWEEN 80®), a pheoxypolyethoxyethanol (e.g., TRITON® X-100, X-301, X-165, X-102, and X-200, and TYLOXAPOL®), or sodium dodecyl sulfate, and the like.

In certain embodiments a halogen-containing component is present. the nature of the halogen-containing compound, in some preferred embodiments the halogen-containing compound comprises a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, tetradecyltrimethylammonium bromide, and the like.

In certain embodiments the emulsion comprises a quaternary ammonium compound. Quaternary ammonium compounds include, but are not limited to, N-alkyldimethyl benzyl ammonium saccharinate, 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quaternium 14; N,N-dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, and 5,152,923 and in Fanun et al. (2009) *Microemulsions: Properties and Applications (Surfactant Science)*, CRC Press, Boca Ratan Fl.

In certain embodiments, one or more active agents described herein can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the rapamycin analogs described herein (e.g. compound represented by the structure of Formula I and the like) are formulated as inclusion complexes.

While not limited to cyclodextrin inclusion complexes, it is noted that cyclodextrin is the agent most frequently used to form pharmaceutical inclusion complexes. Cyclodextrins (CD) are cyclic oligomers of glucose, that typically contain 6, 7, or 8 glucose monomers joined by α-1,4 linkages. These oligomers are commonly called α-CD, β-CD, and γ-CD, respectively. Higher oligomers containing up to 12 glucose monomers are known, and contemplated to in the formulations described herein. Functionalized cyclodextrin inclusion complexes are also contemplated. Illustrative, but non-limiting functionalized cyclodextrins include, but are not limited to sulfonates, sulfonates and sulfinates, or disulfonates of hydroxybutenyl cyclodextrin; sulfonates, sulfonates and sulfinates, or disulfonates of mixed ethers of cyclodextrins where at least one of the ether substituents is hydroxybutenyl cyclodextrin. Illustrative cyclodextrins include a polysaccharide ether which comprises at least one 2-hydroxybutenyl substituent, wherein the at least one hydroxybutenyl substituent is sulfonated and sulfinated, or disulfonated, and an alkylpolyglycoside ether which comprises at least one 2-hydroxybutenyl substituent, wherein the at least one hydroxybutenyl substituent is sulfonated and sulfinated, or disulfonated. In various embodiments inclusion complexes formed between sulfonated hydroxybutenyl cyclodextrins and one or more of the active agent(s) described herein are contemplated. Methods of preparing cyclodextrins, and cyclodextrin inclusion complexes are found for example in U.S. Patent Publication No: 2004/0054164 and the references cited therein and in U.S. Patent Publication No: 2011/0218173 and the references cited therein.

In certain embodiments the rapamycin analogs described herein can also be administered using medical devices known in the art. For example, in one embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or U.S. Pat. No. 4,596,556. Examples of well-known implants and modules useful for such deliver include, but are not limited to U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. In a specific embodiment a rapamycin analogue may be administered using a drug-eluting stent, for example one corresponding to those described in WO 01/87263 and related publications or those described by Perin (Perin, E C, 2005). Many other such implants, delivery systems, and modules are known to those skilled in the art.

The dosage to be administered of a rapamycin analog described herein will vary according to the particular compound, the disease involved, the subject, and the nature and severity of the disease and the physical condition of the subject, and the selected route of administration. The appropriate dosage can be readily determined by a person skilled in the art. For example, without limitation, a dose of up to 15 mg daily e.g. 0.1 to 15 mg daily (or a higher dose given less frequently) may be contemplated.

In certain embodiments the compositions may contain from 0.1%, e.g. from 0.1-70%, or from 5-60%, or preferably from 10-30%, of one or more rapamycin analogs, depending on the method of administration.

It will be recognized by one of skill in the art that the optimal quantity and spacing of individual dosages of a rapamycin analog described herein will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Therapeutic Applications

The compositions and methods of the present disclosure can be useful for a plurality of different subjects including, but are not limited to, a mammal, human, non-human mammal, a domesticated animal (e.g., laboratory animals, household pets, or livestock), non-domesticated animal (e.g., wildlife), dog, cat, rodent, mouse, hamster, cow, bird, chicken, fish, pig, horse, goat, sheep, rabbit, and any combination thereof.

The compositions and methods described herein can be useful as a therapeutic, for example, a treatment that can be administered to a subject in need thereof. A therapeutic effect of the present disclosure can be obtained in a subject by reduction, suppression, remission, or eradication of a disease state, including, but not limited to, a symptom thereof. A therapeutic effect in a subject having a disease or condition, or pre-disposed to have or is beginning to have the disease or condition, can be obtained by a reduction, a suppression, a prevention, a remission, or an eradication of the condition or disease, or pre-condition or pre-disease state.

In practicing the methods described herein, therapeutically-effective amounts of the compositions described herein can be administered to a subject in need thereof, often for treating and/or preventing a condition or progression thereof. A pharmaceutical composition can affect the physiology of the subject, such as the immune system, an inflammatory response, or other physiologic affect. A therapeutically-effective amount can vary depending on the severity of the disease, the age and relative health of the subject, the potency of the compounds used, and other factors.

Treat and/or treating can refer to any indicia of success in the treatment or amelioration of the disease or condition. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treat can be used herein to refer to a method that results in some level of treatment or amelioration of the disease or condition, and can contemplate a range of results directed to that end, including but not restricted to prevention of the condition entirely.

Prevent, preventing and the like can refer to the prevention of the disease or condition, e.g., tumor formation, in the patient. For example, if an individual at risk of developing a tumor or other form of cancer is treated with the methods of the present disclosure and does not later develop the tumor or other form of cancer, then the disease has been prevented, at least over a period of time, in that individual. Preventing can also refer to preventing re-occurrence of a disease or condition in a patient that has previously been treated for the disease or condition, e.g., by preventing relapse.

A therapeutically effective amount can be the amount of a composition or an active component thereof sufficient to provide a beneficial effect or to otherwise reduce a detrimental non-beneficial event to the individual to whom the composition is administered. A therapeutically effective dose can be a dose that produces one or more desired or desirable (e.g., beneficial) effects for which it is administered, such administration occurring one or more times over a given period of time. An exact dose can depend on the purpose of the treatment, and can be ascertainable by one skilled in the art using known techniques.

Pharmaceutical compositions can be used in the methods described herein and can be administered to a subject in need thereof using a technique known to one of ordinary skill in the art which can be suitable as a therapy for the disease or condition affecting the subject. One of ordinary skill in the art would understand that the amount, duration and frequency of administration of a pharmaceutical composition described herein to a subject in need thereof depends on several factors including, for example but not limited to, the health of the subject, the specific disease or condition of the patient, the grade or level of a specific disease or condition of the patient, the additional therapeutics the subject is being or has been administered, and the like.

The methods and compositions described herein can be for administration to a subject in need thereof. Often, administration of the compositions described herein can include routes of administration, non-limiting examples of administration routes include intravenous, intraarterial, subcutaneous, subdural, intramuscular, intracranial, intrasternal, intratumoral, or intraperitoneally. Additionally, a pharmaceutical composition can be administered to a subject by additional routes of administration, for example, by inhalation, oral, dermal, intranasal, or intrathecal administration.

Compositions of the present disclosure can be administered to a subject in need thereof in a first administration, and in one or more additional administrations. The one or more additional administrations can be administered to the subject in need thereof minutes, hours, days, weeks or months following the first administration. Any one of the additional administrations can be administered to the subject in need thereof less than 21 days, or less than 14 days, less than 10 days, less than 7 days, less than 4 days or less than 1 day after the first administration. The one or more administrations can occur more than once per day, more than once per week or more than once per month. The administrations can be weekly, biweekly (every two weeks), every three weeks, monthly or bimonthly.

A compound according to any therapeutic compound disclosed herein for use in one or more of the following: the treatment and/or prevention of a tauopathy (including but not limited to Alzheimer's disease, Parkinson's disease, progressive supranuclear palsy (PSP), corticobasal degeneration, corticobasal syndrome, frontotemporal dementia, frontotemporal lobar degeneration (FTLD) including but not limited to FTLD-17, behavior variant FTD, primary progressive aphasia (semantic, agrammatic or logopenic variants), argyrophilic grain disease, Pick's disease, globular glial tauopathies, primary age-related tauopathy (including neurofibrillary tangle dementia), chronic traumatic encephalopathy (CTE)-traumatic brain injury and aging-related tau astrogliopathy), an mTORopathy (including but not limited to tuberous sclerosis complex (TSC)), an mTORopathy associated with epileptic seizures, focal cortical dysplasia (FCD), ganglioglioma, hemimegalencephaly, neurofibromatosis 1, Sturge-Weber syndrome, Cowden syndrome, PMSE (Polyhydramnios, Megalencephaly, Symptomatic Epilepsy)), familial multiple discoid fibromas (FMDF), an epilepsy/epileptic seizures (both genetic and acquired forms of the disease such as familial focal epilepsies, epileptic spasms, infantile spasms (IS), status epilepticus (SE), temporal lobe epilepsy (PLE) and absence epilepsy), rare diseases associated with a dysfunction of mTORC1 activity (e.g., lymphangioleiomyomatosis (LAM), Leigh's syndrome, Friedrich's ataxia, Diamond-Blackfan anemia, etc.), metabolic diseases (e.g., obesity, Type II diabetes, etc.), autoimmune and inflammatory diseases (e.g., Systemic Lupus Erythematosus (SLE), multiple sclerosis (MS) psoriasis, etc.), cancer, a fungal infection, a proliferative disease, the maintenance of immunosuppression, transplant rejection, traumatic brain injury, autism, lysosomal storage diseases and neurodegenerative diseases associated with an mTORC1 hyperactivity (e.g., Parkinson's, Huntington's disease, etc.), aberrant compound accumulation, dysfuntion of the autophagy mechanisms, and generally including but not limited to disorders that can be modulated by selective inhibition of the mTORC1 pathway.

A compound according to any therapeutic compound disclosed herein for use in the treatment and/or prevention of a tauopathy selected from the group consisting of: progressive supranuclear palsy, dementia pugilistica (chronic traumatic encephalopathy), frontotemporal dementia, lytico-bodig disease (parkinson-dementia complex of guam), tangle-predominant dementia (with nfts similar to ad, but without plaques), ganglioglioma and gangliocytoma, meningioangiomatosis, subacute sclerosing panencephalitis, lead encephalopathy, tuberous sclerosis, Pick's disease, corticobasal degeneration(tau proteins are deposited in the form of inclusion bodies within swollen or "ballooned" neurons), Alzheimer's disease, Parkinson's disease, Huntington's disease, frontotemporal dementia, and frontotemporal lobar degeneration.

A compound according to any therapeutic compound disclosed herein for use in the treatment and/or prevention of a tauopathy selected from the group consisting of: Alzheimer's disease, Parkinson's disease, progressive supranuclear palsy (PSP), corticobasal degeneration, corticobasal syndrome, frontotemporal dementia, frontotemporal lobar degeneration (FTLD) including but not limited to FTLD-17, behavior variant FTD, primary progressive aphasia (semantic, agrammatic or logopenic variants), argyrophilic grain disease, Pick's disease, globular glial tauopathies, primary age-related tauopathy (including neurofibrillary tangle dementia), chronic traumatic encephalopathy (CTE)-traumatic brain injury and aging-related tau astrogliopathy.

A compound according any therapeutic compound disclosed herein for use in the treatment and/or prevention of a mTORopathy. The mTORopathy may be, for example, Tuberous Sclerosis, Focal Cortical Dysplasia, or a PTEN (Phosphatase and tensin homolog) disease, etc. The mTORopathy may be a disease or disorder described elsewhere herein.

Non-limiting examples of cancers can include Acute lymphoblastic leukemia (ALL); Acute myeloid leukemia; Adrenocortical carcinoma; Astrocytoma, childhood cerebellar or cerebral; Basal-cell carcinoma; Bladder cancer; Bone tumor, osteosarcoma/malignant fibrous histiocytoma; Brain cancer; Brain tumors, such as, cerebellar astrocytoma, malignant glioma, ependymoma, medulloblastoma, visual pathway and hypothalamic glioma; Brainstem glioma; Breast cancer; Bronchial adenomas/carcinoids; Burkitt's lymphoma; Cerebellar astrocytoma; Cervical cancer; Cholangiocarcinoma; Chondrosarcoma; Chronic lymphocytic leukemia; Chronic myelogenous leukemia; Chronic myeloproliferative disorders; Colon cancer; Cutaneous T-cell lymphoma; Endometrial cancer; Ependymoma; Esophageal cancer; Eye cancers, such as, intraocular melanoma and retinoblastoma; Gallbladder cancer; Glioma; Hairy cell leukemia; Head and neck cancer; Heart cancer; Hepatocellular (liver) cancer; Hodgkin lymphoma; Hypopharyngeal cancer; Islet cell carcinoma (endocrine pancreas); Kaposi sarcoma; Kidney cancer (renal cell cancer); Laryngeal cancer; Leukemia, such as, acute lymphoblastic, acute myeloid, chronic lymphocytic, chronic myelogenous and, hairy cell; Lip and oral cavity cancer; Liposarcoma; Lung cancer, such as, non-small cell and small cell; Lymphoma, such as, AIDS-related, Burkitt; Lymphoma, cutaneous T-Cell, Hodgkin and Non-Hodgkin, Macroglobulinemia, Malignant fibrous histiocytoma of bone/osteosarcoma; Melanoma; Merkel cell cancer; Mesothelioma; Multiple myeloma/plasma cell neoplasm; Mycosis fungoides; Myelodysplastic syndromes; Myelodysplastic/myeloproliferative diseases; Myeloproliferative disorders, chronic; Nasal cavity and paranasal sinus cancer; Nasopharyngeal carcinoma; Neuroblastoma; Oligodendroglioma; Oropharyngeal cancer; Osteosarcoma/malignant fibrous histiocytoma of bone; Ovarian cancer; Pancreatic cancer; Parathyroid cancer; Pharyngeal cancer; Pheochromocytoma; Pituitary adenoma; Plasma cell neoplasia; Pleuropulmonary blastoma; Prostate cancer; Rectal cancer; Renal cell carcinoma (kidney cancer); Renal pelvis and ureter, transitional cell cancer; Rhabdomyosarcoma; Salivary gland cancer; Sarcoma, Ewing family of tumors; Sarcoma, Kaposi; Sarcoma, soft tissue; Sarcoma, uterine; Sezary syndrome; Skin cancer (non-melanoma); Skin carcinoma; Small intestine cancer; Soft tissue sarcoma; Squamous cell carcinoma; Squamous neck cancer with occult primary, metastatic; Stomach cancer; Testicular cancer; Throat cancer; Thymoma and thymic carcinoma; Thymoma; Thyroid cancer; Thyroid cancer, childhood; Uterine cancer; Vaginal cancer; Waldenstrom macroglobulinemia; Wilms tumor and any combination thereof.

A compound according any therapeutic compound disclosed herein for use in the treatment and/or prevention of an age-related disease or disorder. The age-related disease or disorder may include but not limited to: immune senescence, Parkinson's disease, Alzheimer's disease, tauopathies, mTORopathies, brain atrophy, cognitive decline, stroke, traumatic brain injury, cancer, immune-senescence leading to cancer sarcopenia, infections due to an decline in immune-function, metabolic dysfunction, obesity and type II diabetes including complications arising from diabetes, such as kidney failure, blindness and neuropathy, skin atrophy, cherry angiomas, seborrheic keratoses, atherosclerosis, arteriosclerosis, pulmonary emphysema, osteoporosis, arthritis, osteoarthritis, high blood pressure, cataracts, macular degeneration, glaucoma, chronic kidney disease, diabetes-associated kidney disease, impaired hepatic function, liver fibrosis, autoimmune hepatitis, endometrial hyperplasia, renovascular disease, hearing loss, mobility disability (such as frailty), tendon stiffness, heart dysfunction such as cardiac hypertrophy and/or systolic and/or diastolic dysfunction and/or hypertension, heart dysfunction which results in a decline in ejection fraction, ischemia, mitochondrial myopathy and conditions that increase the likelihood of age-related disorders such as increase in senescence inducing cytokines.

A compound according any therapeutic compound disclosed herein for use in the treatment and/or prevention of seizures and/or seizure related disorders. The seizure related disorders may include but not limited to: West syndrome, Focal Cortical Dysplasia (FCD), tuberous sclerosis complex (TSC), childhood absence epilepsy, benign focal epilepsies of childhood, juvenile myoclonic epilepsy (JME), temporal lobe epilepsy, frontal lobe epilepsy, refractory epilepsy, Lennox-Gastaut syndrome, occipital lobe epilepsy, 5 Proteus syndrome, hemi-megalencephaly syndrome (HMEG), megalencephaly syndrome (MEG), megalencephaly-capillary malformation (MCAP), megalencephalypolymicrogyria-polydactyly-hydrocephalus syndrome (MPPH) and PTEN disorders.

A compound according any therapeutic compound disclosed herein for use in the treatment and/or prevention of disorders that include the processes of fibrosis and/or inflammation (e.g., liver and kidney disorders). The disorders may include but not limited to liver fibrosis (which may occur in end-stage liver disease); liver cirrhosis; liver failure due to toxicity; non-alcohol-associated hepatic steatosis or NASH; and alcohol-associated steatosis. Another example may be kidney fibrosis, which may occur as a result of acute kidney injury or diabetic nephropathy can induce kidney fibrosis and inflammation.

A compound according any therapeutic compound disclosed herein for use in the treatment and/or prevention of acute or chronic organ or tissue transplant rejection, for example, heart, lung, combined heart-lung, liver, kidney, pancreatic, skin or corneal transplants, prevention of graft-versus-host disease, such as following bone marrow transplantation, etc.

A compound according any therapeutic compound disclosed herein for use in the treatment and/or prevention of autoimmune diseases and/or and inflammatory conditions include in particular inflammatory conditions with an etiology that may include an autoimmune component such as arthritis (for example rheumatoid arthritis, arthritis chronica progrediente and arthritis deformans) and rheumatic diseases. Examples may include autoimmune hematological disorders (including e. g. hemolytic anemia, aplastic anemia, pure red cell anaemia and idiopathic thrombocytopenia), systemic lupus erythematosus, polychondritis, scleroderma, Wegener granulamatosis, dermatomyositis, chronic active hepatitis, myasthenia gravis, psoriasis, Steven-Johnson syndrome, idiopathic sprue, autoimmune inflammatory bowel disease (including e. g. ulcerative colitis and Crohn's disease) endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

A compound according any therapeutic compound disclosed herein for use in the treatment and/or prevention of mitochondrial diseases or disorders.

A compound according any therapeutic compound disclosed herein for use in the treatment and/or prevention of smooth muscle cell proliferation migration leading to vessel intimal thickening, blood vessel obstruction, obstructive coronary atherosclerosis, or restenosis.

The invention provides any therapeutic compound disclosed herein for use in a method of treatment of the human or animal body by therapy. Therapy may be by any mechanism disclosed herein, such as by stimulation of the immune system. The invention provides any therapeutic compound disclosed herein for use in stimulation of the immune system, vaccination or immunotherapy, including for example enhancing an immune response. The invention further provides any therapeutic compound disclosed herein for prevention or treatment of any condition disclosed herein, for example cancer, autoimmune disease, inflammation, sepsis, allergy, asthma, graft rejection, graft-versus-host disease, immunodeficiency or infectious disease (typically caused by an infectious pathogen). The invention also provides any therapeutic compound disclosed herein for obtaining any clinical outcome disclosed herein for any condition disclosed herein, such as reducing tumour cells in vivo. The invention also provides use of any therapeutic compound disclosed herein in the manufacture of a medicament for preventing or treating any condition disclosed herein.

In certain embodiments, the disclosure provides a method of treating disease characterized by hyperactivation of mTORC1. The following references include methods for evaluating mTORC (e.g., mTORC1) activity: T. O'Reilly et al., *Translational Oncology*, v3, i2, p 65-79, (2010); J. Peralba, *Clinical Cancer Research*, v9, i8, p 2887-2892 (2003); D. R. Moore et al., *Acta Physiologica*, v201, i3, p 365-372 (2010); M. Dieterlen., Clinical Cytometry, v82B, i3, p 151-157, (2012); the contents of each of which are incorpoarated by reference herein.

In certain embodiments, the disclosure provides a method of treating age-related diseases. It may be established that modulation of mTORC1 signaling may prolong lifespan and may delay the onset of age-related diseases across a wide array of organisms, ranging from flies to mammals, thus possibly providing therapeutic options for preventing or treating age-related diseases in humans. In a recent clinical study Mannick et al. (mTOR inhibition improves immune function in the elderly, Sci Transl Med. 2014 Dec. 24; 6(268):268ra179. doi: 10.1126/scitranslmed.3009892) may have showed that mTOR inhibition improves the immune function in the elderly.

In certain embodiments, the disclosure provides a method of treating mitochondrial diseases. Mitochondrial myopathy and mitochondrial stress may be mitochondrial disorders as described in Chinnery, P. F. (2015); EMBO Mol. Med. 7, 1503-1512; Koopman, W. J. et al., 10 (2016); EMBO Mol. Med. 8, 311-327 and Young, M. J., and Yound and Copeland, W. C. (2016); Curr. Opin. Genet. Dev. 38, 52-62.

In certain embodiments, the disclosure provides a method of treating diseases of impaired autophagy. In some cases they may include impaired autophagies that result in mitochondrial damage, lysosomal storage diseases, cancer, Crohn's disease, etc. In some cases the impaired autophagies may be as described in Jiang P. & Mizushima, N., Autophagy and human diseases, *Cell Research volume* 24, p. 69-79 (2014).

Kits

In some aspects, the present disclosure provides a kit comprising a compound or salt disclosed herein and instructions.

In some aspects, the present disclosure provides a kit comprising a pharmaceutical composition comprising the compound or salt disclosed herein and instructions.

In certain aspects, the present disclosure provides a kit comprising a compound, salt or pharmaceutical composition disclosed herein and instructions for administering the compound, salt or pharmaceutical composition disclosed form to a subject in need thereof. In some embodiments, the kit comprises a compound, salt or pharmaceutical composition disclosed herein, packaged in a low moisture vapor transmission container with a desiccant. Optionally, a label is on or associated with the container. For example, a label is on a container when letters, numbers or other characters forming the label are attached, molded or etched on the container itself, and a label is associated with a container when it is present within a receptacle or carrier, such as a box, that also holds the container, e.g., as a package insert. In addition, a label may be used to indicate that the contents are to be used for a specific therapeutic application. In some embodiments, the label includes directions for use of the contents, such as in the methods described herein. In some embodiments, a compound, salt or pharmaceutical composition disclosed herein is presented in a pack or container that contains one or more unit dosage forms comprising the compound, salt or pharmaceutical composition disclosed herein. The pack may contain metal or plastic foil, such as a blister pack. The pack or container may be accompanied by instructions for administration of the unit dosage form. In some embodiments, the pack or container is accompanied with a notice in a form prescribed by a governmental agency regulating the manufacture, use or sale of pharmaceuticals, which notice is reflective of approval by the agency of the form of the drug for human or veterinary administration. Such notice, for example, may be the labeling approved by the U.S. Food and Drug Administration for prescription of drugs, or the approved product insert. In some embodiments, compositions comprising the compound, salt or pharmaceutical composition disclosed herein are prepared, placed in an appropriate container, and labeled for treatment of an indicated condition.

Production of Rapamycin Analogs.

In various embodiments the rapamycin analogs described herein are produced by the use of a recombinant host strain of *Streptomyces* (e.g., *S. hygroscopicus*) containing genomic deletions of one or more of genes selected from the group consisting of rapQ, rapO, rapN, rapM, rapL, rapK, rapJ, rapI introduced into *S. hygroscopicus* and complementation or partial complementation by expressing single genes or combinations of genes, including but not limited to rapK, rapI, rapQ, rapM, the contiguous genes rapN and O (herein designated as rapN/O), rapL and rapJ, in gene cassettes. The method typically further involves culturing the recombinant host strain, and optionally isolating the rapamycin analogues produced. Thus, for example, as illustrated in PCT Publication No: W) 2004/007709 (PCT/GB2003/003230) the recombinant strain MG2-10[pSGsetrapK], produced by complementation of the genomic deletion strain *S. hygroscopicus* MG2-10, with rapK, was cultured to produce 9-deoxo-16-0-desmethyl-27-desmethoxy-39-0-desmethyl-rapamycin (prerapamycin).

As noted above, the strategy typically involves the integration of a vector comprising a sub-set of genes including, but not limited to, rapK, rapI, rapQ, rapM, rapN, rapO, rapL and rapJ into the *S. hygroscopicus* deletion mutant above. Such integration may be performed using a variety of available integration functions including but not limited to: ΦC31-based vectors, vectors based on pSAM2 integrase (e.g. in pPM927 (Smovkina et al. (1990) *Gene* 94: 53-59), R4 integrase (e.g., in pAT98 (Matsuura et al. (1996 *J Bad.* 178(11): 3374-3376), OVWB integrase (e.g., in pKT02 (Van Mellaert et al. (1998) *Microbiology* 144:3351-3358, BT1 integrase (e.g., pRT801), and L5 integrase (e.g., Lee et al. (1991) *Proc. Natl. Acad. Sci. USA*, 88:3111-3115). In some cases the integration is facililitated by alteration of the host strain, e.g., by addition of the specific attB site for the integrase to enable high efficiency integration. In certain embodiments replicating vectors can also be used, either as replacements to, or in addition to ΦC31-based vectors.

These include, but are not limited to, vectors based on pIJ101 (e.g., pIJ487, Kieser et al. (2000) Practical *Streptomyces* Genetics, John Innes Foundation ISBN 0-7084-0623-8), pSG5 (e.g. pKC1139, Bierman et al. (1992) *Gene* 116: 43-49) and SCP2* (e.g., pIJ698, Kieser et al. (2000), supra.).

Although the introduction of gene cassettes into *S. hygroscopicus* has been exemplified using the ΦBT1 and the ΦC31 site-specific integration functions, those skilled in the art will appreciate that there are a number of different strategies described in the literature, including those mentioned above that could also be used to introduce such gene cassettes into prokaryotic, or more preferably actinomycete, host strains. These include the use of alternative site-specific integration vectors as described above and in the following articles (Kieser et al. (2000), supra.; Van Mellaert et al. (1998) *Microbiology* 144:3351-3358; Lee et al. (1991) *Proc. Natl. Acad. Sci. USA*, 88:3111-3115; Smovkina et al. (1990) *Gene* 94: 53-59; Matsuura et al. (1996 *J Bad.* 178(11): 3374-3376). Alternatively, plasmids containing the gene cassettes may be integrated into a neutral site on the chromosome using homologous recombination sites. Further, for a number of actinomycete host strains, including *S. hygroscopicus*, the gene cassettes may be introduced on self-replicating plasmids (Kieser et al. (2000), supra.; WO 1998/001571).

Typically, a gene cassette is used for the complementation of the recombinant *S. hygroscopicus* deletion strains. Methods of constructing gene cassettes and their heterologous use to produce hybrid glycosylated macrolides have been previously described (Gaisser et al. (2002) *Mol. Microbiol.* 44: 771-781; PCT Pub. Nos. WO 2001/079520, WO 2003/0048375, and WO 2004/007709). In certain embodiments the gene cassette is assembled directly in an expression vector rather than pre-assembling the genes in pUC18/19 plasmids, thus providing a more rapid cloning procedure.

The approach is exemplified in PCT Pub. No. WO 2004/007709. As described herein, a suitable vector (for example but without limitation pSGLitl) can be constructed for use in the construction of said gene cassettes, where a suitable restriction site (for example but without limitation XbaI), sensitive to dam methylation is inserted 5' to the gene(s) of interest and a second restriction site (for example XbaI) can be inserted 3' to the genes of interest. The skilled artisan will appreciate that other restriction sites may be used as an alternative to XbaI and that the methylation sensitive site may be 5' or 3' of the gene(s) of interest.

The cloning strategy also allows the introduction of a histidine tag in combination with a terminator sequence 3' of the gene cassette to enhance gene expression. Those skilled in the art will appreciate other terminator sequences could be used.

In certain embodiments various different promotor sequences can be used in the assembled gene cassette to optimize gene expression. Using these methods (e.g., as further described in WO 2004/007709) *S. hygroscopicus* deletion strains, the deletion comprising, but not limited to, a gene or a sub-set of the genes rapQ, rapN/O, rapM, rapL, rapK, rapJ and rapI can readily be constructed. In various embodiments the gene cassettes for complementation or partial complementation would generally comprise single genes or a plurality of genes selected from the sub-set of the genes deleted.

In another approach, the rapamycin analogues described herein can be obtained by a process comprising the steps of:

a) constructing a deletion strain, where the deletion(s) include, but not limited to, the genes rapK, rapQ, rapN/O, rapM, rapL, rapJ and rapI, or a sub-set thereof;

b) culturing the strain under conditions suitable for polyketide production;

c) optionally, isolating the rapamycin analogue intermediate produced;

d) constructing a biotransformation strain containing a gene cassette comprising all or a sub-set of the genes deleted;

e) feeding the rapamycin analogue intermediate in culture supernatant or isolated as in step c) to a culture of the biotransformation strain under suitable biotransformation conditions; and f) optionally isolating the rapamycin analogue produced.

It is well known to those skilled in the art that polyketide gene clusters may be expressed in heterologous hosts (Pfeifer and Khosla, 2001). Accordingly, suitable host strains for the construction of the biotransformation strain include the native host strain in which the rapamycin biosynthetic gene cluster has been deleted, or substantially deleted or inactivated, so as to abolish polyketide synthesis, or a heterologous host strain. Methods for the expressing of gene cassettes comprising one or a plurality of modifying or precursor supply genes in heterologous hosts are described in WO 2001/079520. In this context heterologous hosts suitable for biotransformation of the rapamycin anlaogues include, but are not limited to, *S. hygroscopicus, S. hygroscopicus* sp., *S. hygroscopicus* var. *ascomyceticus, Streptomyces tsukubaensis, Streptomyces coelicolor, Streptomyces lividans, Saccharopolyspora erythraea, Streptomyces fradiae, Streptomyces avermitilis, Streptomyces cinnamonensis, Streptomyces rimosus, Streptomyces albus, Streptomyces griseofuscus, Streptomyces longisporoflavus, Streptomyces venezuelae, Micromonospora griseorubida, Amycolatopsis mediterranei, Escherichia coli* and *Actinoplanes* sp. N902-109, and the like.

The close structural relationship between rapamycin and FK506, FK520, FK523, 'hyg', meridamycin, antascomicin, FK525 and tsukubamycin, among others, and the established homologies between genes involved in the biosynthesis of rapamycin and FK506 and FK520 (vide supra), renders the application of the synthesis methods described herein straightforward in these closely related systems.

It has been demonstrated that rapK is involved in the supply of the biosynthetic precursors (e.g., 4,5-dihydroxy-cyclohex-1-ene carboxylic acid starter) for rapamycin production. Moreover, deletion or inactivation of rapK or a rapK homologue provides a strain lacking in competition between the natural starter unit and fed non-natural starter units. In another aspect, the invention provides, a method for the efficient incorporation of fed acids including, but not limited to those described below. Thus, for example, Table 1 illustrates various starter units that can be used to produce the rapamycin analogs described herein.

TABLE 1

Illustrative, but non-limiting fed starter units and the resulting substituent attached to carbon 36.

| Starter acid feed | At Carbon 36 |
|---|---|
| cyclohexanecarboxylic acid | 4-hydroxycyclohexyl |
| 4-hydroxycyclohexanecarboxylic acid | 4-hydroxycyclohexyl |
| 3-fluoro-4-hydroxycyclohexanecarboxylic acid | 2-fluoro-4-hydroxycyclohexyl |
| 4-methoxycyclohexanecarboxylic acid | 4-methoxycyclohexyl |
| 3-fluoro-4-methoxycyclohexanecarboxylic acid | 2-fluoro-4-methoxycyclohexyl |

While deletion of rapK to facilitate incorporation of these starter units is a typical approach in the production of the compounds described herein, it will be recognized that other methods are available to remove the competition between the endogenously produced natural starter unit and the alternative starter acid analogues fed. For example, it is possible to disrupt the biosynthesis of the natural 4,5-dihydroxycyclohex-1-enecarboxylic acid starter unit. This may be achieved by deletion or inactivation 6f one or more of the genes involved in the biosynthesis of the natural 4,5-dihydroxycyclohex-1-enecarboxylic acid starter unit from shikimic acid (Lowden et al. (2001) *Angewandte Chemie-international Edition* 40: 777-779) or the biosynthesis of shikimic acid itself. In the latter case, it may be necessary to supplement cultures with aromatic amino acids (phenyl alanine, tyrosine, tryptophan). Alternatively, endogenous production of the natural 4,5-ihydroxycyclohex-1-ene carboxylic acid starter unit may be suppressed by the addition of a chemical inhibitor of shikimic acid biosynthesis.

In various embodiments, the methods described herein produce a racemic mixture of the desired rapamycin analogs and such racemic mixtures can readily be used in the pharmaceutical formulations and treatment methods described herein.

However, in certain embodiments a pure chiral form of the molecule as a single diastereomer is desired. Accordingly, in certain embodiments, methods of preparing a compound in pure chiral form are provided where the methods involve providing the feed starter (1R,4R)-4-hydroxycyclohexanecarboxylic acid in pure chiral form of formula (VII)

VII to a rapamycin producing strain of *Streptomyces* (e.g., *Streptomyces rapamycinicus*) that has been genetically altered to delete the genes rapI, rapJ, rapK, rapL, rapM, rapN, rapO, and rapQ and conjugated with a plasmid containing rapJ, rapM, rapN, rapO and rapLhis.

In certain embodiments, a method of preparing a compound in pure chiral form as a single diastereomer is provided where the method comprises providing the feed starter (1R,4R)-4-methoxycyclohexanecarboxylic acid in pure chiral form of formula (VIII)

VIII

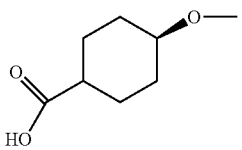

to a rapamycin producing strain of *Streptomyces* (e.g., *Streptomyces rapamycinicus*) that has been genetically altered to delete the genes rapI, rapJ, rapK, rapL, rapM, rapN, rapO, and rapQ and conjugated with a plasmid containing rapJ, rapM, rapN, rapO and rapLhis.

In certain embodiments, a method of preparing a compound in pure chiral form as a single diastereomer is provided where the method involves providing the feed starter (1R,3R,4R)-3-fluoro-4-hydroxycyclohexane carboxylic acid in pure chiral form of formula (IX)

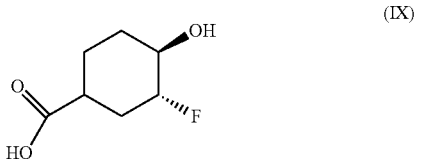 [SMILES: O=C(O)C1CC[C@@H](O)[C@H](F)C1]
(IX)

to a rapamycin producing strain of *Streptomyces* (e.g., *Streptomyces rapamycinicus*) that has been genetically altered to delete the genes rapI, rapJ, rapK, rapL, rapM, rapN, rapO, and rapQ and conjugated with a plasmid containing rapJ, rapM, rapN, rapO and rapLhis. Culture conditions are as described in WO 2004/007709.

The desired rapamycin analog(s) can be purified using methods known to those of skill in the art, e.g., as described in WO 2004/007709.

It will be recognized that these preparation methods are illustrative and not limiting. Using the teaching provided herein, numerous other methods of producing the rapamycin analogs described herein will be available to one of skill in the art.

EXAMPLES

The following examples are offered to illustrate, but not to limit the claimed invention.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Illustrative Synthetic Schemes

The compounds and salts of Formula (I), (II) and sub-formulas thereof can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1 to 12, the steps in some cases may be performed in a different order than the order shown in Schemes 1 to 12. Numberings or R groups in each scheme do not necessarily correspond to that of the claims or other schemes or tables herein. In some embodiments, C16 modification may be performed before C40 modification. In some embodiments, C40 modification may be performed before C16 modification.

In some embodiments, compounds of Tables 2 to Table 4 may be prepared according to Schemes 1 to 12.

C40 Modifications

Scheme 1

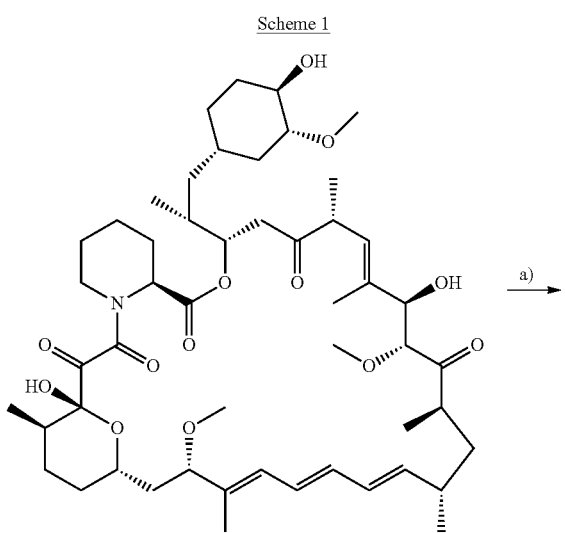
a)

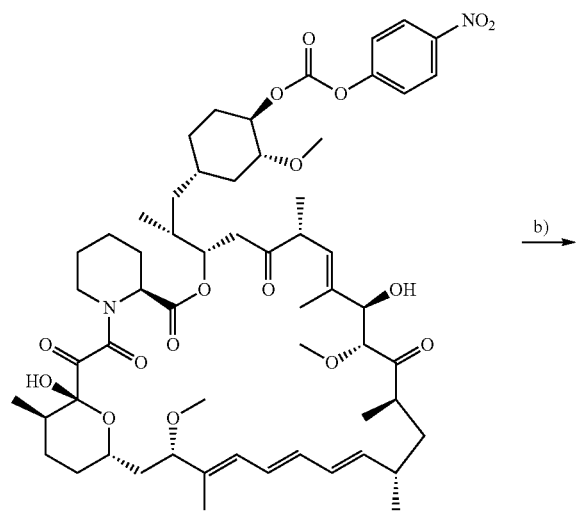
b)

-continued

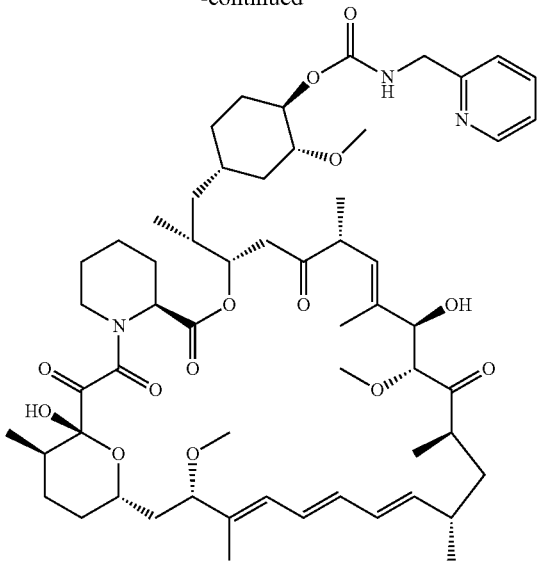

Example 1

Step A: Preparation of [(1R,2R,4S)-4-[(2R)-2-[(1R,9S,12S,15R,16E,18R,19R, 21R,23S,24E,26E, 28E,30S,32S,35R)-1,18-dihydroxy-19, 30-dimethoxy-15,17,21,23,29,35-hexamethyl-2,3,10,14,20-pentaoxo-11,36-dioxa-4-azatricyclo[30.3.1.0ˆ4,9] hexatriaconta-16,24,26,28-tetraen-12-yl]propyl]-2-methoxy-cyclohexyl] (4-nitrophenyl) carbonate. Sirolimus (500 mg; 0.55 mmol) and anhydrous pyridine (0.44 mL, 5.47 mmol) were dissolved in anhydrous DCM (2.5 mL) under nitrogen atmosphere. The reaction mixture was cooled to −78° C. and a solution of (4-nitrophenyl) carbonochloridate (229 mg, 1.09 mmol) in anhydrous DCM (0.4 mL) was added to the mixture. The ice bath was removed and reaction mixture was stirred under $N_2$ for 45 min. The reaction was diluted with DCM and water was added. The mixture was extracted twice with DCM, gathered and concentrated and purified over silica gel column (gradient of Cyclohexane/ ethylacetate 100/0 to 50/50) to afford the desired product as a white solid (518 mg). Yield 83%. 1H NMR (600 MHz, DMSO-d6) δ 6.43 (d, J=1.5 Hz, 1H), 6.40 (dd, J=14.8, 11.2 Hz, 1H), 6.26-6.04 (m, 3H), 5.46 (dd, J=14.9, 9.6 Hz, 1H), 5.24 (d, J=4.5 Hz, 1H), 5.09 (d, J=10.2 Hz, 1H), 5.02-4.96 (m, 1H), 4.93 (d, J=6.1 Hz, 1H), 4.59-4.54 (m, 1H), 4.53-4.47 (m, 1H), 4.11-3.96 (m, 2H), 3.94 (d, J=4.7 Hz, 1H), 3.78 (d, J=13.8 Hz, 1H), 3.52-3.36 (m, 3H), 3.36-3.09 (m, 11H), 2.87-2.78 (m, 1H), 2.73 (d, J=15.1 Hz, 1H), 2.45-2.30 (m, 2H), 2.21 (s, 1H), 2.16-1.82 (m, 5H), 1.82-0.90 (m, 27H), 0.87 (d, J=6.6 Hz, 3H), 0.83 (q, J=7.6, 6.7 Hz, 4H), 0.78 (d, J=6.8 Hz, 3H), 0.73 (d, J=6.7 Hz, 3H), 0.60 (q, J=11.9 Hz, 1H).

Step B: Preparation of (1R,2R,4S)-4-[(2R)-2-[(1R,9S, 12SR,15R,16E,18R,19R,21R,23S,24E,26E,28E,30S,32SR, 35R)-1,18-dihydroxy-19,30-dimethoxy-15,17,21,23,29,35-hexamethyl-2,3,10,14,20-pentaoxo-11,36-dioxa-4-azatricyclo[30.3.1.0ˆ4,9]hexatriaconta-16,24,26,28-tetraen-12-yl]propyl]-2-methoxy-cyclohexyl] N-(2-pyridylmethyl) carbamate (compound 333). [(1R,2R,4S)-4-[(2R)-2-[(1R, 9S,12S,15R,16E,18R,19R,21R,23S,24E,26E,28E,30S,32S, 35R)-1,18-dihydroxy-19,30-dimethoxy-15,17,21,23,29,35-hexamethyl-2,3,10,14,20-pentaoxo-11,36-dioxa-4-azatricyclo[30.3.1.0ˆ4,9]hexatriaconta-16,24,26,28-tetraen-12-yl]propyl]-2-methoxy-cyclohexyl](4-nitrophenyl) carbonate (0,0278 mmol) was dissolved in anhydrous dimethylformamide (0.5 mL) and triethylamine (1.0 mmol). The 2-(Aminomethyl)Pyridine (0.17 mmol dissolved in 0.1 mL of DMF) was added dropwise at −20° C. under atmosphere of nitrogen. After 1.5 hours of stirring at −20° C., ethylacetate was added, the organic phases were separated and washed with water twice. The organics were combined and concentrated to dryness. The crude residue was purified on silica gel by flash column chromatography (0-10% of MeOH in DCM gradient) to afford the desired product compound 333 (44.7 mg) as a white powder. Yield 100%. 1H NMR (600 MHz, DMSO-d6, 300K) δ ppm 8.48 (d, J=4.5 Hz, 1H), 7.77 (td, J=7.7, 1.8 Hz, 1H), 7.67 (br t, J=5.9 Hz, 1H), 7.16-7.35 (m, 2H), 6.44 (s, 1H), 6.41 (br dd, J=14.5, 11.4 Hz, 1H), 6.23 (dd, J=14.7, 10.6 Hz, 1H), 6.08-6.16 (m, 2H), 5.47 (dd, J=14.9, 9.6 Hz, 1H), 5.25 (d, J=4.4 Hz, 1H), 5.10 (br d, J=9.8 Hz, 1H), 5.00 (dt, J=7.4, 3.7 Hz, 1H), 4.92-4.96 (m, 1H), 4.39-4.48 (m, 1H), 4.27 (br dd, J=6.1, 2.4 Hz, 2H), 3.92-4.05 (m, 3H), 3.63 (br dd, J=11.5, 1.8 Hz, 1H), 3.41-3.49 (m, 1H), 3.31 (br s, 3H), 3.22-3.29 (m, 2H), 2.99-3.21 (m, 8H), 2.70-2.76 (m, 1H), 2.35-2.44 (m, 2H), 2.18-2.33 (m, 1H), 2.08-2.14 (m, 1H), 1.93-2.07 (m, 2H), 1.80-1.92 (m, 3H), 1.47-1.77 (m, 10H), 0.90-1.45 (m, 16H), 0.65-0.89 (m, 13H)

Alternative Step B: Preparation of [(1R,2R,4S)-4-[(2R)-2-[(1R,9S,12S,15R,16E,18R,19R,21R,23S,24E,26E,28E, 30S,32S,35R)-1,18-dihydroxy-19,30-dimethoxy-15,17,21, 23,29,35-hexamethyl-2,3,10,14,20-pentaoxo-11,36-dioxa-4-azatricyclo[30.3.1.0ˆ4,9]hexatriaconta-16,24,26,28-tetraen-12-yl]propyl]-2-methoxy-cyclohexyl] N,N-bis(2-hydroxyethyl)carbamate (compound 357). A mixture of [(1R,2R,4S)-4-[(2R)-2-[(1R,9S,12S,15R,16E,18R,19R, 21R,23S, 24E,26E,28E,30S,32S,35R)-1,18-dihydroxy-19, 30-dimethoxy-15,17,21,23,29,35-hexamethyl-2,3,10,14,20-pentaoxo-11,36-dioxa-4-azatricyclo[30.3.1.0ˆ4,9] hexatriaconta-16,24,26,28-tetraen-12-yl]propyl]-2-methoxy-cyclohexyl] (4-nitrophenyl) carbonate (0,066 mmol) and N,N-diethylethanamine (13.36 mg; 0.13 mmol) was dissolved in anhydrous dimethylformamide (1.54 mL). Then 2,2'-iminodiethanol (14.613 mg, 0.13 mmol) was added dropwise at −20° C. under atmosphere of nitrogen. After 1.5 hours of stirring at −20° C., ethylacetate was added, the organic phases were separated and washed with water twice. The organics were combined and concentrated to dryness. The crude residue was purified on silica gel by flash column chromatography (0-10% of MeOH in DCM gradient) to afford the desired product compound 357 as a white powder (37.2 mg). Yield 53%. 1H NMR (600 MHz, DMSO-d6, 300K) δ ppm 6.44 (s, 1H), 6.41 (br dd, J=14.7, 11.2 Hz, 1H), 6.22 (br dd, J=14.7, 10.6 Hz, 1H), 6.09-6.17 (m, 2H), 5.47 (br dd, J=15.0, 9.7 Hz, 1H), 5.26 (d, J=4.4 Hz, 1H), 5.10 (br d, J=10.0 Hz, 1H), 4.98 (ddd, J=8.1, 4.5, 3.2 Hz, 1H), 4.92-4.95 (m, 1H), 4.69 (t, J=5.4 Hz, 2H), 4.36 (ddd, J=11.2, 9.3, 4.7 Hz, 1H), 3.92-4.06 (m, 3H), 3.61-3.65 (m, 1H), 3.40-3.52 (m, 5H), 3.24-3.30 (m, 8H), 2.99-3.21 (m, 8H), 2.74 (br dd, J=17.6, 2.6 Hz, 1H), 2.35-2.44 (m, 2H), 2.18-2.34 (m, 1H), 2.07-2.14 (m, 1H), 1.78-2.07 (m, 4H), 1.74 (s, 3H), 1.49-1.72 (m, 8H), 0.81-1.48 (m, 23H), 0.78 (d, J=6.7 Hz, 3H), 0.65-0.75 (m, 4H).

Certain compounds of Table 2 or 4 with carbamate moieties at C40 can be prepared starting with sirolimus or a C16 modified form of sirolimus following Scheme 1 and employing alternative amine reagents to those described in Example 1.

Scheme 2

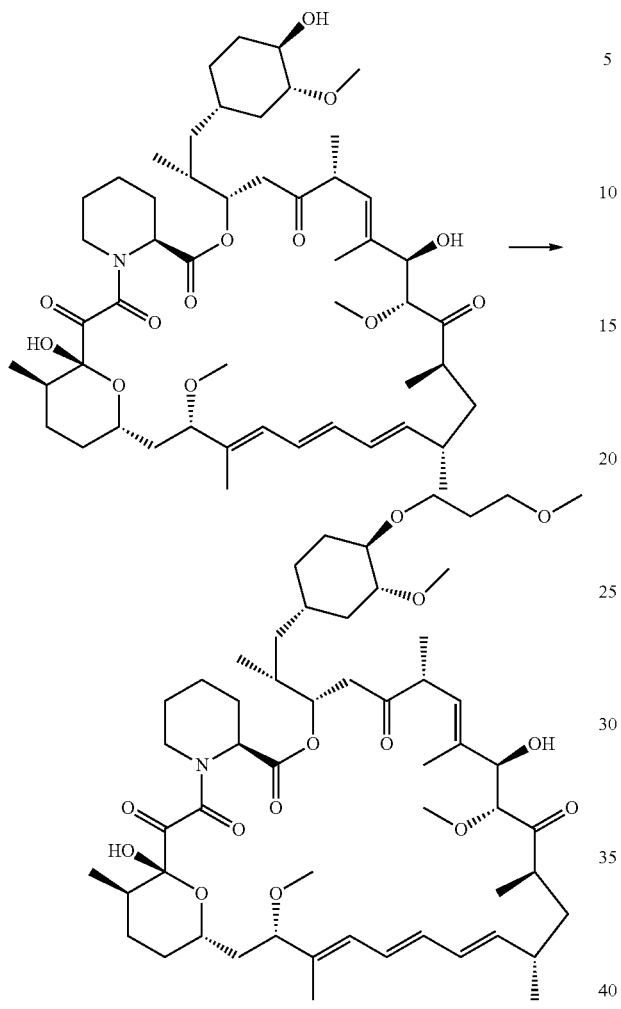

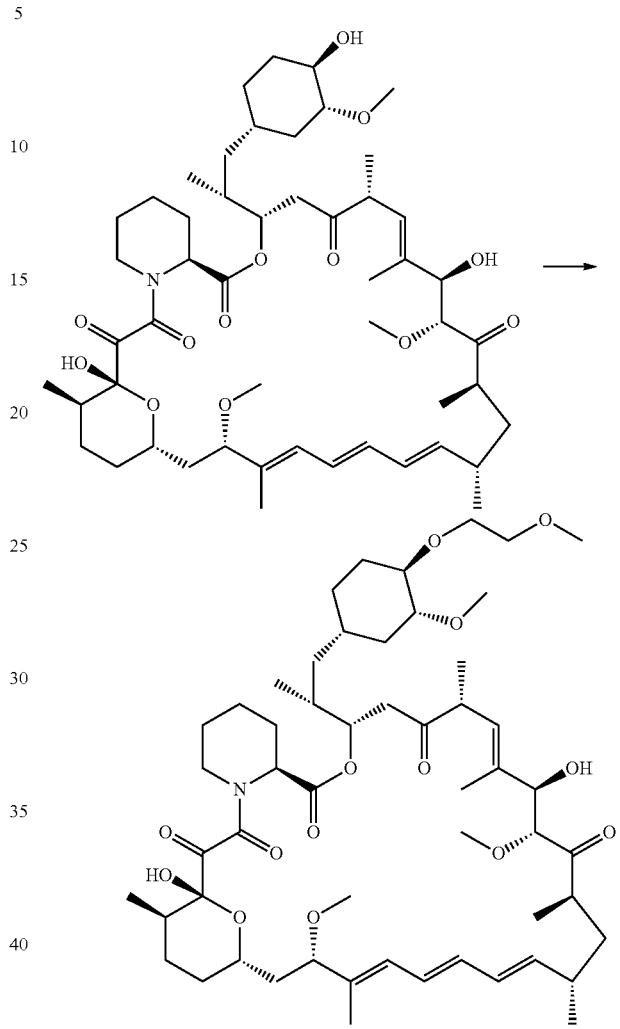

Preparation of (1R,9S,12S,15R,16E,18R,19R,21R,23S, 24E,26E,28E,30S,32S,35R)-1,18-dihydroxy-19,30-dimethoxy-12-[(1R)-2-[(1S,3R,4R)-3-methoxy-4-(3-methoxypropoxy)cyclohexyl]-1-methyl-ethyl]-15,17,21,23,29,35-hexamethyl-11,36-dioxa-4-azatricyclo[30.3.1.0^4,9]hexatriaconta-16,24,26,28-tetraene-2,3,10,14,20-pentone (Compound 308). 3-methoxypropyl trifluoromethanesulfonate (72.912 mg, 0.33 mmol) was added to a mixture of Sirolimus (100.0 mg, 0.11 mmol) and N-ethyl-N-isopropylpropan-2-amine (0.11 mL, 0.6 mmol) previously dissolved in dry Toluene (0.4051 mL) under argon. After 1.5 hours of stirring at 60° C., the crude mixture was concentrated and purified on silica gel by flash column chromatography (Cyclohexane/Ethylacetate 100:00 to 60/40) to afford the desired product Compound 308 as an amorphous white solid (34.9 mg). Yield 35%. 1H NMR (600 MHz, DMSO-d6, 300K) δ ppm 6.44 (d, J=0.9 Hz, 1H), 6.40 (dd, J=14.6, 11.2 Hz, 1H), 6.22 (br dd, J=14.6, 10.6 Hz, 1H), 6.09-6.16 (m, 2H), 5.46 (dd, J=14.9, 9.6 Hz, 1H), 5.25 (d, J=4.5 Hz, 1H), 5.09 (br d, J=10.1 Hz, 1H), 4.96-5.00 (m, 1H), 4.94 (br d, J=5.6 Hz, 1H), 3.97-4.04 (m, 2H), 3.93 (d, J=4.5 Hz, 1H), 3.62 (dd, J=11.7, 2.1 Hz, 1H), 3.52-3.57 (m, 1H), 3.48 (dt, J=9.5, 6.3 Hz, 1H), 3.41-3.46 (m, 1H), 3.37 (t, J=6.4 Hz, 2H), 3.33 (s, 3H), 3.25-3.29 (m, 1H), 3.13-3.21 (m, 7H), 3.05 (s, 3H), 2.92-3.03 (m, 2H), 2.73 (br dd, J=17.7, 2.6 Hz, 1H), 2.35-2.43 (m, 2H), 2.18-2.26 (m, 1 H), 1.78-2.13 (m, 6H), 1.47-1.76 (m, 11H), 1.37-1.44 (m, 2H), 0.91-1.33 (m, 15H), 0.59-0.89 (m, 14H).

Preparation of (1R,9S,12S,15R,16E,18R,19R,21R,23S, 24E,26E,28E,30S,32S,35R)-1,18-dihydroxy-19,30-dimethoxy-12-[(1R)-2-[(1S,3R,4R)-3-methoxy-4-(2-methoxyethoxy)cyclohexyl]-1-methyl-ethyl]-15,17,21,23,29,35-hexamethyl-11,36-dioxa-4-azatricyclo[30.3.1.0^4,9]hexatriaconta-16,24,26,28-tetraene-2,3,10,14,20-pentone (Compound 315). 2-methoxyethyl trifluoromethanesulfonate (0.04 mL, 0.66 mmol) was added to a mixture of Sirolimus (200.0 mg, 0.22 mmol) and N-ethyl-N-isopropylpropan-2-amine (0.17 mL, 1.2 mmol) previously dissolved in dry Toluene (0.8 mL) under argon. After 1.5 hours of stirring at 60° C., the crude mixture was concentrated and purified on silica gel by flash column chromatography (Cyclohexane/Ethylacetate 100:00 to 60/40) followed by C18 RP chromatography (ACN/H2O 40:60 to 98:02) to afford the desired product Compound 315 as an amorphous white solid (68 mg). Yield 32%. 1H NMR (600 MHz, DMSO-d6, 300K) δ ppm 6.44 (s, 1H), 6.40 (br dd, J=14.5, 11.1 Hz, 1H), 6.22 (br dd, J=14.7, 10.8 Hz, 1H), 6.08-6.17 (m, 2H), 5.46 (br dd, J=14.8, 9.7 Hz, 1H), 4.91-5.31 (m, 4H), 3.89-4.06 (m, 3H), 3.55-3.65 (m, 3H), 3.37-3.44 (m, 4H), 3.32-3.34 (m, 3H), 2.90-3.25 (m, 12H), 2.54-2.87 (m, 2H), 2.29-2.45 (m, 1H), 1.90-2.26 (m, 5H), 1.44-1.88 (m, 14H), 1.21-1.43 (m, 6H), 0.56-1.19 (m, 22H).

Certain compounds of Table 2 or 4 with alkoxyalkyloxy moieties at C40 can be prepared starting with sirolimus or a C16 modified form of sirolimus following Scheme 2 and employing alternative alkylating agents to those described in Example 2.

Scheme 3

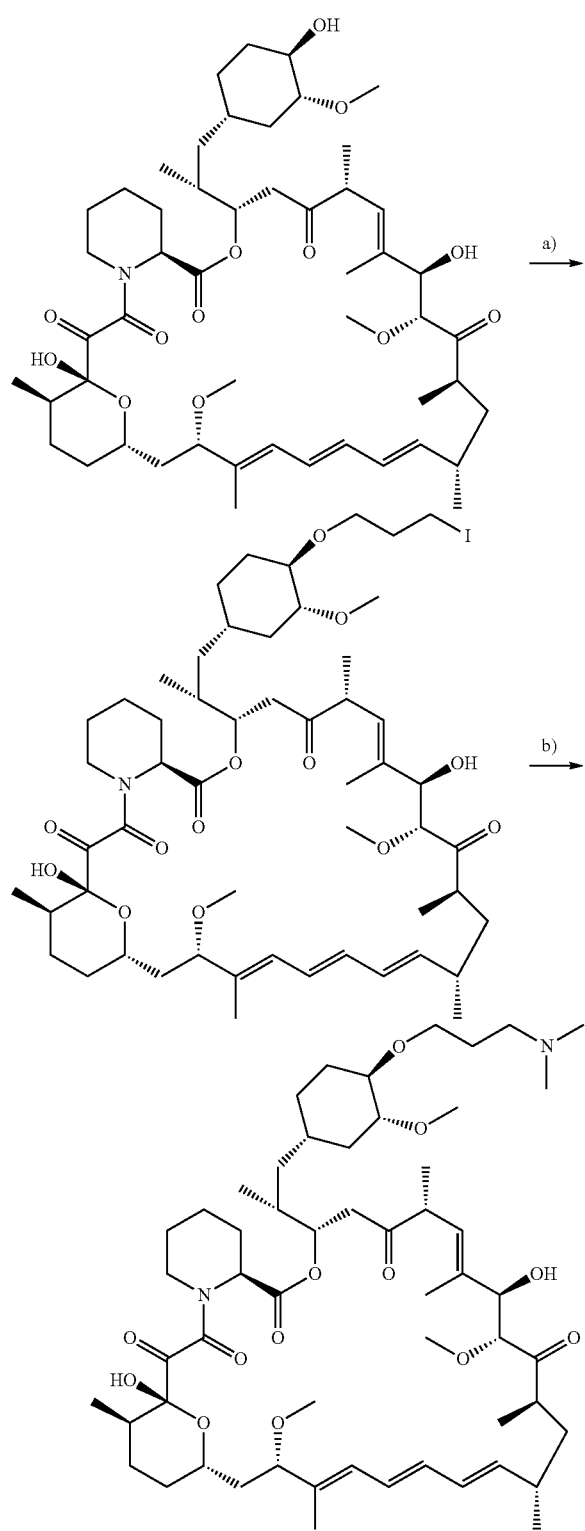

Example 3

Step A: Preparation of (1R,9S,12S,15R,16E,18R,19R, 21R,23S,24E,26E,28E,30S,32S,35R)-1,18-dihydroxy-12- [(1R)-2-[(1S,3R,4R)-4-(3-iodopropoxy)-3-methoxy-cyclohexyl]-1-methyl-ethyl]-19,30-dimethoxy-15,17,21,23,29, 35-hexamethyl-11,36-dioxa-4-azatricyclo[30.3.1.0^4,9] hexatriaconta-16,24,26,28-tetraene-2,3,10,14,20-pentone. Sirolimus (2 g; 2.18 mmol) was dissolved in dry Toluene (8 mL) with N-ethyl-N-isopropyl-propan-2-amine (2.1 mL, 12.03 mmol). 3-iodopropyl trifluoromethanesulfonate (2.1 g, 6.56 mmol) was added to the mixture under argon. The reaction mixture was stirred at 60° C. for 2 h. The reaction was allowed to cool to room temperature, concentrated and was purified on silica gel by flash column chromatography (Cyclohexane/ethylacetate; Gradient: 100:0 to 50:50) to afford the desired product as a yellow foam (1.25 g). Yield 49%. 1H NMR (600 MHz, DMSO-d6, 300K) δ ppm 6.44 (s, 1H), 6.40 (br dd, J=14.7, 11.2 Hz, 1H), 6.19-6.25 (m, 1H), 6.08-6.16 (m, 1H), 5.46 (br dd, J=15.0, 9.7 Hz, 1H), 5.25 (d, J=4.7 Hz, 1H), 5.10 (br d, J=10.0 Hz, 1H), 4.96-5.01 (m, 1H), 4.92-4.95 (m, 1H), 4.01 (d, J=2.5 Hz, 2H), 3.93 (br d, J=4.7 Hz, 1H), 3.63 (br dd, J=11.3, 2.2 Hz, 1H), 3.40-3.57 (m, 3H), 3.32-3.34 (m, 3H), 3.28 (br d, J=6.7 Hz, 1H), 3.17 (br s, 1H), 3.16 (s, 3H), 3.05 (s, 3H), 2.92-3.03 (m, 5H), 2.73 (br dd, J=17.6, 2.3 Hz, 1H), 2.33-2.45 (m, 2H), 2.18-2.31 (m, 3H), 2.12 (br s, 6H), 1.78-2.06 (m, 6H), 1.74 (s, 3H), 0.79-1.71 (m, 30H), 0.77 (d, J=6.7 Hz, 3H), 0.73 (br d, J=6.7 Hz, 3H), 0.59-0.69 (m, 1H).

Step B: Preparation of (1R,9S,12S,15R,16E,18R,19R, 21R,23S,24E,26E,28E,30S,32S,35R)-12-[(1R)-2-[(1S,3R, 4R)-4-[3-(dimethylamino)propoxy]-3-methoxy-cyclohexyl]-1-methyl-ethyl]-1,18-dihydroxy-19,30-dimethoxy- 15,17,21,23,29,35-hexamethyl-11,36-dioxa-4-azatricyclo [30.3.1.0^4,9]hexatriaconta-16,24,26,28-tetraene-2,3,10,14, 20-pentone (Compound 363). N-methylmethanamine (2M, 0.04 mL, 0.08 mmol) was added to a solution of N-ethyl-N-isopropyl-propan-2-amine (0.03 mL, 0.19 mmol and (1R, 9S,12S,15R,16E,18R,19R,21R,23S, 24E,26E,28E,30S,32S, 35R)-1,18-dihydroxy-12-[(1R)-2-[(1S,3R,4R)-4-(3-iodopropoxy)-3-methoxy-cyclohexyl]-1-methyl-ethyl]-19, 30-dimethoxy-15,17,21,23,29,35-hexamethyl-11,36-dioxa-4-azatricyclo[30.3.1.0^4,9]hexatriaconta-16,24,26,28-tetraene-2,3,10,14,20-pentone (70 mg; 0.0647 mmol) in dry DCM (0.4 mL). After 5 hours of stirring at room temperature under argon, the reaction mixture was diluted with DCM and acidifed with HCl 1N to pH=4. The organic phase was washed with H2O, gathered, concentrated and purified on silica gel by flash column chromatography (Eluent A=Ethylacetate Eluent B=MeOH:Et3N (50:50) Gradient: A/B from 100/0 to 70:30) to afford the desired product Compound 363 as an amorphous white solid (17.3 mg). Yield 24%. 1H NMR (600 MHz, DMSO-d6, 300K) δ ppm 6.44 (s, 1H), 6.40 (br dd, J=14.7, 11.2 Hz, 1H), 6.19-6.25 (m, 1H), 6.08-6.16 (m, 1H), 5.46 (br dd, J=15.0, 9.7 Hz, 1H), 5.25 (d, J=4.7 Hz, 1H), 5.10 (br d, J=10.0 Hz, 1H), 4.96-5.01 (m, 1H), 4.92-4.95 (m, 1H), 4.01 (d, J=2.5 Hz, 2H), 3.93 (br d, J=4.7 Hz, 1H), 3.63 (br dd, J=11.3, 2.2 Hz, 1H), 3.40-3.57 (m, 3H), 3.32-3.34 (m, 3H), 3.28 (br d, J=6.7 Hz, 1H), 3.17 (br s, 1H), 3.16 (s, 3H), 3.05 (s, 3H), 2.92-3.03 (m, 5H), 2.73 (br dd, J=17.6, 2.3 Hz, 1H), 2.33-2.45 (m, 2H), 2.18-2.31 (m, 3H), 2.12 (br s, 6H), 1.78-2.06 (m, 6H), 1.74 (s, 3H), 0.79-1.71 (m, 30H), 0.77 (d, J=6.7 Hz, 3H), 0.73 (br d, J=6.7 Hz, 3H), 0.59-0.69 (m, 1H)

Certain compounds of Table 2 or 4 with aminopropoxy moieties at $C_{40}$ can be prepared starting with sirolimus or a C16 modified form of sirolimus following Scheme 3 and employing alternative amine reagents in Step B and/or an alternative alkylating agent in Step A to those described in Example 3.

Scheme 4

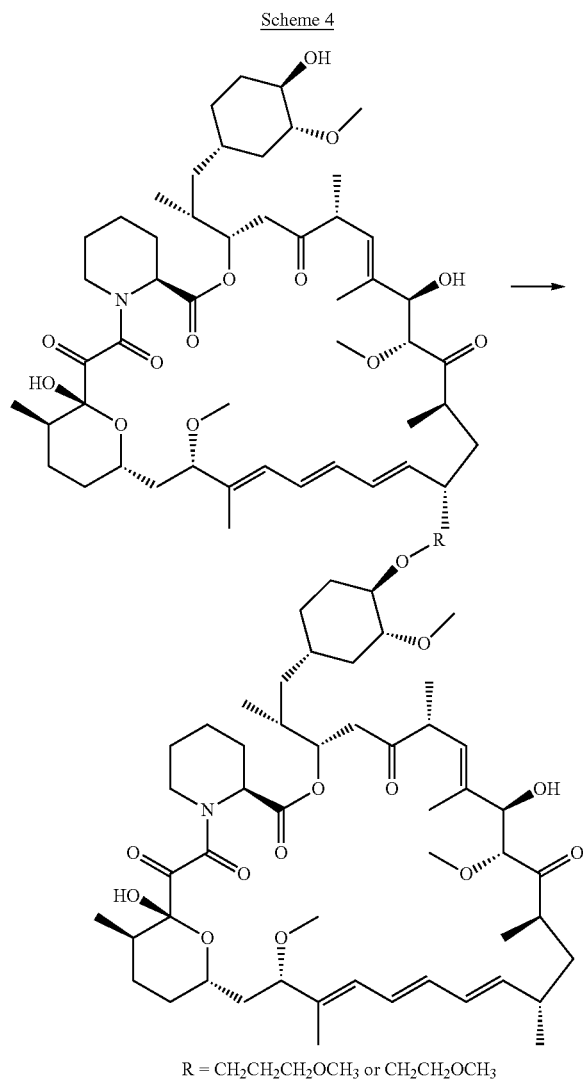

R = CH₂CH₂CH₂OCH₃ or CH₂CH₂OCH₃

Example 4

Preparation of (1R,9S,12S,15R,16E,18R,19R,21R,23S, 24E,26E,28E,30S,32S,35R)-1,18-dihydroxy-19,30-dimethoxy-12-[(1R)-2-[(1S,3R,4R)-3-methoxy-4-(3-methoxypropoxy)cyclohexyl]-1-methyl-ethyl]-15,17,21,23,29,35-hexamethyl-11,36-dioxa-4-azatricyclo[30.3.1.0^4,9] hexatriaconta-16,24,26,28-tetraene-2,3,10,14,20-pentone (Compound 308). 3-methoxypropyl trifluoromethanesulfonate (72.912 mg, 0.33 mmol) was added to a mixture of Sirolimus (100.0 mg, 0.11 mmol) and N-ethyl-N-isopropyl-propan-2-amine (0.11 mL, 0.6 mmol) previously dissolved in dry Toluene (0.4051 mL) under argon. After 1.5 hours of stirring at 60° C., the crude mixture was concentrated and purified on silica gel by flash column chromatography (Cyclohexane/Ethylacetate 100:00 to 60/40) to afford the desired product Compound 308 as an amorphous white solid (34.9 mg). Yield 35%. 1H NMR (600 MHz, DMSO-d6, 300K) δ ppm 6.44 (d, J=0.9 Hz, 1H), 6.40 (dd, J=14.6, 11.2 Hz, 1H), 6.22 (br dd, J=14.6, 10.6 Hz, 1H), 6.09-6.16 (m, 2H), 5.46 (dd, J=14.9, 9.6 Hz, 1H), 5.25 (d, J=4.5 Hz, 1H), 5.09 (br d, J=10.1 Hz, 1H), 4.96-5.00 (m, 1H), 4.94 (br d, J=5.6 Hz, 1H), 3.97-4.04 (m, 2H), 3.93 (d, J=4.5 Hz, 1H), 3.62 (dd, J=11.7, 2.1 Hz, 1H), 3.52-3.57 (m, 1H), 3.48 (dt, J=9.5, 6.3 Hz, 1H), 3.41-3.46 (m, 1H), 3.37 (t, J=6.4 Hz, 2H), 3.33 (s, 3H), 3.25-3.29 (m, 1H), 3.13-3.21 (m, 7H), 3.05 (s, 3H), 2.92-3.03 (m, 2H), 2.73 (br dd, J=17.7, 2.6 Hz, 1H), 2.35-2.43 (m, 2H), 2.18-2.26 (m, 1H), 1.78-2.13 (m, 6H), 1.47-1.76 (m, 11H), 1.37-1.44 (m, 2H), 0.91-1.33 (m, 15H), 0.59-0.89 (m, 14H)

Preparation of (1R,9S,12S,15R,16E,18R,19R,21R,23S, 24E, 26E,28E,30S,32S,35R)-1,18-dihydroxy-19,30-dimethoxy-12-[(1R)-2-[(1S,3R,4R)-3-methoxy-4-(2-methoxyethoxy)cyclohexyl]-1-methyl-ethyl]-15,17,21,23,29,35-hexamethyl-11,36-dioxa-4-azatricyclo[30.3.1.0^4,9] hexatriaconta-16,24,26,28-tetraene-2,3,10,14,20-pentone (Compound 315). 2-methoxyethyl trifluoromethanesulfonate (0.04 mL, 0.66 mmol) was added to a mixture of Sirolimus (200.0 mg, 0.22 mmol) and N-ethyl-N-isopropyl-propan-2-amine (0.17 mL, 1.2 mmol) previously dissolved in dry Toluene (0.8 mL) under argon. After 1.5 hours of stirring at 60° C., the crude mixture was concentrated and purified on silica gel by flash column chromatography (Cyclohexane/Ethylacetate 100:00 to 60/40) followed by C18 RP chromatography (ACN/H2O 40:60 to 98:02) to afford the desired product Compound 315 as an amorphous white solid (68 mg). Yield 32%. 1H NMR (600 MHz, DMSO-d6, 300K) δ ppm 6.44 (s, 1H), 6.40 (br dd, J=14.5, 11.1 Hz, 1H), 6.22 (br dd, J=14.7, 10.8 Hz, 1H), 6.08-6.17 (m, 2H), 5.46 (br dd, J=14.8, 9.7 Hz, 1H), 4.91-5.31 (m, 4H), 3.89-4.06 (m, 3H), 3.55-3.65 (m, 3H), 3.37-3.44 (m, 4H), 3.32-3.34 (m, 3H), 2.90-3.25 (m, 12H), 2.54-2.87 (m, 2H), 2.29-2.45 (m, 1H), 1.90-2.26 (m, 5H), 1.44-1.88 (m, 14H), 1.21-1.43 (m, 6H), 0.56-1.19 (m, 22H).

Certain compounds of Table 2 or 4 with alkoxyalkyloxy moieties at C40 can be prepared starting with sirolimus or a C16 modified form of sirolimus following Scheme 4 and employing alternative alkylating agents to those described in Example 4.

Scheme 5

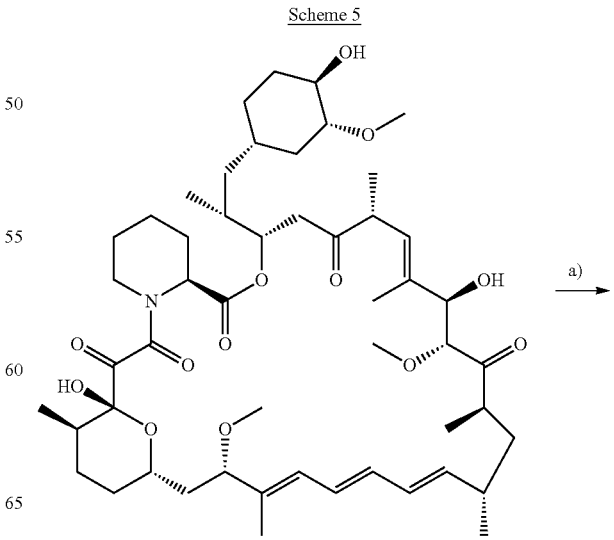

a)

-continued

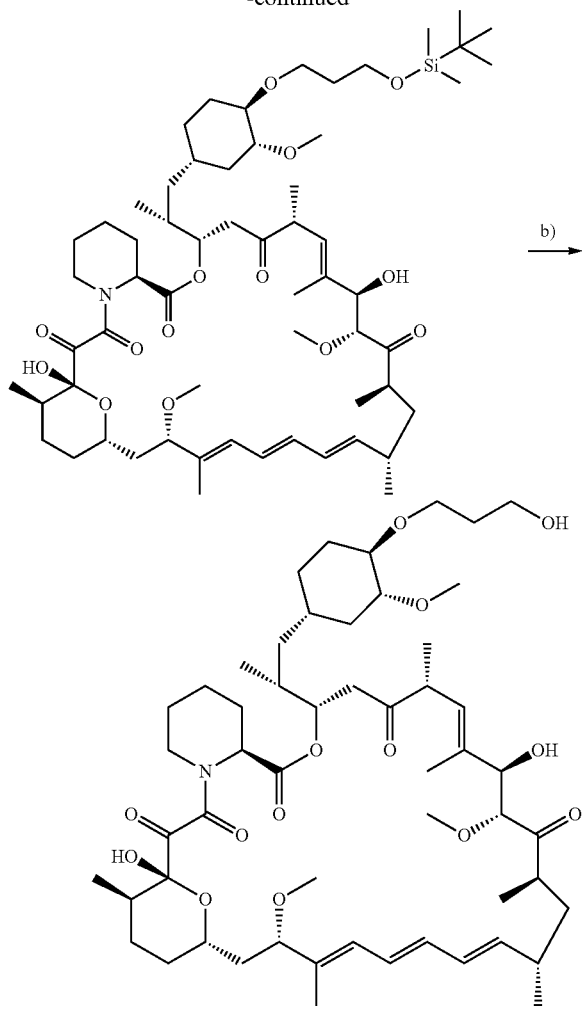

Example 5

Step A: Preparation of (1R,9S,12S,15R,16E,18R,19R,21R,23S,24E,26E,28E,30S,32S,35R)-12-[(1R)-2-[(1S,3R,4R)-4-[3-[tert-butyl(dimethyl)silyl]oxypropoxy]-3-methoxy-cyclohexyl]-1-methyl-ethyl]-1,18-dihydroxy-19,30-dimethoxy-15,17,21,23,29,35-hexamethyl-11,36-dioxa-4-azatricyclo[30.3.1.0^4,9]hexatriaconta-16,24,26,28-tetraene-2,3,10,14,20-pentone. 3-[tert-butyl(dimethyl)silyl]oxypropyl trifluoromethanesulfonate (0.212 g, 0.66 mmol) was added to a mixture of Sirolimus (200.0 mg, 0.22 mmol) and N-ethyl-N-isopropyl-propan-2-amine (0.17 mL, 1.2 mmol) previously dissolved in dry Toluene (0.8 mL) under argon. After 2 hours of stirring at 60° C., the crude mixture was concentrated and purified on silica gel by flash column chromatography (Cyclohexane/Ethylacetate 100:0 to 70:30) to afford the desired product as an amorphous white solid (103.6 mg). Yield 42%.

Step B: Preparation of (1R,9S,12S,15R,16E,18R,19R,21R,23S,24E,26E,28E,30S,32S,35R)-1,18-dihydroxy-12-[(1R)-2-[(1S,3R,4R)-4-(3-hydroxypropoxy)-3-methoxy-cyclohexyl]-1-methyl-ethyl]-19,30-dimethoxy-15,17,21,23,29,35-hexamethyl-11,36-dioxa-4-azatricyclo[30.3.1.0^4,9]hexatriaconta-16,24,26,28-tetraene-2,3,10,14,20-pentone (Compound 323). (1R,9S,12S,15R,16E,18R,19R,21R,23S,24E,26E,28E,30S,32S,35R)-12-[(1R)-2-[(1S,3R,4R)-4-[3-[tert-butyl(dimethyl)silyl]oxypropoxy]-3-methoxy-cyclohexyl]-1-methyl-ethyl]-1,18-dihydroxy-19,30-dimethoxy-15,17,21,23,29,35-hexamethyl-11,36-dioxa-4-azatricyclo[30.3.1.0^4,9]hexatriaconta-16,24,26,28-tetraene-2,3,10,14,20-pentone (103.6 mg, 0.1 mmol) was dissolved in Methanol (0.1 mL) and cooled to 0° C. Aqueous 1M hydrogen chloride (0.05 mL, 0.05 mmol) was added and the mixture stirred for 30 min at 0° C. The reaction mixture was diluted with DCM then neutralized with NaHCO$_3$ sat to pH=8. The two phases were separated and the aqueous phase was extracted with DCM. The organic phases were combined, concentrated and purified on silica gel by flash column chromatography (Cyclohexan/Ethylacetate 100:0 to 40:60) to afford the desired product Compound 323 as an amorphous white solid (73.6 mg). Yield 79%. 1H NMR (600 MHz, DMSO-d6): δ (ppm) 6.44 (d, J=1.0 Hz, 1H), 6.40 (br dd, J=14.5, 11.3 Hz, 1H), 6.22 (br dd, J=14.5, 10.7 Hz, 1H), 6.08-6.16 (m, 2H), 5.46 (dd, J=14.9, 9.6 Hz, 1H), 5.25 (br d, J=4.4 Hz, 1H), 5.09 (br d, J=10.0 Hz, 1H), 4.98 (dt, J=7.7, 4.0 Hz, 1H), 4.94 (br d, J=5.4 Hz, 1H), 4.29 (t, J=5.1 Hz, 1H), 3.98-4.05 (m, 2H), 3.94 (d, J=4.7 Hz, 1H), 3.62 (br dd, J=11.7, 2.0 Hz, 1H), 3.54-3.59 (m, 1H), 3.41-3.51 (m, 4H), 3.32 (s, 3H), 3.26-3.29 (m, 1H), 3.17-3.22 (m, 1H), 3.16 (s, 3H), 3.05 (s, 3H), 2.92-3.00 (m, 2H), 2.73 (br dd, J=17.5, 2.4 Hz, 1H), 2.35-2.45 (m, 2H), 2.18-2.27 (m, 1H), 2.09 (br d, J=13.6 Hz, 1H), 2.00-2.07 (m, 1H), 1.81-1.98 (m, 4H), 1.74 (s, 3H), 1.51-1.69 (m, 11H), 1.37-1.45 (m, 2H), 0.96-1.31 (m, 12H), 0.87 (br d, J=6.5 Hz, 3H), 0.83 (br d, J=6.3 Hz, 3H), 0.81-0.84 (m, 1H), 0.77 (br d, J=6.7 Hz, 3H), 0.73 (br d, J=6.6 Hz, 3H), 0.61-0.68 (m, 1H).

Certain compounds of Table 2 or 4 with hydroxyalkyloxy moieties at C40 can be prepared starting with sirolimus or a C16 modified form of sirolimus following Scheme 5 and employing alternative alkylating agents in Step A to those described in Example 5.

C16 Modifications

Compounds prepared following the procedures described below result in a mixture of diastereomers at the C16 stereocenter. The ratio of diastereomers can vary from a large excess of one diastereomer to the other to a racemic mixture of diastereomers. The diastereomic products of the procedures were not isolated prior to testing in Example 12.

Scheme 6

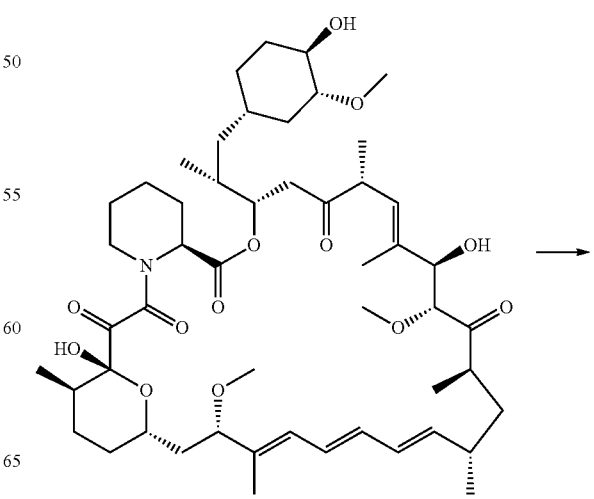

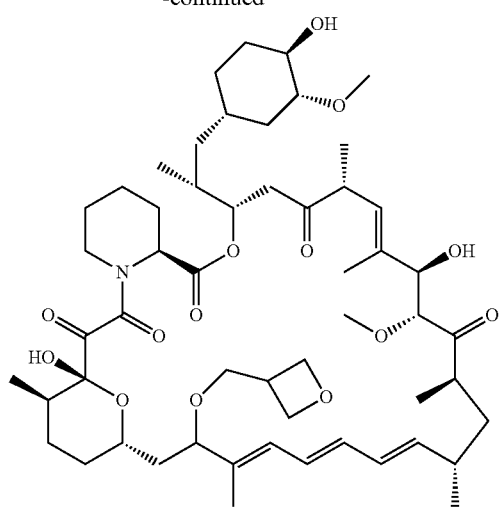

Example 6

Preparation of (1R,9S,12S,15R,16E,18R,19R,21R,23S, 24E,26E,28E,32S,35R)-1,18-dihydroxy-12-[(1R)-2-[(1S, 3R,4R)-4-hydroxy-3-methoxy-cyclohexyl]-1-methyl-ethyl]-19-methoxy-15,17,21,23,29,35-hexamethyl-30-(oxetan-3-ylmethoxy)-11,36-dioxa-4-azatricyclo [30.3.1.0^4,9]hexatriaconta-16,24,26,28-tetraene-2,3,10,14, 20-pentone (Compound 215). Sirolimus (150.0 mg, 0.16 mmol) was dissolved in DCM (6.5 mL) with oxetan-3-ylmethanol (602.611 mg, 6.5 mmol) and mixture was cooled to −40° C. Para-toluenesulfonic acid (138.45 mg, 0.8 mmol) were added under vigorous stirring and the reaction mixture stirred at 0° C. for 1 h. The reaction mixture was diluted with DCM (30 mL) and quenched with saturated NaHCO$_3$ aq (10 mL). The mixture was diluted with DCM, and the organics were washed with NaHCO$_3$ saturated solution, brine, and passed through a phase separator to remove water. The obtained residue was purified by reverse phase C18 preparative HPLC (gradient water/ACN from 90/10 to 0/100) to afford the desired product Compound 215 as a white amorphous solid (42.8 mg). Yield 24.5%. 1H NMR (600 MHz, DMSO-d6) δ 6.45 (s, 1H), 6.41 (dd, J=14.6, 11.1 Hz, 2H), 6.26-6.09 (m, 3H), 5.47 (dd, J=14.9, 9.6 Hz, 1H), 5.24 (d, J=4.4 Hz, 1H), 5.09 (d, J=10.2 Hz, 1H), 5.01-4.96 (m, 1H), 4.94 (d, J=5.5 Hz, 1H), 4.63-4.55 (m, 3H), 4.26 (ddt, J=7.8, 5.9, 3.1 Hz, 2H), 4.06-3.97 (m, 2H), 3.90 (dd, J=25.2, 4.8 Hz, 1H), 3.81-3.67 (m, 1H), 3.49-3.36 (m, 2H), 3.35-3.24 (m, 5H), 3.28-3.00 (m, 6H), 2.87-2.70 (m, 2H), 2.43-2.36 (m, 2H), 2.33-1.79 (m, 7H), 1.74 (s, 3H), 1.70-1.48 (m, 9H), 1.46-1.10 (m, 8H), 1.10-0.69 (m, 18H), 0.67-0.53 (m, 1H).

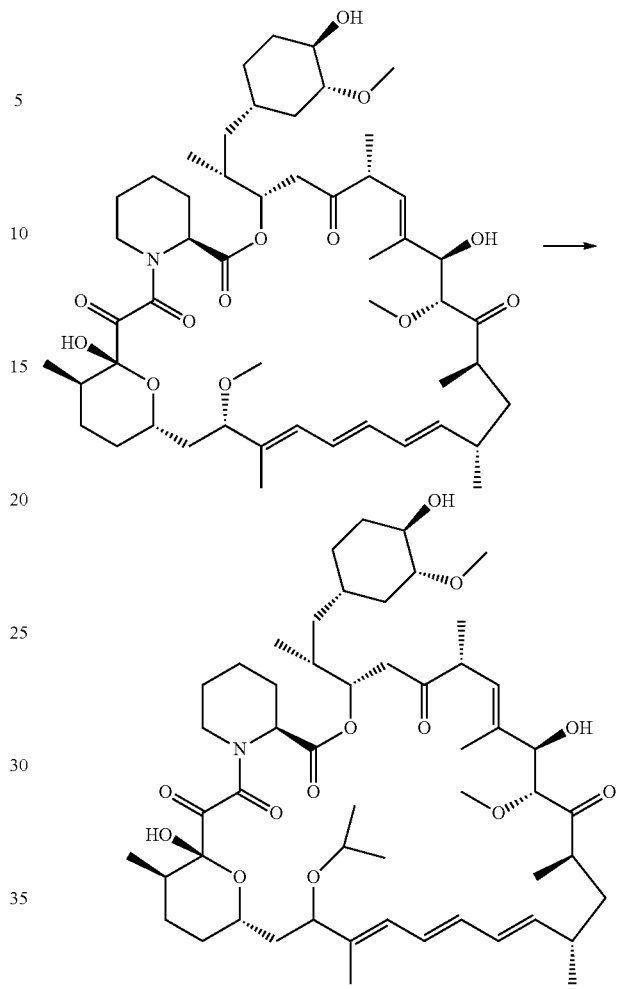

Preparation of (1R,9S,12S,15R,16E,18R,19R,21R,23S, 24E,26E,28E,32S,35R)-1,18-dihydroxy-12-[(1R)-2-[(1S, 3R,4R)-4-hydroxy-3-methoxy-cyclohexyl]-1-methyl-ethyl]-30-isopropoxy-19-methoxy-15,17,21,23,29,35-hexamethyl-11,36-dioxa-4-azatricyclo[30.3.1.0^4,9] hexatriaconta-16,24,26,28-tetraene-2,3,10,14,20-pentone (Compound 208). Sirolimus (150.0 mg, 0.16 mmol) was dissolved in DCM (6.5 mL) and 2-propanol (4.5 mL) at room temperature. Para-toluenesulfonic acid (92.3 mg, 0.54 mmol) was added under vigorous stirring and the reaction mixture stirred for 3 h. The reaction mixture was diluted with EtOAc. The organics were washed with saturated NaHCO$_3$aq and bine, dried over Na2SO4. The solvents were removed and The crude material was purified with flash column chromatography eluting 0-100% Acetone in DCM to afford the desired product Compound 208 as a white amorphous solid (8.3 mg). Yield 8%. 1H NMR (600 MHz, DMSO-d6, 300K) δ ppm 6.44 (br s, 1H), 6.39 (br dd, J=14.8, 11.3 Hz, 1H), 6.08-6.24 (m, 2H), 5.45 (br dd, J=14.7, 9.7 Hz, 1H), 5.09 (br d, J=10.3 Hz, 1H), 4.95-5.01 (m, 1H), 4.89-4.94 (m, 1H), 3.80-4.13 (m, 5H), 3.36-3.47 (m, 4H), 3.07-3.30 (m, 7H), 2.68-2.89 (m, 2H), 2.33-2.41 (m, 1H), 0.69-2.29 (m, 55H), 0.51-0.65 (m, 1H).

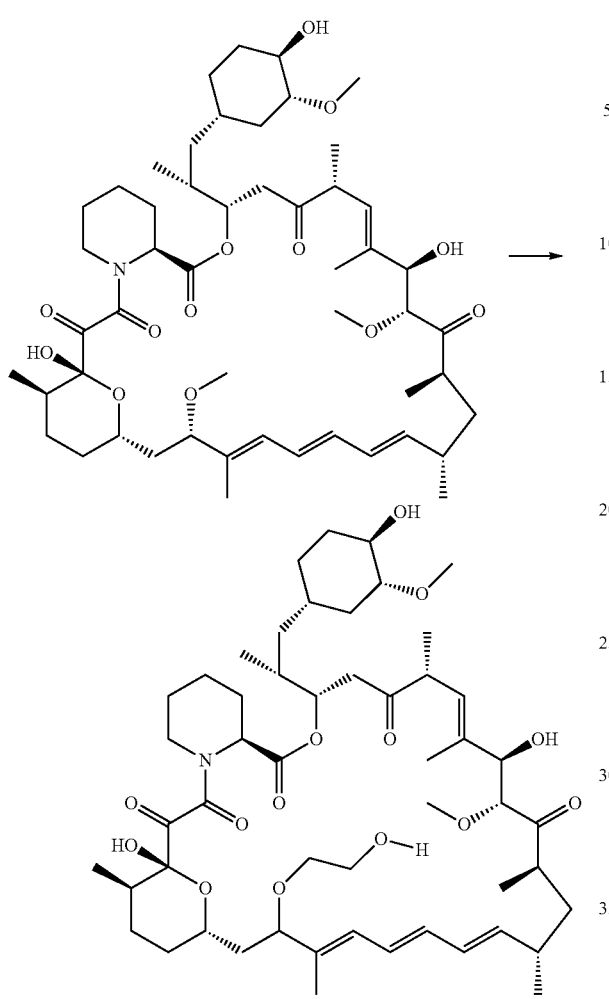

Preparation of (1R,9S,12S,15R,16E,18R,19R,21R,23S, 24E,26E,28E,32S,35R)-1,18-dihydroxy-30-(2-hydroxyethoxy)-12-[(1R)-2-[(1S,3R,4R)-4-hydroxy-3-methoxy-cyclohexyl]-1-methyl-ethyl]-19-methoxy-15,17,21,23,29,35-hexamethyl-11,36-dioxa-4-azatricyclo[30.3.1.0^4,9]hexatriaconta-16,24,26,28-tetraene-2,3,10,14,20-pentone (Compound 219).

Sirolimus (300 mg, 0.328 mmol) was dissolved in DCM (2.7723 mL) at room temperature and ethylene glycol was added (6.7 mL, 0.120 mol). Para-toluenesulfonic acid (283 mg, 1.64 mmol) was added under vigorous stirring and the reaction mixture stirred for 2.5 h. The reaction mixture quenched with saturated NaHCO₃aq., washed with brine, and passed through a phase separator to remove water. The obtained residue was purified by reverse phase $C_{18}$ preparative HPLC (gradient water/ACN from 90/10 to 0/100) to afford the desired product Compound 219 as a white amorphous solid (69.9 mg). Yield 20.5%. 1H NMR (600 MHz, DMSO-d6) δ 6.43 (d, J=1.5 Hz, 1H), 6.40 (dd, J=14.8, 11.2 Hz, 1H), 6.26-6.04 (m, 3H), 5.46 (dd, J=14.9, 9.6 Hz, 1H), 5.24 (d, J=4.5 Hz, 1H), 5.09 (d, J=10.2 Hz, 1H), 5.02-4.96 (m, 1H), 4.93 (d, J=6.1 Hz, 1H), 4.59-4.54 (m, 1H), 4.53-4.47 (m, 1H), 4.11-3.96 (m, 2H), 3.94 (d, J=4.7 Hz, 1H), 3.78 (d, J=13.8 Hz, 1H), 3.52-3.36 (m, 3H), 3.36-3.09 (m, 11H), 2.87-2.78 (m, 1H), 2.73 (d, J=15.1 Hz, 1H), 2.45-2.30 (m, 2H), 2.21 (s, 1H), 2.16-1.82 (m, 5H), 1.82-0.90 (m, 27H), 0.87 (d, J=6.6 Hz, 3H), 0.83 (q, J=7.6, 6.7 Hz, 4H), 0.78 (d, J=6.8 Hz, 3H), 0.73 (d, J=6.7 Hz, 3H), 0.60 (q, J=11.9 Hz, 1H).

Certain compounds of Table 3 or 4 can be prepared starting with sirolimus or a C40 modified form of sirolimus following Scheme 6 and employing alternative reagents to those described in Example 6.

C16/C40 Combination of Modifications

Scheme 7

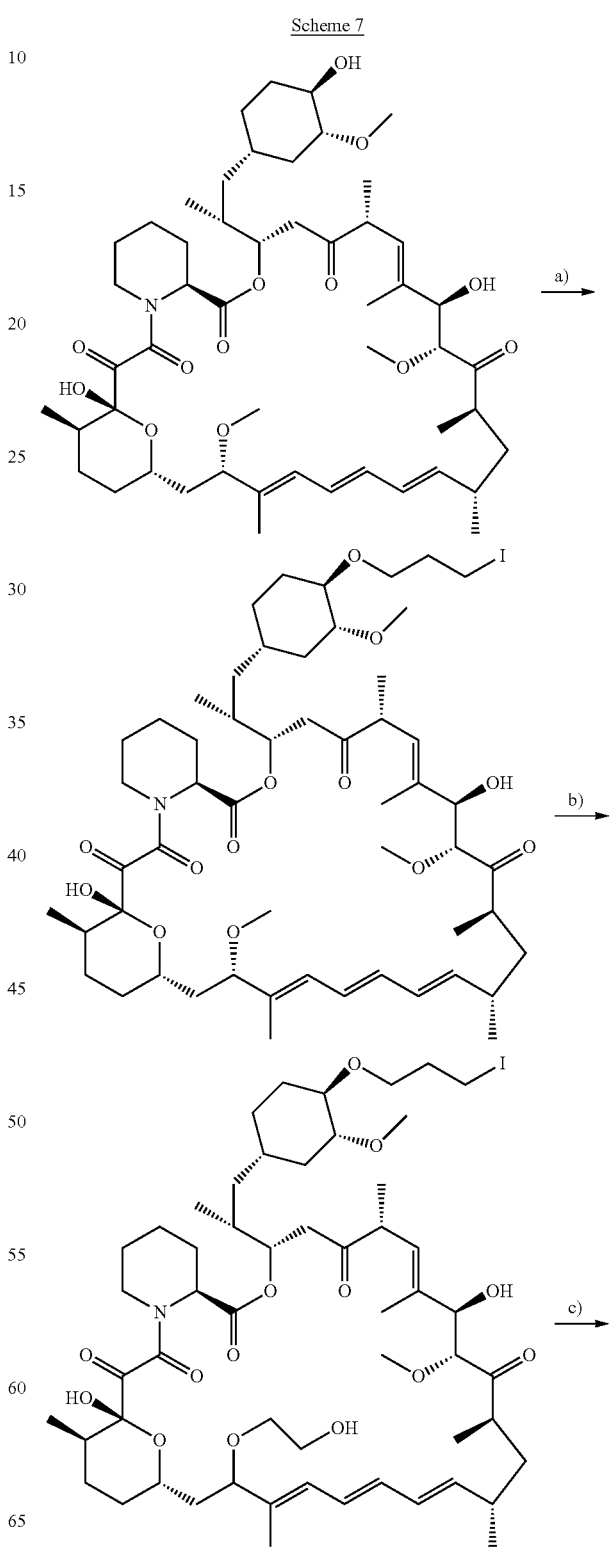

-continued

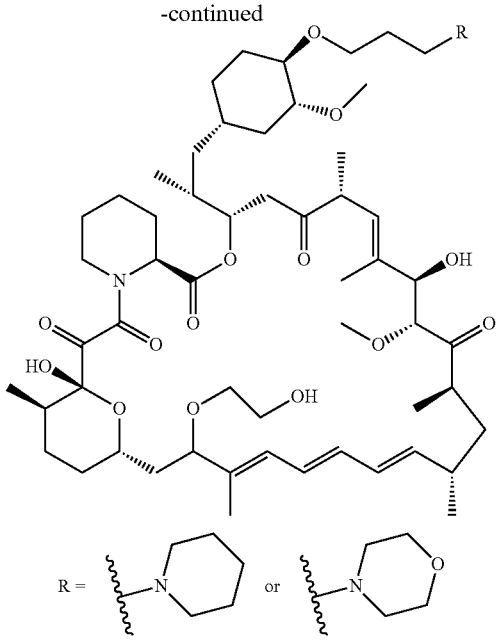

Example 7

Step A: Preparation of (1R,9S,12SR,15R,16E,18R,19R, 21R,23S,24E,26E,28E,30S,32SR,35R)-1,18-dihydroxy-12-[(1R)-2-[(1S,3R,4R)-4-(3-iodopropoxy)-3-methoxy-cyclohexyl]-1-methyl-ethyl]-19,30-dimethoxy-15,17,21,23,29, 35-hexamethyl-11,36-dioxa-4-azatricyclo[30.3.1.0^4,9] hexatriaconta-16,24,26,28-tetraene-2,3,10,14,20-pentone. 3-iodopropyl trifluoromethanesulfonate (2.714 g, 8.53 mmol) was added to a mixture of Sirolimus (2.60 g, 2.84 mmol) and N-ethyl-N-isopropyl-propan-2-amine (2.7 mL, 15.6 mmol) previously dissolved in dry Toluene (10.342 mL) under argon. After 1.5 hours of stirring at 60° C., the reaction mixture was cooled to RT, diluted with DCM and directly deposited onto silica. The solvents were evaporated to give a dry sample which was then and purified on silica gel by flash column chromatography (Cy/EtOAc; Gradient: 100: to 77:23) to afford the desired product as an amorphous white solid (1.56 g). Yield 49.7%.

Step B: Preparation of 1R,9S,12SR,15R,16E,18R,19R, 21R,23S,24E,26E,28E,32S,35R)-1,18-dihydroxy-30-(2-hydroxyethoxy)-12-[(1R)-2-[(1S,3R,4R)-4-(3-iodopropoxy)-3-methoxy-cyclohexyl]-1-methyl-ethyl]-19-methoxy-15,17, 21,23,29,35-hexamethyl-11,36-dioxa-4-azatricyclo [30.3.1.0^4,9]hexatriaconta-16,24,26,28-tetraene-2,3,10,14, 20-pentone. (1R,9S,12SR,15R,16E,18R,19R,21R,23S,24E, 26E,28E,30S,32SR,35R)-1,18-dihydroxy-12-[(1R)-2-[(1S, 3R,4R)-4-(3-iodopropoxy)-3-methoxy-cyclohexyl]-1-methyl-ethyl]-19,30-dimethoxy-15,17,21,23,29,35-hexamethyl-11,36-dioxa-4-azatricyclo[30.3.1.0^4,9] hexatriaconta-16,24,26,28-tetraene-2,3,10,14,20-pentone (600 mg, 0.554 mmol) was dissolved in in anhydrous DCM (6.8083 mL). Ethylene glycol (11 mL, 0.203 mol) then 4-methylbenzenesulfonic acid (477 mg, 2.77 mmol) were added and mixture was stirred at RT for 3.5 h. The reaction mixture was quenched with saturated NaHCO3aq. The organic phase was washed with NaCl, passed through a phase separator, then concentrated to dryness to give a pale yellow foam (760 mg). The obtained residue was purified by reverse phase C18 preparative HPLC (EluentH2O/ACN; Gradient: 30:70 to 0:100) to afford the desired product as a white amorphous solid (98 mg). Yield 15%.

Step C: Preparation of (1R,9S,12S,15R,16E,18R,19R, 21R,23S,24E,26E,28E,32S,35R)-1,18-dihydroxy-30-(2-hydroxyethoxy)-19-methoxy-12-[(1R)-2-[(1S,3R,4R)-3-methoxy-4-[3-(1-piperidyl)propoxy]cyclohexyl]-1-methyl-ethyl]-15,17,21,23,29,35-hexamethyl-11,36-dioxa-4-azatricyclo[30.3.1.0^4,9]hexatriaconta-16,24,26,28-tetraene-2,3,10,14,20-pentone (Compound 87). Piperidine (0.010 mL, 0.106 mmol) was added to a solution of N-ethyl-N—isopropyl-propan-2-amine (0.046 mL, 0.264 mmol) and (1R,9S,12SR,15R,16E,18R,19R,21R,23S,24E,26E, 28E, 30S,32S,35R)-1,18-dihydroxy-30-(2-hydroxyethoxy)-12-[(1R)-2-[(1S,3R,4R)-4-(3-iodopropoxy)-3-methoxy-cyclohexyl]-1-methyl-ethyl]-19-methoxy-15,17,21,23,29,35-hexamethyl-11,36-dioxa-4-azatricyclo[30.3.1.0^4,9] hexatriaconta-16,24,26,28-tetraene-2,3,10,14,20-pentone (98 mg, 0.0881 mmol) in dry DCM (0.5507 mL). After 4 hours of stirring at room temperature under argon, the reaction mixture was diluted with DCM and quenched with HCl 1N (pH=4-5). The organic phase was washed with H2O, passed through a phase separator. The solution was deposited directly onto silica and the solvent was removed to give a dry sample which was then purified on silica gel by flash column chromatography (Eluent A=Ethylacetate Eluent B=MeOH:Et3N (50:50) Gradient: A/B from 100/0 to 70:30) to afford the desired product Compound 87 as an amorphous white solid (29.8 mg). Yield 30%.

Alternative Step C: Preparation of (1R,9S,12S,15R,16E, 18R,19R,21R,23S,24E,26E,28E,32S,35R)-1,18-dihydroxy-30-(2-hydroxyethoxy)-19-methoxy-12-[(1R)-2-[(1S,3R, 4R)-3-methoxy-4-(3-morpholinopropoxy)cyclohexyl]-1-methyl-ethyl]-15,17,21,23,29,35-hexamethyl-11,36-dioxa-4-azatricyclo[30.3.1.0^4,9]hexatriaconta-16,24,26,28-tetraene-2,3,10,14,20-pentone (Compound 55). Morpholine (0.0070 mL, 0.0806 mmol) was added to a solution of N-ethyl-N-isopropyl-propan-2-amine (0.035 mL, 0.201 mmol) and 1R,9S,12SR,15R,16E,18R,19R,21R,23S, 24E, 26E,28E,30S,32SR,35R)-1,18-dihydroxy-30-(2-hydroxyethoxy)-12-[(1R)-2-[(1S,3R,4R)-4-(3-iodopropoxy)-3-methoxy-cyclohexyl]-1-methyl-ethyl]-19-methoxy-15,17, 21,23,29,35-hexamethyl-11,36-dioxa-4-azatricyclo [30.3.1.0^4,9]hexatriaconta-16,24,26,28-tetraene-2,3,10,14, 20-pentone (75 mg, 0.0672 mmol) in dry DCM (0.4 mL). After 7.5 hours of stirring at room temperature under argon, the reaction mixture was diluted with DCM and acidified with HCl 1N to pH=5. The organic phase was washed with H2O, passed through a phase separator and deposited directly onto silica. The solvent was removed to give a crude residue which was then purified on silica gel by flash column chromatography (Eluent A=Ethylacetate Eluent B=MeOH: Et3N (50:50) Gradient: A/B from 100/0 to 80:20) to afford the desired product Compound 55 as an amorphous white solid (18.6 mg). Yield 24%. 1H NMR (DMSO, 500 MHz): δ (ppm) 6.44 (s, J=1.4 Hz, 1H), 6.40 (dd, J=14.5, 11.1 Hz, 1H), 6.24-6.07 (m, 3H), 5.46 (dd, J=14.8, 9.6 Hz, 1H), 5.26 (d, J=4.6 Hz, 1H), 5.09 (d, J=10.1 Hz, 1H), 4.98 (dt, J=7.8, 3.8 Hz, 1H), 4.93 (d, J=5.0 Hz, 1H), 4.50 (td, J=5.4, 2.3 Hz, 1H), 4.06-3.99 (m, 2H), 3.93 (d, J=4.6 Hz, 1H), 3.77 (d, J=13.5 Hz, 1H), 3.45 (dt, J=8.2, 5.9 Hz, 4H), 3.31 (s, 2H), 3.28-3.12 (m, 5H), 2.98 (m, J=23.9, 8.9, 4.7 Hz, 2H), 2.73 (d, J=15.2 Hz, 1H), 2.45-2.34 (m, 2H), 2.32-2.20 (m, 7H), 2.12-1.99 (m, 2H), 1.91 (m, J=30.1, 16.6, 9.9 Hz, 5H), 1.73 (s, 3H), 1.68-0.90 (m, 34H), 0.85 (dd, J=21.1, 6.5 Hz, 7H), 0.75 (dd, J=21.1, 6.7 Hz, 6H), 0.69-0.59 (m, 1H)

Certain compounds of Table 2 can be prepared starting with sirolimus following Scheme 7 and employing alternative reagents in Steps A, B, and/or C to those described in Example 7.

Scheme 8

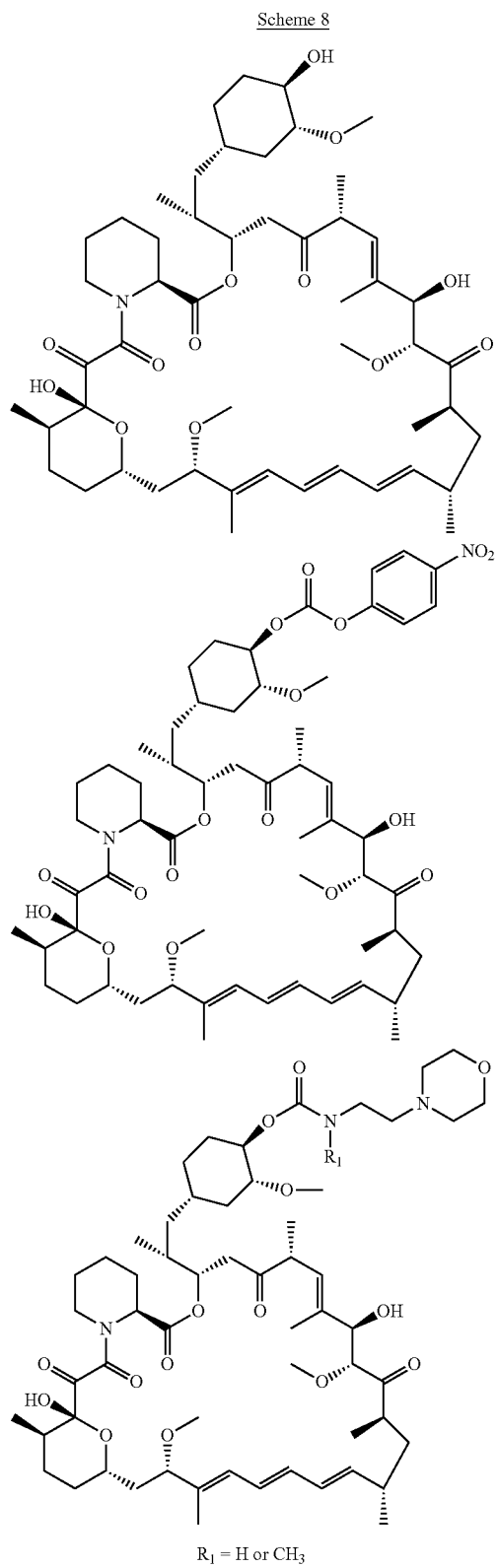

a)

b)

c)

$R_1$ = H or CH$_3$

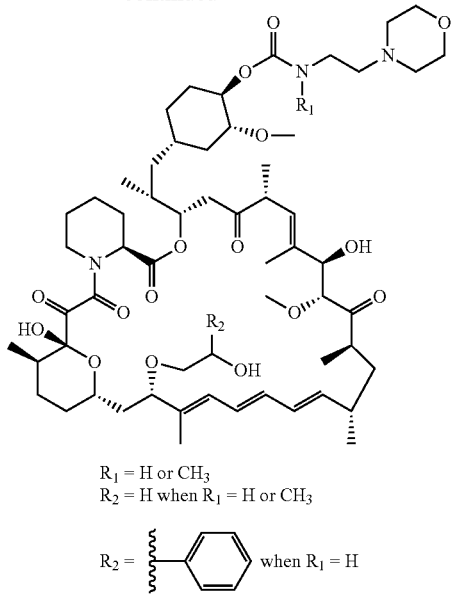

$R_1$ = H or CH$_3$
$R_2$ = H when $R_1$ = H or CH$_3$ $R_2$ = [phenyl group] when $R_1$ = H Example 8

Step A: Follow the procedure in Example 1.

Step B: Preparation of [(1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^4,9]hexatriaconta-16,24,26,28-tetraen-12-yl]propyl]-2-methoxy-cyclohexyl] N-methyl-N-(2-morpholinoethyl)carbamate. [(1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^4,9]hexatriaconta-16,24,26,28-tetraen-12-yl]propyl]-2-methoxy-cyclohexyl](4-nitrophenyl) carbonate (500.0 mg, 0.46 mmol) was dissolved anhydrous dimethylformamide (10 mL) and triethylamine (129 uL, 0.93 mmol). The N-methyl-2-(morpholin-4-yl)ethanamine (134 mg, 0.926 mmol) was added dropwise at −20° C. under atmosphere of nitrogen. After 1 hours of stirring at −20° C., ethylacetate was added, the organic phases were separated and washed with water twice. The organics were combined and concentrated to dryness. The crude residue was purified on silica gel by flash column chromatography (0-10% of MeOH in DCM gradient) to afford the desired product (460 mg) as a white powder. Yield 91%.

Alternative Step B: Preparation of [(1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^4,9]hexatriaconta-16,24,26,28-tetraen-12-yl]propyl]-2-methoxy-cyclohexyl] N-(2-morpholinoethyl)carbamate. [(1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^4,9]hexatriaconta-16,24,26,28-tetraen-12-yl]propyl]-2-methoxy-cyclohexyl](4-nitrophenyl) carbonate (600.0 mg, 0.56 mmol) was dissolved anhydrous dimethylformamide (12.3 mL) and triethylamine (0.15 mL, 1.11 mmol). The 2-morpholinoethanamine (144.753 mg, 1.11 mmol) was added dropwise at −20° C. under atmosphere of nitrogen. After 2 hours of stirring at −20° C., ethylacetate was added, the organic phases were separated and washed with water twice. The organics were combined and concentrated to dryness. The crude residue was purified on silica gel by flash column chromatography (0-10% of MeOH in DCM gradient) to afford the desired product (510 mg) as a white powder. Yield 86%.

Step C: Preparation of [(1R,2R,4S)-4-[(2R)-2-[(1R,9S, 12S,15R,16E,18R,19R,21R,23S,24E,26E,28E,32S,35R)-1, 18-dihydroxy-30-(2-hydroxyethoxy)-19-methoxy-15,17,21, 23,29,35-hexamethyl-2,3,10,14,20-pentaoxo-11,36-dioxa-4-azatricyclo[30.3.1.0^4,9]hexatriaconta-16,24,26,28-tetraen-12-yl]propyl]-2-methoxy-cyclohexyl] N-methyl-N-(2-morpholinoethyl)carbamate (Compound 41). [(1R,2R, 4S)-4-[(2R)-2-[(1R,9S,12S,15R,16E,18R,19R,21R,23S, 24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^4,9] hexatriaconta-16,24,26,28-tetraen-12-yl]propyl]-2-methoxy-cyclohexyl]N-methyl-N-(2-morpholinoethyl) carbamate (230 mg, 0.212 mmol) was dissolved in DCM-Anhydrous (1.5 mL) and ethylene glycol (4.6 mL, 77.6 mmol) was added. Then 4-methylbenzenesulfonic acid (183 mg, 1.06 mmol) was added and the mixture was stirred under argon at r.t. for 1 h25. The crude mixture with DCM and and quenched with saturated NaHCO₃ aq. Then the mixture was extracted with DCM. The organic layer was dried under a separator phase, then concentrated to dryness. The obtained residue was purified by reverse phase $C_{18}$ preparative HPLC to afford the desired product Compound 41 as a white amorphous solid (29.8 mg). Yield 12.4%.

Alternative Step C: Preparation of [(1R,2R,4S)-4-[(2R)-2-[(1R,9S,12S,15R,16E,18R,19R,21R,23S,24E,26E,28E, 32S,35R)-1,18-dihydroxy-30-[(2S)-2-hydroxy-2-phenyl-ethoxy]-19-methoxy-15,17,21,23,29,35-hexamethyl-2,3,10, 14,20-pentaoxo-11,36-dioxa-4-azatricyclo[30.3.1.0^4,9] hexatriaconta-16,24,26,28-tetraen-12-yl]propyl]-2-methoxy-cyclohexyl] N-(2-morpholinoethyl)carbamate. [(1R,2R,4S)-4-[(2R)-2-[(1R,9S,12S,15R,16E,18R,19R, 21R,23S,24E,26E,28E,30S,32S,35R)-1,18-dihydroxy-19, 30-dimethoxy-15,17,21,23,29,35-hexamethyl-2,3,10,14,20-pentaoxo-11,36-dioxa-4-azatricyclo[30.3.1.0^4,9] hexatriaconta-16,24,26,28-tetraen-12-yl]propyl]-2-methoxy-cyclohexyl] N-(2-morpholinoethyl)carbamate (350 mg, 0.327 mmol) was dissolved in DCM-Anhydrous (13 mL) at −20° C. under argon and (1S)-1-phenylethane-1,2-diol (1.79 g, 12.9 mmol) was added. Then 4-methylbenzenesulfonic acid (276 mg, 1.60 mmol) was added and the mixture was stirred under argon at r.t. for 3 h30. The crude mixture with DCM and and quenched with saturated NaHCO₃aq. Then the mixture was extracted with DCM. The organic layer was dried under a separator phase, then concentrated to dryness. The obtained residue was purified by reverse phase C18 preparative HPLC to afford the desired product as a white amorphous solid (57.8 mg). Yield 13.1%.

Certain compounds of Table 2 can be prepared starting with sirolimus following Scheme 8 and employing alternative reagents in Steps A, B, and/or C to those described in Example 8.

Scheme 9

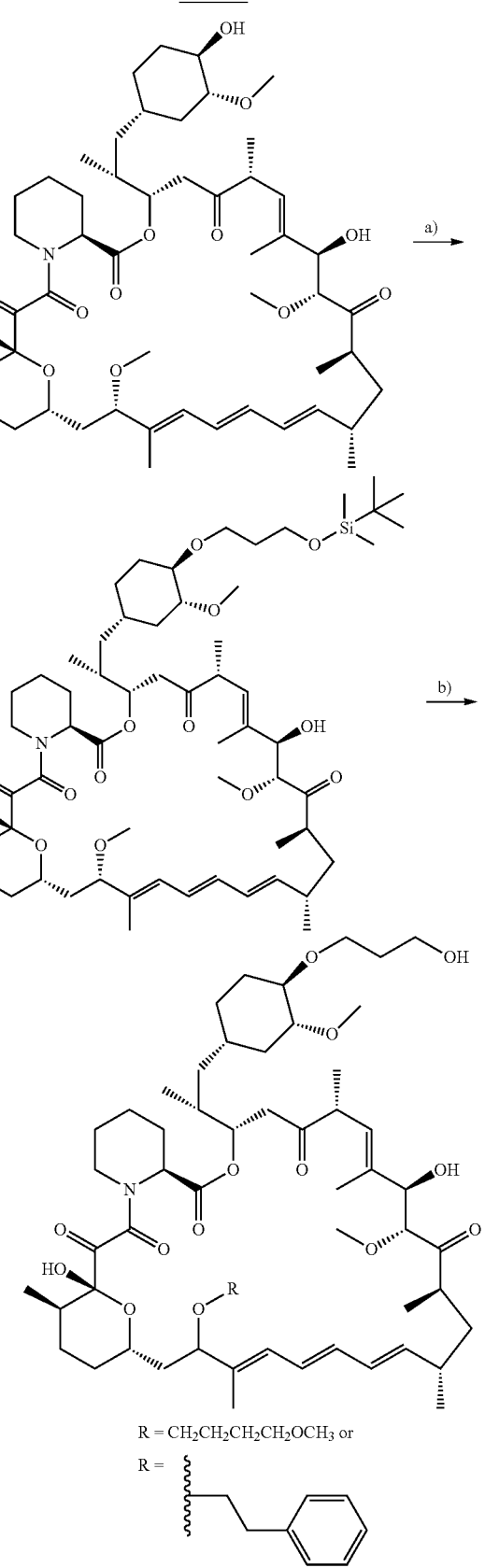

R = CH₂CH₂CH₂CH₂OCH₃ or

R =

Example 9

Step A: Preparation of (1R,9S,12S,15R,16E,18R,19R,21R,23S,24E,26E,28E,30S,32S,35R)-12-[(1R)-2-[(1S,3R,4R)-4-[3-[tert-butyl(dimethyl)silyl]oxypropoxy]-3-methoxy-cyclohexyl]-1-methyl-ethyl]-1,18-dihydroxy-19,30-dimethoxy-15,17,21,23,29,35-hexamethyl-11,36-dioxa-4-azatricyclo[30.3.1.0^4,9] hexatriaconta-16,24,26,28-tetraene-2,3,10,14,20-pentone. 3-[tert-butyl(dimethyl)silyl]oxypropyl trifluoromethanesulfonate (1799 mg, 5.58 mmol) was added to a mixture of Sirolimus (1.7 g, 1.86 mmol) and N-ethyl-N-isopropyl-propan-2-amine (1.8 mL, 10.2 mmol) previously dissolved in dry Toluene (6.9 mL) under argon. After 3 hours of stirring at 60° C., the crude mixture was concentrated and purified on silica gel by flash column chromatography (Cyclohexane/Ethylacetate 100:0 to 70:30) to afford the desired product as an amorphous white solid (799 mg). Yield 39%.

Step B: Preparation of (1R,9S,12SR,15R,16E,18R,19R,21R,23S,24E,26E,28E,32S,35R)-1,18-dihydroxy-12-[(1R)-2-[(1S,3R,4R)-4-(3-hydroxypropoxy)-3-methoxy-cyclohexyl]-1-methyl-ethyl]-19-methoxy-15,17,21,23,29,35-hexamethyl-30-(2-phenylethoxy)-11,36-dioxa-4-azatricyclo[30.3.1.0^4,9]hexatriaconta-16,24,26,28-tetraene-2,3,10,14,20-pentone (Compound 94). A mixture of (1R,9S,12SR,15R,16E,18R,19R,21R,23S,24E,26E,28E,30S,32S,35R)-12-[(1R)-2-[(1S,3R,4R)-4-[3-[tert-butyl(dimethyl)silyl]oxypropoxy]-3-methoxy-cyclohexyl]-1-methyl-ethyl]-1,18-dihydroxy-19,30-dimethoxy-15,17,21,23,29,35-hexamethyl-11,36-dioxa-4-azatricyclo[30.3.1.0^4,9]hexatriaconta-16,24,26,28-tetraene-2,3,10,14,20-pentone (250 mg, 0.230 mmol) 2-phenylethanol (1.1 mL, 9.11 mmol) in DCM (9.2 ml) was cooled to −20° C. 4-methylbenzenesulfonic acid (198 mg, 1.15 mmol) was added and the RM was stirred for 1 h45 from −20° C. to 10° C. The reaction mixture was diluted with DCM then quenched with saturated NaHCO₃ aq. The 2 phases were separated and the organic phase was washed with H2O, passed through a phase separator phase and combined. The organic layer was dried under a separator phase, then concentrated to dryness. The residue was purified by reverse phase C18 preparative HPLC to afford the desired product as a white amorphous solid (76.5 mg). Yield 31%. 1H NMR (600 MHz, DMSO-d6, 300K) δ ppm 7.08-7.34 (m, 5H), 6.40 (d, J=1.3 Hz, 1H), 6.37 (br dd, J=14.6, 11.1 Hz, 1H), 6.19 (br dd, J=14.6, 10.6 Hz, 1H), 6.06-6.14 (m, 2H), 5.45 (br dd, J=14.9, 9.6 Hz, 1H), 5.24 (d, J=4.5 Hz, 1H), 5.08 (br d, J=10.0 Hz, 1H), 4.94-4.98 (m, 1H), 4.93 (d, J=5.1 Hz, 1H), 4.28-4.31 (m, 1H), 3.95-4.02 (m, 2H), 3.93 (d, J=4.5 Hz, 1H), 3.73 (br dd, J=11.7, 2.1 Hz, 1H), 3.51-3.60 (m, 2H), 3.40-3.51 (m, 5H), 3.32 (s, 3H), 3.22-3.27 (m, 1H), 3.07-3.22 (m, 4H), 2.86-3.06 (m, 2H), 2.71-2.85 (m, 3H), 2.32-2.44 (m, 2H), 2.17-2.25 (m, 1H), 1.75-2.12 (m, 5H), 1.73 (s, 3H), 1.48-1.70 (m, 13H), 1.35-1.48 (m, 3H), 1.20-1.34 (m, 3H), 0.88-1.19 (m, 7H), 0.59-0.87 (m, 14H)

Alternative Step B: Preparation of (1R,9S,12S,15R,16E,18R,19R,21R,23S,24E, 26E,28E,32S,35R)-1,18-dihydroxy-12-[(1R)-2-[(1S,3R,4R)-4-(3-hydroxypropoxy)-3-methoxy-cyclohexyl]-1-methyl-ethyl]-19-methoxy-30-(4-methoxybutoxy)-15,17,21,23,29,35-hexamethyl-11,36-dioxa-4-azatricyclo[30.3.1.0^4,9]hexatriaconta-16,24,26,28-tetraene-2,3,10,14,20-pentone (Compound 70). A mixture of 1R,9S,12S,15R,16E,18R,19R,21R,23S,24E,26E,28E,30S,32S,35R)-12-[(1R)-2-[(1S,3R,4R)-4-[3-[tert-butyl(dimethyl)silyl]oxypropoxy]-3-methoxy-cyclohexyl]-1-methyl-ethyl]-1,18-dihydroxy-19,30-dimethoxy-15,17,21,23,29,35-hexamethyl-11,36-dioxa-4-azatricyclo[30.3.1.0^4,9]hexatriaconta-16,24,26,28-tetraene-2,3,10,14,20-pentone (250 mg, 0.230 mmol) in DCM (7 ml) and 4-methoxybutan-1-ol (0.97 g, 9.11 mmol) was cooled to −10° C. 4-methylbenzenesulfonic acid (198 mg, 1.15 mmol) was added and the RM was stirred for 3 h from −20° C. to 0° C. The reaction mixture was diluted with DCM then quenched with saturated NaHCO₃ aq. The 2 phases were separated and the organic phase was washed with H₂O, passed through a phase separator phase and combined. The organic layer was dried under a separator phase, then concentrated to dryness. The residue was purified by reverse phase C18 preparative HPLC to afford the desired product Compound 70 as a white amorphous solid (60.2 mg). Yield 23.8%. 1H NMR (600 MHz, DMSO-d6): δ (ppm) 6.44 (d, J=1.0 Hz, 1H), 6.36-6.42 (m, 1H), 6.17-6.24 (m, 1H), 6.08-6.16 (m, 1H), 5.45 (br dd, J=14.8, 9.5 Hz, 1H), 4.88-5.32 (m, 4H), 4.25-4.33 (m, 1H), 3.68-4.06 (m, 4H), 3.41-3.60 (m, 6H), 3.28-3.31 (m, 5H), 3.04-3.25 (m, 9H), 2.92-3.03 (m, 2H), 2.70-2.77 (m, 1H), 2.31-2.47 (m, 2H), 1.91-2.25 (m, 5H), 0.62-1.81 (m, 49H).

Certain compounds of Table 2 can be prepared starting with sirolimus following Scheme 9 and employing alternative reagents in Steps A and B to those described in Example 9.

Scheme 10

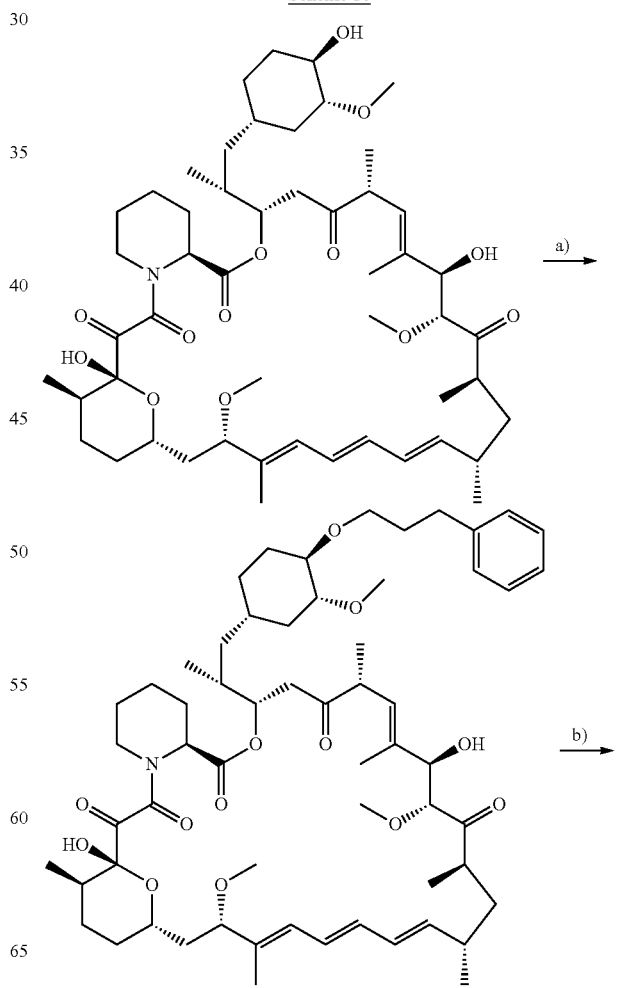

-continued

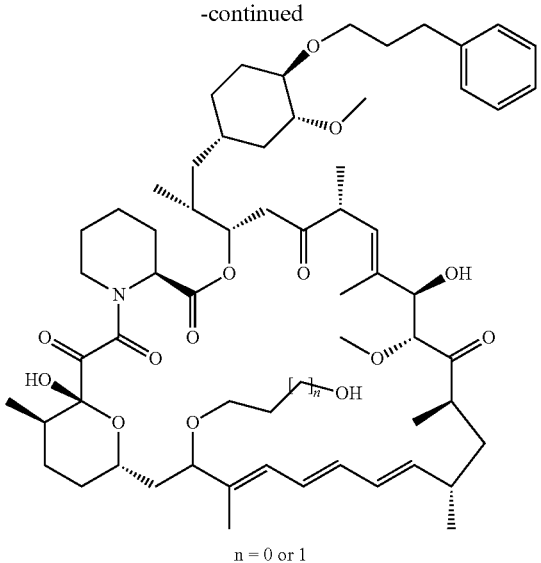

n = 0 or 1

Example 10

Step A: Preparation of (1R,9S,12S,15R,16E,18R,19R, 21R,23S,24E,26E,28E,30S,32S,35R)-1,18-dihydroxy-19, 30-dimethoxy-12-[(1R)-2-[(1S,3R,4R)-3-methoxy-4-(3-phenylpropoxy)cyclohexyl]-1-methyl-ethyl]-15,17,21,23, 29,35-hexamethyl-11,36-dioxa-4-azatricyclo[30.3.1.0^4,9] hexatriaconta-16,24,26,28-tetraene-2,3,10,14,20-pentone. 3-phenylpropyl trifluoromethanesulfonate (391 mg, 1.31 mmol) was added to a mixture of Sirolimus (400.0 mg, 0.44 mmol) and N-ethyl-N-isopropyl-propan-2-amine (0.42 mL, 2.41 mmol) previously dissolved in dry Toluene (1.6 mL) under argon. After 1.5 hours of stirring at 60° C., the crude mixture was concentrated and purified on silica gel by flash column chromatography (Cyclohexane/Ethylacetate 100:0 to 70:30) to afford the desired product as an amorphous white solid (283 mg). Yield 62.7%.

Step B: Preparation of (1R,9S,12SR,15R,16E,18R,19R, 21R,23S,24E,26E,28E,32SR,35R)-1,18-dihydroxy-30-(3-hydroxypropoxy)-19-methoxy-12-[(1R)-2-[(1S,3R,4R)-3-methoxy-4-(3-phenylpropoxy)cyclohexyl]-1-methyl-ethyl]-15,17,21,23,29,35-hexamethyl-11,36-dioxa-4-azatricyclo [30.3.1.0^4,9]hexatriaconta-16,24,26,28-tetraene-2,3,10,14, 20-pentone (Compound 67). A mixture of (1R,9S,12SR, 15R,16E,18R,19R,21R,23S,24E,26E,28E,30S,32SR,35R)-1,18-dihydroxy-19,30-dimethoxy-12-[(1R)-2-[(1S,3R,4R)-3-methoxy-4-(3-phenylpropoxy)cyclohexyl]-1-methyl-ethyl]-15,17,21,23,29,35-hexamethyl-11,36-dioxa-4-azatricyclo[30.3.1.0^4,9]hexatriaconta-16,24,26,28-tetraene-2,3,10,14,20-pentone (174.0 mg, 0.17 mmol) propane-1,3-diol (4.5 mL, 61.7 mmol) in DCM (1.7 ml) was cooled to −20° C. 4-methylbenzenesulfonic acid (145 mg, 0.843 mmol) was added and the RM was stirred for 3 h20 at RT. The reaction mixture was diluted with DCM then quenched with saturated NaHCO₃ aq. The 2 phases were separated. Then the mixture was extracted with DCM (X3). The organic phase was washed with H₂O, passed through a phase separator phase and combined. The organic layer was dried under a separator phase, then concentrated to dryness. The residue was purified by reverse phase C₁₈ preparative HPLC to afford the desired product Compound 67 as a white amorphous solid (43.2 mg). Yield 23.8%. 1H NMR (600 MHz, DMSO-d6) δ 7.31-7.23 (m, 2H), 7.23-7.11 (m, 3H), 6.44 (s, 1H), 6.39 (dd, J=14.7, 11.2 Hz, 1H), 6.24-6.04 (m, 3H), 5.45 (dd, J=14.9, 9.6 Hz, 1H), 5.25 (dd, J=10.5, 4.7 Hz, 1H), 5.09 (d, J=10.2 Hz, 1H), 5.06-4.95 (m, 1H), 4.93 (d, J=5.9 Hz, 1H), 4.34 (t, J=5.1 Hz, 1H), 4.05-3.97 (m, 2H), 3.94 (d, J=4.6 Hz, 1H), 3.72 (d, J=13.9 Hz, 1H), 3.56-3.33 (m, 8H), 3.29-3.08 (m, 7H), 3.06-2.94 (m, 2H), 2.73 (d, J=15.2 Hz, 1H), 2.67-2.56 (m, 2H), 2.45-2.26 (m, 2H), 2.21 (s, 1H), 2.14-1.34 (m, 24H), 1.34-0.90 (m, 12H), 0.86 (t, J=6.0 Hz, 3H), 0.83 (d, J=6.5 Hz, 4H), 0.78 (d, J=6.7 Hz, 3H), 0.76-0.71 (m, 3H), 0.71-0.60 (m, 1H).

Alternative Step B: Preparation of 1R,9S,12SR,15R,16E, 18R,19R,21R,23S,24E,26E,28E,32SR,35R)-1,18-dihydroxy-30-(2-hydroxyethoxy)-19-methoxy-12-[(1R)-2-[(1S, 3R,4R)-3-methoxy-4-(3-phenylpropoxy)cyclohexyl]-1-methyl-ethyl]-15,17,21,23,29,35-hexamethyl-11,36-dioxa-4-azatricyclo[30.3.1.0^4,9]hexatriaconta-16,24,26,28-tetraene-2,3,10,14,20-pentone (Compound 38). A mixture of (1R,9S,12SR,15R,16E,18R,19R,21R,23S,24E,26E,28E, 30S,32SR,35R)-1,18-dihydroxy-19,30-dimethoxy-12-[(1R)-2-[(1S,3R,4R)-3-methoxy-4-(3-phenylpropoxy)cyclohexyl]-1-methyl-ethyl]-15,17,21,23,29,35-hexamethyl-11,36-dioxa-4-azatricyclo[30.3.1.0^4,9]hexatriaconta-16, 24,26,28-tetraene-2,3,10,14,20-pentone (174.0 mg, 0.17 mmol) and ethylenglycol (3.4 mL, 61.7 mmol) in DCM (1.7 ml) at RT. 4-methylbenzenesulfonic acid (145 mg, 0.843 mmol) was added and the RM was stirred for 3 h20 at RT. The reaction mixture was diluted with DCM then quenched with saturated NaHCO₃aq. The 2 phases were separated. Then the mixture was extracted with DCM (X3). The organic phase was washed with H₂O, passed through a phase separator phase and combined. The organic layer was dried under a separator phase, combined, then concentrated to dryness. The residue was purified by reverse phase C₁₈ preparative HPLC to afford the desired product Compound 38 as a white amorphous solid (31.8 mg). Yield 17.8%. 1H NMR (DMSO, 600 MHz): δ (ppm) 7.27 (t, J=7.5 Hz, 2H), 7.22-7.11 (m, 3H), 6.43 (s, 1H), 6.40 (dd, J=14.6, 11.2 Hz, 1H), 6.28-6.04 (m, 3H), 5.46 (dd, J=14.9, 9.6 Hz, 1H), 5.25 (d, J=4.5 Hz, 1H), 5.10 (d, J=10.1 Hz, 1H), 4.98 (dt, J=8.0, 4.1 Hz, 1H), 4.93 (d, J=6.1 Hz, 1H), 4.49 (t, J=5.2 Hz, 1H), 4.07-3.99 (m, 2H), 3.94 (d, J=4.6 Hz, 1H), 3.76 (dd, J=17.2, 10.2 Hz, 1H), 3.56-3.32 (m, 8H), 3.28-3.07 (m, 7H), 3.00 (m, 2H), 2.82-2.70 (m, 1H), 2.67-2.55 (m, 2H), 2.44-2.34 (m, 2H), 2.22 (d, J=7.1 Hz, 1H), 2.12-1.36 (m, 22H), 1.33-0.92 (m, 13H), 0.88-0.81 (m, 6H), 0.78 (d, J=6.7 Hz, 3H), 0.73 (d, J=6.7 Hz, 3H), 0.71-0.60 (m, 1H).

Certain compounds of Table 2 can be prepared starting with sirolimus following Scheme 10 and employing alternative reagents in Steps A and B to those described in Example 10.

Scheme 11

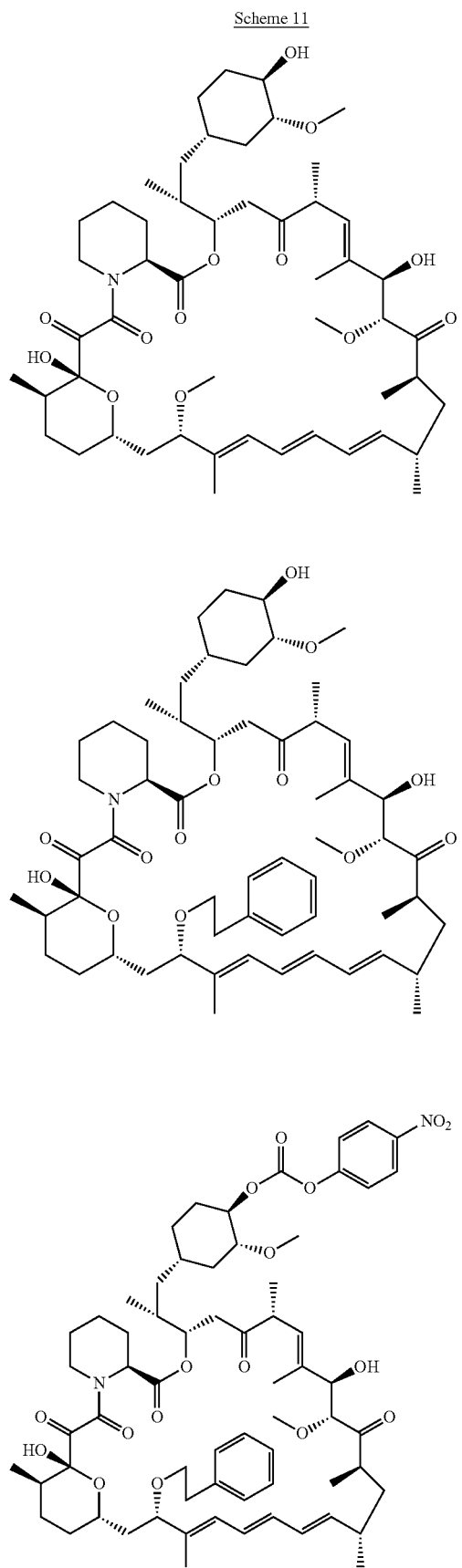

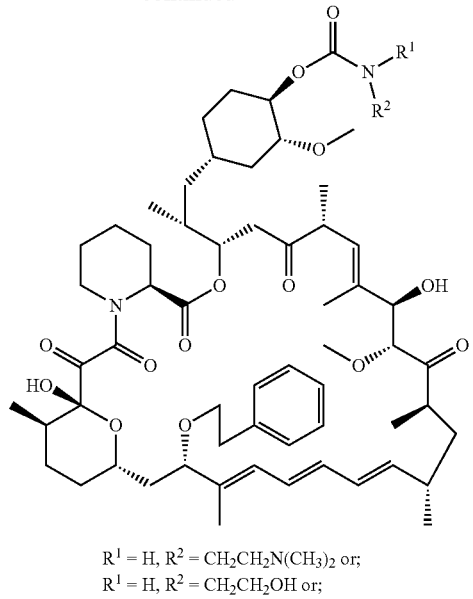

$R^1$ = H, $R^2$ = CH$_2$CH$_2$N(CH$_3$)$_2$ or;
$R^1$ = H, $R^2$ = CH$_2$CH$_2$OH or;
$R^1$ = CH$_2$CH$_2$OH, $R^2$ = CH$_2$CH$_2$OH

Example 11

Step A: Preparation of (1R,9S,12S,15R,16E,18R,19R, 21R,23S,24E,26E,28E,32S,35R)-1,18-dihydroxy-12-[(1R)-2-[(1S,3R,4R)-4-hydroxy-3-methoxy-cyclohexyl]-1-methyl-ethyl]-19-methoxy-15,17,21,23,29,35-hexamethyl-30-(2-phenylethoxy)-11,36-dioxa-4-azatricyclo[30.3.1.0^4, 9]hexatriaconta-16,24,26,28-tetraene-2,3,10,14,20-pentone. Sirolimus (2.0 g, 2.19 mmol) was dissolved in DCM (87 mL) with 2-phenylethanol (10.35 mL, 86.64 mmol) and the mixture was cooled to −40° C. 4-methylbenzenesulfonic acid (1.85 g, 10.72 mmol) was added at −40° C. under vigorous stirring and the reaction mixture stirred to −10° C. within 4 h. The reaction mixture was diluted with DCM (30 mL) and quenched with saturated NaHCO$_3$aq (10 mL). The mixture was diluted with DCM, and the organics were washed with NaHCO$_3$ saturated solution, brine, and passed through a phase separator to remove water. The obtained residue was purified by reverse phase C$_{18}$ preparative HPLC to afford the desired product as a white amorphous solid (1.22 g). Yield 39%. 1H NMR (600 MHz, DMSO-d6, 300K) δ ppm 7.14-7.33 (m, 5H), 6.94 (br d, J=4.5 Hz, 1H), 6.41 (s, 1H), 6.37 (dd, J=14.6, 11.1 Hz, 1H), 6.16-6.22 (m, 1H), 6.06-6.15 (m, 2H), 5.45 (dd, J=14.8, 9.7 Hz, 1H), 5.24 (br d, J=4.5 Hz, 1H), 5.09 (br d, J=10.1 Hz, 1H), 4.97 (dt, J=8.0, 3.8 Hz, 1H), 4.91-4.94 (m, 1H), 4.30-4.40 (m, 1H), 3.91-4.04 (m, 3H), 3.67-3.79 (m, 1H), 3.44 (br d, J=2.9 Hz, 3H), 3.22-3.27 (m, 4H), 2.95-3.16 (m, 7H), 2.70-2.83 (m, 3H), 2.30-2.44 (m, 4H), 2.06-2.29 (m, 8H), 1.92-2.05 (m, 2H), 1.79-1.90 (m, 2H), 1.73 (s, 3H), 0.88-1.70 (m, 24H), 0.65-0.88 (m, 14H)

Step B: Preparation of [(1R,2R,4S)-4-[(2R)-2-[(1R,9S, 12S,15R,16E,18R,19R,21R,23S,24E,26E,28E,32S,35R)-1, 18-dihydroxy-19-methoxy-15,17,21,23,29,35-hexamethyl-2,3,10,14,20-pentaoxo-30-(2-phenylethoxy)-11,36-dioxa-4-azatricyclo[30.3.1.0^4,9]hexatriaconta-16,24,26,28-tetraen-12-yl]propyl]-2-methoxy-cyclohexyl] (4-nitrophenyl) carbonate. (1R,9S,12S,15R,16E,18R,19R,21R, 23S,24E, 26E,28E,30S*,32S,35R)-1,18-dihydroxy-12-[(1R)-2-[(1S, 3R,4R)-4-hydroxy-3-methoxy-cyclohexyl]-1-methylethyl]-19-methoxy-15,17,21,23,29,35-hexamethyl-30-(2-phenylethoxy)-11,36-dioxa-4-azatricyclo[30.3.1.0^4,9]hexatriaconta-16,24,26,28-tetraene-2,3,10,14,20-pentone (400 mg, 0.398 mmol) and anhydrous pyridine (0.32 mL, 3.98 mmol) were dissolved in anhydrous DCM (1.5 mL) under nitrogen atmosphere. The reaction mixture was cooled to −78° C. and a solution of (4-nitrophenyl) carbonochloridate (161 mg, 0.797 mmol) in anhydrous DCM (0.4 mL) was added to the mixture. The reaction mixture was stirred under N2 for 1.5 h. Additional (4-nitrophenyl) carbonochloridate (161 mg, 0.797 mmol) in anhydrous-DCM (0.1 mL) was added at −78° C. and the RM was stirred at −78° C. for 30 min. The ice bath was removed and RM was warmed to RT. Then RM was diluted with DCM and washed with water. The 2 phases were separated. The aqueous phase was extracted with DCM. The organic phases were gathered and concentrated and purified over silica gel column (gradient of Cyclohexane/ethylacetate 100/0 to 0/100) to afford the desired product as a white solid (105 mg). Yield 23%.

Step C: Preparation of [(1R,2R,4S)-4-[(2R)-2-[(1R,9S,12S,15R,16E,18R,19R,21R,23S,24E,26E,28E,32S,35R)-1,18-dihydroxy-19-methoxy-15,17,21,23,29,35-hexamethyl-2,3,10,14,20-pentaoxo-30-(2-phenylethoxy)-11,36-dioxa-4-azatricyclo[30.3.1.0^4,9]hexatriaconta-16,24,26,28-tetraen-12-yl]propyl]-2-methoxy-cyclohexyl] N-[2-(dimethylamino) ethyl]carbamate (Compound 104). A solution of [(1R,2R,4S)-4-[(2R)-2-[(1R,9S,12S,15R,16E,18R,19R,21R,23S,24E,26E, 28E,30S*,32S,35R)-1,18-dihydroxy-19-methoxy-15,17,21,23,29,35-hexamethyl-2,3,10,14,20-pentaoxo-30-(2-phenylethoxy)-11,36-dioxa-4-azatricyclo[30.3.1.0^4,9]hexatriaconta-16,24,26,28-tetraen-12-yl]propyl]-2-methoxy-cyclohexyl] (4-nitrophenyl) carbonate (105.1 mg, 0.09 mmol) and triethylamine (25 uL, 0.18 mmol) in anhydrous dimethylformamide (1.94 mL) was cooled to −20° C. 2 N',N'-dimethylethane-1,2-diamine (20 uL, 0.18 mmol) was added dropwise at −20° C. under atmosphere of nitrogen. After 45 min of stirring at −20° C., ethylacetate was added, the organic phases were separated and washed with water twice. The organic phases were combined and concentrated to dryness. The crude residue was purified on silica gel by flash column chromatography (0-10% of MeOH in DCM gradient) to afford the desired product Compound 104 (80.7 mg) as a white powder. Yield 63.8%.

Alternative Step C: Preparation of [(1R,2R,4S)-4-[(2R)-2-[(1R,9S,12S,15R,16E,18R,19R,21R,23S, 24E,26E,28E, 32S,35R)-1,18-dihydroxy-19-methoxy-15,17,21,23,29,35-hexamethyl-2,3,10,14,20-pentaoxo-30-(2-phenylethoxy)-11,36-dioxa-4-azatricyclo[30.3.1.0^4,9]hexatriaconta-16,24,26,28-tetraen-12-yl]propyl]-2-methoxy-cyclohexyl] N,N-bis(2-hydroxyethyl)carbamate (Compound 112). A solution of [(1R,2R,4S)-4-[(2R)-2-[(1R,9S,12S,15R,16E,18R,19R,21R,23S,24E,26E,28E, 30S*,32S,35R)-1,18-dihydroxy-19-methoxy-15,17,21,23,29,35-hexamethyl-2,3,10,14,20-pentaoxo-30-(2-phenylethoxy)-11,36-dioxa-4-azatricyclo[30.3.1.0^4,9]hexatriaconta-16,24,26,28-tetraen-12-yl]propyl]-2-methoxy-cyclohexyl] (4-nitrophenyl) carbonate (110.0 mg, 0.09 mmol) and triethylamine (26 uL, 0.19 mmol) in anhydrous dimethylformamide (2.03 mL) was cooled to −20° C. 2,2'-iminodiethanol (18 uL, 0.19 mmol) was added dropwise at −20° C. under atmosphere of nitrogen. The reaction mixture was stirred for 2 h. Additional 2,2'-iminodiethanol (18 uL, 0.19 mmol) was added and the reaction mixture was stirred for 3 h. Ethylacetate was added, the organic phases were separated and washed with water twice. The organic phases were combined and concentrated to dryness. The crude residue was purified on silica gel by flash column chromatography (0-10% of MeOH in DCM gradient) to afford the desired product Compound 112 (46.9 mg) as a white powder. Yield 37.9%. 1H NMR (600 MHz, DMSO-d6): δ (ppm) 7.12-7.30 (m, 5H), 6.41 (d, J=1.2 Hz, 1H), 6.37 (dd, J=14.5, 11.2 Hz, 1H), 6.16-6.23 (m, 1H), 6.06-6.15 (m, 2H), 5.45 (dd, J=14.8, 9.7 Hz, 1H), 5.25 (d, J=4.5 Hz, 1H), 5.09 (br d, J=10.1 Hz, 1H), 4.95-5.05 (m, 1H), 4.94 (br d, J=5.3 Hz, 1H), 4.69 (t, J=5.3 Hz, 2H), 4.36 (ddd, J=11.0, 9.4, 4.8 Hz, 1H), 3.96-4.04 (m, 2H), 3.94 (d, J=4.5 Hz, 1H), 3.74 (dd, J=11.4, 1.9 Hz, 1H), 3.39-3.57 (m, 6H), 3.30-3.31 (m, 1H), 3.22-3.29 (m, 8H), 3.12-3.20 (m, 4H), 2.69-2.83 (m, 3H), 2.31-2.43 (m, 2H), 2.18-2.30 (m, 1H), 2.10 (br d, J=12.9 Hz, 1H), 1.94-2.05 (m, 2H), 1.80-1.92 (m, 2H), 1.73 (s, 3H), 1.59-1.68 (m, 4H), 1.58 (s, 3H), 1.50-1.57 (m, 3H), 1.43-1.49 (m, 2H), 1.36-1.42 (m, 1H), 1.18-1.36 (m, 5H), 1.00-1.17 (m, 3H), 0.97 (d, J=6.6 Hz, 3H), 0.88-0.95 (m, 2H), 0.86 (d, J=6.6 Hz, 3H), 0.82 (d, J=6.5 Hz, 3H), 0.77 (d, J=6.6 Hz, 3H), 0.73 (d, J=6.6 Hz, 3H), 0.65-0.70 (m, 1H)

Alternative Step C: Preparation of [(1R,2R,4S)-4-[(2R)-2-[(1R,9S,12S,15R,16E,18R,19R,21R,23S,24E, 26E,28E, 32S,35R)-1,18-dihydroxy-19-methoxy-15,17,21,23,29,35-hexamethyl-2,3,10,14,20-pentaoxo-30-(2-phenylethoxy)-11,36-dioxa-4-azatricyclo[30.3.1.0^4,9] hexatriaconta-16,24,26,28-tetraen-12-yl]propyl]-2-methoxy-cyclohexyl] N-(2-hydroxyethyl)carbamate (Compound 111). A solution of [(1R,2R,4S)-4-[(2R)-2-[(1R,9S,12S,15R,16E,18R,19R, 21R,23S,24E,26E, 28E,30S*,32S,35R)-1,18-dihydroxy-19-methoxy-15,17,21,23,29,35-hexamethyl-2,3,10,14,20-pentaoxo-30-(2-phenylethoxy)-11,36-dioxa-4-azatricyclo[30.3.1.0^4,9]hexatriaconta-16,24,26,28-tetraen-12-yl]propyl]-2-methoxy-cyclohexyl] (4-nitrophenyl) carbonate (50 mg, 0.0428 mmol) and trimethylamine (12 uL, 0.0855 mmol) in anhydrous dimethylformamide (0.8 mL) was cooled to −20° C. 2-aminoethanol (5.2 mg, 0.0855 mmol) in 0.123 mL of DMF-anhdrous (20 uL, 0.18 mmol) was added dropwise at −20° C. under atmosphere of nitrogen. After 1.5 h of stirring at −20° C., ethylacetate was added, the organic phases were separated and washed with water twice. The organic phases were combined and concentrated to dryness. The crude residue was purified on silica gel by flash column chromatography (0-10% of MeOH in DCM gradient) to afford the desired product Compound 111 (41.8 mg) as a white powder. Yield 86%. 1H NMR (600 MHz, DMSO-d6) δ 7.35-7.08 (m, 5H), 6.95 (t, J=5.7 Hz, 1H), 6.44-6.33 (m, 2H), 6.23-6.02 (m, 3H), 5.45 (dd, J=14.8, 9.6 Hz, 1H), 5.26-5.20 (m, 1H), 5.09 (d, J=10.2 Hz, 1H), 4.96 (dd, J=7.7, 4.2 Hz, 1H), 4.93 (d, J=5.7 Hz, 1H), 4.57 (s, 1H), 4.36 (td, J=10.9, 5.0 Hz, 1H), 4.06-3.90 (m, 3H), 3.78-3.68 (m, 1H), 3.50-3.05 (m, 15H), 3.02 (q, J=6.1 Hz, 2H), 2.85-2.67 (m, 3H), 2.43-2.29 (m, 2H), 2.19 (d, J=21.4 Hz, 1H), 2.16-0.57 (m, 45H).

Certain compounds of Table 2 can be prepared starting with sirolimus following Scheme 11 and employing alternative reagents in Steps A, B, and/or C to those described in Example 11.

Scheme 12

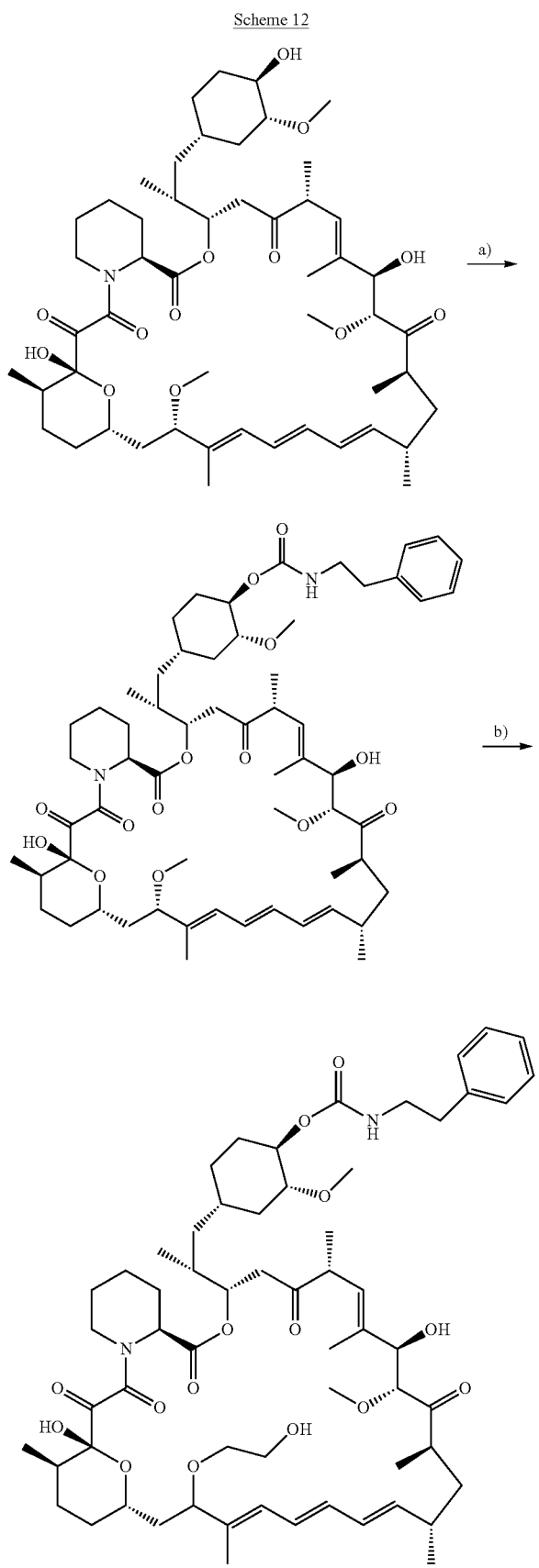

Example 12

Step A: Preparation of [(1R,2R,4S)-4-[(2R)-2-[(1R,9S, 12SR,15R,16E,18R,19R,21R,23S,24E,26E,28E,30S,32SR, 35R)-1,18-dihydroxy-19,30-dimethoxy-15,17,21,23,29,35-hexamethyl-2,3,10,14,20-pentaoxo-11,36-dioxa-4-azatricyclo[30.3.1.0^4,9]hexatriaconta-16,24,26,28-tetraen-12-yl]propyl]-2-methoxy-cyclohexyl] N-(2-phenylethyl)carbamate. Sirolimus (500.0 mg, 0.55 mmol) was dissolved in 0.8 mL of anhydrous THF. dibutyl[bis(dodecanoyloxy)]stannane (34 uL, 0.05 mmol) followed by a solution of (2-isocyanatoethyl)benzene (100 uL, 0.66 mmol) in 0.2 mL of anhydrous THF were added at RT. The RM was stirred at RT overnight. RM was diluted with ethyl acetate and washed with brine. The organic layer was dried (Na2SO4), filtered and concentrated to dryness. The crude mixture was purified on silica gel by flash column chromatography (DCM/MeOH: 0% to 50% in 30CV) to afford the desired product as a white amorphous solid (259 mg). Yield 47.4%.

Step B: Preparation of [(1R,2R,4S)-4-[(2R)-2-[(1R,9S, 12SR,15R,16E,18R,19R,21R,23S,24E,26E,28E,32SR, 35R)-1,18-dihydroxy-30-(2-hydroxyethoxy)-19-methoxy-15,17,21,23,29,35-hexamethyl-2,3,10,14,20-pentaoxo-11, 36-dioxa-4-azatricyclo[30.3.1.0^4,9]hexatriaconta-16,24, 26,28-tetraen-1$^2$-yl]propyl]-2-methoxy-cyclohexyl] N-(2-phenylethyl)carbamate (Compound 1). [(1R,2R,4S)-4-[(2R)-2-[(1R,9S,12SR,15R,16E,18R,19R,21R,23S,24E, 26E,28E,30S, 32SR,35R)-1,18-dihydroxy-19,30-dimethoxy-15,17,21,23,29,35-hexamethyl-2,3,10,14,20-pentaoxo-11,36-dioxa-4-azatricyclo[30.3.1.0^4,9] hexatriaconta-16,24,26,28-tetraen-12-yl]propyl]-2-methoxy-cyclohexyl] N-(2-phenylethyl)carbamate (259 mg, 0.24 mmol) was dissolved in ethylene glycol (5.0 mL, 89.42 mmol) at RT under $N_2$. The mixture was heterogeneous. Anhydrous DCM (3 mL) was added to help solubilized and homogenized every component. 4-methylbenzenesulfonic acid (210.352 mg, 1.22 mmol) was added at RT and the RM was stirred at RT for 45 min. The crude mixture was quenched with saturated NaHCO$_3$ aq. Then the mixture was extracted with DCM. The organic layer was dried under a separator phase, then concentrated to dryness. The obtained residue was purified by reverse phase C18 preparative HPLC to afford the desired product Compound 1 as a white amorphous solid (55 mg). Yield 20.6%. 1H NMR (600 MHz, DMSO-d6) δ 7.33-7.15 (m, 5H), 7.12 (d, J=5.2 Hz, 1H), 6.49-6.34 (m, 2H), 6.27-6.05 (m, 3H), 5.46 (dd, J=14.8, 9.8 Hz, 1H), 5.24 (d, J=4.4 Hz, 1H), 5.10 (d, J=10.2 Hz, 1H), 5.02-4.96 (m, 1H), 4.94 (d, J=5.0 Hz, 1H), 4.49 (t, J=5.4 Hz, 1H), 4.37 (s, 1H), 4.10-3.97 (m, 2H), 3.95 (d, J=4.3 Hz, 1H), 3.78 (d, J=13.8 Hz, 1H), 3.45 (ddd, J=13.5, 8.7, 5.4 Hz, 3H), 3.28-3.06 (m, 13H), 2.84-2.63 (m, 4H), 2.44-2.33 (m, 2H), 2.22 (s, 1H), 2.16-1.11 (m, 25H), 1.11-0.64 (m, 20H).

Certain compounds of Table 2 can be prepared starting with sirolimus following Scheme 12 and employing alternative reagents in Steps A, B, and/or C to those described in Example 12.

Exemplary compounds may include, but are not limited to, a compound or salt thereof selected from Table 2 to Table 4 which may be prepared following Schemes 1 to 12 and the accompanying procedures described herein.

TABLE 2

Rapamycin analogs with substitution at C40 and C16.

[Structure of rapamycin core with R¹ at C40, R² at C39, R³ at C27, and R⁴ at C16]

| No. # | R¹ | R² | R³ |
|---|---|---|---|
| 1 | -O-C(=O)-NH-CH₂CH₂-phenyl | -O-CH₃ | -O-CH₃ |
| 2 | -O-CH₂CH₂CH₂-N(morpholine with 3-methyl) | -O-CH₃ | -O-CH₃ |
| 3 | -O-CH₂CH₂CH₂-O-CH₃ | -O-CH₃ | -O-CH₃ |
| 4 | -O-CH₂CH₂-O-CH₃ | -O-CH₃ | -O-CH₃ |
| 5 | -O-CH₂CH₂CH₂-N(morpholine with 3-methyl) | -O-CH₃ | -O-CH₃ |
| 6 | -O-CH₃ | -O-CH₃ | -O-CH₃ |
| 7 | -O-CH₂CH₂CH₂-OH | -O-CH₃ | -O-CH₃ |
| 8 | -O-CH₂CH₂-N(morpholine) | -O-CH₃ | -O-CH₃ |
| 9 | -O-CH₂CH₂-OH | -O-CH₃ | -O-CH₃ |

TABLE 2-continued
Rapamycin analogs with substitution at C40 and C16.
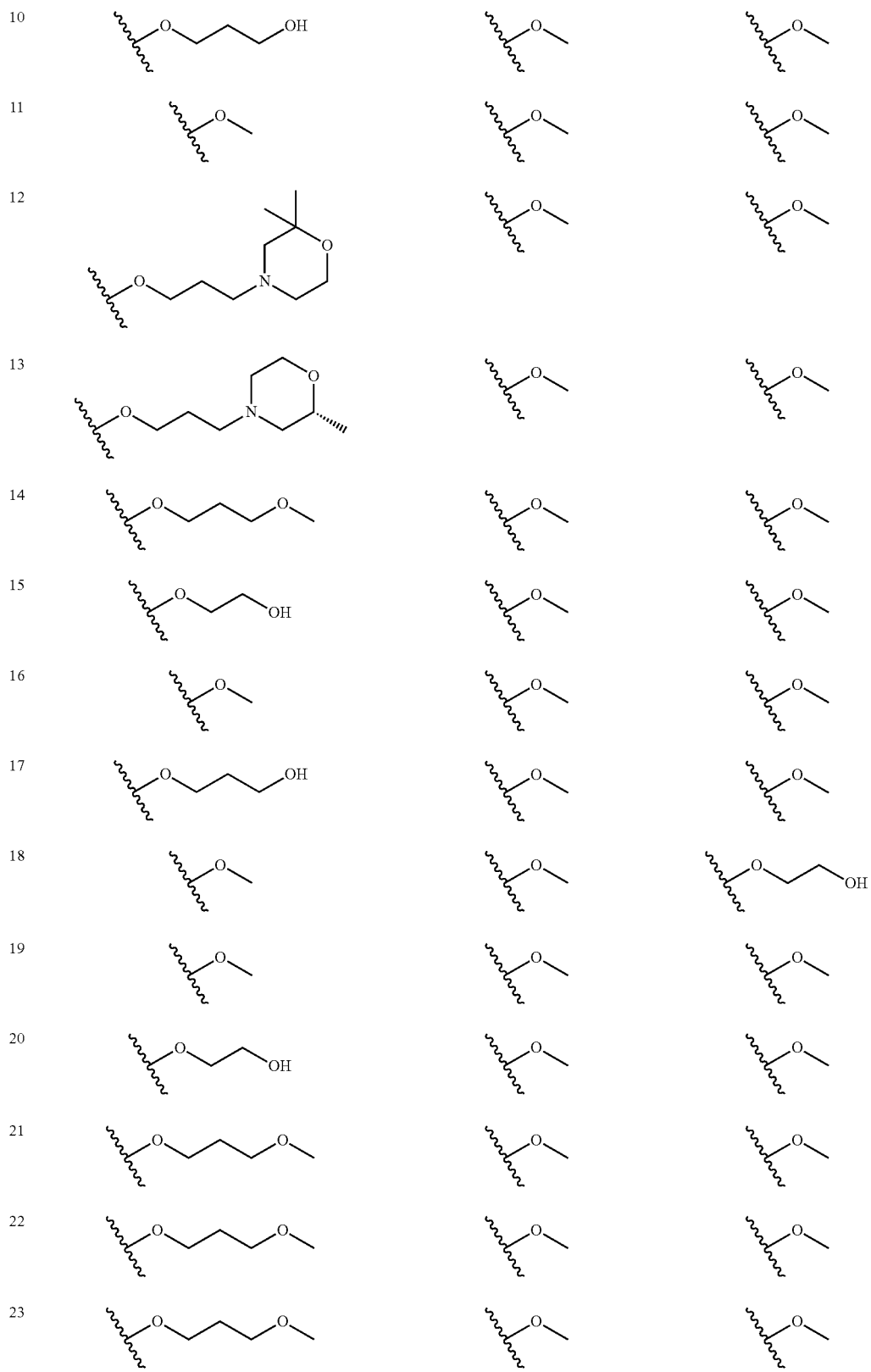

TABLE 2-continued
Rapamycin analogs with substitution at C40 and C16.
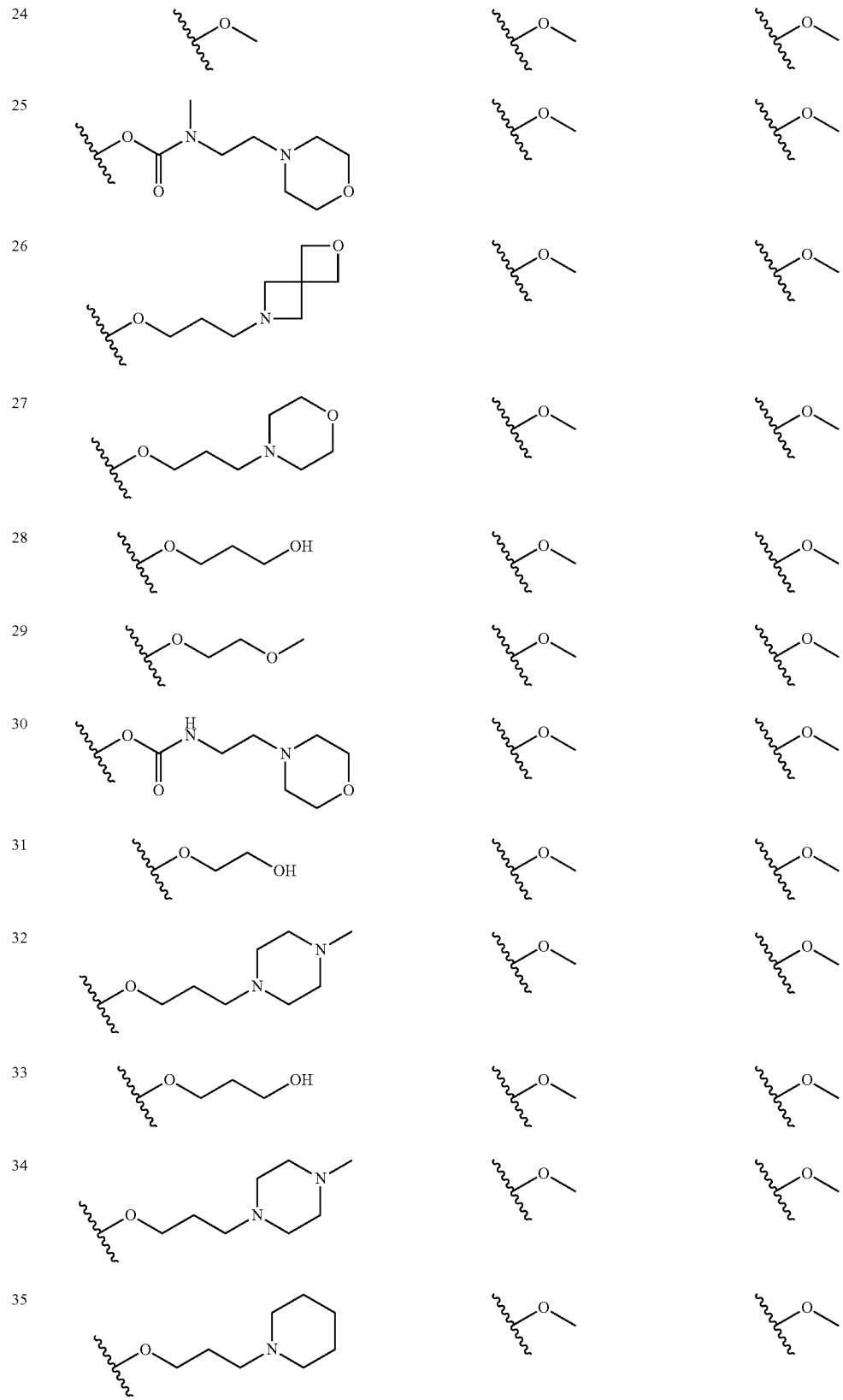

TABLE 2-continued

Rapamycin analogs with substitution at C40 and C16.

| # | R(C40) | R(C16) middle | R(C16) right |
|---|---|---|---|
| 36 | ~O~~N-morpholine (2-methyl) | ~O~Me | ~O~Me |
| 37 | ~O~~~OH | ~O~Me | ~O~Me |
| 38 | ~O~~~Ph | ~O~Me | ~O~Me |
| 39 | ~O~~~N-piperazine-N-iPr | ~O~Me | ~O~Me |
| 40 | ~O~OH | ~O~Me | ~O~Me |
| 41 | ~O-C(O)-N(Me)-CH2CH2-morpholine | ~O~Me | ~O~Me |
| 42 | ~O~~N-morpholine (3-methyl) | ~O~Me | ~O~Me |
| 43 | ~O~~N-morpholine (2-methyl) | ~O~Me | ~O~OH |
| 44 | ~O~~N-(2-oxa-6-azaspiro[3.3]heptane) | ~O~Me | ~O~Me |
| 45 | ~O~CH(OH)CH2OH | ~O~Me | ~O~Me |
| 46 | ~O~~~N-piperazine-N-Me | ~O~Me | ~O~Me |

TABLE 2-continued

Rapamycin analogs with substitution at C40 and C16.

| | | | |
|---|---|---|---|
| 47 | [2-(4-methylpiperazin-1-yl)ethoxy] | [methoxy] | [methoxy] |
| 48 | [3-morpholinopropoxy] | [methoxy] | [methoxy] |
| 49 | [2-hydroxyethoxy] | [methoxy] | [methoxy] |
| 50 | [4-morpholinobutoxy] | [methoxy] | [methoxy] |
| 51 | [2-(piperidin-1-yl)ethoxy] | [methoxy] | [methoxy] |
| 52 | [3-((S)-3-methylmorpholino)propoxy] | [methoxy] | [methoxy] |
| 53 | [3-hydroxypropoxy] | [methoxy] | [methoxy] |
| 54 | [3-((R)-3-hydroxypiperidin-1-yl)propoxy] | [methoxy] | [methoxy] |
| 55 | [3-morpholinopropoxy] | [methoxy] | [methoxy] |
| 56 | [4-morpholinobutoxy] | [methoxy] | [methoxy] |
| 57 | [2-(piperidin-1-yl)ethylcarbamate] | [methoxy] | [methoxy] |
| 58 | [(S)-2,3-dihydroxypropoxy] | [methoxy] | [methoxy] |

TABLE 2-continued
Rapamycin analogs with substitution at C40 and C16.
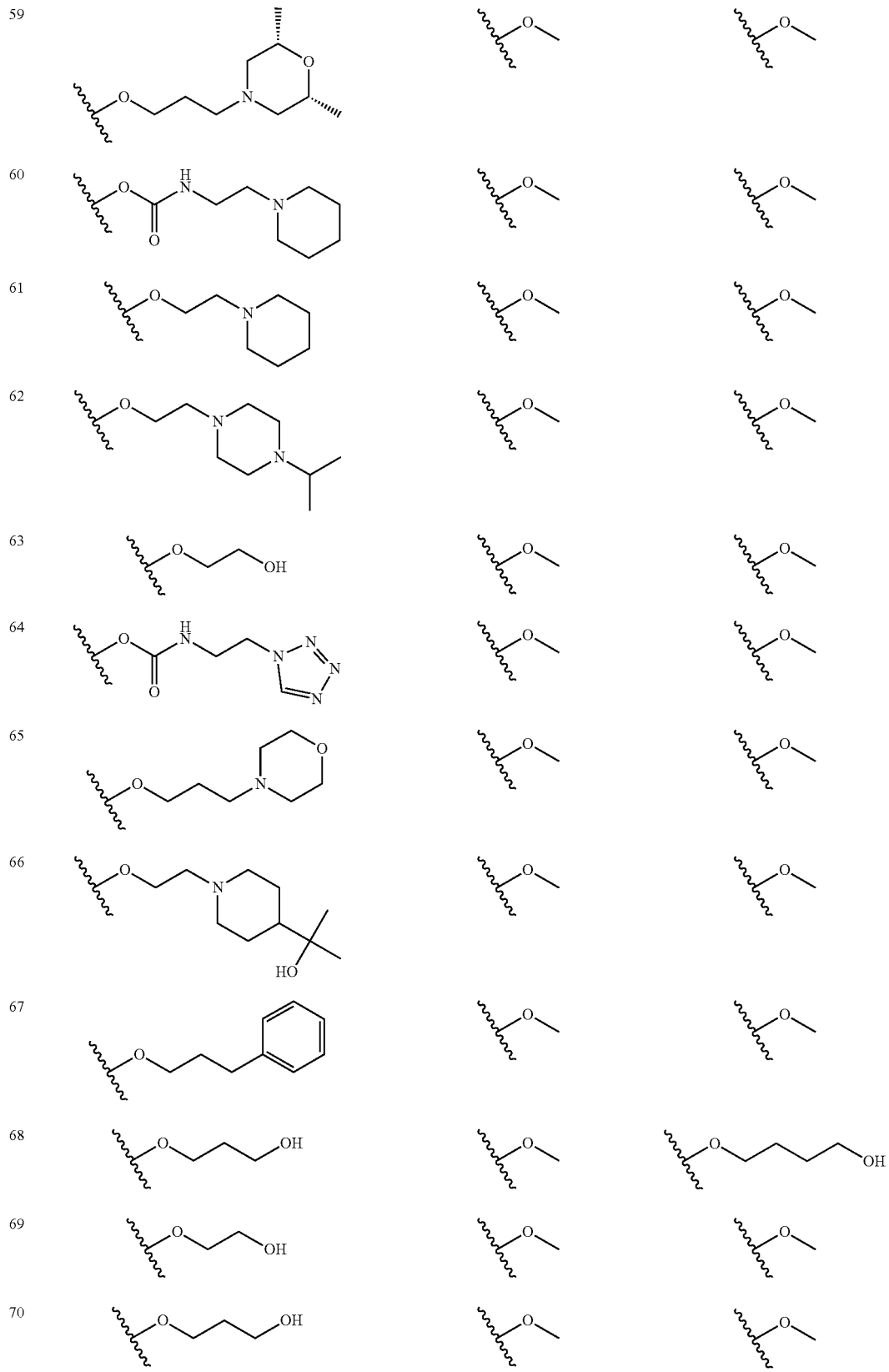

TABLE 2-continued
Rapamycin analogs with substitution at C40 and C16.
| | | | |
|---|---|---|---|
| 71 | 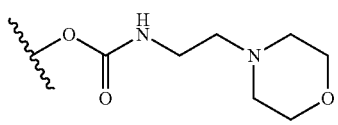 | 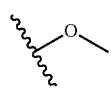 [SMILES: *OC] | 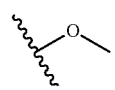 [SMILES: *OC] |
| 72 | 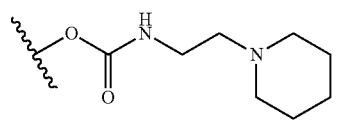 | 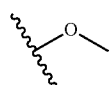 [SMILES: *OC] | 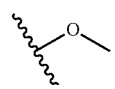 [SMILES: *OC] |
| 73 | 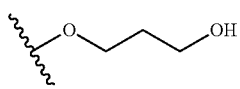 [SMILES: *OCCCO] | 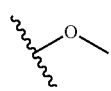 [SMILES: *OC] | 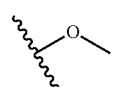 |
| 74 | 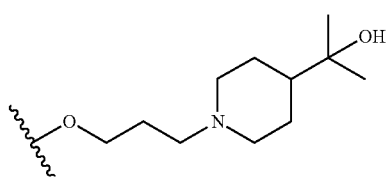 | 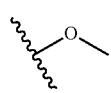 [SMILES: *OC] | 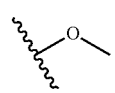 [SMILES: *OC] |
| 75 | 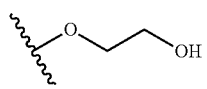 | 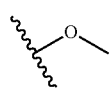 [SMILES: *OC] | 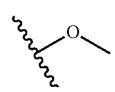 |
| 76 | 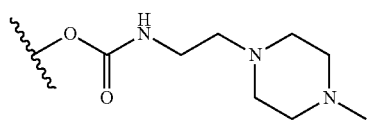 [SMILES: *OC(=O)NCCN1CCN(C)CC1] | 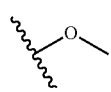 | 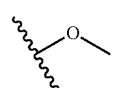 |
| 77 | 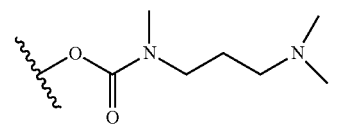 [SMILES: *OC(=O)N(C)CCCN(C)C] | 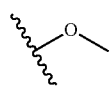 [SMILES: *OC] | 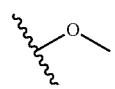 [SMILES: *OC] |
| 78 | 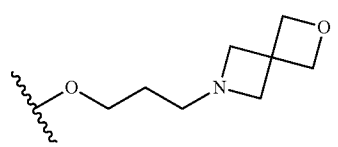 [SMILES: *OCCCN1CC2(COC2)C1] | 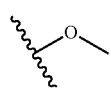 | 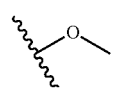 |
| 79 | 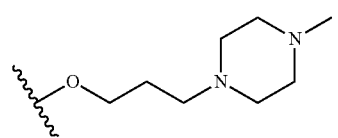 [SMILES: *OCCCN1CCN(C)CC1] | 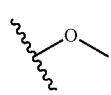 | 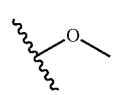 |
| 80 | 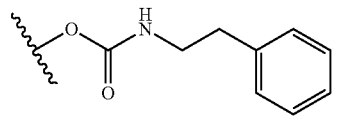 [SMILES: *OC(=O)NCCc1ccccc1] | 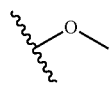 | 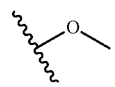 [SMILES: *OC] |
| 81 | 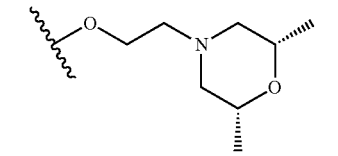 [SMILES: *OCCN1C[C@@H](C)O[C@@H](C)C1] | 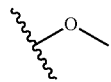 | 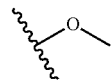 |

TABLE 2-continued

Rapamycin analogs with substitution at C40 and C16.

| # | C40 | C16 | |
|---|-----|-----|---|
| 82 | carbamate-CH₂CH₂-morpholine | OMe | OMe |
| 83 | N-methyl carbamate-CH₂CH₂OH | OMe | OMe |
| 84 | O-CH₂CH₂CH₂-OH | OMe | OMe |
| 85 | O-CH₂CH₂CH₂-N(4-hydroxypiperidine) | OMe | OMe |
| 86 | O-CH₂CH₂-OH | OMe | OMe |
| 87 | O-CH₂CH₂CH₂-piperidine | OMe | OMe |
| 88 | carbamate-CH₂CH₂-piperidine | OMe | OMe |
| 89 | carbamate-CH₂CH₂-tetrazole | OMe | OMe |
| 90 | O-CH₂CH₂CH₂-OH | OMe | OMe |
| 91 | O-CH₂CH₂-OH | OMe | OMe |
| 92 | O-CH₂CH₂CH₂-morpholine | OMe | OMe |
| 93 | carbamate-CH₂CH₂-morpholine | OMe | O-CH₂CH₂-phenyl |
| 94 | O-CH₂CH₂CH₂-OH | OMe | OMe |

TABLE 2-continued

Rapamycin analogs with substitution at C40 and C16.

| # | C40 | C16a | C16b |
|---|---|---|---|
| 95 | ~O-C(=O)-N(Me)-CH2CH2CH2-N(Me)2 | ~O-Me | ~O-Me |
| 96 | ~O-CH2CH2CH2-Ph | ~O-Me | ~O-Me |
| 97 | ~O-CH2CH2CH2-N(piperazinyl-N'-Me) | ~O-Me | ~O-Me |
| 98 | ~O-CH2CH2CH2-OH | ~O-Me | ~O-Me |
| 99 | ~O-CH2CH2-OH | ~O-Me | ~O-Me |
| 100 | ~O-C(=O)-NH-CH2CH2-O-CH2CH2-O-CH2CH2-O-CH2CH2CH2-OH | ~O-Me | ~O-Me |
| 101 | ~O-CH2CH2CH2-N(piperidinyl) | ~O-Me | ~O-Me |
| 102 | ~O-CH2CH2-OH | ~O-Me | ~O-Me |
| 103 | ~O-CH2CH2-OH | ~O-Me | ~O-Me |
| 104 | ~O-C(=O)-NH-CH2CH2-N(Me)2 | ~O-Me | ~O-Me |
| 105 | ~O-C(=O)-N(Me)-CH2CH2-OH | ~O-Me | ~O-Me |
| 106 | ~O-CH2CH2CH2-OH | ~O-Me | ~O-Me |
| 107 | ~O-C(=O)-NH-CH2CH2-N(piperazinyl-N'-Me) | ~O-Me | ~O-Me |

TABLE 2-continued

Rapamycin analogs with substitution at C40 and C16.

| # | C40 | C16 | (third) |
|---|---|---|---|
| 108 | -O-CH2CH2CH2-morpholine | -O-CH3 | -O-CH3 |
| 109 | -O-C(=O)-N(CH3)-CH2CH2-N(CH3)2 | -O-CH3 | -O-CH3 |
| 110 | -O-C(=O)-NH-CH2CH2-(1H-imidazol-4-yl) | -O-CH3 | -O-CH3 |
| 111 | -O-C(=O)-NH-CH2CH2-OH | -O-CH3 | -O-CH3 |
| 112 | -O-C(=O)-N(CH2CH2OH)2 | -O-CH3 | -O-CH3 |
| 113 | -O-C(=O)-NH-CH2CH2-piperidine | -O-CH3 | -O-CH3 |
| 114 | -O-C(=O)-NH-CH2CH2-(1H-tetrazol-1-yl) | -O-CH3 | -O-CH3 |
| 115 | -O-C(=O)-NH-CH2CH2-morpholine | -O-CH3 | -O-CH3 |
| 116 | -O-CH2CH2CH2-phenyl | -O-CH3 | -O-CH3 |
| 117 | -O-C(=O)-NH-CH2CH2-phenyl | -O-CH3 | -O-CH3 |
| 118 | -O-C(=O)-NH-CH2CH2-N(CH3)2 | -O-CH3 | -O-CH3 |
| 119 | -O-CH2CH2CH2-OH | -O-CH3 | -O-CH2CH2-phenyl |

TABLE 2-continued

Rapamycin analogs with substitution at C40 and C16.

| No. # | R⁴ | LCMS Characterization Ion, mass obtained |
|---|---|---|
| 1 | -O-CH₂CH₂-OH | [M + Na]+, 1113.3 |
| 2 | -O-CH₂CH₂-OH | [M +H]+, 1086.0 |
| 3 | -O-CH₂CH₂-OH | [M + Na]+, 1038.7 |
| 4 | -O-CH₂CH₂-OH | [M + Na]+, 1026.6 |
| 5 | -O-CH₂CH₂-OH | [M + H]+, 1086.0 |
| 6 | -O-CH₂CH₂-OH | [M + H]+, 980.6 |
| 7 | -O-CH₂CH₂CH₂-OH | [M + Na]+, 1039.8 |
| 8 | -O-CH₂CH₂-OH | [M + H]+, 1058.1 |
| 9 | -O-CH₂CH₂-OH | [M + Na]+, 1010.5 |
| 10 | -O-CH₂CH₂-OH | [M + Na]+, 1024.6 |
| 11 | -O-CH₂CH₂-O-CH₃ | [M + Na]+, 994.6 |
| 12 | -O-CH₂CH₂-OH | [M + H]+, 1099.8 |
| 13 | -O-CH₂CH₂-OH | [M + H]+, 1085.7 |
| 14 | -O-CH₂CH₂-O-CH₃ | [M + Na]+, 1052.7 |
| 15 | -O-CH₂CH₂CH₂-OH | [M + Na]+, 1024.8 |

TABLE 2-continued

Rapamycin analogs with substitution at C40 and C16.

| # | Structure | MS |
|---|---|---|
| 16 | ~O~OH | [M + H]+, 980.6 |
| 17 | ~O~O~O~ | [M + Na]+, 1082.7 |
| 18 | ~O~OH | [M + H]+, 1100.0 |
| 19 | ~O~OH | [M + Na]+, 994.8 |
| 20 | ~O~O~O~ | [M + Na]+, 1068.7 |
| 21 | ~O~~~OH | [M + Na]+, 1066.7 |
| 22 | ~O~O~OH | [M + Na]+, 1080.7 |
| 23 | ~O~O~O~ | [M + Na]+, 1096.7 |
| 24 | ~O~~OH | [M + Na]+, 1008.9 |
| 25 | ~O~O~ | [M + H]+, 1128.7 |
| 26 | ~O~O~ | [M + H]+, 1098.1 |
| 27 | ~O~~OH | [M + Na]+, 1099.8 |
| 28 | ~O~O~ | [M + Na]+, 1038.8 |
| 29 | ~O~O~ | [M + Na]+, 1038.7 |
| 30 | ~O~O~ | [M + H]+, 1114.7 |
| 31 | ~O~~O~ | [M + Na]+, 1038.7 |

TABLE 2-continued
Rapamycin analogs with substitution at C40 and C16.
| | | |
|---|---|---|
| 32 | 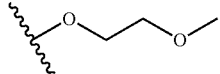 [SMILES: *OCCOC] | [M + H]+, 1098.8 |
| 33 | 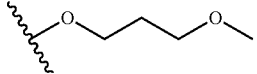 [SMILES: *OCCCOC] | [M + H]+, 1053.2 |
| 34 | 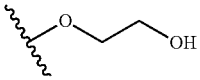 [SMILES: *OCCO] | [M + H]+, 1084.8 |
| 35 | 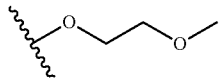 [SMILES: *OCCOC] | [M + H]+, 1083.8 |
| 36 | 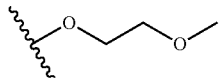 [SMILES: *OCCOC] | [M + H]+, 1099.9 |
| 37 | 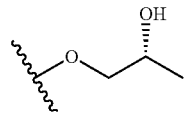 | [M + Na]+, 1039.7 |
| 38 | 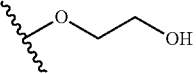 [SMILES: *OCCO] | [M + Na]+, 1084.6 |
| 39 | 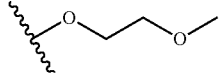 [SMILES: *OCCOC] | [M + H]+, 1127.1 |
| 40 | 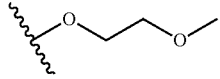 | [M + H]+, 1024.8 |
| 41 | 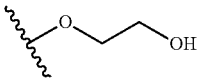 [SMILES: *OCCO] | [M + H]+, 1114.7 |
| 42 | 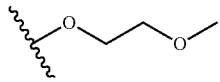 [SMILES: *OCCOC] | [M + H]+, 1099.9 |
| 43 | 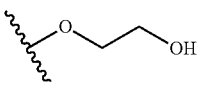 | [M + H]+, 1085.7 |
| 44 | 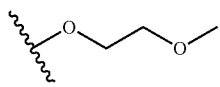 [SMILES: *OCCOC] | [M + H]+, 1084.1 |
| 45 | 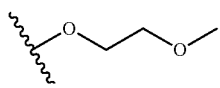 [SMILES: *OCCOC] | [M + H]+, 1054.8 |
| 46 | 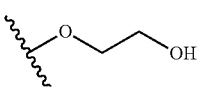 | [M + H]+, 1084.8 |

TABLE 2-continued
Rapamycin analogs with substitution at C40 and C16.
| | | |
|---|---|---|
| 47 | 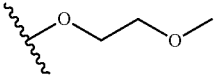 [SMILES: *OCCOC] | [M + H]+, 1084.8 |
| 48 | 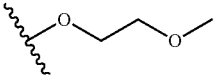 [SMILES: *OCCOC] | [M + H]+, 1085.9 |
| 49 | 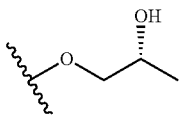 | [M + Na]+, 1024.9 |
| 50 | 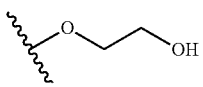 [SMILES: *OCCO] | [M + H]+, 1085.9 |
| 51 | 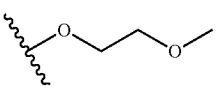 | [M + H]+, 1069.8 |
| 52 | 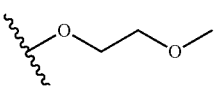 [SMILES: *OCCOC] | [M + H]+, 1100.0 |
| 53 | 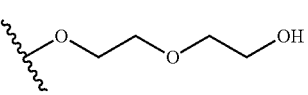 [SMILES: *OCCOCCO] | [M + Na]+, 1068.9 |
| 54 | 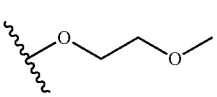 [SMILES: *OCCOC] | [M + H]+, 1099.5 |
| 55 | 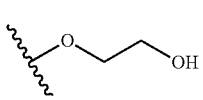 | [M + H]+, 1071.7 |
| 56 | 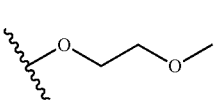 [SMILES: *OCCOC] | [M + H], 1100.6 |
| 57 | 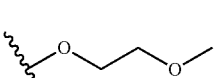 | [M + H]+, 1112.8 |
| 58 | 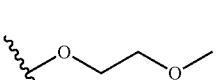 | [M + Na]+, 1054.9 |
| 59 | 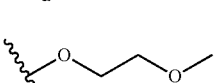 | [M + H]+, 1113.7 |
| 60 | 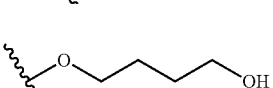 | [M + Na]+, 1054.9 |
| 61 | 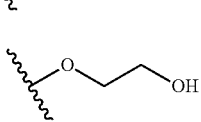 | [M + H]+, 1056.0 |

TABLE 2-continued

Rapamycin analogs with substitution at C40 and C16.

| # | Structure | MS |
|---|---|---|
| 62 | ~O~~~O~ | [M + Na]+, 1038.7 |
| 63 | ~O~~~OH | [M + Na]+, 1038.7 |
| 64 | ~O~~OH | [M + Na]+, 1053.6 |
| 65 | ~O~~~O~ | [M + H]+, 1113.6 |
| 66 | ~O~~O~ | [M + H]+, 1126.0 |
| 67 | ~O~~OH | [M + H]+, 1098.7 |
| 68 | ~O~~~OH | [M + Na]+, 1053.0 |
| 69 | ~O~~O~~OH | [M + Na]+, 1054.9 |
| 70 | ~O~~~O~ | [M + Na]+, 1066.7 |
| 71 | ~O-oxetanyl | [M + H]+, 1112.7 |
| 72 | ~O~~OH | [M + H]+, 1098.8 |
| 73 | ~O-CH2-(tetrahydropyran-4-yl) | [M + Na]+, 1079.0 |
| 74 | ~O~~O~ | [M + H]+, 1142.1 |
| 75 | ~O-CH2-(oxetan-3-yl) | [M + Na]+, 1036.7 |
| 76 | ~O~~OH | [M + H]+, 1113.8 |

TABLE 2-continued

Rapamycin analogs with substitution at C40 and C16.

| # | Structure | MS |
|---|---|---|
| 77 | -O-CH₂CH₂-OH | [M + H]+, 1086.7 |
| 78 | -O-CH₂CH₂-OH | [M + H]+, 1084.0 |
| 79 | -O-CH₂CH₂-Ph | [M + Na]+, 1144.8 |
| 80 | -O-iPr | [M + Na]+, 1111.5 |
| 81 | -O-CH₂CH₂-OMe | [M + H]+, 1100.0 |
| 82 | -O-CH₂CH₂-OH | [M + H]+, 1100.7 |
| 83 | -O-CH₂CH₂-OH | [M + Na]+, 1067.6 |
| 84 | -O-CH₂-(oxetan-3-yl) | [M + Na]+, 1050.7 |
| 85 | -O-CH₂CH₂-OMe | [M + H]+, 1099.6 |
| 86 | -O-CH₂-(tetrahydropyran-4-yl) | [M + Na]+, 1064.7 |
| 87 | -O-CH₂CH₂-OH | [MH+]+, 1069.7 |
| 88 | -O-CH₂-CH(OH)-Ph (S) | [M + Na]+, 1086.6 |
| 89 | -O-CH₂CH₂-OH | [M + Na]+, 1105.6 |
| 90 | -O-CH₂-CH(OH)-Ph (R) | [M + Na]+, 1100.7 |

TABLE 2-continued
Rapamycin analogs with substitution at C40 and C16.
| | | |
|---|---|---|
| 91 | 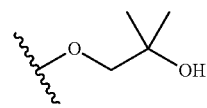 [SMILES: *OCC(C)(C)O] | [M + Na]+, 1038.7 |
| 92 | 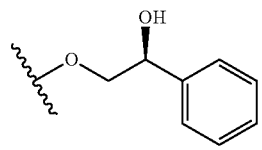 [SMILES: *OC[C@@H](O)c1ccccc1] | [M + H]+, 1147.8 |
| 93 | 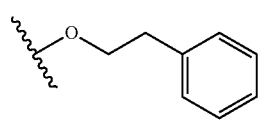 | [M + H]+, 1161.7 |
| 94 | 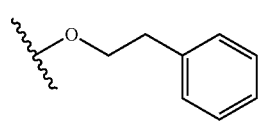 [SMILES: *OCCc1ccccc1] | [M + Na]+, 1084.7 |
| 95 | 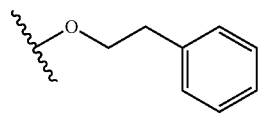 [SMILES: *OCCc1ccccc1] | [M + H]+, 1146.8 |
| 96 | 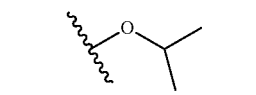 [SMILES: *OC(C)C] | [M + Na]+, 1082.4 |
| 97 | 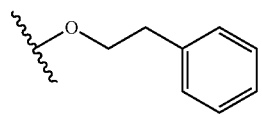 [SMILES: *OCCc1ccccc1] | [M + H]+, 1144.8 |
| 98 | 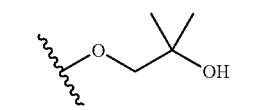 [SMILES: *OCC(C)(C)O] | [M + Na]+, 1052.9 |
| 99 | 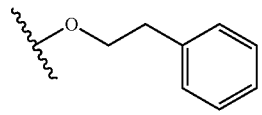 [SMILES: *OCCc1ccccc1] | [M + Na]+, 1070.6 |
| 100 | 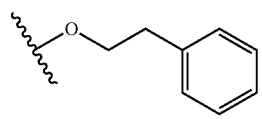 [SMILES: *OCCc1ccccc1] | [M + Na]+, 1289.8 |
| 101 | 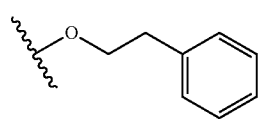 [SMILES: *OCCc1ccccc1] | [M + H]+, 1129.8 |
| 102 | 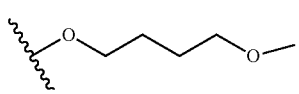 [SMILES: *OCCCCOC] | [M + Na]+, 1052.6 |

TABLE 2-continued
Rapamycin analogs with substitution at C40 and C16.
| | | |
|---|---|---|
| 103 | 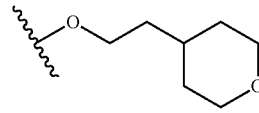 | [M + Na]+, 1086.5 |
| 104 | 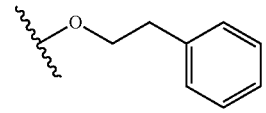 [SMILES: *OCCc1ccccc1] | [M + H]+, 1118.8 |
| 105 | 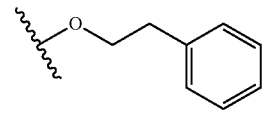 [SMILES: *OCCc1ccccc1] | [M + Na]+, 1127.6 |
| 106 | 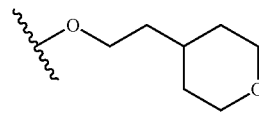 | [M + Na]+, 1092.9 |
| 107 | 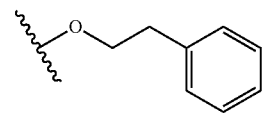 [SMILES: *OCCc1ccccc1] | [M + H]+, 1073.8 |
| 108 | 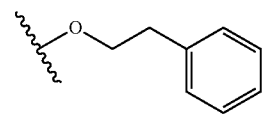 [SMILES: *OCCc1ccccc1] | [M + H]+, 1131.8 |
| 109 | 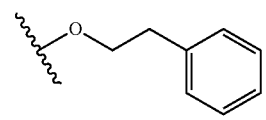 [SMILES: *OCCc1ccccc1] | [M + H]+, 1132.8 |
| 110 | 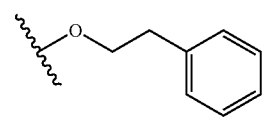 [SMILES: *OCCc1ccccc1] | [M + H]+, 1141.7 |
| 111 | 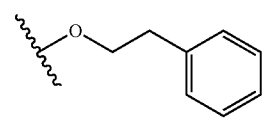 [SMILES: *OCCc1ccccc1] | [M + Na]+, 1113.7 |
| 112 | 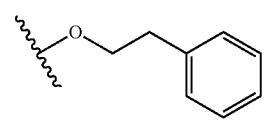 | [M + Na]+, 1157.7 |
| 113 | 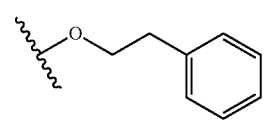 [SMILES: *OCCc1ccccc1] | [M + H]+, 1158.8 |
| 114 | 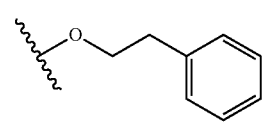 [SMILES: *OCCc1ccccc1] | [M + Na]+, "65.8 |

TABLE 2-continued

Rapamycin analogs with substitution at C40 and C16.

| No. | Structure | LCMS |
|---|---|---|
| 115 | –O–CH₂–C₆H₅ | [M + H]+, 1146.7 |
| 116 | –O–CH₂–C₆H₅ | [M + Na]+, 1130.6 |
| 117 | –O–CH₂–C₆H₅ | [M + Na]+, 1159.5 |
| 118 | –O–CH₂CH₂–C₆H₅ | |
| 119 | –O–CH₂CH₂CH₂–O–CH₃ | |

TABLE 3

Rapamycin analogs with substitution at C16.

| No. # | R¹ | R² | R³ | R⁴ | LCMS Characterization Ion, mass obtained |
|---|---|---|---|---|---|
| 200 | –OH | –OCH₃ | –OCH₃ | 5-methylfuran-2-yl | [M + H]+, 986.3 |

TABLE 3-continued

Rapamycin analogs with substitution at C16.

| No. # | R¹ | R² | R³ | R⁴ | LCMS Characterization Ion, mass obtained |
|---|---|---|---|---|---|
| 201 | ⋯OH | ⋯O-Me | ⋯O-Me | ⋯S-iPr | [M + H]+, 958.3 |
| 202 | ⋯OH | ⋯O-Me | ⋯O-Me | 5-methylthiophen-2-yl | [M + H]+, 980.3 |
| 203 | ⋯OH | ⋯O-Me | ⋯O-Me | 4-methylthiophen-2-yl | [M + H]+, 980.3 |
| 204 | ⋯OH | ⋯O-Me | ⋯O-Me | ⋯O-CH(Ph)-CH2OH | [M + Na]+, 1042.8 |
| 205 | ⋯OH | ⋯O-Me | ⋯O-Me | ⋯O-CH2-Ph | [M + Na]+, 1012.4 |
| 206 | ⋯OH | ⋯O-Me | ⋯O-Me | ⋯O-CH2-CH(OMe)-Ph | [M + Na]+, 1056.6 |

TABLE 3-continued
Rapamycin analogs with substitution at C16.
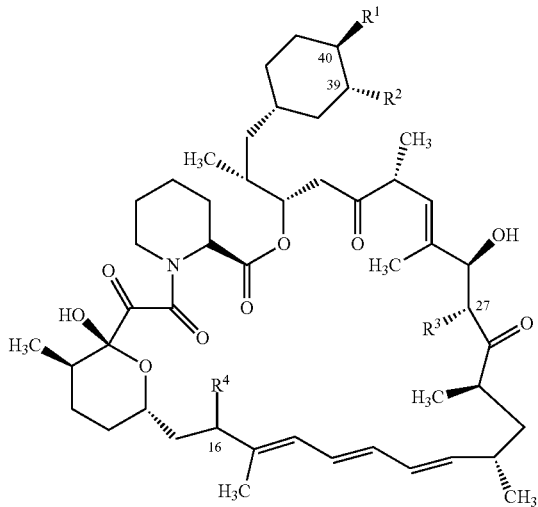
| No. # | R¹ | R² | R³ | R⁴ | LCMS Characterization Ion, mass obtained |
|---|---|---|---|---|---|
| 207 | ⟿OH | ⟿O―  | ⟿O― | ⟿O―⟨phenylpropyl⟩ | [M + Na]+, 1040.4 |
| 208 | ⟿OH | ⟿O― | ⟿O― | ⟿O―iPr | [M + Na]+, 964.4 |
| 209 | ⟿OH | ⟿O― | ⟿O― | ⟿O―cyclopropyl | [M + Na]+, 962.4 |
| 210 | ⟿OH | ⟿O― | ⟿O― | ⟿O―(CH₂)₃OH | [M + Na]+, 980.4 |
| 211 | ⟿OH | ⟿O― | ⟿O― | ⟿O―CH₂CH₂―Ph | [M + Na]+, 1026.6 |
| 212 | ⟿OH | ⟿O― | ⟿O― | ⟿―(N-methylpyrrole) | [M + H]+, 963.4 |
| 213 | ⟿OH | ⟿O― | ⟿O― | ⟿O―CH₂CH₂―(tetrahydropyran) | [M + Na]+, 1034.6 |

TABLE 3-continued

Rapamycin analogs with substitution at C16.

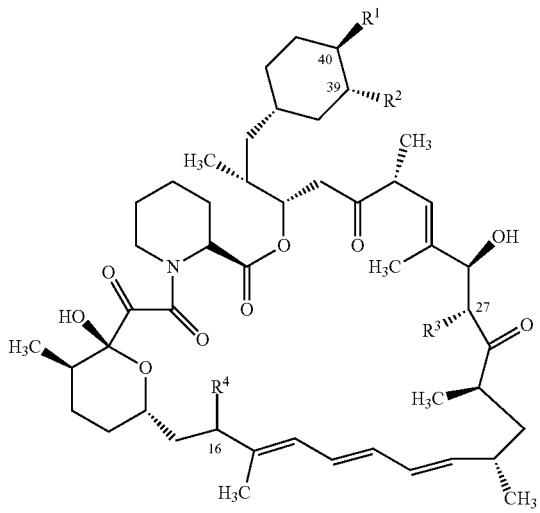

| No. # | R¹ | R² | R³ | R⁴ | LCMS Characterization Ion, mass obtained |
|---|---|---|---|---|---|
| 214 | ⋯OH | ⋯O−CH₃ | ⋯O−CH₃ | ⋯O−CH₂−CH(OH)−Ph | [M + Na]+, 1042.6 |
| 215 | ⋯OH | ⋯O−CH₃ | ⋯O−CH₃ | ⋯O−CH₂−(oxetanyl) | [M + H]+, 992.5 |
| 216 | ⋯OH | ⋯O−CH₃ | ⋯O−CH₃ | ⋯O−CH₂−C(OH)(CH₃)₂ | [M + Na]+, 994.6 |
| 217 | ⋯OH | ⋯O−CH₃ | ⋯O−CH₃ | ⋯O−CH₂−CH(OH)−Ph | [M + Na]+, 1042.6 |
| 218 | ⋯OH | ⋯O−CH₃ | ⋯O−CH₃ | ⋯O−(oxetanyl) | [M + Na]+, 978.3 |
| 219 | ⋯OH | ⋯O−CH₃ | ⋯O−CH₃ | ⋯O−CH₂CH₂−OH | [M + Na]+, 966.3 |
| 220 | ⋯OH | ⋯O−CH₃ | ⋯O−CH₃ | ⋯O−CH₂CH₂−O−CH₃ | [M + Na]+, 980.5 |
| 221 | ⋯OH | ⋯O−CH₃ | ⋯O−CH₃ | ⋯O−(CH₂)₄−OH | [M + Na]+, 994.3 |

TABLE 3-continued
Rapamycin analogs with substitution at C16.
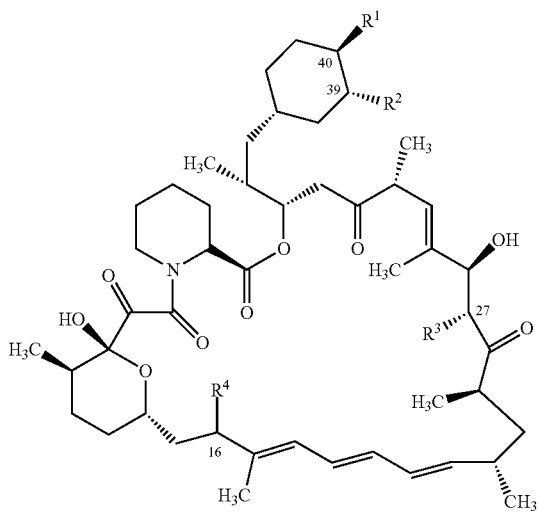
| No. # | R¹ | R² | R³ | R⁴ | LCMS Characterization Ion, mass obtained |
|---|---|---|---|---|---|
| 222 | OH | O-Me | O-Me | O-(CH₂)₄-OMe | [M + Na]+, 1003.6 |
| 223 | OH | O-Me | O-Me | O-CH₂-CH(OH)-CH₃ | [M + Na]+, 980.5 |
| 224 | OH | O-Me | O-Me | O-CH₂CH₂-O-CH₂CH₂-OH | [M + Na]+, 1010.6 |
| 225 | OH | O-Me | O-Me | O-CH₂CH₂CH₂-OMe | [M + Na]+, 994.8 |
| 226 | OH | O-Me | O-Me | O-CH₂-(tetrahydropyran-4-yl) | [M + Na]+, 1020.6 |
| 227 | OH | O-Me | O-Me | O-CH₂CH₂-O-CH₂CH₂-OMe | [M + Na]+, 1024.7 |

TABLE 4

Rapamycin analogs with substitution at C40.

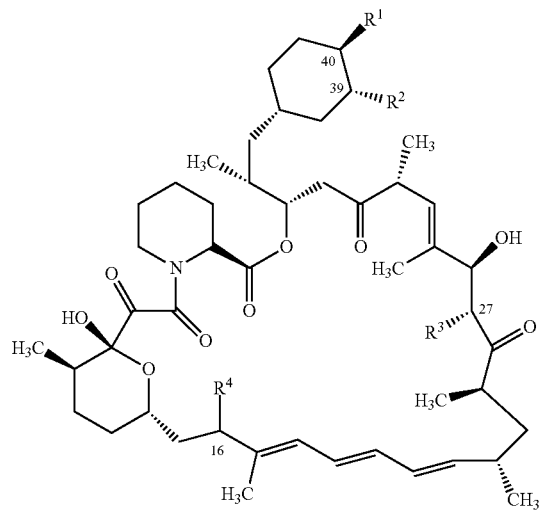

| No. # | R¹ | R² | R³ | R⁴ | LCMS Characterization Ion, mass obtained |
|---|---|---|---|---|---|
| 300 | -O-(CH₂)₄-morpholine | -OCH₃ | -OCH₃ | -OCH₃ | [M + H]+, 1055.9 |
| 301 | -OCH₂OCH₃ | -OCH₃ | -OCH₃ | -OCH₃ | [M + Na]+, 980.5 |
| 302 | -O-Si(CH₃)₂-C(CH₃)₃ | -OCH₃ | -OCH₃ | -OCH₃ | [M + Na]+, 1051.0 |
| 303 | -O-CH₂CH₂-O-Si(CH₃)₂-C(CH₃)₃ | -OCH₃ | -OCH₃ | -OCH₃ | [M + Na]+, 1051.0 |
| 304 | -OCH₃ | -OCH₃ | -OCH₃ | -OCH₃ | [M + H]+, 950.6 |
| 305 | -O-CH₂-Ph | -OCH₃ | -OCH₃ | -OCH₃ | [M + Na]+, 1026.3 |
| 306 | -O-CH₂CH₂-OH | -OCH₃ | -OCH₃ | -OCH₃ | [M + Na]+, 980.6 |
| 307 | -tetrazolyl | -OCH₃ | -OCH₃ | -OCH₃ | [M + Na]+, 988.3 |

TABLE 4-continued

Rapamycin analogs with substitution at C40.

| No. # | R¹ | R² | R³ | R⁴ | LCMS Characterization Ion, mass obtained |
|---|---|---|---|---|---|
| 308 | -O-CH₂CH₂-O-CH₂CH₂CH₂-O-CH₃ | -O-CH₃ | -O-CH₃ | -O-CH₃ | [M + Na]+, 1008.5 |
| 309 | -O-C(=O)-C(CH₃)(CH₂O-)(CH₂O-)C(CH₃)₂ (2,2,5-trimethyl-1,3-dioxane-5-carboxylate) | -O-CH₃ | -O-CH₃ | -O-CH₃ | [M + Na]+, 1092.3 |
| 310 | -O-CH₂CH₂CH₂-N(morpholine with 2-methyl) | -O-CH₃ | -O-CH₃ | -O-CH₃ | [M + H]+, 1056.0 |
| 311 | -N(tetrazolyl) | -O-CH₃ | -O-CH₃ | -O-CH₃ | [M + Na]+, 988.3 |
| 312 | -O-C(=O)-NH-CH₂CH₂-N(tetrazol-1-yl) | -O-CH₃ | -O-CH₃ | -O-CH₃ | [M + Na]+, 1075.6 |
| 313 | -O-C(=O)-N(CH₃)-CH₂CH₂-OH | -O-CH₃ | -O-CH₃ | -O-CH₃ | [M + Na]+, 1037.4 |
| 314 | -O-CH₃ | -O-CH₃ | -O-CH₃ | -O-CH₃ | [M + H]+, 950.6 |

TABLE 4-continued

Rapamycin analogs with substitution at C40.

| No. # | R¹ | R² | R³ | R⁴ | LCMS Characterization Ion, mass obtained |
|---|---|---|---|---|---|
| 315 | ⟅O⟍⟍O⟍ | ⟅O⟍ | ⟅O⟍ | ⟅O⟍ | [M + Na]+, 994.6 |
| 316 | ⟅O-C(=O)-CH₂CH₂-Ph | ⟅O⟍ | ⟅O⟍ | ⟅O⟍ | [M + Na]+, 1068.0 |
| 317 | ⟅O⟍⟍O⟍⟍O⟍⟍OH | ⟅O⟍ | ⟅O⟍ | ⟅O⟍ | [M + Na]+, 1068.6 |
| 318 | ⟅O-C(=O)-N(CH₃)-CH₂CH₂-piperidine | ⟅O⟍ | ⟅O⟍ | ⟅O⟍ | [M + H]+, 1082.9 |
| 319 | ⟅O⟍⟍⟍O⟍⟍OH | ⟅O⟍ | ⟅O⟍ | ⟅O⟍ | [M + Na]+, 1038.6 |
| 320 | ⟅O⟍⟍N(piperazine-N-CH₃) | ⟅O⟍ | ⟅O⟍ | ⟅O⟍ | [M + H]+, 1040.9 |
| 321 | ⟅O-C(=O)-N(CH₃)-CH₂CH₂CH₂-N(CH₃)₂ | ⟅O⟍ | ⟅O⟍ | ⟅O⟍ | [M + H]+, 1056.6 |
| 322 | ⟅O⟍⟍⟍N-morpholine | ⟅O⟍ | ⟅O⟍ | ⟅O⟍ | [M + H]+, 1041.6 |

TABLE 4-continued

Rapamycin analogs with substitution at C40.

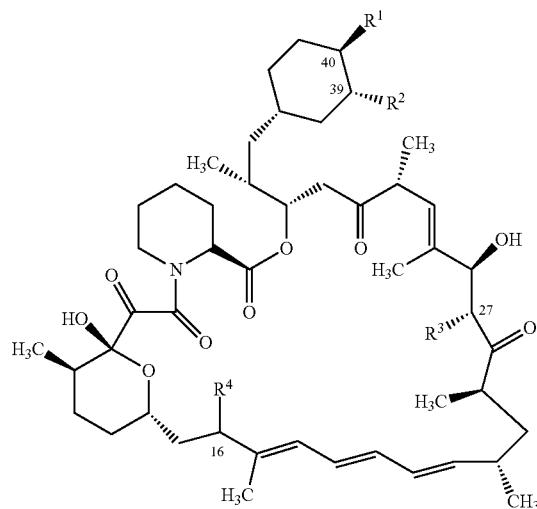

| No. # | R¹ | R² | R³ | R⁴ | LCMS Characterization Ion, mass obtained |
|---|---|---|---|---|---|
| 323 | ~O~~~OH | ~OMe | ~OMe | ~OMe | [M + H]+, 994.6 |
| 324 | ~O-C(O)-NH-CH₂CH₂-Ph | ~OMe | ~OMe | ~OMe | [M + Na]+, 1083.5 |
| 325 | ~O-CH₂CH₂-morpholine | ~OMe | ~OMe | ~OMe | [M + Na]+, 1050.4 |
| 326 | ~O-CH₂CH₂-O-CH₂-Ph | ~OMe | ~OMe | ~OMe | [M + Na]+, 1074.5 |
| 327 | ~O-C(O)-NH-CH₂CH₂CH₂-Ph | ~OMe | ~OMe | ~OMe | [M + Na]+, 1097.5 |
| 328 | ~O-CH₂CH₂CH₂-N(piperidinyl-3-OH) | ~OMe | ~OMe | ~OMe | [M + H]+, 1055.7 |
| 329 | ~O-CH₂CH₂-O-CH₂CH₂-O-CH₂CH₂-O-CH₂CH₂-OH | ~OMe | ~OMe | ~OMe | [M + Na]+, 1112.6 |
| 327 | ~O-CH₂CH₂CH₂CH₂-Ph | ~OMe | ~OMe | ~OMe | [M + Na]+, 1068.6 |

TABLE 4-continued

Rapamycin analogs with substitution at C40.

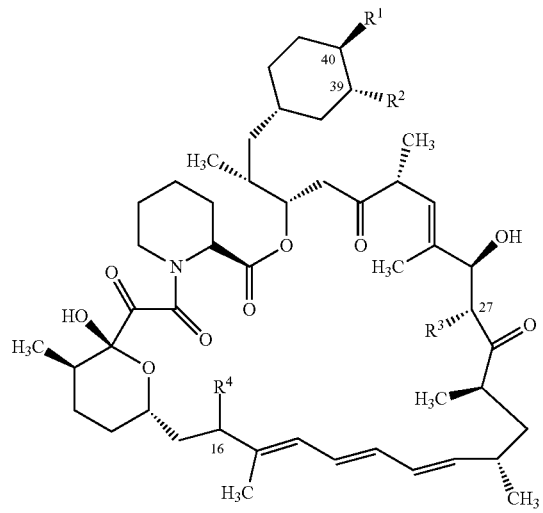

| No. # | R¹ | R² | R³ | R⁴ | LCMS Characterization Ion, mass obtained |
|---|---|---|---|---|---|
| 328 | ⁓O-(CH₂)₅-Ph | ⁓O-CH₃ | ⁓O-CH₃ | ⁓O-CH₃ | [M + Na]+, 1082.5 |
| 329 | ⁓O-(CH₂)₃-Ph | ⁓O-CH₃ | ⁓O-CH₃ | ⁓O-CH₃ | [M + Na]+, 1054.4 |
| 330 | ⁓O-C(O)-CH₂-N(piperidine) | ⁓O-CH₃ | ⁓O-CH₃ | ⁓O-CH₃ | [M + H]+, 1025.5 |
| 331 | ⁓O-C(O)-NH-(CH₂)₃-OCH₃ | ⁓O-CH₃ | ⁓O-CH₃ | ⁓O-CH₃ | [M + Na]+, 1028.4 |
| 332 | ⁓O-(CH₂)₃-N(N-methylpiperazine) | ⁓O-CH₃ | ⁓O-CH₃ | ⁓O-CH₃ | [M + H]+, 1054.7 |
| 333 | ⁓O-C(O)-NH-CH₂-(2-pyridyl) | ⁓O-CH₃ | ⁓O-CH₃ | ⁓O-CH₃ | [M + H]+, 1048.6 |
| 334 | ⁓O-C(O)-NH-(CH₂)₂-(4-pyridyl) | ⁓O-CH₃ | ⁓O-CH₃ | ⁓O-CH₃ | [M + H]+, 1062.5 |

TABLE 4-continued

Rapamycin analogs with substitution at C40.

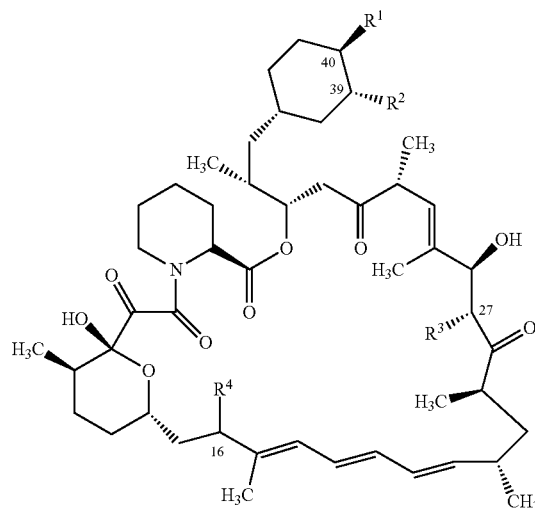

| No. # | R¹ | R² | R³ | R⁴ | LCMS Characterization Ion, mass obtained |
|---|---|---|---|---|---|
| 335 | carbamate-NH-CH₂CH₂-(2-pyridyl) | OMe | OMe | OMe | [M + H]+, 1061.5 |
| 336 | carbamate-NH-CH₂CH₂-morpholinyl | OMe | OMe | OMe | [M + H]+, 1070.5 |
| 337 | carbamate-NH-CH₂CH₂-cyclopropyl | OMe | OMe | OMe | [M + Na]+, 1047.4 |
| 338 | carbamate-N(Me)-CH₂CH₂CH₂-OH | OMe | OMe | OMe | [M + Na]+, 1051.4 |
| 339 | O-CH₂CH₂CH₂-N(2,2-dimethylmorpholinyl) | OMe | OMe | OMe | [M + Na]+, 980.5 |
| 340 | O-CH₂CH₂CH₂-N(3-hydroxypiperidinyl) | OMe | OMe | OMe | [M + H]+, 1056.0 |
| 341 | O-CH₂CH₂CH₂-N(piperidinyl) | OMe | OMe | OMe | [M + H]+, 1039.6 |

TABLE 4-continued

Rapamycin analogs with substitution at C40.

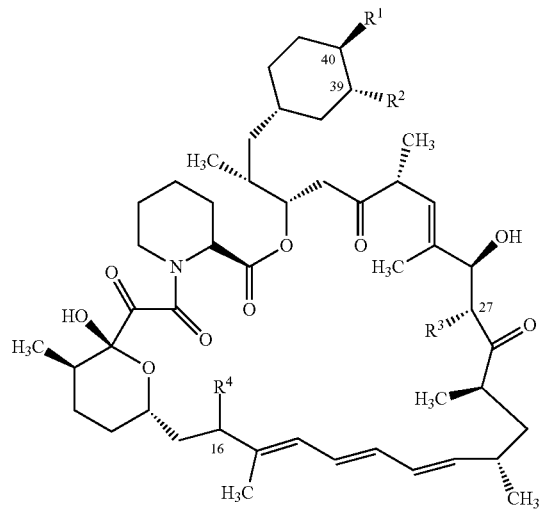

| No. # | R¹ | R² | R³ | R⁴ | LCMS Characterization Ion, mass obtained |
|---|---|---|---|---|---|
| 342 | -O-P(=O)(CH₃)(CH₃) | -OCH₃ | -OCH₃ | -OCH₃ | [M + Na]+, 1012.4 |
| 343 | -O-C(=O)-CH₂-N(CH₃)₂ | -OCH₃ | -OCH₃ | -OCH₃ | [M + H]+, 999.5 |
| 344 | -O-C(=O)-NH-(CH₂)₃-morpholine | -OCH₃ | -OCH₃ | -OCH₃ | [M + H]+, 1084.8 |
| 345 | -O-CH₂CH₂-morpholine | -OCH₃ | -OCH₃ | -OCH₃ | [M + H]+, 1025.8 |
| 346 | -O-C(=O)-NH-CH₂CH₂-O-CH₂CH₂-OCH₃ | -OCH₃ | -OCH₃ | -OCH₃ | [M + Na]+, 1081.6 |
| 347 | -O-C(=O)-NH-CH₂CH₂-(OCH₂CH₂)₃-OH | -OCH₃ | -OCH₃ | -OCH₃ | [M + Na]+, 1199.6 |
| 348 | -O-CH₂CH₂-phenyl | -OCH₃ | -OCH₃ | -OCH₃ | [M + Na]+, 1040.3 |
| 349 | -OH | -OCH₃ | -OCH₃ | -OCH₃ | |

TABLE 4-continued

Rapamycin analogs with substitution at C40.

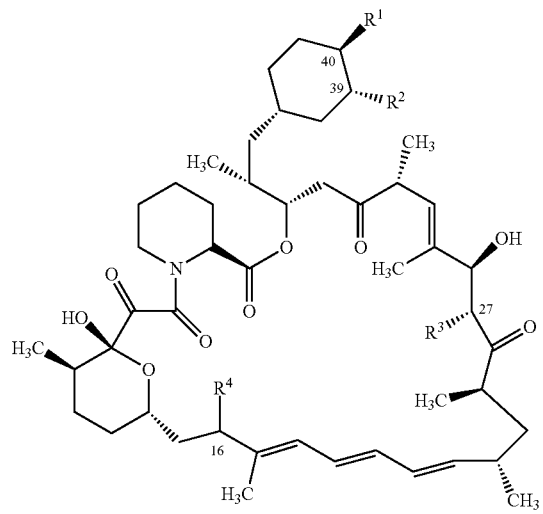

| No. # | R¹ | R² | R³ | R⁴ | LCMS Characterization Ion, mass obtained |
|---|---|---|---|---|---|
| 350 | ~O~O~O~O~O~OH | ~O~ | ~O~ | ~O~ | [M + Na]+, 1156.7 |
| 351 | ~O-C(=O)-NH-CH₂CH₂-(3-pyridyl) | ~O~ | ~O~ | ~O~ | [M + H]+, 1061.6 |
| 352 | ~O~O~O~OH | ~O~ | ~O~ | ~O~ | [M + Na]+, 1038.6 |
| 353 | ~O~CH₂CH₂-N(4-hydroxypiperidinyl) | ~O~ | ~O~ | ~O~ | [M + H]+, 1041.9 |
| 354 | ~O-C(=O)-C(CH₃)(CH₂OH)(CH₂CH₂OH) | ~O~ | ~O~ | ~O~ | [M + Na]+, 1052.4 |
| 355 | ~O-C(=O)-NH-CH₂-C₆H₅ | ~O~ | ~O~ | ~O~ | [M + Na]+, 1069.4 |
| 356 | ~O-C(=O)-N(CH₃)-CH₂CH₂-morpholinyl | ~O~ | ~O~ | ~O~ | [M + H]+, 1084.7 |

TABLE 4-continued

Rapamycin analogs with substitution at C40.

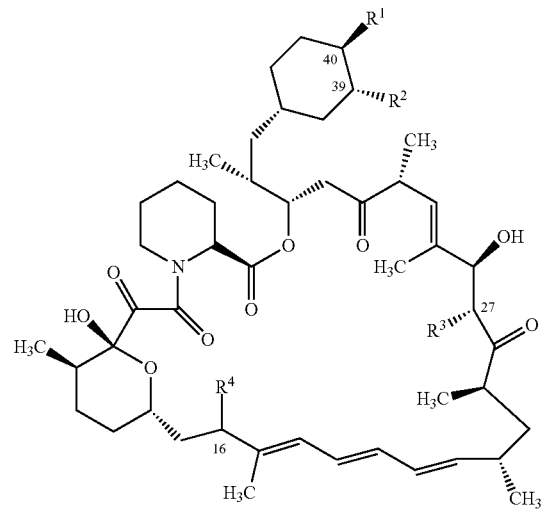

| No. # | R¹ | R² | R³ | R⁴ | LCMS Characterization Ion, mass obtained |
|---|---|---|---|---|---|
| 357 | carbamate-N(CH₂CH₂OH)₂ | -OCH₃ | -OCH₃ | -OCH₃ | [M + Na]+, 1067.6 |
| 358 | carbamate-NH-CH₂CH₂CH₂-N(CH₂CH₂OH)(CH₂CH₂OH) | -OCH₃ | -OCH₃ | -OCH₃ | [M + H]+, 1102.6 |
| 359 | carbamate-N(CH₃)CH₂CH₂N(CH₃)₂ | -OCH₃ | -OCH₃ | -OCH₃ | [M + H]+, 1042.7 |
| 360 | carbamate-NH-CH₂CH₂-N(CH₃)₂ | -OCH₃ | -OCH₃ | -OCH₃ | [M + Na]+, 1028.7 |
| 361 | carbamate-NH-glucosamine | -OCH₃ | -OCH₃ | -OCH₃ | [M + Na]+, 1141.4 |
| 362 | carbamate-NH-CH₂CH₂OH | -OCH₃ | -OCH₃ | -OCH₃ | [M + Na]+, 1023.6 |
| 363 | -O-CH₂CH₂CH₂-N(CH₃)₂ | -OCH₃ | -OCH₃ | -OCH₃ | [M + H]+, 999.7 |

TABLE 4-continued

Rapamycin analogs with substitution at C40.

[Structure of rapamycin analog backbone with R¹, R², R³, R⁴ substitution positions at C40, C39, C27, and C16]

| No. # | R¹ | R² | R³ | R⁴ | LCMS Characterization Ion, mass obtained |
|---|---|---|---|---|---|
| 364 | carbamate-NH-CH₂CH₂-(imidazole) | OMe | OMe | OMe | [M + H]+, 1051.4 |
| 365 | carbamate-NH-CH₂CH₂-(piperidine) | OMe | OMe | OMe | [M + H]+, 1068.7 |
| 366 | carbamate-NH-CH₂CH₂CH₂-(piperidine) | OMe | OMe | OMe | [M + H]+, 1082.7 |
| 367 | carbamate-NH-CH₂CH₂-(N-methylpiperazine) | OMe | OMe | OMe | [M + H]+, 1083.7 |
| 368 | -O-CH₂CH₂CH₂-N(4-hydroxypiperidine) | OMe | OMe | OMe | [M + H]+, 1055.7 |

Example 12: Inhibition Assay for mTORC1 and mTORC2

The IC50s of the inhibition of mTORC1 and mTORC2 were determined in vitro by determining the phosphorylation of pS6K at position Thr389 (mTORC1 inhibition) and pAkt at Ser473 (mTORC2 inhibition). In vitro studies were performed with AlphaLISA® technology using PC3 cells (Prostate Adenocarcinoma; Human (*Homo sapiens*)). The cells were seeded in 96 well plates and were treated for 24 hours with the different compounds. Inhibition of phosphorylation of S6K and Akt was determined directly using AlphaLISA® SurFire® assays according to the manufacturer instructions (Alpha. Sure Fire ULTRA ART 1/2/3 pS$^{473}$; Perkin Elmer ALSU-PAKT-B10 K; Alpha. SF ULTRA p70 S6K pT389; Perkin Elmer ALSU-PP70-A10K; Alpha. SF ULTRA Total AKT1; Perkin Elmer ALSU-TAK1-A10K). All analysis were performed using GraphPad Prism 7.0 (GraphPad Software, San Diego, USA).

Tables 5-7 include pIC$_{50}$ values for mTORC1 of selected compounds; with compounds having an pIC$_{50}$ for mTORC1 of >9.5 as A, 8.5 to 9.5 as B, and less than 8.5 as C. Tables 5-7 include PIC$_{50}$ values for mTORC2 of selected compounds; with compounds having an PIC$_{50}$ for mTORC2 of <5 as A, 5 to 6 as B, and greater than 6 as C.

TABLE 5 pIC$_{50}$ for mTORC1 and mTORC2 of Rapamycin analogs substituted at C40 and C16

| Compound No. # | pIC50 mTORC1 | pIC50 mTORC2 |
|---|---|---|
| 1 | A | A |
| 2 | A | A |
| 3 | A | A |
| 4 | A | A |
| 5 | A | A |
| 6 | A | A |
| 7 | A | A |
| 8 | A | A |
| 9 | A | A |
| 10 | A | A |
| 11 | A | A |
| 12 | A | A |
| 13 | A | A |
| 14 | A | A |
| 15 | A | A |
| 16 | A | A |
| 17 | A | A |
| 18 | A | A |
| 19 | A | A |
| 20 | A | A |
| 21 | A | A |
| 22 | A | A |
| 23 | A | A |
| 24 | A | A |
| 25 | A | B |
| 26 | A | A |
| 27 | A | B |
| 28 | A | B |
| 29 | A | A |
| 30 | A | B |
| 31 | A | B |
| 32 | A | B |
| 33 | A | B |
| 34 | B | A |
| 35 | A | B |
| 36 | A | B |
| 37 | B | A |
| 38 | B | A |
| 39 | A | B |
| 40 | A | B |
| 41 | A | B |
| 42 | A | B |
| 43 | A | B |
| 44 | A | B |
| 45 | A | B |
| 46 | B | A |
| 47 | A | B |
| 48 | A | B |
| 49 | B | A |
| 50 | A | B |
| 51 | A | B |
| 52 | A | B |
| 53 | B | A |
| 54 | A | B |
| 55 | A | B |
| 56 | A | B |
| 57 | A | B |
| 58 | A | B |
| 59 | A | B |
| 60 | A | B |
| 61 | B | A |
| 62 | A | B |
| 63 | A | B |
| 64 | B | A |
| 65 | A | B |
| 66 | A | B |
| 67 | B | A |
| 68 | A | B |
| 69 | B | A |
| 70 | A | B |
| 71 | B | A |
| 72 | B | A |
| 73 | A | B |
| 74 | A | B |
| 75 | B | B |
| 76 | B | A |
| 77 | B | A |
| 78 | B | A |
| 79 | A | B |
| 80 | B | A |
| 81 | B | B |
| 82 | B | B |
| 83 | B | B |
| 84 | B | B |
| 85 | B | B |
| 86 | B | B |
| 87 | B | B |
| 88 | A | B |
| 89 | B | B |
| 90 | A | B |
| 91 | B | B |
| 92 | A | B |
| 93 | A | C |
| 94 | A | B |
| 95 | A | C |
| 96 | C | A |
| 97 | A | C |
| 98 | B | B |
| 99 | A | B |
| 100 | A | C |
| 101 | A | C |
| 102 | A | B |
| 103 | B | B |
| 104 | A | C |
| 105 | A | C |
| 106 | B | B |
| 107 | A | C |
| 108 | A | C |
| 109 | A | C |
| 110 | A | C |
| 111 | A | C |
| 112 | A | C |
| 113 | A | C |
| 114 | A | C |
| 115 | A | C |
| 116 | B | C |
| 117 | A | C |

TABLE 6 pIC$_{50}$ for mTORC1 and mTORC2 of Rapamycin analogs substituted at C16

| Compound No. # | pIC50 mTORC1 | pIC50 mTORC2 |
|---|---|---|
| 200 | C | B |
| 201 | C | B |
| 202 | C | B |
| 203 | C | B |
| 204 | A | C |
| 205 | A | C |
| 206 | B | B |
| 207 | B | B |
| 208 | B | B |
| 209 | A | C |
| 210 | B | C |
| 211 | A | C |
| 212 | B | B |
| 213 | B | B |
| 214 | A | B |
| 215 | B | B |
| 216 | B | B |
| 217 | A | B |
| 218 | B | A |

TABLE 6-continued pIC$_{50}$ for mTORC1 and mTORC2 of Rapamycin analogs substituted at C16

| Compound No. # | pIC50 mTORC1 | pIC50 mTORC2 |
|---|---|---|
| 219 | B | A |
| 220 | A | B |
| 221 | A | B |
| 222 | A | B |
| 223 | B | A |
| 224 | B | A |
| 225 | A | B |
| 226 | B | A |
| 227 | A | A |

TABLE 7 pIC$_{50}$ for mTORC1 and mTORC2 of Rapamycin analogs substituted at C40

| Compound No. # | pIC50 mTORC1 | pIC50 mTORC2 |
|---|---|---|
| 300 | A | C |
| 301 | A | C |
| 302 | C | B |
| 303 | A | C |
| 304 | A | C |
| 305 | A | C |
| 306 | A | C |
| 307 | A | C |
| 308 | A | C |
| 309 | A | C |
| 310 | A | C |
| 311 | A | C |
| 312 | A | C |
| 313 | A | C |
| 314 | A | C |
| 315 | A | C |
| 316 | A | C |
| 317 | A | C |
| 318 | A | C |
| 319 | A | C |
| 320 | A | C |
| 321 | A | C |
| 322 | A | C |
| 323 | A | C |
| 324 | A | C |
| 325 | A | C |
| 326 | A | C |
| 327 | A | C |
| 328 | A | C |
| 329 | A | C |
| 330 | A | C |
| 331 | A | C |
| 332 | A | C |
| 333 | A | C |
| 334 | A | C |
| 335 | A | C |
| 336 | A | C |
| 337 | A | C |
| 338 | A | C |
| 339 | A | C |
| 340 | A | C |
| 341 | A | C |
| 342 | A | C |
| 343 | A | C |
| 344 | A | C |
| 345 | A | C |
| 346 | A | C |
| 347 | A | C |
| 348 | A | C |
| 349 | A | C |
| 350 | A | C |
| 351 | A | C |
| 352 | A | C |

TABLE 7-continued pIC$_{50}$ for mTORC1 and mTORC2 of Rapamycin analogs substituted at C40

| Compound No. # | pIC50 mTORC1 | pIC50 mTORC2 |
|---|---|---|
| 353 | A | C |
| 354 | A | C |
| 355 | A | C |
| 356 | A | C |
| 357 | A | C |
| 358 | A | C |
| 359 | A | C |
| 360 | A | C |
| 361 | C | C |
| 362 | A | C |
| 363 | A | C |
| 364 | A | C |
| 365 | A | C |
| 366 | C | B |
| 367 | A | C |
| 368 | A | C |

What is claimed is:
1. A compound represented by the structure of Formula (I):

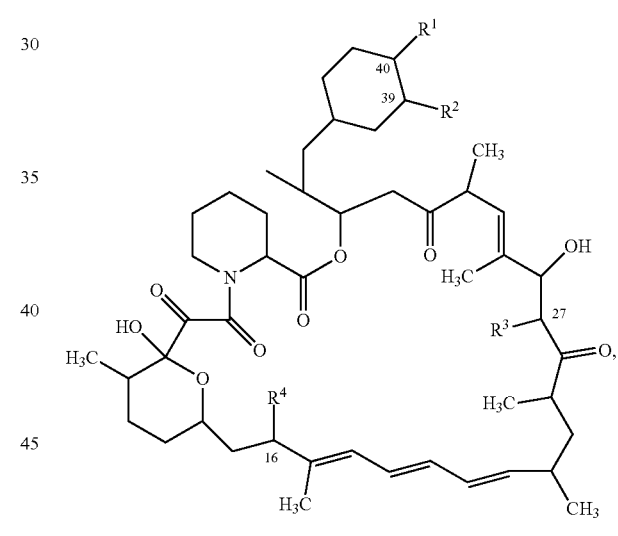

or a pharmaceutically acceptable salt thereof, wherein:
R$^1$ is selected from

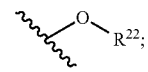

R$^2$ is selected from hydrogen and an optionally substituted C$_1$-C$_6$ alkoxy group, wherein substituents are independently selected at each occurrence from hydroxy, halogen, cyano, nitro, C$_2$-C$_6$ alkoxy group, cycloalkyl, aryl, heteroaryl, and heterocycloalkyl, wherein cycloalkyl, aryl, heterocyloalkyl, and heteroaryl, are each optionally substituted with one or more substituents independently selected from hydroxy, halogen, cyano, nitro, alkyl, haloalkyl, hydroxyalkyl, alkoxy, and alkoxyalkyl;

$R^3$ is selected from hydrogen and an optionally substituted $C_1$-$C_6$ alkoxy group, wherein the substituents independently selected at each occurrence from hydroxy, halogen, cyano, nitro, $C_2$-$C_6$ alkoxy group, cycloalkyl, aryl, heteroaryl, and heterocycloalkyl, wherein cycloalkyl, aryl, heterocyloalkyl, and heteroaryl, are each optionally substituted with one or more substituents independently selected from hydroxy, halogen, cyano, nitro, alkyl, haloalkyl, hydroxyalkyl, alkoxy, and alkoxyalkyl;

$R^4$ is selected from

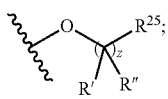

z is 2, 3, 4, or 5;

each R' and R" are independently selected from hydrogen, halogen, —$OR^{31}$, and $C_{1-3}$ alkyl optionally substituted with one or more substituents independently selected from halogen and —$OR^{31}$;

$R^{25}$ is selected from —$OR^{31}$;

$R^{31}$ is independently selected at each occurrence from hydrogen, —Si($C_1$-$C_6$ alkyl)$_3$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OSi($C_1$-$C_6$ alkyl)$_3$, —CN, —$NO_2$, —$NH_2$, =O, =S, $C_{1-10}$ alkyl, —$C_{1-10}$ haloalkyl, —$C_{2-10}$ alkenyl, $C_{2-10}$ alkynyl, $C_{3-12}$ carbocycle, and 3- to 12-membered heterocycle;

$R^{22}$ is selected from $C_3$-$C_6$ alkyl substituted with one or more substituents selected from;
  halogen, —$OR^{30}$, —$N(R^{30})_2$, —(O—$CH_2$—($CH_2$)$_p$)$_n$—W, —$SR^{30}$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, —CN;
  $C_{2-10}$ alkenyl, $C_{2-10}$ alkynyl, each of which is optionally substituted with one or more substituents independently selected from halogen, —$OR^{30}$, —$SR^{30}$, —$N(R^{30})_2$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, —CN, $C_{3-10}$ carbocycle and 3- to 10-membered heterocycle;
  $C_{3-10}$ carbocycle which is optionally substituted with one or more substituents independently selected from halogen, —$OR^{30}$, —$SR^{30}$, —$N(R^{30})_2$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, —CN, $C_{1-6}$ alkyl, $C_{1-6}$ alkyl-$R^{30}$, $C_{2-6}$ alkenyl, and $C_{2-6}$ alkynyl;

each p is selected from 1 or 2;

n is selected from 1-4;

W is selected from —OH and —$CH_3$ $R^{30}$ is independently selected at each occurrence from hydrogen, —Si($C_1$-$C_6$ alkyl)$_3$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —OSi($C_1$-$C_6$ alkyl)$_3$, —CN, —$NO_2$, —$NH_2$, =O, =S, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle.

2. The compound or salt of claim 1, wherein $R^1$ is selected from

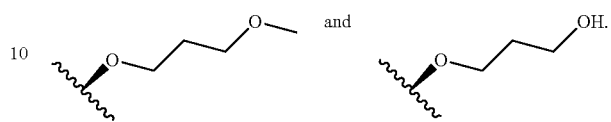

3. The compound or salt of claim 1, wherein $R^4$ is selected from

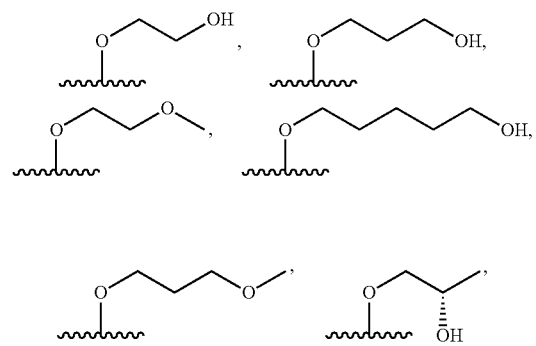

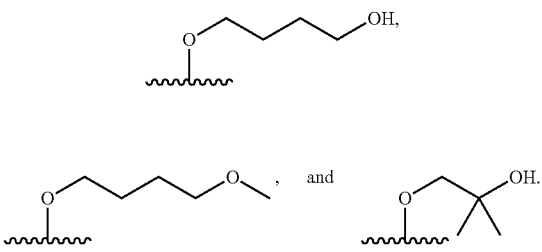

4. The compound or salt of claim 1, wherein $R^{22}$ is selected from $C_3$-$C_6$ alkyl substituted with one or more substituents selected from halogen, —$OR^{30}$, —$N(R^{30})_2$, —(O—$CH_2$—($CH_2$)$_p$)$_n$—W, —$SR^{30}$, —$N(R^{30})_2$, —$C(O)R^{30}$, —$C(O)N(R^{30})_2$, —$N(R^{30})C(O)R^{30}$, —$C(O)OR^{30}$, —$OC(O)R^{30}$, —$S(O)R^{30}$, —$S(O)_2R^{30}$, —$P(O)(OR^{30})_2$, —$OP(O)(OR^{30})_2$, —$NO_2$, =O, =S, =$N(R^{30})$, and —CN.

5. The compound or salt of claim 1, wherein $R^{22}$ is selected from $C_3$-$C_6$ alkyl substituted with one or more substituents selected from halogen, —$OR^{30}$, —$N(R^{30})_2$, —$SR^{30}$, —$S(O)R^{30}$, —$S(O)_2R^{30}$, —$NO_2$, =O, and —CN.

6. The compound or salt of claim 1, wherein $R^{22}$ is selected from substituted $C_3$ alkyl.

7. The compound or salt of claim 1, wherein $R^{30}$ is selected from hydrogen and $C_{1-10}$ alkyl.

8. The compound or salt of claim 1, wherein $R^{31}$ is selected from hydrogen, and $C_{1-10}$ alkyl.

9. The compound or salt of claim 1, wherein each R' and R" are independently selected from hydrogen, and $C_{1-3}$ alkyl.

10. The compound or salt of claim 1, wherein the compound is
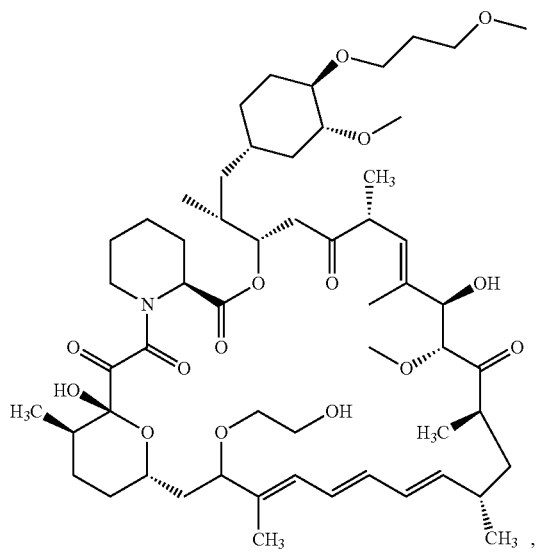
or a salt thereof.
11. The compound or salt of claim 1, wherein the compound is
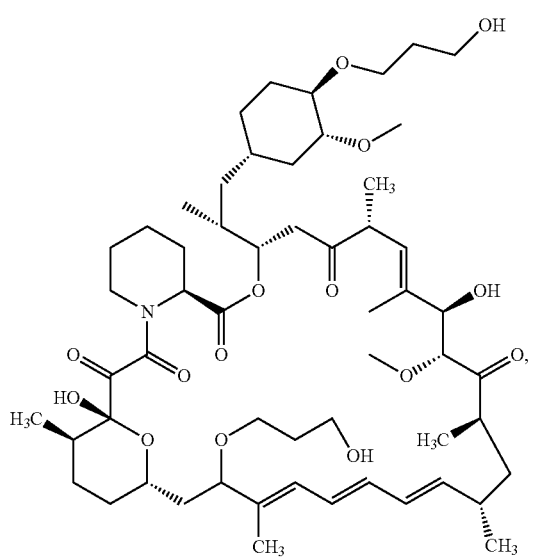 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCO)C[C@@H]3CC[C@@H](C)[C@@](O)(O3)C(=O)C(=O)N3CCCC[C@H]3C(=O)O2)CC[C@H]1OCCCO]
or a salt thereof.
12. The compound or salt of claim 1, wherein the compound is
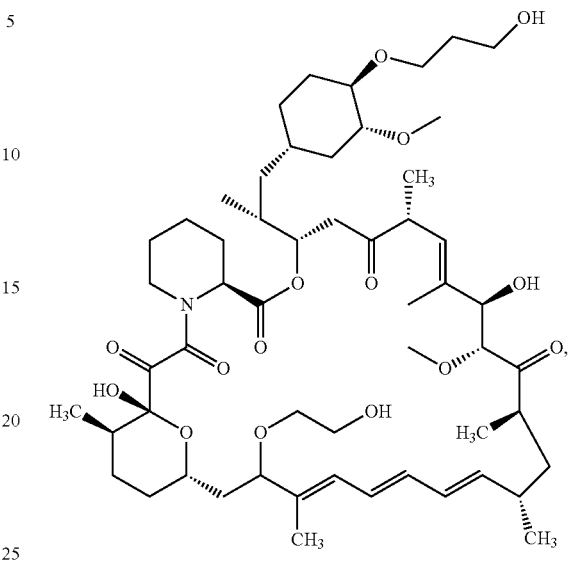
or a salt thereof.
13. The compound or salt of claim 1, wherein the compound is
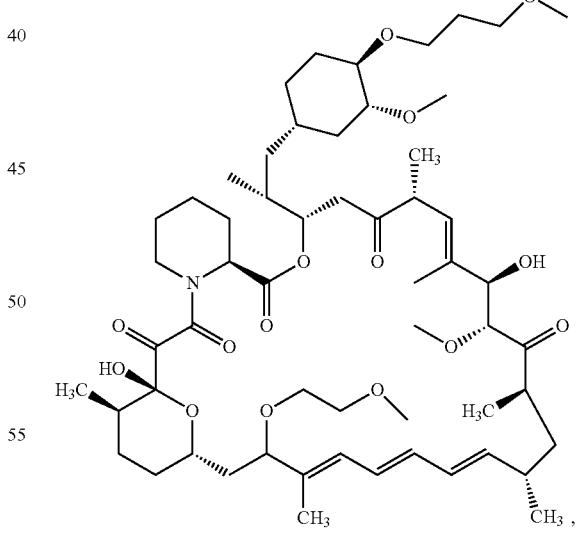
or a salt thereof.

14. The compound or salt of claim 1, wherein the compound is
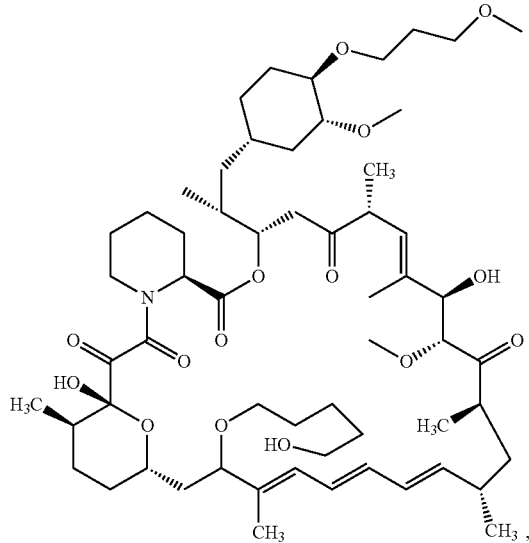
or a salt thereof.
15. The compound or salt of claim 6, wherein the compound is
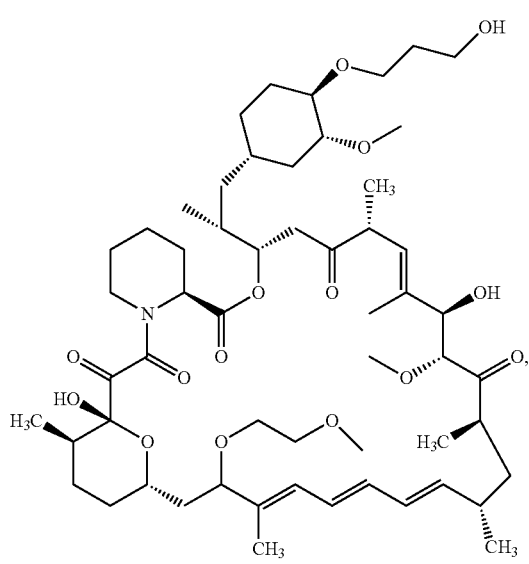 [SMILES: COCCOC1C[C@@H]2CC[C@@H](C)[C@@](O)(O2)C(=O)C(=O)N2CCCC[C@H]2C(=O)O[C@H]([C@H](C)C[C@@H]2CC[C@@H](OCCCO)[C@H](OC)C2)CC(=O)[C@H](C)/C=C(\C)[C@@H](O)[C@@H](OC)C(=O)[C@H](C)C[C@H](C)/C=C/C=C/C=C/1C]
or a salt thereof.
16. The compound or salt of claim 1, wherein the compound is selected from:
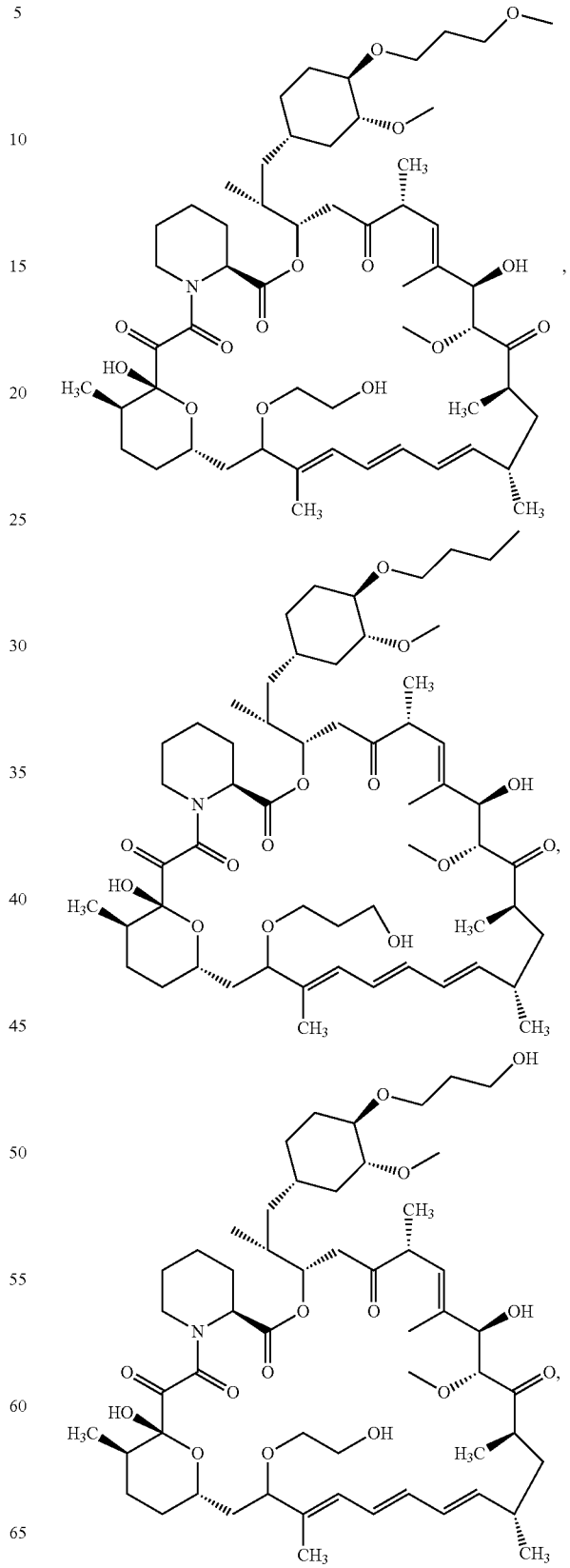

243
-continued
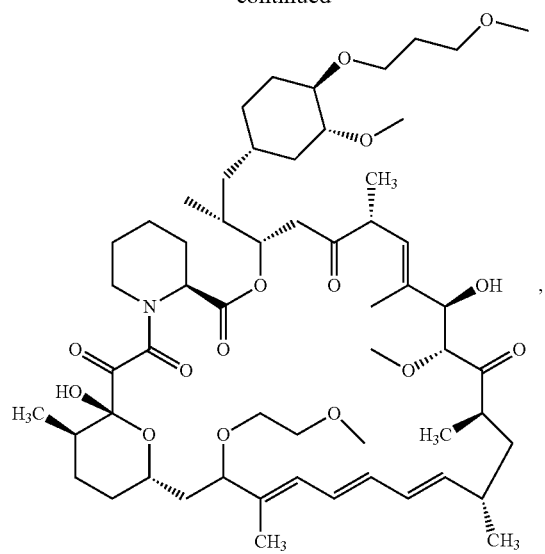
,
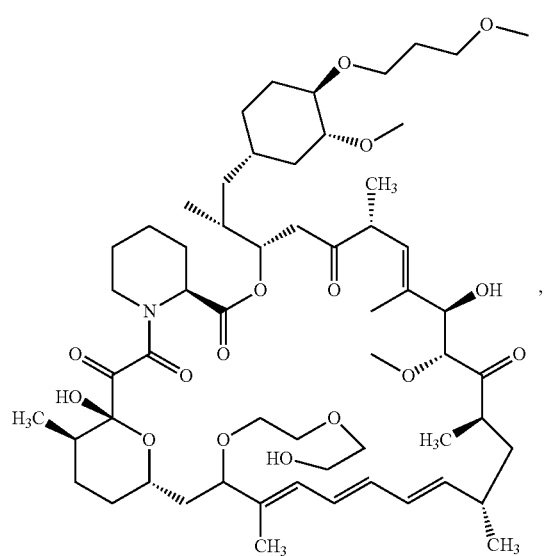
,
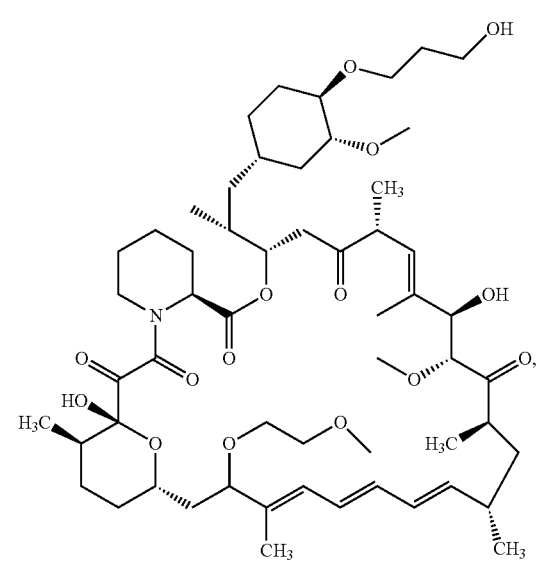
244
-continued
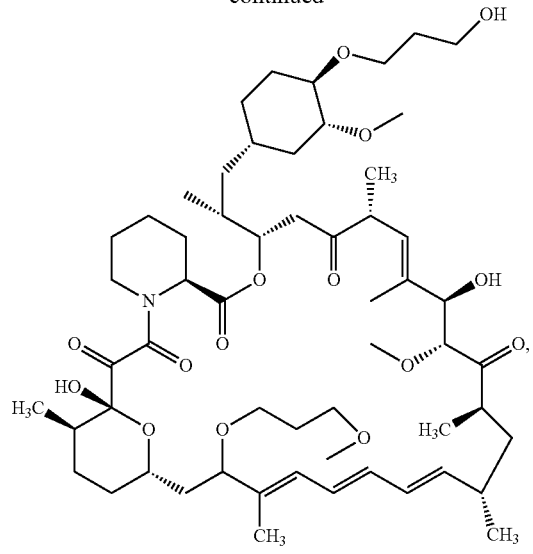
,
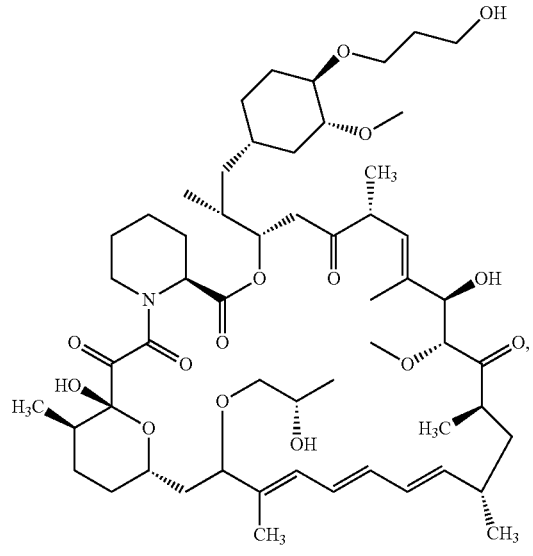
,
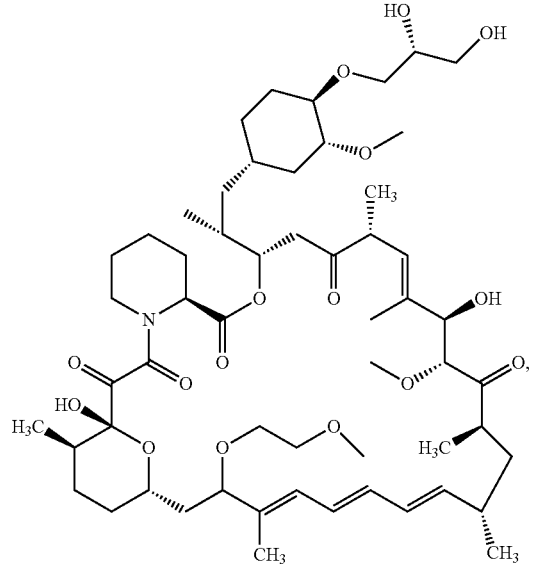 [SMILES: COCCOC1C[C@@H]2CC[C@@H](C)[C@@](O)(O2)C(=O)C(=O)N2CCCC[C@H]2C(=O)O[C@H]([C@H](C)C[C@@H]2CC[C@@H](OC[C@@H](O)CO)[C@H](OC)C2)CC(=O)[C@H](C)/C=C(\C)[C@@H](O)[C@@H](OC)C(=O)[C@H](C)C[C@H](C)/C=C/C=C/C=C/1C]

245
-continued
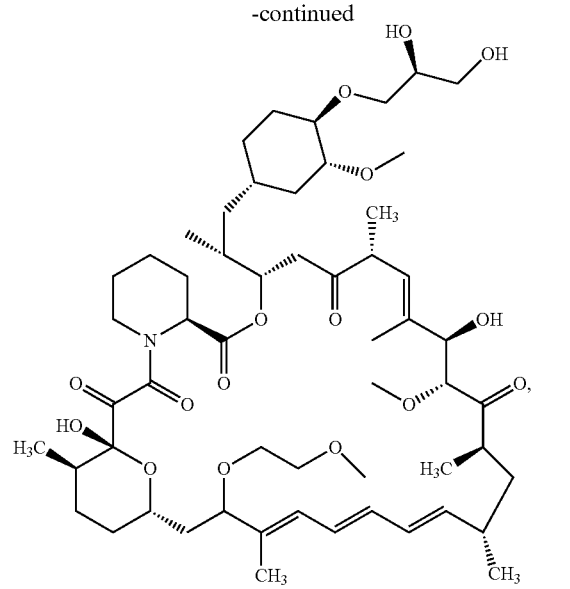
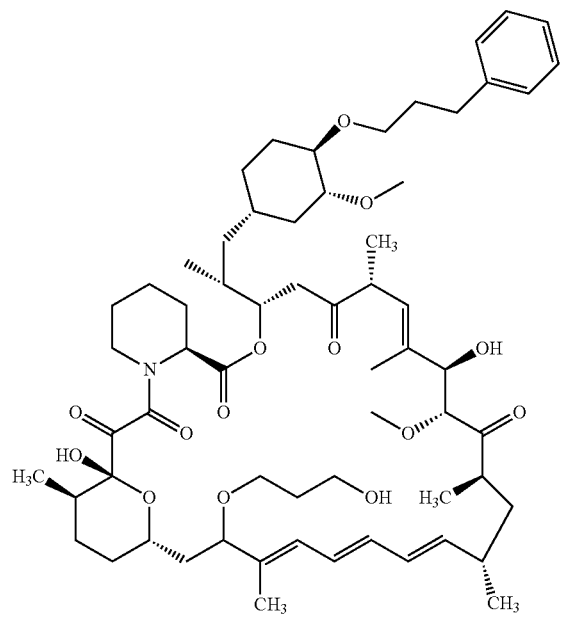
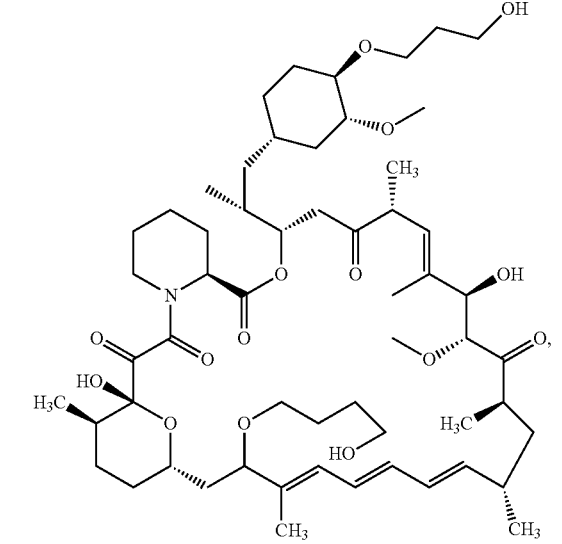
246
-continued
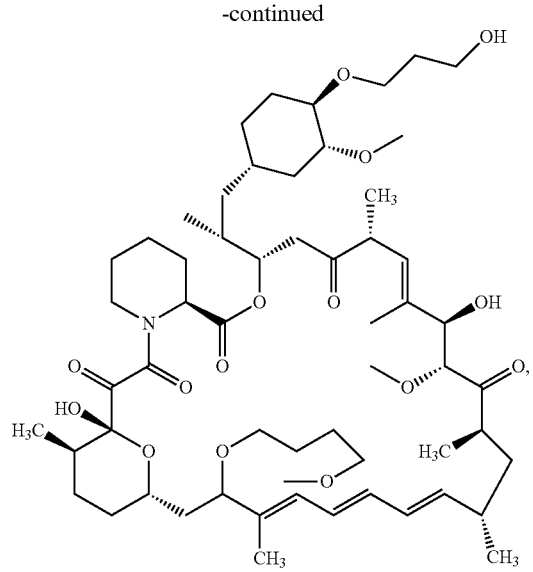
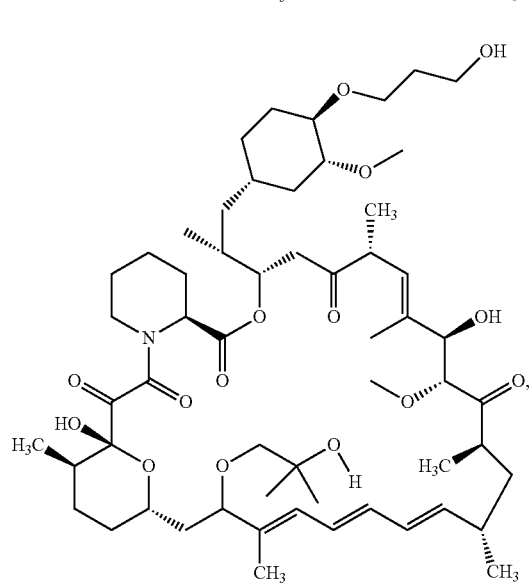
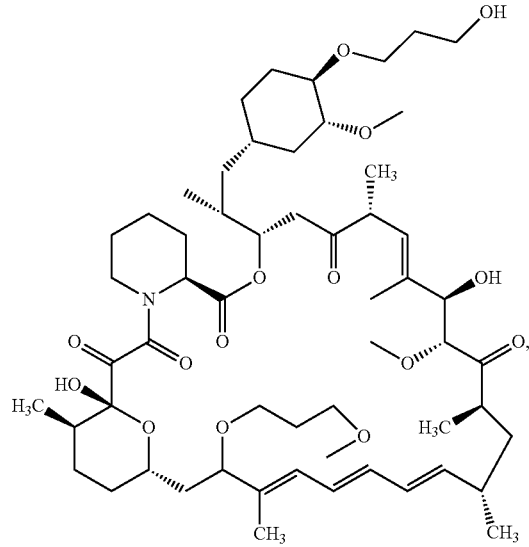
or salt of any one thereof.

17. A pharmaceutical composition comprising a compound or salt of claim 1 and a pharmaceutically acceptable excipient.

18. A method of treating a subject with a chronic disease wherein the subject would benefit from inhibition of the activity of mTORC1, comprising administering to the subject a pharmaceutical composition of claim 17.

19. The method of claim 18, wherein said benefit includes the improvement of one or more symptoms associated with the chronic disease.

20. The method of claim 19, wherein the chronic disease is an mTORopathy.

\* \* \* \* \*